(12) United States Patent
Wrobleski et al.

(10) Patent No.: US 7,923,556 B2
(45) Date of Patent: Apr. 12, 2011

(54) PHENYL-SUBSTITUTED PYRIMIDINE COMPOUNDS USEFUL AS KINASE INHIBITORS

(75) Inventors: Stephen T. Wrobleski, Whitehouse Station, NJ (US); Shuqun Lin, Newtown, PA (US); Katerina Leftheris, Skillman, NJ (US); Liqi He, Furlong, PA (US); Steven P. Seitz, Swarthmore, PA (US); Tai-An Lin, Pequannock, NJ (US); Wayne Vaccaro, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/570,010

(22) Filed: Sep. 30, 2009

(65) Prior Publication Data

US 2010/0029649 A1 Feb. 4, 2010

Related U.S. Application Data

(63) Continuation of application No. 11/344,881, filed on Feb. 1, 2006, now abandoned.

(60) Provisional application No. 60/650,077, filed on Feb. 4, 2005.

(51) Int. Cl.
| | |
|---|---|
| *C07D 403/04* | (2006.01) |
| *C07D 403/14* | (2006.01) |
| *A61K 31/506* | (2006.01) |
| *A61P 19/02* | (2006.01) |
| *A61K 31/53* | (2006.01) |
| *C07D 401/04* | (2006.01) |
| *C07D 401/14* | (2006.01) |

(52) U.S. Cl. ........ 544/315; 544/316; 544/319; 544/320; 514/269; 514/275

(58) Field of Classification Search .................. 544/315, 544/316, 319, 320; 514/269, 275
See application file for complete search history.

(56) References Cited

U.S. PATENT DOCUMENTS

| | | | |
|---|---|---|---|
| 4,200,750 A | 4/1980 | Warner, Jr. et al. | |
| 4,873,248 A | 10/1989 | Katoh et al. | |
| 5,022,915 A | 6/1991 | Prisbylla | |
| 5,250,530 A | 10/1993 | Giencke et al. | |
| 5,250,533 A | 10/1993 | Heinemann et al. | |
| 5,658,903 A | 8/1997 | Adams et al. | |
| 5,712,279 A | 1/1998 | Biller et al. | |
| 5,739,135 A | 4/1998 | Biller et al. | |
| 5,760,246 A | 6/1998 | Biller et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,184,231 B1 | 2/2001 | Hewawasam et al. | |
| 6,251,914 B1 | 6/2001 | Adams et al. | |
| 6,277,989 B1 | 8/2001 | Chakravarty et al. | |
| 6,531,479 B2 | 3/2003 | Wang et al. | |
| 6,548,529 B1 | 4/2003 | Robl et al. | |
| 6,670,357 B2 | 12/2003 | Leftheris et al. | |
| 6,706,720 B2 | 3/2004 | Atwal et al. | |
| 6,720,427 B2 | 4/2004 | Sanner et al. | |
| 2002/0010170 A1 | 1/2002 | Salituro et al. | |
| 2004/0039033 A1 | 2/2004 | Atwal et al. | |
| 2007/0027155 A1 | 2/2007 | Bakthavatchalam et al. | |
| 2008/0132509 A1 | 6/2008 | Blum et al. | |

FOREIGN PATENT DOCUMENTS

| | | |
|---|---|---|
| FR | 2201083 | 4/1974 |
| JP | 2001089452 | 4/2001 |
| JP | 2003206230 | 7/2003 |
| WO | WO 00/12074 | 3/2000 |
| WO | WO 00/12497 | 3/2000 |
| WO | WO 00/56738 | 9/2000 |
| WO | WO 01/27089 | 4/2001 |
| WO | WO 01/34605 | 5/2001 |
| WO | WO 02/22607 | 3/2002 |
| WO | WO 03/029248 | 4/2003 |
| WO | WO 03/099820 | 12/2003 |
| WO | WO 2004/011443 | 2/2004 |

(Continued)

OTHER PUBLICATIONS

Mass, R. D., Int. J. Radiation Oncology Bio. Phys.vol. 58(3): 932-940, 2004.*

(Continued)

*Primary Examiner* — Venkataraman Balasubramanian
(74) *Attorney, Agent, or Firm* — Lauralee L. Duncan

(57) ABSTRACT

Compounds having the formula (I),

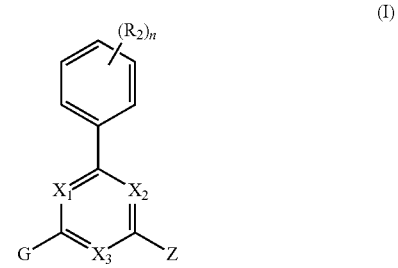

and pharmaceutically acceptable salts, and solvates thereof, are useful as kinase inhibitors, wherein:
two of $X_1$, $X_2$, and $X_3$ are N, and the remaining one of $X_1$, $X_2$, and $X_3$ is —$CR_1$;
$R_1$ is hydrogen or —CN; and
N, G, Z, $R_2$, $R_3$, $R_4$, $R_5$, and $R_6$ are described in the specification.

Also disclosed are pharmaceutical compositions containing compounds of formula (I), and methods of treating conditions associated with the activity of p38 kinase and/or conditions associated with the activity of LIM kinase.

10 Claims, No Drawings

FOREIGN PATENT DOCUMENTS

| | | |
|---|---|---|
| WO | WO 2004/043467 | 5/2004 |
| WO | WO 2004043467 | 5/2004 |
| WO | WO 2004/071440 | 8/2004 |
| WO | WO 2004/080979 | 9/2004 |
| WO | WO 2004/087679 | 10/2004 |
| WO | WO 2004084824 A2 | 10/2004 |
| WO | WO 2004/096797 | 11/2004 |
| WO | WO 2005/079801 | 9/2005 |
| WO | WO 2005/113514 | 12/2005 |

OTHER PUBLICATIONS

Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141" 802-810, 1999.*
Golub et al., Science, 286, 531-537, 1999.*
Cecil Textbook of Medicine, edited by Bennet, J.C., and Plum F., 20th edition,vol. 1, 1004-1010, 1996.*
Ahn, H., et al., "Potent Tetracyclic Guanine Inhibitors of PDE1 and PDE5 Cyclic Guanosine Monophosphate Phosphodiesterases with Oral Antihypertensive Activity", Journal of Medicinal Chemistry, vol. 40(14), pp. 2196-2210, (1997).
Bundgaard, H, et al., "A Textbook of Drug Design and Development", Chapter 5, Design and Application of Prodrugs, pp. 113-191, (1991).
Bundgaard, H., "Design of Prodrugs", Table of Contents, (1985).
Bundgaard, H., "Means to Enhance Penetration", Advanced Drug Delivery Reviews, vol. 8, pp. 1-38, (1992).
Collman, J.P., et al., "The Formation of Peptide Bonds in the Coordination Sphere of Cobalt(III)", Journal of the American Chemical Society, vol. 89(24), pp. 6096-6103, (1967).
Davila, M, et al., "LIM Kinase 1 Is Essential for the Invasive Growth of Prostate Epithelial Cells", The Journal of Biological Chemistry, vol. 278(38), 36868-36875, (2003).
Greene, T. W, et al,, Protective Groups in Organic Synthesis, Second Edition, Wiley, NY, Table of Contents, (1991).
Henry, J. R., et al., "p38 mitogen-activated protein kinase as a target for drug discover", Drugs of the Future, vol. 24(12), pp. 1345-1354, (1999).
Moreland, L.W., et al., "Etanercept Therapy in Rheumatoid Arthritis", Annals of Internal Medicine, vol. 130(6), pp. 478-486, (1999).
Raingeaud, J. et a.., "MKK3- and MKK6-Regulated Gene Expression is Mediated by the p38 Mitogen-Activated Protein Kinase Signal Transduction Pathway", Molecular and Cellular Biology, vol. 16(3), pp. 1247-1255, (1996).
Rankin, E.C.C, et al. "The Therapeutic Effects of an engineered Human Anti-Tumour Necrosis Factor Alpha Antibody (DCP571) in Rheumatoid Arthritis", British Journal of Rheumatology, vol. 34, pp. 334-342, (1995).
Salituro, F. G., "Inhibitors of p38 MAP Kinase: Therapeutic Intervention in Cytokine-Mediated Diseases", Current Medicinal Chemistry, vol. 6, pp. 807-823, (1999).
Suyama, E., et al., "LIM kinase-2 targeting as a possible anti-metastasis therapy", The Journal of Gene Medicine, vol. 6, pp. 357-363, (2004).
Widder, KS., "Methods in Enzymology", Drug and Enzyme Targeting, vol. 112, pp. 309-396, (1985).
Yoshioka, K., et al., "A role for LIM kinase in cancer invasion", Proceedings of the National Academy of Sciences. vol. 100(12), pp. 7247-7252, (2003).

* cited by examiner

PHENYL-SUBSTITUTED PYRIMIDINE COMPOUNDS USEFUL AS KINASE INHIBITORS

RELATED APPLICATION

This application is a Continuation of patent application U.S. Ser. No. 11/344,881 filed Feb. 1, 2006 which claims a benefit of priority under Title 35 §119(e) from U.S. Provisional Application No. 60/650,077, filed Feb. 4, 2005, the entire disclosure of which is herein incorporated by reference.

FIELD OF THE INVENTION

This invention relates to phenyl-substituted pyrimidine compounds, more particularly, to phenyl-substituted pyrimidine compounds useful for treating kinase-associated conditions, such as p38 kinase-associated conditions. The invention further pertains to pharmaceutical compositions containing at least one compound according to the invention useful for treating kinase-associated conditions, such as p38 kinase-associated conditions, and methods of inhibiting the activity of kinase in a mammal.

BACKGROUND OF THE INVENTION

Protein kinases, a class of enzymes that phosphorylate proteins, are involved in a wide variety of processes including the cell cycle and cellular signal pathways. Examples of protein kinases include p38 kinases and LIM kinases.

A large number of cytokines participate in the inflammatory response, including IL-1, IL-6, IL-8, and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.*, 6:807-823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334-342 (1995)], and soluble TNF-α receptor-Fc fusion protein (Etanercept) [Moreland et al., *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production include the mitogen-activated protein (MAP) kinases, a family of Ser/Thr protein kinases that activate their substrates by phosphorylation. The MAP kinases are activated in response to various stress stimuli, including but not limited to proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α.

Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); WO 00/12074 (piperazine and piperidine compounds useful as p38 inhibitors), U.S. Pat. application publication No. US2002/0010170 A1, U.S. Pat. No. 6,670,357 (pyrrolotriazine compounds useful as p38 kinase inhibitors); WO 03/0099820 (aniline-substituted pyrazolo-pyrimidine compounds useful for treating p38 kinase-associated conditions); and WO 04/071440 (thiazolyl-based compounds useful for treating p38 kinase-associated conditions).

The metastasis of cancer cells involves the modulation of signal pathways that regulate the actin cytoskeleton. Cofilin, an actin binding protein, acts as a regulator of actin dynamics by promoting F-actin depolymerization. Kinases, such as LIM kinase 1 (LIMK1) and LIM kinase 2 (LIMK2), have been identified as participating in signal pathways affecting actin dynamics by deactivating cofilin. Over expression of LIMK1 has been found in invasive breast and prostate cancer cell lines [Yoshioka et al., *Proc. Nat. Acad. Sci.* 100(12) 7247-7252 (2003); Davila et al., *J. Biol. Chem.*, 278(38) 36868-36875 (2003)]. Suppression of LIMK 2 expression has been found to limit migration of human fibrosarcoma cells [Suyama et al., *J. Gene Med.*, 6:357-363 (2004). Accordingly, the inhibition of LIMK1 and/or LIMK2 enzymes have been suggested as targets for treating cancer, including reduction or prevention of metastasis.

The present invention provides certain phenyl-substituted pyrimidine compounds useful as kinase inhibitors, particularly kinases p38α and β, and/or LIM kinases, such as LIM kinase 1 and/or LIM kinase 2. JP2001089452 to Sankyo Co. Ltd, published Apr. 3, 2001 in Japanese, discloses certain phenyl-substituted pyrimidine compounds. JP2003206230 to Yamanouchi Pharmaceutical Co. Ltd., published Jul. 22, 2003 in Japanese, discloses cyano heterocyclic compounds, including certain phenyl-substituted cyano pyrimidine compounds, as a calcium channel blocking-drug. A method of treating a cyclin-dependent kinases (CDK) dependent or sensitive disorder and a method of treating viral disorders using 2-substituted 4-heteroarylpyrimidines, are disclosed in U.S. Pat. No. 6,531,479 and WO 2004/043467, respectively, to Cyclacel Ltd. Pyrazole compounds, including certain phenyl-substituted pyrimidine compounds, useful as protein kinase inhibitors, are disclosed in WO 02/22607 to Vertex Pharmaceuticals Incorporated. Each of the patent applications, patents, and publications referred to herein is incorporated herein by reference.

SUMMARY OF THE INVENTION

The instant invention generally pertains to compounds of formula (I),

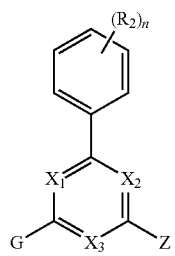

wherein:
two of $X_1$, $X_2$, and $X_3$ are N, and the remaining one of $X_1$, $X_2$, and $X_3$ is —$CR_1$;
$R_1$ is hydrogen or —CN;
n is zero, 1, 2, or 3; and
wherein G, Z, $R_2$, $R_3$, $R_4$, $R_5$, and $R_6$ are defined herein below.

The invention further pertains to pharmaceutical compositions containing compounds of formula (I), and to methods of treating conditions associated with the activity of kinase, such as p38 (α and β), comprising administering to a mammal a pharmaceutically-acceptable amount of a compound of formula (I).

DETAILED DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like.

"Substituted alkyl" refers to an alkyl group substituted with one or more substituents, preferably 1 to 4 substituents, at any available point of attachment on the alkyl straight or branched chain. Exemplary substituents include one or more of the following groups: halo (e.g., a single halo substituent or multiple halo substituents forming, in the latter case, groups such as a perfluoroalkyl group or an alkyl group bearing $Cl_3$ or $CF_3$), nitro, cyano, hydroxy, alkoxy, haloalkoxy (e.g., trifluoromethoxy), —O-aryl, —O-heterocyclo, —O-alkylene-aryl, —O-haloalkyl, alkylthio, carboxy (i.e., —COOH), alkoxycarbonyl, alkylcarbonyloxy, carbamoyl, substituted carbamoyl, carbamate, substituted carbamate, urea, substituted urea, amidinyl, substituted amidinyl, aryl, heterocycle, cycloalkyl, —$NR^cR^d$, —$OC(=O)NR^cR^d$, —$C(=O)NR^cR^d$, —$NR^eC(=O)NR^cR^d$, —$NR^eC(O)^2$—$NR^cR^d$, —$N(R^e)S(O)_2NR^cR^d$, —$N(R^e)P(O)_2NR^cR^d$, (wherein each of $R^c$ and $R^d$ is independently selected from hydrogen, alkyl, aryl, and heterocyclo, and $R^e$ is hydrogen, alkyl, or phenyl); and —$SR^f$, —$S(=O)R^g$, —$S(O)_2R^g$, —$NR^eS(O)_2$—$R^g$, —$P(O)_2$—$R^g$, —$NR^eP(O)_2$—$R^g$, —$NR^eC(=O)R^f$, —$NR^eC(O)_2R^f$, —$OC(=O)R^f$, —$OC(=O)OR^f$, —$C(=O)OR^f$ or —$C(=O)R^f$ (wherein $R^f$ is defined as immediately above, $R^f$ is hydrogen, alkyl, aryl or heterocyclo, and $R^g$ is alkyl, aryl, or heterocyclo). In the aforementioned substituents, in each instance, the alkyl, aryl, heterocyclo or cycloalkyl groups ($R^c$, $R^d$, $R^e$, $R^f$, and $R^g$) in turn can be optionally substituted with one to four, preferably one to three further groups, selected from $R^k$, —O—$R^k$, cyano, nitro, haloalkyl, haloalkoxy, halogen, —$NR^kR^m$, —$OC(=O)NR^kR^m$, —$C(=O)NR^kR^m$, —$NR^kC(=O)R^m$, —$SR^k$, —$S(=O)R^n$, —$S(O)_2R^n$, —$OC(=O)R^k$, —$C(=O)OR^k$, —$C(=O)R^k$, phenyl, benzyl, phenyloxy, or benzyloxy, or a lower alkyl substituted with one to two of —O—$R^k$, cyano, nitro, haloalkyl, haloalkoxy, halogen, —$NR^kR^m$, —$OC(=O)NR^kR^m$, —$C(=O)NR^kR^m$, —$NR^kC(=O)R^m$, —$SR^k$, —$S(=O)R^n$, —$S(O)_2R^n$, —$OC(=O)R^k$, —$C(=O)OR^k$, —$C(=O)R^k$, phenyl, benzyl, phenyloxy, or benzyloxy, wherein $R^k$ and $R^m$ are selected from hydrogen, lower alkyl, hydroxy(lower alkyl), halo(lower alkyl), cyano(lower alkyl), and amino(lower alkyl), and $R^n$ is lower alkyl.

When a subscript is used following a group, as in $C_{1-4}$alkyl, this refers to the number of carbon atoms that the group may contain, in addition to heteroatoms or other substituents. Thus, for example, $C_{1-4}$alkyl refers to alkyl groups having from one to four carbon atoms; —O—$C_{1-3}$alkyl (or —O—$C_{1-3}$alkoxy) refers to alkoxy groups having from one to three carbon atoms, i.e., methoxy, ethoxy and propoxy; and optionally-substituted $C_{1-4}$alkyl refers to alkyl groups of one to four carbon atoms optionally substituted with one to four groups selected from those recited above for substituted alkyl.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. The term "lower alkylene" herein refers to those alkylene groups having from about 1 to about 6 carbon atoms. "Substituted alkylene" refers to an alkylene group substituted with one or more substituents, preferably 1 to 4 substituents, at any available point of attachment. Exemplary substituents include, but are not limited to alkyl, substituted alkyl, and those groups recited above as exemplary alkyl substituents.

When the term alkyl is used as a subscript following another particularly-named group, as in "arylalkyl," "substituted arylalkyl," "cycloalkylalkyl," etc., or as in hydroxy (lower alkyl), this refers to an alkyl group having one or two (preferably one) substituents selected from the other, particularly-named group. Thus, for example, arylalkyl includes benzyl, biphenyl and phenylethyl. A "substituted arylalkyl" will be substituted on the alkyl portion of the radical with one or more groups selected from those recited above for alkyl, and/or will be substituted on the aryl portion of the radical with one or more groups selected from those recited below for substituted aryl.

The term "alkenyl" refers to a straight or branched chain hydrocarbon radical containing from 2 to 12 carbon atoms and at least one carbon-carbon double bond. Exemplary groups include ethenyl or allyl. "Substituted alkenyl" refers to an alkenyl group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkenylene" refers to a straight or branched chain bivalent hydrocarbon radical containing from 2 to 12 carbon atoms and at least one carbon-carbon double bond. Exemplary groups include ethenylene or allylene. "Substituted alkenylene" refers to an alkenylene group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkynyl" refers to a straight or branched chain hydrocarbon radical containing from 2 to 12 carbon atoms and at least one carbon to carbon triple bond. Exemplary groups include ethynyl. "Substituted alkynyl" refers to an alkynyl group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkynylene" refers to a straight or branched chain bivalent hydrocarbon radical containing from 2 to 12 carbon atoms and at least one carbon to carbon triple bond. Exemplary groups include ethynylene. "Substituted alkynylene" refers to an alkynylene group substituted with one or more substituents, preferably 1 to 4 substituents, at any available point of attachment. Exemplary substituents include, but are not limited to, alkyl, substituted alkyl, and those groups recited above as exemplary alkyl substituents.

The term "cycloalkyl" refers to a fully saturated cyclic hydrocarbon group containing from 1 to 3 rings and 3 to 8 carbons per ring. Exemplary groups include cyclopropyl, cyclobutyl, cyclopentyl, and cyclohexyl. The term "cycloalkyl" also includes groups having a carbon-carbon bridge of one to two bridgehead carbon atoms, and bicyclic and tricyclic groups in which at least one of the rings is a saturated, carbon-containing ring, in which case the second or third ring may be carbocyclic or heterocyclic, provided that the point of attachment is to the cycloalkyl group. The further rings may be attached to the saturated, carbon-containing ring in a spiro or fused fashion. "Substituted cycloalkyl" refers to a cycloalkyl group substituted with one or more substituents, preferably 1 to 4 substituents, at any available point of attachment. Exemplary substituents include, but are not limited to, alkyl, substituted alkyl, oxo(=O), and those groups recited above as exemplary alkyl substituents.

The term "cycloalkylene" refers to a bivalent cycloalkyl group as defined above. Exemplary groups include cyclopropylene, cyclobutylene, cyclopentylene and cyclohexylene. "Substituted cycloalkylene" refers to a cycloalkylene group substituted with one or more substituents, preferably 1 to 4 substituents, at any available point of attachment selected from those recited for substituted cycloalkyl.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group. "Substituted cycloalkenyl" refers to a cycloalkenyl group substituted with one or more substituents, preferably 1 to 4 substituents, at any available point of attachment selected from those recited above for cycloalkyl groups.

The term "cycloalkenylene" refers to a bivalent cycloalkenyl group, as defined above. Exemplary groups include cyclobutenylene, cyclopentenylene, and cyclohexenylene. "Substituted cycloalkenylene" refers to a cycloalkenylene group substituted with one or more substituents, preferably 1 to 4 substituents, at any available point of attachment, selected from those recited for substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively. "Thiol" refers to —SH.

The term "alkoxycarbonyl" refers to an alkoxy group bonded through a carbonyl group (i.e., —C(=O)—O-alkyl).

The term "alkylcarbonyl" refers to an alkyl group bonded through a carbonyl group (i.e., —C(=O)alkyl).

The term "alkylcarbonyloxy" refers to an alkylcarbonyl group bonded through an oxygen linkage (i.e., —O—C(=O)-alkyl).

The term "amido" refers to the group —NHC(=O)H, and amidinyl refers to the group —C(=NH)(NH$_2$). A "substituted amido" refers to the group —NR$^p$C(=O)R$^q$, and a "substituted amidinyl" refers to the group —C(=NR$^p$)(NR$^q$R$^r$), wherein R$^p$, R$^q$, and R$^r$ are selected from hydrogen, alkyl, substituted alkyl, cycloalkyl, substituted cycloalkyl, aryl, substituted aryl, heterocyclo, and substituted heterocyclo, provided that at least one of R$^p$, R$^q$, and R$^r$ is other than hydrogen.

The term "aryl" encompasses monocyclic and polycyclic aryl groups. The term "monocyclic aryl" refers to phenyl, and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. Additionally, a ring carbon atom of the second and third further rings may be replaced with a carbonyl [—C(=O)group] (e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups include:

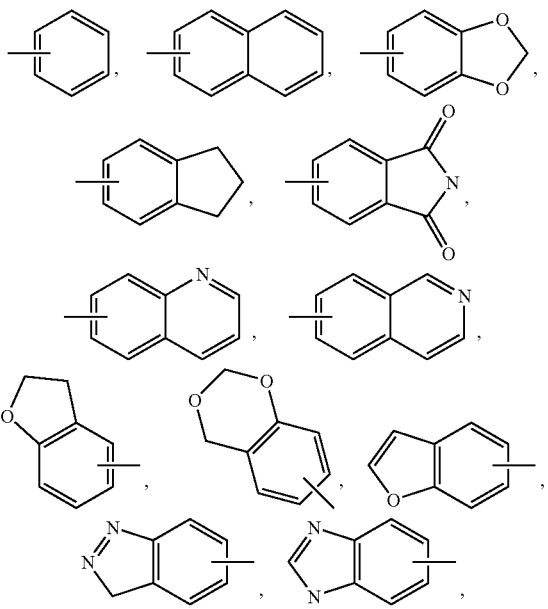

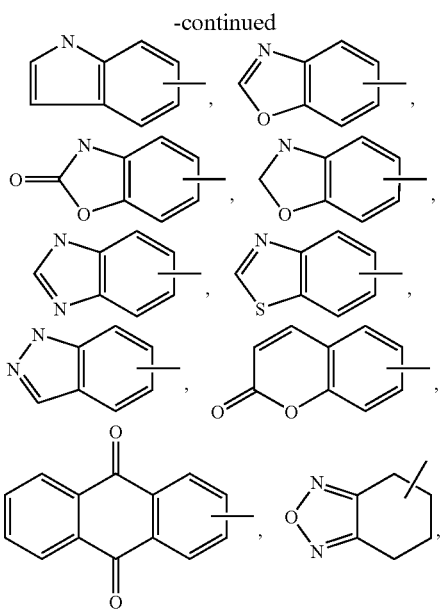

and the like.

The term "arylene" refers to bivalent aryl groups as defined above.

"Carbamoyl" refers to the group —C(=O)—NR$^h$R$^i$, wherein R$^h$ and R$^i$ are selected from hydrogen, alkyl, cycloalkyl, aryl, and heterocyclo.

"Carbamate" refers to the group —O—C(=O)—NR$^h$R$^i$, and urea refers to the groups NH—C(=O)—NR$^h$R$^i$ and N(alkyl)-C(=O)—NR$^h$R$^i$, wherein R$^h$ and R$^i$ are selected from the same groups recited for carbamoyl.

"Substituted carbamoyl," "substituted carbamate," and "substituted urea" refer to the groups —C(=O)—NR$^h$R$^i$, —O—C(=O)—NR$^h$R$^i$, and —N(R$^j$)—C(=O)—NR$^h$R$^i$, respectively, wherein R$^h$, R$^i$, and R$^j$ are selected from hydrogen, alkyl, substituted alkyl, cycloalkyl, substituted cycloalkyl, aryl, substituted aryl, heterocyclo, and substituted heterocyclo, provided that at least one of R$^h$, R$^i$, and R$^j$ is substituted alkyl, substituted cycloalkyl, substituted aryl, or substituted heterocyclo.

The terms "heterocycle", "heterocyclic" and "heterocyclo" refer to fully saturated, partially unsaturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term "heteroaryl" is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) Additionally, one or more (preferably one) carbon rings atoms of the heterocyclo ring may as valence allows be replaced with carbonyl group, i.e., —C(=O)—. The heterocyclic group may be attached to the remainder of the molecule at any heteroatom or carbon atom of the ring or ring system.

Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxoquinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heterocyclene" refers to bivalent heterocycle groups as defined above.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment, wherein the substituents are selected from those recited above for substituted cycloalkyl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The term "heteroaryl" refers to five and six membered monocyclic aromatic heterocyclo groups, as well as bicyclic and tricyclic heterocyclic ring systems in which the point of attachment of the ring system to another group is via a five or six membered aromatic ring of the ring system. Thus, for example, the term heteroaryl includes groups such as five or six membered heteroaryl groups, such as thienyl, pyrrolyl, oxazolyl, pyridyl, pyrazinyl, and the like, wherein fused rings completing bicyclic and tricyclic groups may contain only carbon atoms and may be saturated, partially saturated, or unsaturated. Heteroaryl groups which are bicyclic or tricyclic must include at least one fully aromatic ring but the other fused ring or rings may be aromatic or non-aromatic. The term "substituted heteroaryl" refers to five and six membered monocyclic aromatic heterocyclo groups substituted with one or more substituents, preferably 1 to 4 substituents, at any available point of attachment, wherein the substituents are selected from those recited above for substituted cycloalkyl groups.

Exemplary monocyclic heteroaryl groups include pyrrolyl, pyrazolyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, and the like.

Exemplary bicyclic heteroaryl groups include indolyl, benzothiazolyl, benzodioxolyl, benzoxazolyl, benzothienyl, quinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, and the like.

Exemplary tricyclic heteroaryl groups include carbazolyl, benzidolyl, phenanthrolinyl, acridinyl, phenanthridinyl, xanthenyl and the like.

The terms "halogen" or "halo" refer to chlorine, bromine, fluorine or iodine.

The terms "hydroxylamine" and "hydroxylamide" refer to the groups —NH—OH and —C(=O)—NH—OH, respectively.

The term "heteroatoms" shall include oxygen, sulfur and nitrogen.

The term "haloalkyl" means an alkyl having one or more halo substituents.

The term "haloalkoxy" means an alkoxy group having one or more halo substituents. For example, "haloalkoxy" includes —OCF$_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When it is stated that a group may be optionally-substituted, this is intended to include unsubstituted groups and substituted groups wherein the substituents are selected from those recited above for the particularly named group. Thus, when reference is made to an optionally substituted aryl, this intended to refer to unsubstituted aryl groups, such as phenyl, or napthyl, and such groups having one or more (preferably 1 to 4, and more preferably 1 or 2), substituents selected from alkyl, substituted alkyl, and those substituents recited for substituted alkyl groups. When the term "optionally substituted" precedes a Markush group, the term "optionally-substituted" is intended to modify each one of the species recited in the Markush group. Thus, for example, the phrase "optionally-substituted aryl, cycloalkyl, or heterocycle" includes aryl, substituted aryl, cycloalkyl, substituted cycloalkyl, heterocycle, and substituted heterocycle.

Among the compounds of the invention, in the case of a compound which has a sulfide, the sulfur atom may be converted into oxido at an appropriate oxidation state, and all of these oxido derivatives are included herein.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

"Solvate" refers to a molecular or ionic complex of molecules or ions of solvent with molecules or ions of solute.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

Unless otherwise indicated, any heteroatom with unsatisfied valences is assumed to have hydrogen atoms sufficient to satisfy the valences.

Carboxylate anion refers to a negatively charged group —COO$^-$.

The compounds of the present invention may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of the present invention may form salts with alkali metals such as sodium, potassium, and lithium, with alkaline earth metals such as calcium and magnesium, with organic bases such as dicyclohexylamine, tributylamine, pyridine, and amino acids such as arginine, lysine, and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid, and various others (e.g., nitrates, phosphates, borates, tartrates, citrates, succinates, benzoates, ascorbates, salicylates, and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, pp. 1-38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

The phenyl-substituted pyrimidine compounds of formula (I) include the compounds of formulae (Ia), (Ib), and (Ic),

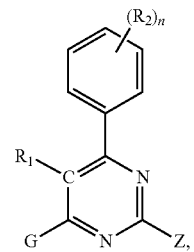

(Ia)

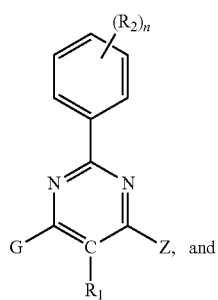

(Ib)

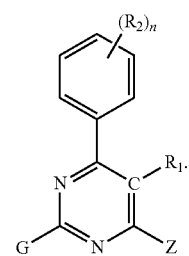

(Ic)

The compounds of formula (Ia) are preferred for use in treating p38 kinase-associated conditions.

One nonlimiting embodiment provides phenyl-substituted pyrimidine compounds of formula (I) having the formula (II),

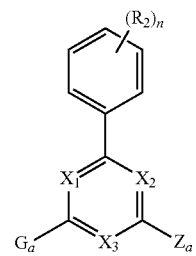

(II)

and enantiomers, diastereomers, pharmaceutically-acceptable salts, prodrugs, and solvates thereof,
wherein:
two of $X_1$, $X_2$, and $X_3$ are N, and the remaining one of $X_1$, $X_2$, and $X_3$ is —$CR_1$;
$R_1$ is hydrogen or —CN;
n is zero, 1, 2, or 3;
each $R_2$ is independently $C_1$-$C_8$ alkyl, substituted $C_1$-$C_8$ alkyl, cycloalkyl, substituted cycloalkyl, alkenyl, substituted alkenyl, alkynyl, substituted alkynyl, —$OR_4$, —$SR_4$, —$CO_2R_4$, —$C(=O)NR_4R_5$, —$NR_4R_5$, —$S(=O)R_6$, —$SO_2R_6$, —$SO_2NR_4R_5$, —$NR_4SO_2NR_5R_6$, —$NR_4SO_2R_6$, —$NR_4C(=O)R_5$, —$NR_4CO_2R_5$, —$NR_4C(=O)NR_5R_6$, halogen, cyano, aryl, substituted aryl, heterocyclo, and/or substituted heterocyclo;

$G_a$ is a monocyclic five- or six-membered heteroaryl, which is optionally substituted with one to three $R_3$;

each $R_3$ is independently hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, —$OR_4$, —$SR_4$, —$CO_2R_4$, —$C(=O)NR_4R_5$, —$NR_4R_5$, —$S(=O)R_6$, —$SO_2R_6$, —$NR_4SO_2NR_5R_6$, —$NR_4SO_2R_6$, —$NR_4C(=O)R_5$, —$NR_4CO_2R_5$, —$NR_4C(=O)NR_5R_6$, halogen, aryl, substituted aryl, heterocyclo, and/or substituted heterocyclo;

each $R_4$ is independently hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, and/or substituted heterocyclo;

each $R_5$ is independently hydrogen, $C_1$-$C_8$ alkyl, substituted $C_1$-$C_8$ alkyl, cycloalkyl, and/or substituted cycloalkyl;

wherein when $R_4$ and $R_5$ are alkyl and/or substituted alkyl and are bonded to the same atom, $R_4$ and $R_5$ can be optionally linked together to form a four-, five-, or six-membered ring heterocyclo or substituted heterocyclo;

each $R_6$ is independently $C_{1-8}$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, and/or substituted heterocyclo;

wherein when $R_5$ and $R_6$ are alkyl and/or substituted alkyl and are bonded to the same atom, $R_5$ and $R_6$ can be optionally linked together to form a four-, five-, or six-membered ring heterocyclo or substituted heterocyclo;

$Z_a$ is hydrogen, $C_1$-$C_8$ alkyl, $C_1$-$C_8$ substituted alkyl, cycloalkyl, substituted cycloalkyl, —$OR_7$, —$SR_7$, —$CO_2R_7$, —$C(=O)NR_7R_8$, —$NR_7R_8$, —$S(=O)R_9$, —$SO_2R_8$, —$SO_2NR_7R_8$, —$NR_7SO_2NR_8R_9$, —$NR_7SO_2R_9$, —$NR_7C(=O)R_8$, —$NR_7CO_2R_8$, —$NR_7C(=O)NR_8R_9$, halogen, cyano, aryl, substituted aryl, heterocyclo, or substituted heterocyclo;

$R_7$ is hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo;

$R_8$ is hydrogen, $C_1$-$C_8$ alkyl, substituted $C_1$-$C_8$ alkyl, cycloalkyl, or substituted cycloalkyl;

wherein when $R_7$ and $R_8$ are alkyl and/or substituted alkyl and are bonded to the same atom, $R_7$ and $R_8$ can be optionally linked together to form a four-, five-, or six-membered ring heterocyclo or substituted heterocyclo;

$R_9$ is $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo; and wherein when $R_8$ and $R_9$ are alkyl and are bonded to the same atom, $R_8$ and $R_9$ can be optionally linked together to form a four-, five-, or six-membered ring heterocyclo or substituted heterocyclo; with the provisos that:

(a) $G_a$ is not thiazolyl with 4-methyl substitution or oxazolyl with 4-methyl substitution;

(b) $G_a$ is not 2-pyridyl, substituted 2-pyridyl, or dichlorothienyl when $Z_a$ is hydrogen;

(c) $G_a$ is not substituted 2-pyridyl when Z is —$OR_7$ or chlorine;

(d) $G_a$ is not:

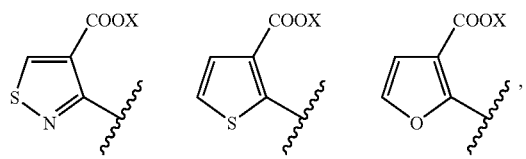

wherein X is hydrogen or alkali, when $Z_a$ is hydrogen and $R_1$ is hydrogen;

(e) $G_a$ is not unsubstituted pyrazolyl or 4-pyridyl when n is zero and $Z_a$ is hydrogen;

(f) $G_a$ is not isoxazolyl substituted with phenyl or isoxazolyl substituted with substituted phenyl when n is 1, $R_2$ is chlorine, and $Z_a$ is hydrogen;

(g) $G_a$ is not 3-pyridyl or dichloro-4-pyridyl when $Z_a$ is hydrogen, $R_1$ is hydrogen, and at least one $R_2$ is —C(=O)OX, wherein X is hydrogen or alkali;

(h) n is 1, 2, or 3 when $R_1$ is —CN;

(i) $R_2$ is not optionally substituted phenoxy attached at the para-position of the phenyl ring;

(j) $R_7$ is not pyrazolyl, substituted pyrazolyl, alkyl substituted triazolyl, indazolyl, or substituted indazolyl when $Z_a$ is —$NR_7R_8$;

(k) $Z_a$ is not $NR_7R_8$ when $R_1$ is —CN, and (l) n is 1, 2, or 3 when Z is unsubstituted phenyl.

Preferred compounds of formula (Ia) include compounds wherein $X_2$ and $X_3$ are each N, and $X_1$ is —$CR_1$. More preferably, $X_1$ is —CH.

For example, the compounds of formula (Ia) may be provided wherein each $R_2$ is independently alkyl, halogen, or cyano. Preferably, at least one $R_2$ is located at the 2-position of the phenyl ring, represented by the compounds of formula (IIa),

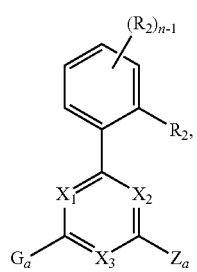
(IIa)

wherein each $R_2$ is independently selected. Examples of the compounds of formula (Ia) include the compounds of formulae (IIb), (IIc), and (IId),

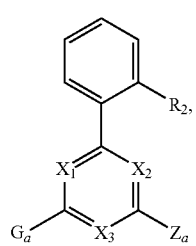
(IIb)

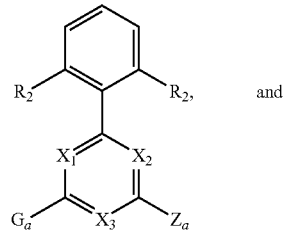
(IIc)

and

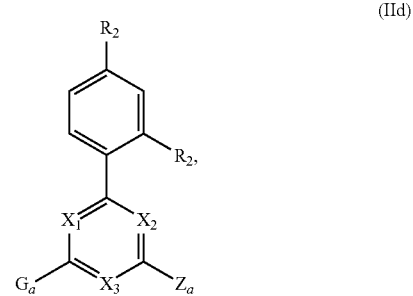
(IId)

wherein each $R_2$ is independently selected. Preferred groups for the $R_2$ located in the 2-position of the phenyl ring include fluoro, chloro, alkyl such as methyl, cyano, and substituted alkyl wherein the substituent is —NHC(=O)$R_5$, —$NHCO_2R_5$, or —NHC(=O)$NR_5R_6$.

Examples of the compounds of formula (Ia) include compounds wherein $G_a$ is a monocyclic five-membered heteroaryl, which is optionally substituted with one to three $R_3$. Preferably, $G_a$ is selected from substituted or unsubstituted thiazolyl, substituted or unsubstituted thiadiazolyl, and substituted or unsubstituted oxadiazolyl, which include, for example,

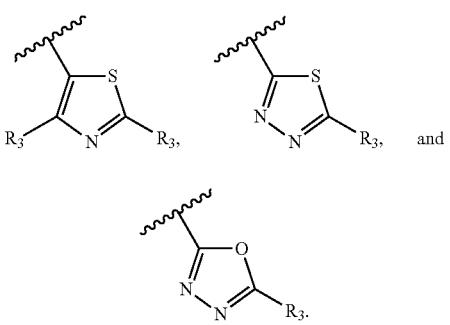

More preferably, $G_a$ is a substituted or unsubstituted thiazolyl. Still more preferably, $G_a$ is a thiazolyl having a substituted amino group at the 2-position and a hydrogen at the 4-position, represented by

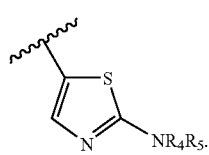

Most preferably, $G_a$ is

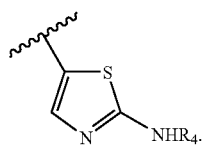

Exemplary compounds of formula (Ia) include compounds wherein $Z_a$ is —$NR_4R_5$, —$NR_4SO_2NR_5R_6$, or pyridyl.

In one embodiment, compounds of formula (Ia) are provided wherein:

n is 2 or 3;

each $R_2$ is independently halogen or ether, preferably halogen or alkyl ether, substituted alkyl ether, cycloalkyl ether, or substituted cycloalkyl ether;

each $R_3$ is independently —$NR_4R_5$, —$NR_4C(=O)R_5$, —$NR_4CO_2R_5$, and —$NR_4C(=O)NR_5R_6$, provided that:

when $R_3$ is —$NR_5$, one of $R_4$ and $R_5$ is hydrogen and the other of $R_4$ and $R_5$ is alkyl or substituted alkyl;

when $R_3$ is —$NR_4CO_2R_5$ or —$NR_4C(=O)R_5$, $R_5$ is alkyl or substituted alkyl; and when $R_3$ is —$NR_4C(=O)NR_5R_6$, $R_5$ is hydrogen and $R_6$ is alkyl or substituted alkyl;

each $R_5$ is hydrogen, $C_1$-$C_8$ alkyl, substituted $C_1$-$C_8$ alkyl, $C_1$-$C_8$ cycloalkyl, and substituted $C_1$-$C_8$ cycloalkyl; and $Z_a$ is heterocyclo or substituted heterocyclo.

The compounds of this embodiment are useful for inhibiting LIMK1 and/or LIMK2 activity.

A different nonlimiting embodiment of the invention provides phenyl-substituted pyrimidine compounds of formula (I) having formula (Ib),

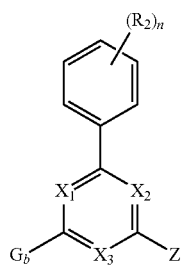

and enantiomers, diastereomers, pharmaceutically-acceptable salts, prodrugs, and solvates thereof, wherein:

two of $X_1$, $X_2$, and $X_3$ are N, and the remaining one of $X_1$, $X_2$, and $X_3$ is —$CR_1$;

$R_1$ is hydrogen or —CN;

n is zero, 1, 2, or 3;

each $R_2$ is independently $C_1$-$C_8$ alkyl, substituted $C_1$-$C_8$ alkyl, cycloalkyl, substituted cycloalkyl, alkenyl, substituted alkenyl, alkynyl, substituted alkynyl, —$OR_4$, —$SR_4$, —$CO_2R_4$, —$C(=O)NR_4R_5$, —$NR_4R_5$, —$S(=O)R_6$, —$SO_2R_6$, —$SO_2NR_4R_5$, —$NR_4SO_2NR_5R_6$, —$NR_4SO_2R_6$, —$NR_4C(=O)R_5$, —$NR_4CO_2R_5$, —$NR_4C(=O)NR_5R_6$, halogen, cyano, aryl, substituted aryl, heterocyclo, and/or substituted heterocyclo;

$G_b$ is —$C(=O)NR_4R_5$, —$NR_4SO_2NR_5R_6$, —$NR_4SO_2R_6$, —$NR_4C(=O)R_5$, —$NR_4C(=O)NR_5R_6$, or a monocyclic five- or six-membered heteroaryl optionally substituted with one to three $R_3$;

each $R_3$ is independently hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, —$OR_4$, —$SR_4$, —$CO_2R_4$, —$C(=O)NR_4R_5$, —$NR_4R_5$, —$S(=O)R_6$, —$SO_2R_6$, —$NR_4SO_2NR_5R_6$, —$NR_4SO_2R_6$, —$NR_4C(=O)R_5$, —$NR_4CO_2R_5$, —$NR_4C(=O)NR_5R_6$, halogen, aryl, substituted aryl, heterocyclo, and/or substituted heterocyclo;

each $R_4$ is independently hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, and/or substituted heterocyclo;

each $R_5$ is independently hydrogen, $C_1$-$C_8$ alkyl, substituted $C_1$-$C_8$ alkyl, cycloalkyl, and/or substituted cycloalkyl;

wherein when $R_4$ and $R_5$ are alkyl and/or substituted alkyl and are bonded to the same atom, $R_4$ and $R_5$ can be optionally linked together to form a four-, five-, or six-membered ring heterocyclo or substituted heterocyclo;

each $R_6$ is independently $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, and/or substituted heterocyclo;

wherein when $R_5$ and $R_6$ are alkyl and/or substituted alkyl and are bonded to the same atom, $R_5$ and $R_6$ can be optionally linked together to form a four-, five-, or six-membered ring heterocyclo or substituted heterocyclo;

$Z_b$ is —$NR_7R_8$ or pyridyl, pyridazinyl, or pyrazinyl optionally substituted with one to three $R_{10}$;

$R_7$ is hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo;

$R_8$ is hydrogen, $C_1$-$C_8$ alkyl, substituted $C_1$-$C_8$ alkyl, cycloalkyl, or substituted cycloalkyl;

wherein when $R_7$ and $R_8$ are alkyl and/or substituted alkyl and are bonded to the same atom, $R_7$ and $R_8$ can be optionally linked together to form a four-, five-, or six-membered ring heterocyclo or substituted heterocyclo; and each $R_{10}$ is independently halogen, cyano, $C_1$-$C_8$ alkyl, substituted $C_1$-$C_8$ alkyl, cycloalkyl, substituted cycloalkyl, alkenyl, substituted alkenyl, alkynyl, and/or substituted alkynyl;

with the provisos that:

(a) $G_b$ is not thiazolyl with 4-methyl substitution or oxazolyl with 4-methyl substitution;

(b) n is 1, 2, or 3 when $R_1$ is —CN;

(c) $R_7$ is not pyrazolyl, substituted pyrazolyl, indazolyl, substituted indazolyl, or alkyl substituted triazolyl when $Z_b$ is —$NR_7R_8$; and (d) $Z_b$ is not $NR_7R_8$ when $R_1$ is —CN.

Preferred compounds of formula (Ib) include compounds wherein $X_2$ and $X_3$ are each N, and $X_1$ is —$CR_1$. More preferably, $X_1$ is —CH.

For example, the compounds of formula (Ib) may be provided wherein each $R_2$ is independently alkyl, halogen, or cyano. More preferably, at least one $R_2$ is located at the 2-position of the phenyl ring, represented by the compounds of formula (IIe),

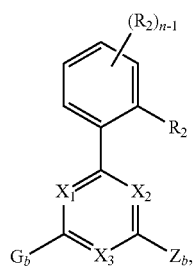
(IIe)

wherein each $R_2$ is independently selected. Examples of the compounds of formula (IIe) include the compounds of formulae (IIf), (IIg), and (IIh),

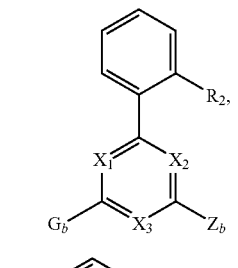
(IIf)

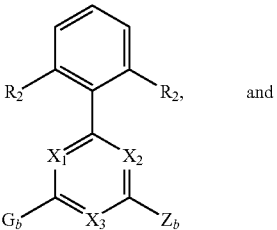
(IIg)

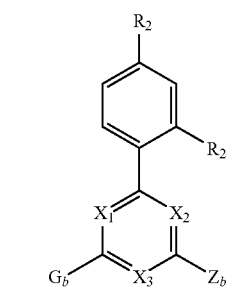
(IIh)

wherein each $R_2$ is independently selected. Preferred groups for the $R_2$ that is located at the 2-position of the phenyl ring include fluoro, chloro, alkyl such as methyl, cyano, and substituted alkyl wherein the substituent is —NHC(=O)$R_5$, —NHCO$_2R_5$, or —NHC(=O)NR$_5R_6$.

Examples of the compounds of formula (Ib) include compounds wherein $G_b$ is selected from —C(=O)NR$_4R_5$, —NR$_4$SO$_2$NR$_5R_6$, —NR$_4$SO$_2R_6$, —NR$_4$C(=O)R$_5$, or —NR$_4$C(=O)NR$_5R_6$.

Other examples of the compounds of formula (Ib) include compounds wherein $G_b$ is a monocyclic five- or six-membered heteroaryl, which is optionally substituted with one to three $R_3$. Preferably, $G_b$ is a monocyclic five-membered heteroaryl, which is optionally substituted with one to three $R_3$.

More preferably, $G_b$ is selected from substituted or unsubstituted thiazolyl, substituted or unsubstituted thiadiazolyl, and substituted or unsubstituted oxadiazolyl, which include, for example,

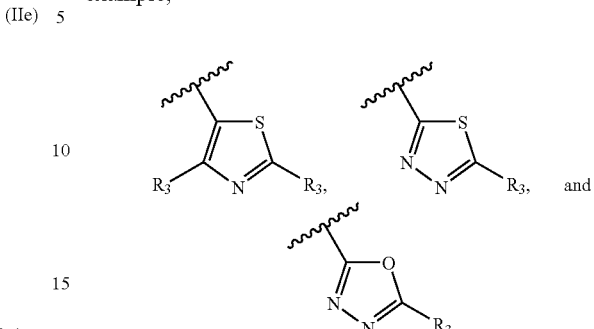

Still more preferably, $G_b$ is a substituted or unsubstituted thiazolyl. Even more preferably, $G_b$ is a thiazolyl having a substituted amino group at the 2-position and a hydrogen at the 4-position, represented by

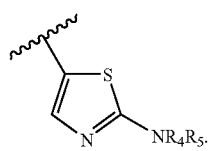

Most preferably, $G_b$ is

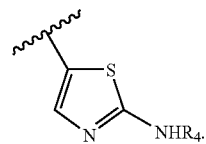

Still other examples of the compounds of formula (Ib) include compounds wherein $Z_b$ is —NR$_4R_5$.

Exemplary compounds of formula (Ib) include compounds wherein $Z_b$ is pyridyl, pyridazinyl, or pyrazinyl, which is optionally substituted with one to three $R_{10}$.

In one embodiment, compounds of formula (Ib) are provided wherein:
n is 2 or 3;
each $R_2$ is independently halogen or ether, preferably halogen or alkyl ether, substituted alkyl ether, cycloalkyl ether, or substituted cycloalkyl ether;
$G_b$ is a monocyclic five- or six-membered heteroaryl optionally substituted with one to three $R_3$;
each $R_3$ is independently —NR$_4R_5$, —NR$_4$C(=O)R$_5$, —NR$_4$CO$_2R_5$, and —NR$_4$C(=O)NR$_5R_6$, provided that:
when $R_3$ is —NR$_4R_5$, one of $R_4$ and $R_5$ is hydrogen and the other of $R_4$ and $R_5$ is alkyl or substituted alkyl;
when $R_3$ is —NR$_4$CO$_2R_5$ or —NR$_4$C(=O)R$_5$, $R_5$ is alkyl or substituted alkyl; and
when $R_3$ is —NR$_4$C(=O)NR$_5R_6$, $R_5$ is hydrogen and $R_6$ is alkyl or substituted alkyl;
each $R_5$ is hydrogen, $C_1$-$C_8$ alkyl, substituted $C_1$-$C_8$ alkyl, $C_1$-$C_8$ cycloalkyl, and substituted $C_1$-$C_8$ cycloalkyl; and
$Z_b$ is pyridyl, pyridazinyl, or pyrazinyl optionally substituted with one to three $R_{10}$.

Another nonlimiting embodiment of the invention provides phenyl-substituted pyrimidine compounds of formula (I) having the formula (Ic),

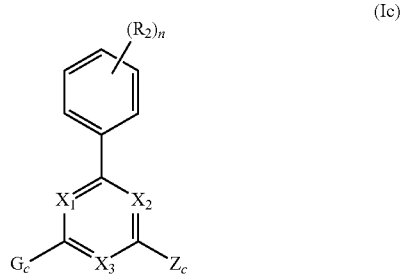

and enantiomers, diastereomers, pharmaceutically-acceptable salts, prodrugs, and solvates thereof,
wherein:

two of $X_1$, $X_2$, and $X_3$ are N, and the remaining one of $X_1$, $X_2$, and $X_3$ is —$CR_1$;

$R_1$ is hydrogen or —CN;

n is zero, 1, 2, or 3;

each $R_2$ is independently $C_1$-$C_8$ alkyl, $C_1$-$C_8$ substituted alkyl, cycloalkyl, substituted cycloalkyl, alkenyl, substituted alkenyl, alkynyl, substituted alkynyl, —$OR_4$, —$SR_4$, —$CO_2R_4$, —$C(=O)NR_4R_5$, —$NR_4R_5$, —$S(=O)R_6$, —$SO_2R_6$, —$SO_2NR_4R_5$, —$NR_4SO_2NR_5R_6$, —$NR_4SO_2R_6$, —$NR_4C(=O)R_5$, —$NR_4CO_2R_5$, —$NR_4C(=O)NR_5R_6$, halogen, cyano, aryl, substituted aryl, heterocyclo, and/or substituted heterocyclo;

each $R_4$ is independently hydrogen, $C_1$-$C_8$ alkyl, $C_1$-$C_8$ substituted alkyl, cycloalkyl, substituted cycloalkyl, alkenyl, substituted alkenyl, alkynyl, substituted alkynyl, aryl, substituted aryl, heterocyclo, and/or substituted heterocyclo;

each $R_5$ is independently hydrogen, $C_1$-$C_8$ alkyl, and/or $C_1$-$C_8$ substituted alkyl;

wherein when $R_4$ and $R_5$ are alkyl and/or substituted alkyl and are bonded to the same atom, $R_4$ and $R_5$ can be optionally linked together to form a four-, five-, or six-membered ring heterocyclo or substituted heterocyclo; and each $R_6$ is independently $C_1$-$C_8$ alkyl, $C_1$-$C_8$ substituted alkyl, cycloalkyl, substituted cycloalkyl, alkenyl, substituted alkenyl, alkynyl, substituted alkynyl, aryl, substituted aryl, heterocyclo, and/or substituted heterocyclo;

wherein when $R_5$ and $R_6$ are alkyl and/or substituted alkyl and are bonded to the same atom, $R_5$ and $R_6$ can be optionally linked together to form a four-, five-, or six-membered ring heterocyclo or substituted heterocyclo;

$G_c$ is —$C(=O)NR_4R_5$, —$NR_4SO_2NR_5R_6$, —$NR_4SO_2R_6$, —$NR_4C(=O)R_5$, or —$NR_4C(=O)NR_5R_6$;

$Z_c$ is hydrogen, $C_1$-$C_8$ alkyl, substituted $C_1$-$C_8$ alkyl, cycloalkyl, substituted cycloalkyl, —$OR_7$, —$SR_7$, —$CO_2R_7$, —$C(=O)NR_7R_8$, —$NR_7R_8$, —$S(=O)R_9$, —$SO_2R_9$, —$SO_2NR_7R_8$, —$NR_7SO_2NR_8R_9$, —$NR_7SO_2R_9$, —$NR_7C(=O)R_8$, —$NR_7CO_2R_8$, —$NR_7C(=O)NR_8R_9$, halogen, cyano, aryl, substituted aryl, heterocyclo, and/or substituted heterocyclo;

$R_7$ is hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo;

$R_8$ is hydrogen, $C_1$-$C_8$ alkyl, substituted $C_1$-$C_8$ alkyl, cycloalkyl, or substituted cycloalkyl;

wherein when $R_7$ and $R_8$ are alkyl or substituted alkyl and are bonded to the same atom, $R_7$ and $R_8$ can be optionally linked together to form a four-, five-, or six-membered ring heterocyclo or substituted heterocyclo;

$R_9$ is $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo; and wherein when $R_8$ and $R_9$ are alkyl or substituted alkyl and are bonded to the same atom, $R_8$ and $R_9$ can be optionally linked together to form a four-, five-, or six-membered ring heterocyclo or substituted heterocyclo; with the provisos that:

(a) when $R_1$ is —CN and $G_c$ is —$NR_4C(=O)R_5$, then $R_5$ is hydrogen;

(b) $R_2$ is not optionally substituted p-phenoxy; and (c) n is 1, 2, or 3 when Z is unsubstituted phenyl.

For example, compounds of formula (Ic) include compounds wherein $X_2$ and $X_3$ are each N, and $X_1$ is —$CR_1$. Preferably, $X_1$ is —CH.

Exemplary compounds of formula (Ic) include compounds wherein each $R_2$ is independently alkyl, halogen, or cyano. Preferably, at least one $R_2$ is located at the 2-position of the phenyl ring, represented by the compounds of formula (II),

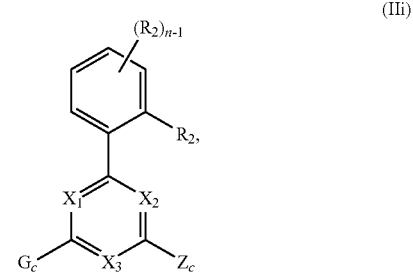

wherein each $R_2$ is independently selected. Examples of the compounds of formula (IIi) include the compounds of formulae (IIj), (IIk), and (IIm),

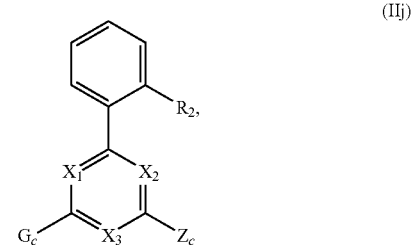

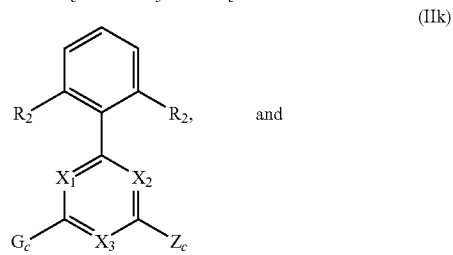

and

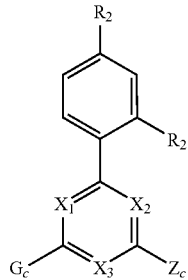

(IIm)

wherein each $R_2$ is independently selected. Preferred groups for the $R_2$ that is located at the 2-position of the phenyl ring include fluoro, chloro, methyl, cyano, and substituted alkyl wherein the substituent is —NHC(=O)$R_5$, —NHCO$_2R_5$, or —NHC(=O)NR$_5R_6$.

For example, the compounds of formula (Ic) may be provided wherein $G_c$ is selected from —NR$_7$SO$_2$NR$_8R_9$ and —NR$_8$SO$_2R_9$; and more preferably $G_c$ is —NR$_7$SO$_2$NR$_8R_9$.

Other examples of the compounds of formula (Ic) include compounds wherein $Z_c$ is a heterocyclo or substituted heterocyclo. Preferably, $Z_c$ is a monocyclic five- or six-membered heteroaryl, which is optionally substituted with one to three $R_3$. More preferably, $Z_c$ is a monocyclic five-membered heteroaryl, which is optionally substituted with one to three $R_3$. Preferred monocyclic five-membered heteroaryl groups for $Z_c$ include substituted or unsubstituted thiazolyl, substituted or unsubstituted thiadiazolyl, and substituted or unsubstituted oxadiazolyl, such as, for example,

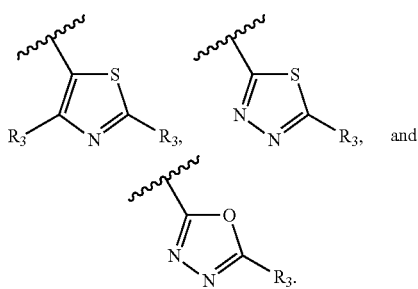

Still more preferably, $Z_c$ is a substituted or unsubstituted thiazolyl. Even more preferably, $Z_c$ is a thiazolyl having a substituted amino group at the 2-position and a hydrogen at the 4-position, represented by

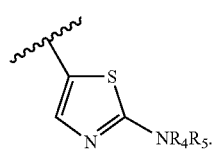

Most preferably, $Z_c$ is

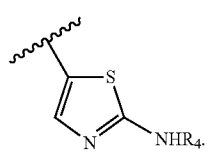

Utility

The compounds of the invention are selective inhibitors of kinases, for example, p38 kinases such as the isoforms p38α and p38β, and/or LIM kinases, such as LIM kinase 1 (LIMK1) and LIM kinase 2 (LIMK2).

Particular compounds of this invention have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its symptoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited. In view of their activity as inhibitors of p-38α/β kinase, compounds of formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenza, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to treat infectious diseases such as sepsis, septic shock, Shigellosis, and *Helicobacter Pylori*.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatitis B, and hepatitis C), HIV infection and CMV retinitis, AIDS, ARC, or malignancy, and herpes.

The inventive compounds also may be used to treat angiogenic disorders including solid tumors, ocular neovascularization, and infantile haemangiomas.

The inventive compounds also may be used to treat cancer including breast cancer.

In one embodiment, the compounds of this invention are used to treat a disease or condition selected from asthma, adult respiratory distress syndrome, chronic obstructive pulmonary disease, chronic pulmonary disease, diabetes, inflammatory bowel disease, osteoporosis, graft vs. host rejection, atherosclerosis, and arthritis.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia, and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction (MI), coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormone replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and/or necrosis.

Additional diseases and disorders that may be treated with the inventive compounds include irritable bowel syndrome, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity. The present invention thus provides methods for treating such conditions, comprising administering to a subject in need thereof an effective amount of at least one compound of formula (I), or a pharmaceutically-acceptable salt, hydrate, or prodrug thereof. The methods of treating p38 kinase-associated conditions may comprise administering compounds of formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Further, particular compounds of this invention have utility in treating conditions associated with LIM kinase activity. Such conditions include diseases or disorders in which actin levels are modulated as a consequence of inhibition of the actin depolymerizing protein cofilin by LIM kinases, and in particular, diseases that are associated with the overproduction of LIMK1 and/or LIMK2. In view of their activity as inhibitors of LIMK1 and LIMK2, particular compounds of this invention are thus useful in the treatment of a variety of cancers, including (but not limited to) the following:

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma.

The phenyl-substituted pyrimidine compounds of this invention may also inhibit tumor angiogenesis, thereby affecting the growth of tumors. Such anti-angiogenesis properties of the phenyl-substituted pyrimidine compounds of this invention may also be useful in the treatment of certain forms of blindness related to retinal vascularization, arthritis, especially inflammatory arthritis, multiple sclerosis, restinosis and psoriasis.

The phenyl-substituted pyrimidine compounds of this invention may induce or inhibit apoptosis, a physiological cell death process critical for normal development and homeostasis. Alterations of apoptotic pathways contribute to the pathogenesis of a variety of human diseases. The phenyl-substituted pyrimidine compounds of this invention, as modulators of apoptosis, will be useful in the treatment of a variety of human diseases with aberrations in apoptosis including cancer (particularly, but not limited to follicular lymphomas, carcinomas with p53 mutations, tumors of the breast, prostate and ovary, and precancerous lesions such as familial adenomatous polyposis).

On a different embodiment, a method is provided for treating cancer comprising administering to a patient in need of such treatment a pharmaceutical composition comprising a compound of this invention, wherein the cancer is selected from breast cancer and prostate cancer.

Further, the particular compounds of this invention have utility in treating conditions associated with LIM kinase activity relating to T-cell activation, such as immunological conditions.

Particular compounds of this invention may have utility in treating cardiovascular conditions associated with LIM kinase activity. Examples of cardiovascular conditions include ischemia, thrombosis, atherosclerosis, peripheral arterial disease, and thrombotic or thromboembolic symptoms, as disclosed hereinabove.

When the terms "LIMK associated condition", "LIM kinase associated condition", "LIMK associated disease or disorder", or "LIM kinase associated disease or disorder" are used herein, each is intended to encompass all of the conditions identified above as if repeated at length, as well as any other condition that is modulated by LIM kinase 1 and/or LIM kinase 2 activity. The present invention thus provides methods for treating such conditions, comprising administering to a subject in need thereof an effective amount of at least one compound of formula (I), or a pharmaceutically-acceptable salt, hydrate, or prodrug thereof. The methods of treating LIM kinase-associated conditions may comprise administering compounds of formula (I) alone or in combination with each other and/or other suitable therapeutic agents such as anti-inflammatory drugs, antibiotics, anti-viral agents, anti-oxidants, cholesterol/lipid lowering agents, other anti-tumor agents including other antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen® or Celebrex®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g., penicillins, cephalosporins and carbopenams); β-lactam and lactamase inhibitors (e.g., augmentin); aminoglycosides (e.g., tobramycin and streptomycin); macrolides (e.g. erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g. zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steroidal or non-steroidal progesterone receptor agonists ("PRA"), such as levonorgestrel and medroxyprogesterone acetate (MPA).

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with other anticancer strategies and chemotherapies such as taxol and/or cisplatin. The compounds may be used in conjunction with antitumor agents such as paclitaxel, adriamycin, epothilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. Patent Application Publication No. 2004/0039033A1 and assigned to the present assignee; alpha- or beta-adrenergic blockers (such as propranolol, nadolol, carvedilol, and prazosin), or β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); K$^+$ channel modulators such as $I_{Ach}$ inhibitors and inhibitors of the K$_v$1 subfamily of K$^+$ channel openers such as $I_{Kur}$ inhibitors (e.g., compounds disclosed in U.S. Pat. No. 6,706,720); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g. abciximab, eptifibatide, and tirofiban), thromboxane receptor antagonists (e.g., ifetroban), P2Y$_1$ and P2Y$_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the inventive compounds may be used in combination with lipid profile modulators and antiatherosclerotic agents including HMG-CoA reductase inhibitors (e.g. pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal Na$^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279, and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

In general, preferred compounds of the present invention, such as particular compounds disclosed in the following examples, have been identified to inhibit the activity of one or more of p38α/β enzymes, TNF-α, LIMK1, and/or LIMK2. Potencies can be calculated and expressed as either inhibition constants ($K_i$ values) or as $IC_{50}$ (inhibitory concentration 50%) values, and refer to activity measured employing the in vitro assay systems described herein. Exemplary values for compounds that inhibit the activity of p38α/β enzymes include concentration equivalent to, or more potent than, 10 µM, preferably 1 µM, and more preferably 0.1 µM, thereby demonstrating particular compounds of the present invention as effective inhibitors of p38α/β enzymes. Exemplary values for compounds that inhibit the activity of TNF-α include concentration equivalent to, or more potent than, 20 µM, preferably 2 µM, and more preferably 0.2 µM, thereby demonstrating particular compounds of the present invention as effective inhibitors of TNF-α. Exemplary values for compounds that inhibit the activity of LIMK1 enzymes include concentration equivalent to, or more potent than, 10 µM, preferably 1 µM, and more preferably 0.1 µM, thereby demonstrating particular compounds of the present invention as effective inhibitors of LIMK1 enzymes. Exemplary values for compounds that inhibit the activity of LIMK2 enzymes include concentration equivalent to, or more potent than, 10 µM, preferably 1 µM, and more preferably 0.1 µM, thereby demonstrating particular compounds of the present invention as effective inhibitors of LIMK2 enzymes.

Biological Assays

Generation of p38 Kinases cDNAs of human p38α, β, and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.,* 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 µl of cell suspension was incubated with 50 µl of test compound (4× concentration in assay medium containing 0.2% DMSO) in 96-well tissue culture plates for 5 minutes at RT. 100 µl of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 µl prepared from three 20 µl additions of enzyme, substrates (MBP and ATP) and test compounds in assay buffer (50 mM Tris pH 7.5, 10 mM MgCl$_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 µM; [γ-$^{33}$P]ATP, 3 nM; MBP (Sigma, #M1891), 2 µg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 µg/kg lipopolysaccharide (LPS; *E coli* strain 0111:B4, Sigma) suspended in sterile saline. Ninety minutes later, mice were sedated by CO$_2$:O$_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Generation of the Kinase Domains of LIMK1 and LIMK2

The cDNA coding regions corresponding to the kinase domains of LIMK1 (accession number P53667, amino acids 321 to 647) and LIMK2 (accession number P53671, amino acids 312 to 638) were isolated and cloned to the Gateway entry vector pENTR TOPO (Invitrogen) using PCR. The cDNA inserts were transferred to the baculovirus donor vector pDEST 10 according to the procedures suggested by the manufacturer (Invitrogen). Recombinant baculovirus expressing the kinase domains of LIMK1 and LIMK2 as glutathione S-transferase (GST) fusion proteins were generated using the Bac-to-Bac system (Invitrogen) according to the manufacturer's procedure.

For production of the recombinant kinases GST-LIMK1 and GST-LIMK2, Sf9 cells growing in log phase were infected with the corresponding baculoviruses at MOI=5 for 2 days. The cells were harvested and re-suspended in ice-cold buffer A [50 mM HEPES, pH 7.5, 50 mM NaF, 100 mM NaCl, 1 mM Na$_3$VO$_4$, 10% glycerol, 1% Triton-X-100 surfactant and Complete protease inhibitors (1 tablet/50 ml, Roche Diagnostics)]. After centrifugation (16,000 g, 20 min, 4° C.), the supernatants were incubated with glutathione sepharose 4B (Amersham Pharmacia Biotech; 1 ml bed volume per liter of lysate) for 1 hr at 4° C. and washed 2 times with 15 bed volumes of buffer A and 2 times with 15 bed volumes of buffer B (50 mM HEPES, pH 7.5, 50 mM NaF, 100 mM NaCl, 1 mM Na$_3$VO$_4$, and 10% glycerol). The sepharose beads were then resuspended in 2 bed volumes of buffer B and poured into disposable columns. The GST fusion proteins were eluted with buffer B containing 10 mM glutathione and stored at −70° C.

Generation of Biotinylated ADF

The cDNA of the full length actin depolymization factor (ADF, accession number P60981) was cloned to the pET28N-BioPn vector for bacteria expression. Expression was carried out in BL21(DE3) cells with plysS in M9CA media (Teknova) after co-transformation with the pBirA vector (for co-expression of biotin lygase). Uninduced cells were chilled on ice for 30 minutes upon reaching OD$_{600}$ of 0.6 to 0.8, induced by addition of 0.4 mM IPTG and 50 µM biotin, and incubated for 16 hours at 20° C. Cells were harvested by centrifugation. The cell pellet was lysed by freezing and thawing in PBS containing 5 mM imidazole and EDTA-free protease inhibitor tablet (1 tablet/50 ml, Roche Diagnostics). The lysate was digested with DNase I and Centrifuged (10,000×g for 20 min). Biotinylated ADF in the supernatant was bound to Ni-NTA resin (Qiagen), washed, and eluted with 200 mM Imidazole. The protein was dialyzed to storage buffer (50 mM HEPES, pH7.5, 100 mM NaCl) and stored at −70° C.

LIMK1 and LIMK2 Kinase Assays

Filter-based TCA precipitation assays were employed to determine the IC$_{50}$ values against LIMK1 and LIMK2 using biotinylated ADF as the protein substrate and the kinase domains of LIMK1 and LIMK2 as the enzyme sources in the presence of 1 µM ATP. The reactions (60 µl) containing 25 mM HEPES, 100 mM NaCl, 5 mM MgCl$_2$, 5 mM MnCl$_2$, 1 µM ATP, 83 µg/ml biotinylated ADF, 167 ng/ml GST-LIMK1 (or 835 ng/ml GST-LIMK2), and various concentrations of tested compound were carried out at room temperature for 30 min (60 min for LIMK2) in a 96-well plate. After the reactions were terminated by addition of 140 µl of 20% TCA and 100 mM NaPPi, the TCA-precipitated proteins were harvested onto GF/C unifilter plates (Perkin-Elmer) and washed. The radioactivity incorporated was then determined using a TopCount (Packard Instrument) after addition of 35 µl of Microscint scintillation fluid.

For ease of reference, the following abbreviations are employed herein, including the methods of preparation and Examples that follow:

ABBREVIATIONS

MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM=dichloromethane
DCE=1,2-dichloroethane
DEAD=diethyl azodicarboxylate
DMF=dimethyl formamide
DMSO=dimethyl sulfoxide
PmB=para-methoxybenzyl
TFA=trifluoroacetic acid
THF=tetrahydrofuran
TMS=trimethylsilyl
HATU=O-(7-Azabenzotriazol-1-yl-N,N,N',N'-tetramethyluronium hexafluorophosphate
KOH=potassium hydroxide
K$_2$CO$_3$=potassium carbonate
POCl$_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOEt=sodium ethoxide
NaOH=sodium hydroxide
Na$_2$S$_2$O$_3$=sodium thiosulfate
HCl=hydrogen chloride NMP=N-methylpyrrolidinone
$CO_2$=carbon dioxide
Pd=palladium
Pd/C=palladium on carbon
sec=second (s)
min=minute(s)
h=hour(s)
L=liter
mL=milliliter
µL=microliter
g=gram(s)
mg=milligram(s)
mol=moles
mmol=millimole(s)
N=Normal
M=Molar
° C.=degrees Celsius
rt=room temperature
Ret. time or $t_R$=retention time (minutes)
anhyd.=anhydrous
sat or sat'd=saturated
aq.=aqueous
HPLC=high performance liquid chromatography
LCMS=high performance liquid chromatography/mass spectrometry
MS=mass spectrometry
NMR=nuclear magnetic resonance
MHz=megahertz
s=singlet
m=multiplet
d=doublet
dd=doublet of doublet Methods of Preparation The compounds of formula (I) may generally be prepared according to the following schemes and the knowledge of one skilled in the art.

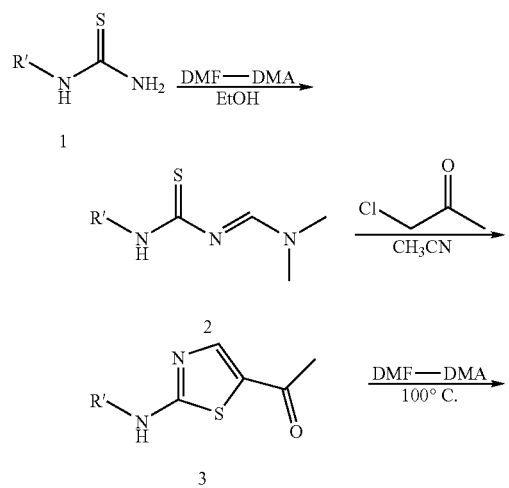

Compound 8 can be prepared from Compound 1 as depicted in Scheme 1. Compound 1 can be reacted with N,N-dimethylformamide dimethyl acetal (DMF-DMA) in a solvent, such as ethanol, to afford Compound 2. Compound 2 can be cyclized with α-chloroacetone in a solvent, such as acetonitrile, to afford Compound 3. Compound 3 can be reacted with N,N-dimethylformamide dimethyl acetal (DMF-DMA) to afford Compound 4. Compound 4 can be reacted with urea in the presence of a base, such as sodium hydride, to afford Compound 5. Compound 5 can be converted to Compound 6 by reacting with phosphorus oxychloride in the presence of a base, such as Hunig's base, in a solvent, such as toluene. Finally, Compound 6 can be coupled to Compound 7 in the presence of catalysts, such as Pd$(PPh_3)_4$, and in the presence of a base, such as $K_3PO_4$, in a solvent, such as toluene, to afford Compound 8.

SCHEME 2

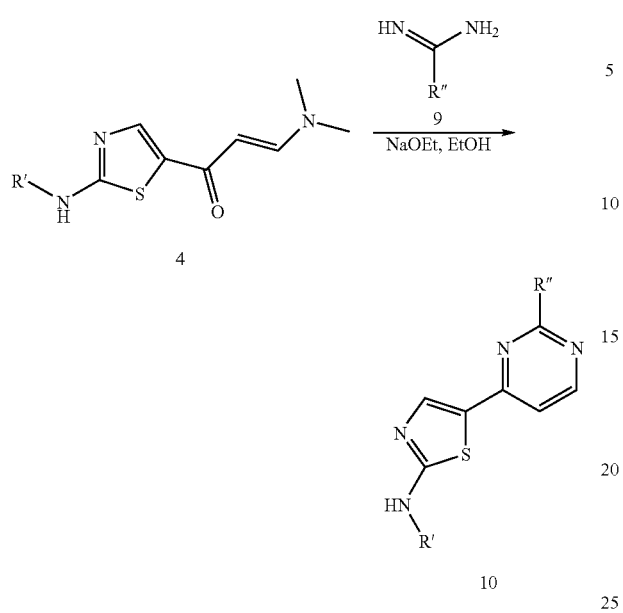

Alternatively, Compound 10 can be prepared from Compound 4 by reacting Compound 9, in the presence of a base, such as sodium ethoxide, in a solvent, such as ethanol as depicted in Scheme 2.

SCHEME 3

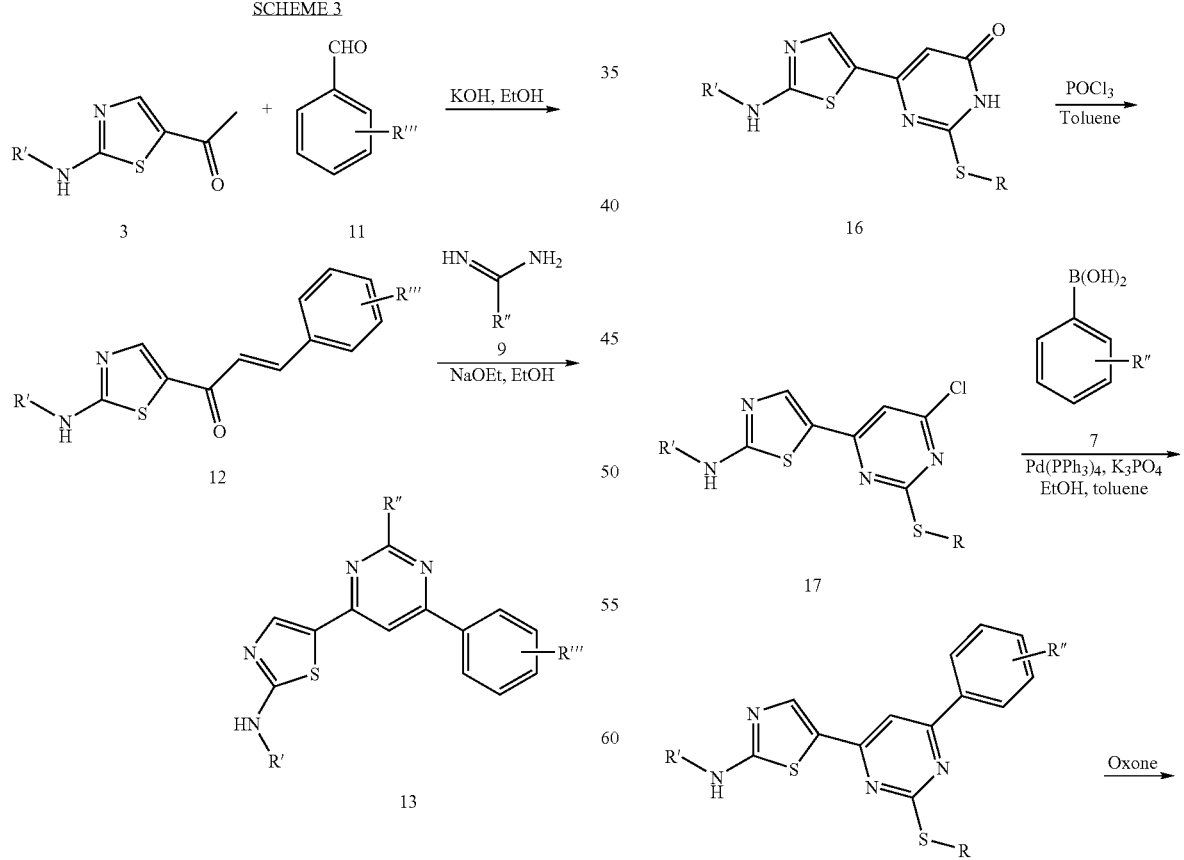

Compound 13 can be prepared from Compound 3 as depicted in Scheme 3. Compound 3 can be reacted with Compound 11, in the presence of a base, such as potassium hydroxide, in a solvent, such as ethanol, to afford Compound 12. Compound 12 can be coupled to Compound 9 to afford Compound 13, in the presence of a base, such as sodium ethoxide, in the presence of a solvent, such as ethanol.

SCHEME 4

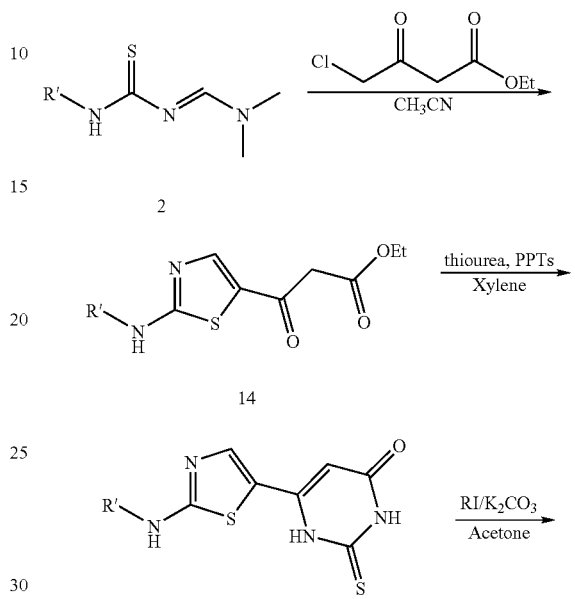

-continued

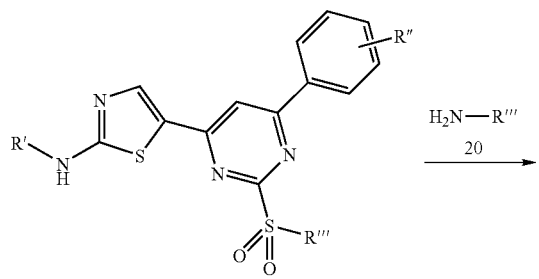

19

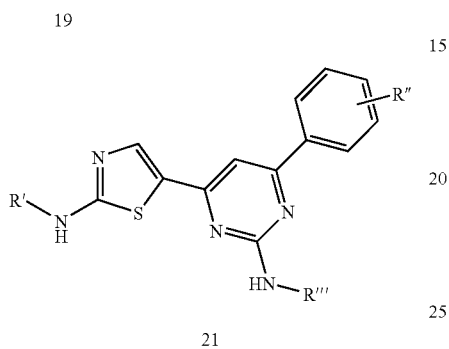

21

Compound 21 can be prepared from the Compound 2 as depicted in Scheme 4. Compound 2 can be cyclized with ethyl-4-chloroacetoacetate, in the presence of a base, such as triethylamine, in a solvent, such as acetonitrile, to afford Compound 14. Compound 14 can be reacted with thiourea in the presence of a catalytic amount of p-toluenesulfonic acid (PPTs) in a solvent, such as xylene, to afford Compound 15. Compound 15 can be alkylated with alkylating agent, such as iodomethane, in the presence of a base, such as potassium carbonate, in a solvent, such as acetone, to afford Compound 16. Compound 16 can be converted to Compound 17 by reacting with phosphorus oxychloride in the presence of a base, such as Hunig's base, in a solvent, such as toluene. Compound 17 can be coupled to Compound 7 in the presence of catalysts, such as Pd(PPh$_3$)$_4$, and in the presence of a base, such as K$_3$PO$_4$, in a solvent, such as toluene. Compound 18 can be oxidized in the presence of an oxidant, such as Oxone™ compound, in a solvent, such as aqueous methanol, to afford Compound 19. Finally, Compound 19 can be coupled with Compound 20, in the presence of a solvent, such as ethanol, to afford Compound 21.

SCHEME 4a

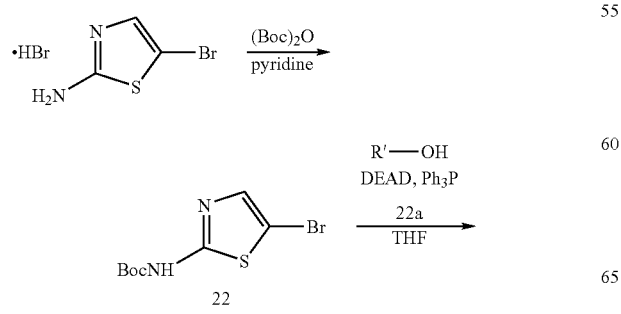

-continued

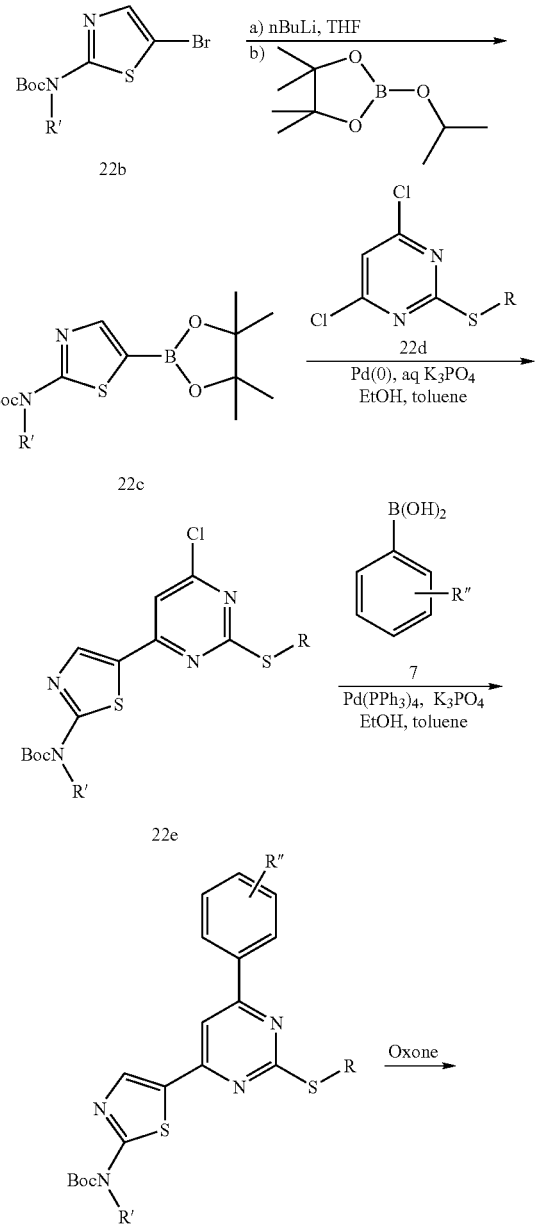

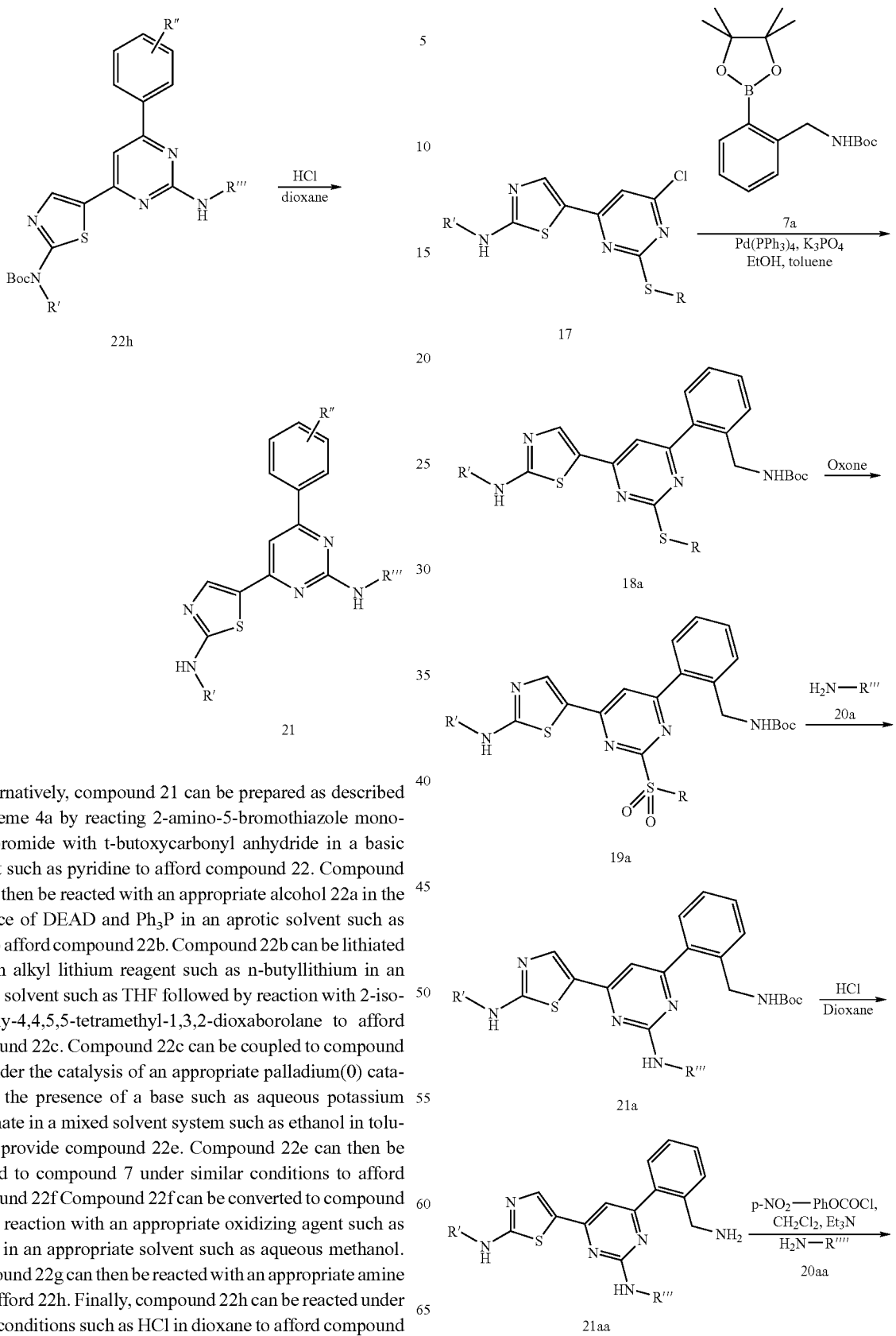

Alternatively, compound 21 can be prepared as described in Scheme 4a by reacting 2-amino-5-bromothiazole monohydrobromide with t-butoxycarbonyl anhydride in a basic solvent such as pyridine to afford compound 22. Compound 22 can then be reacted with an appropriate alcohol 22a in the presence of DEAD and Ph$_3$P in an aprotic solvent such as THF to afford compound 22b. Compound 22b can be lithiated with an alkyl lithium reagent such as n-butyllithium in an aprotic solvent such as THF followed by reaction with 2-isopropoxy-4,4,5,5-tetramethyl-1,3,2-dioxaborolane to afford compound 22c. Compound 22c can be coupled to compound 22d under the catalysis of an appropriate palladium(0) catalyst in the presence of a base such as aqueous potassium phosphate in a mixed solvent system such as ethanol in toluene to provide compound 22e. Compound 22e can then be coupled to compound 7 under similar conditions to afford compound 22f. Compound 22f can be converted to compound 22g be reaction with an appropriate oxidizing agent such as Oxone in an appropriate solvent such as aqueous methanol. Compound 22g can then be reacted with an appropriate amine 20 to afford 22h. Finally, compound 22h can be reacted under acidic conditions such as HCl in dioxane to afford compound 21.

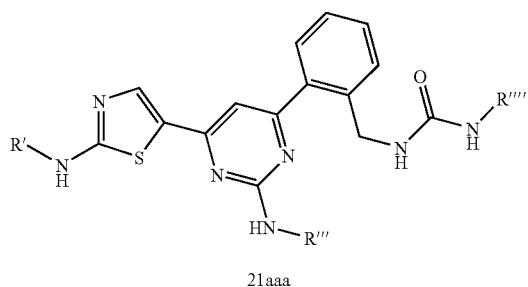

21aaa

Compound 21aaa can be prepared from the Compound 17 as depicted in Scheme 4b. Compound 17 can be coupled to Compound 7a in the presence of a catalyst, such as Pd(PPh$_3$)$_4$, and in the presence of a base, such as K$_3$PO$_4$, in a solvent, such as toluene. Compound 18a can be oxidized in the presence of an oxidant, such as Oxone™ compound, in a solvent, such as aqueous methanol, to afford Compound 19a. Compound 19a can be converted to Compound 21a by reacting with amine 20a in the presence of a solvent, such as ethanol. Compound 21a can be reacted with acid, such as hydrogen chloride, in a solvent, such as dioxane, to afford Compound 21aa. Finally, Compound 21aa can be allowed to react with an activating reagent, such as p-nitrophenylchloroformate, in the presence of a base, such as triethylamine, in a solvent, such as dichloromethane, then reacted with amine 20aa to afford Compound 21aaa.

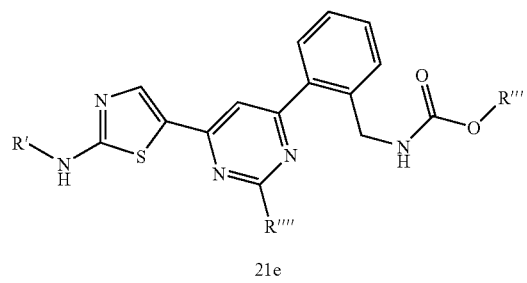

21e

In addition, Compound 21c can be reacted with acid chloride 74 in the presence of a base, such as triethylamine, in a solvent, such as dichloromethane, to afford amide 21d. Furthermore, Compound 1 can be reacted with chloroformate 75 under similar conditions to afford carbamate 21e.

SCHEME 4c

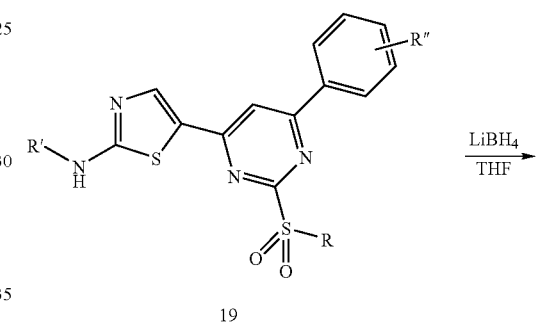

Compound 21b can be prepared from Compound 19 by reacting Compound 19 with a reducing agent, such as lithium borohydride, in a solvent, such as THF, to afford Compound 21b as depicted in Scheme 4c.

SCHEME 4bb

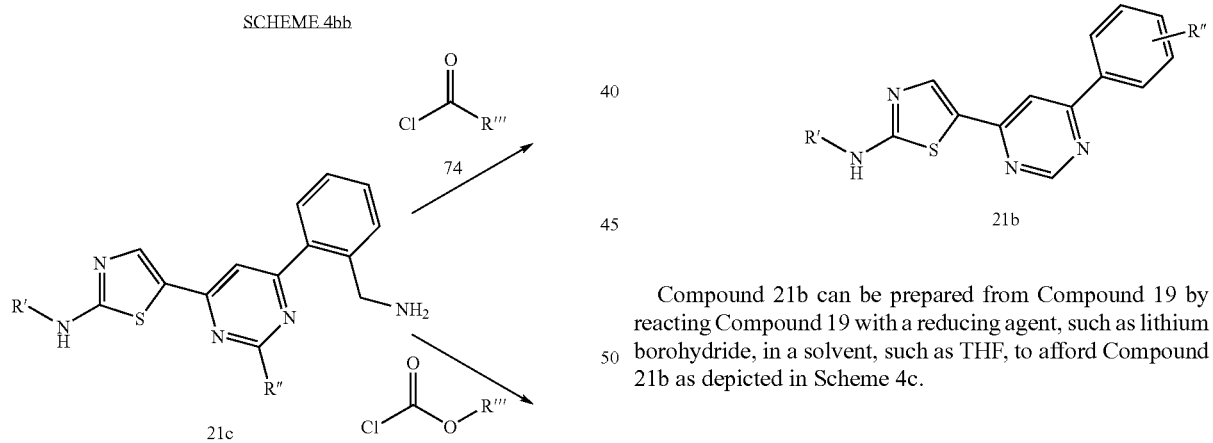

SCHEME 4d

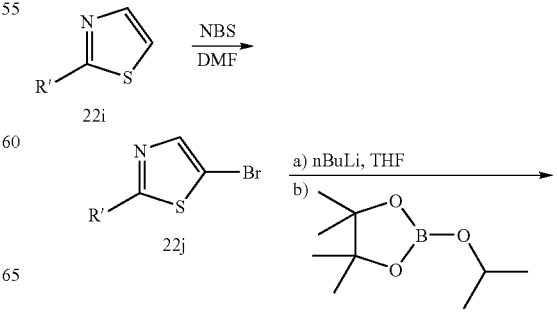

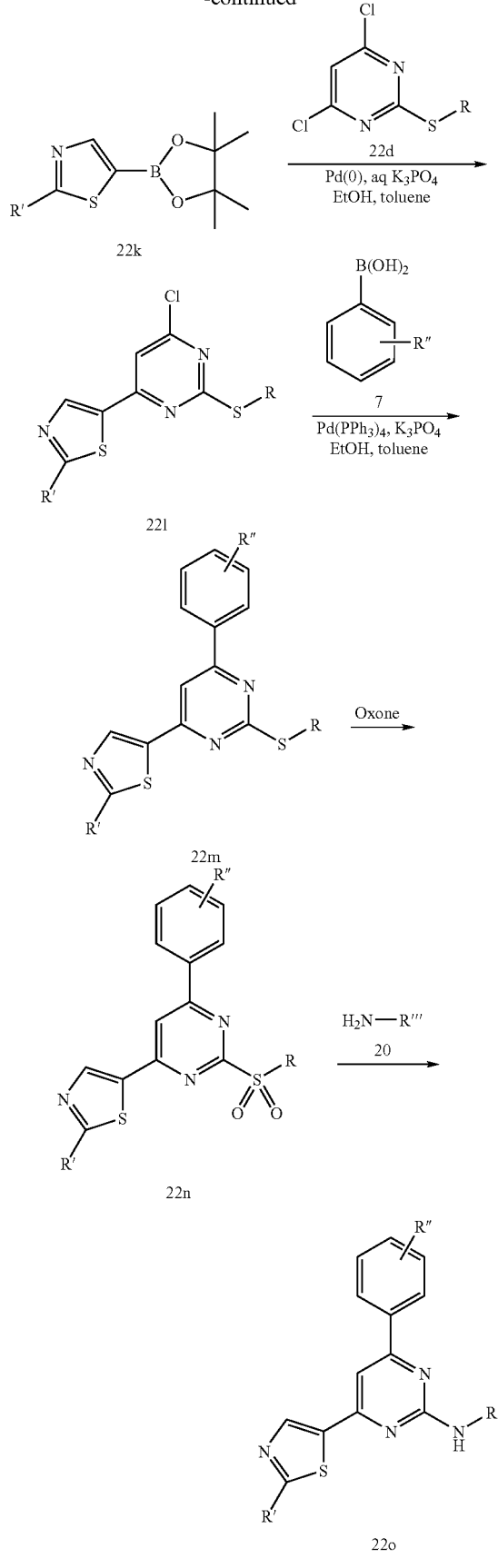

In addition, Compound 22o can be prepared from compound 22i as described in Scheme 4d. Compound 22i can be brominated in the presence of an appropriate brominating reagent such as N-bromosuccinimide (NBS) in an aprotic solvent such as DMF to afford compound 22j. Compound 22j can then be converted into compound 22k by lithiation using an alkyl lithium reagent such as n-butyllithium in an aprotic solvent such as THF followed by reacting with 2-isopropoxy-4,4,5,5-tetramethyl-1,3,2-dioxaborolane. Compound 22k can be coupled to compound 22d under the catalysis of an appropriate palladium(0) catalyst in the presence of a base such as aqueous potassium phosphate in a mixed solvent system such as ethanol in toluene to provide compound 22l. Compound 22l can then be coupled to compound 7 under similar conditions to afford compound 22m. Compound 22m can be converted to compound 22n be reaction with an appropriate oxidizing agent such as Oxone in an appropriate solvent such as aqueous methanol. Finally, compound 22n can then be reacted with an appropriate amine 20 to afford compound 22o.

SCHEME 4e

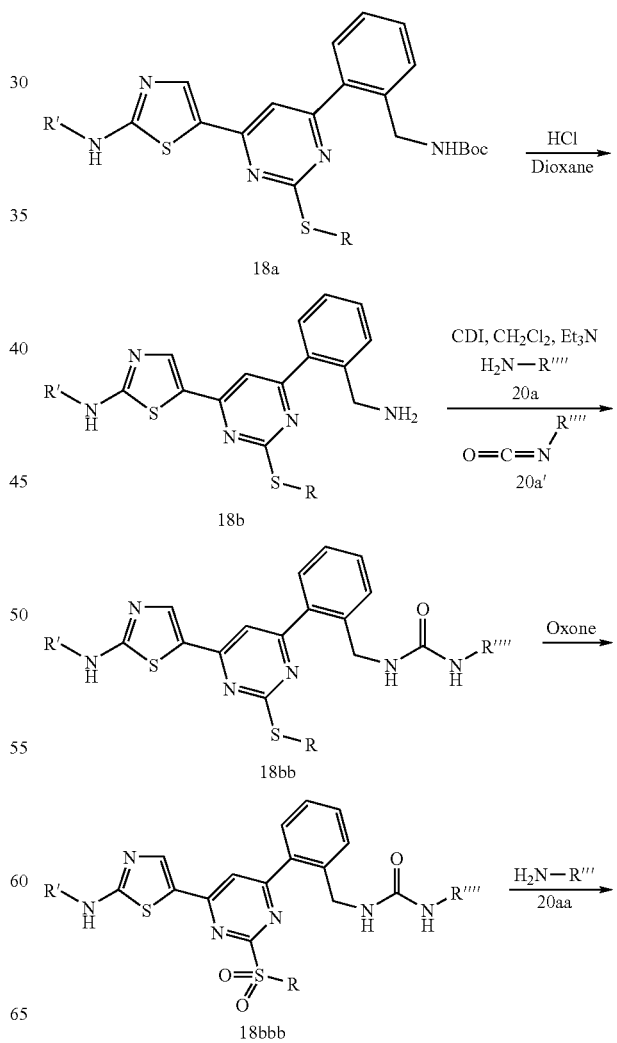

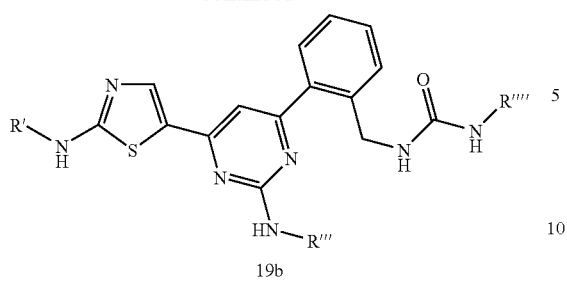

19b

Compound 19b can be prepared from the Compound 18a as depicted in Scheme 4e. Compound 18a can be reacted with acid, such as hydrogen chloride, in a solvent, such as dioxane, to afford Compound 18b. Compound 18b can be allowed to react with an activating reagent, such as carbonyldiimidazole (CDI), in the presence of a base, such as triethylamine, in a solvent, such as dichloromethane, then reacted with amine 20a to afford Compound 18bb. Alternatively, Compound 18b can be allowed to react with isocyanate 20a' in the presence of a base, such as triethylamine, in a solvent such as dichloromethane to afford Compound 18bb. Compound 18bb can be oxidized in the presence of an oxidant, such as Oxone™ compound, in a solvent, such as aqueous methanol, to afford Compound 18bbb. Finally, compound 18bbb can be converted to Compound 19b by reacting with amine 20aa in the presence of a solvent, such as ethanol.

SCHEME 4f

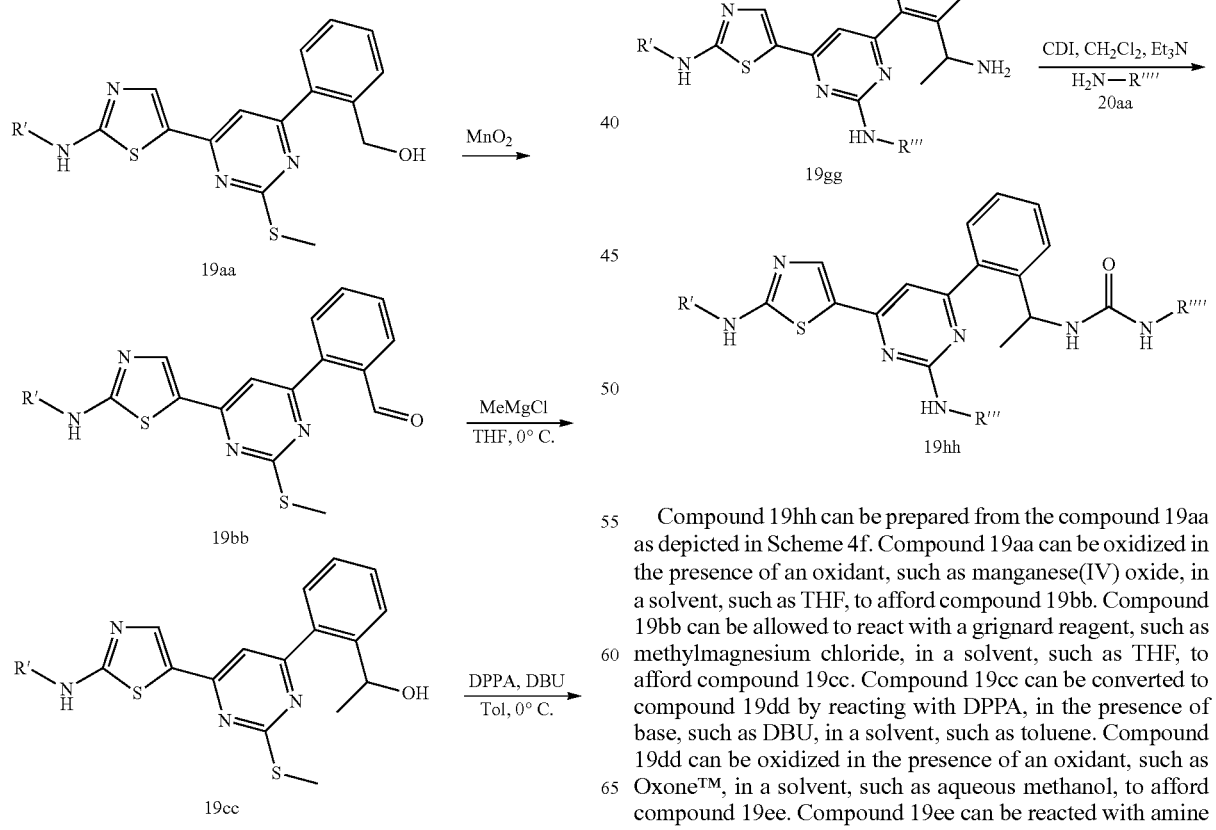

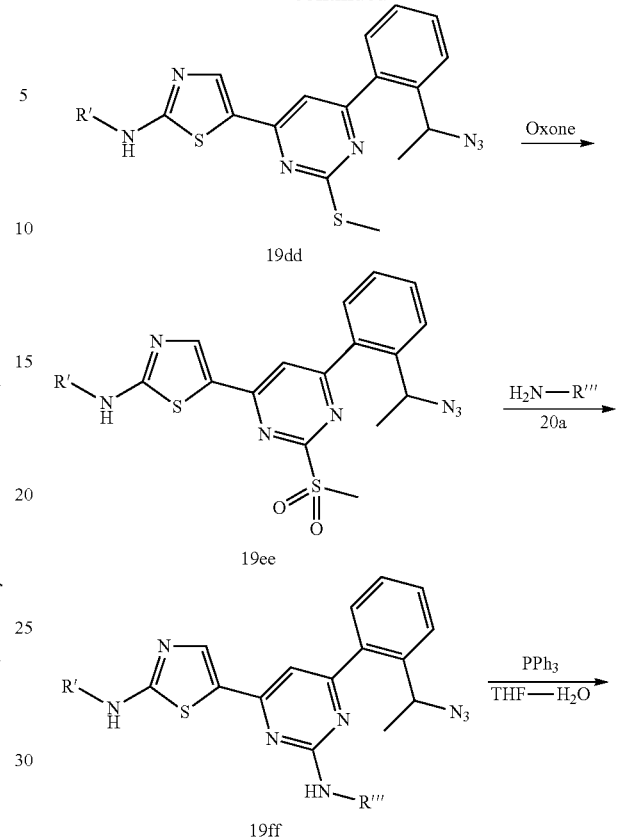

Compound 19hh can be prepared from the compound 19aa as depicted in Scheme 4f. Compound 19aa can be oxidized in the presence of an oxidant, such as manganese(IV) oxide, in a solvent, such as THF, to afford compound 19bb. Compound 19bb can be allowed to react with a grignard reagent, such as methylmagnesium chloride, in a solvent, such as THF, to afford compound 19cc. Compound 19cc can be converted to compound 19dd by reacting with DPPA, in the presence of base, such as DBU, in a solvent, such as toluene. Compound 19dd can be oxidized in the presence of an oxidant, such as Oxone™, in a solvent, such as aqueous methanol, to afford compound 19ee. Compound 19ee can be reacted with amine 20a to afford compound 19ff. Compound 19ff can be reduced to compound 19gg in the presence of reducing agent, such as PPh$_3$ in a solvent such as aqueous THF. Finally, compound 19gg can be allowed to react with an activating reagent, such as carbonyldiimidazole (CDI), in the presence of a base, such as triethylamine, in a solvent, such as dichloromethane, followed by reaction with amine 20aa to afford compound 19hh.

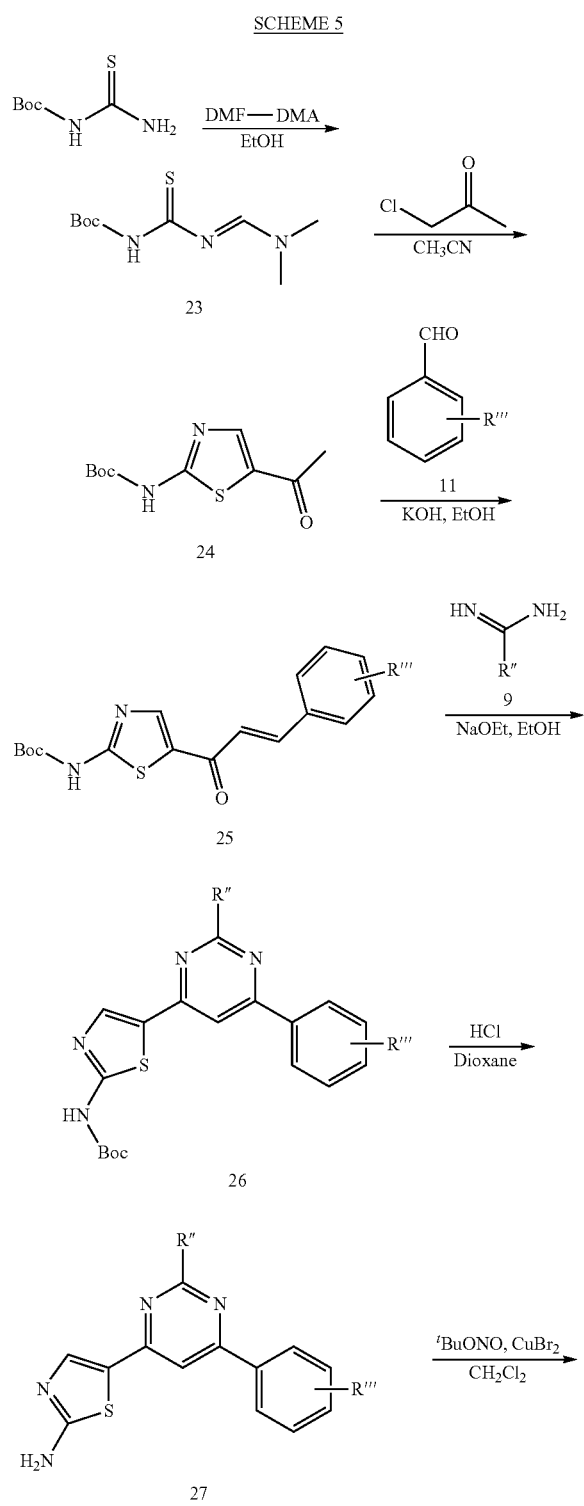

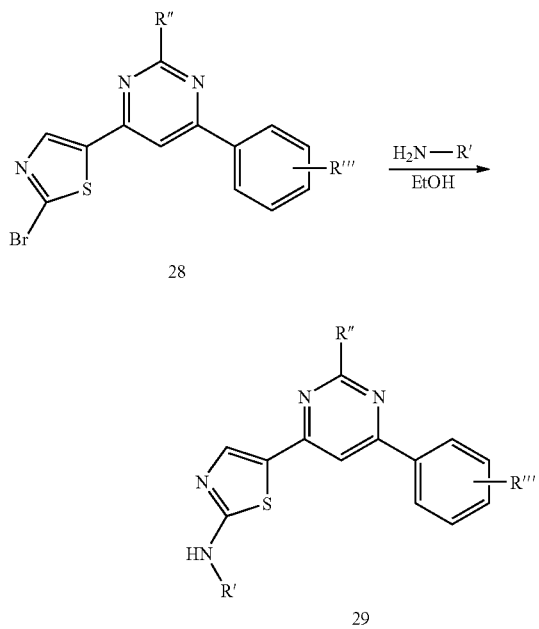

Compound 29 can be prepared from tert-butoxycarbonylthiourea as depicted in Scheme 5. Tert-butoxycarbonylthiourea can be reacted with N,N-dimethylformamide dimethyl acetal (DMF-DMA) in a solvent, such as ethanol, to afford Compound 23. Compound 23 can be cyclized with α-chloroacetone in the presence of a base, such as triethylamine, in a solvent, such as acetonitrile, to afford Compound 24. Compound 24 can be reacted with Compound 11, in the presence of a base, such as potassium hydroxide, in a solvent, such as ethanol, to afford Compound 25. Compound 25 can be coupled to Compound 9 to afford Compound 26, in the presence of a base, such as sodium ethoxide, in the presence of a solvent, such as ethanol. Compound 26 can be reacted with an acid, such as hydrogen chloride, in a solvent, such as dioxane, to afford Compound 27. Compound 27 can be converted to Compound 28 by reacting with t-butyl nitrite in the presence of a catalyst, such as Cu(II)Br$_2$, in the presence of a solvent, such as dichloromethane. Finally, Compound 28 can be converted to Compound 29 by reacting with an amine, in a solvent, such as ethanol.

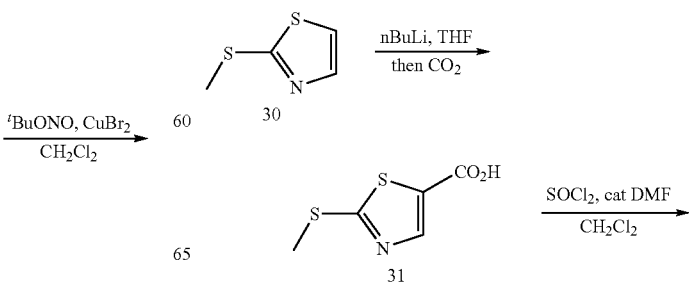

49
-continued

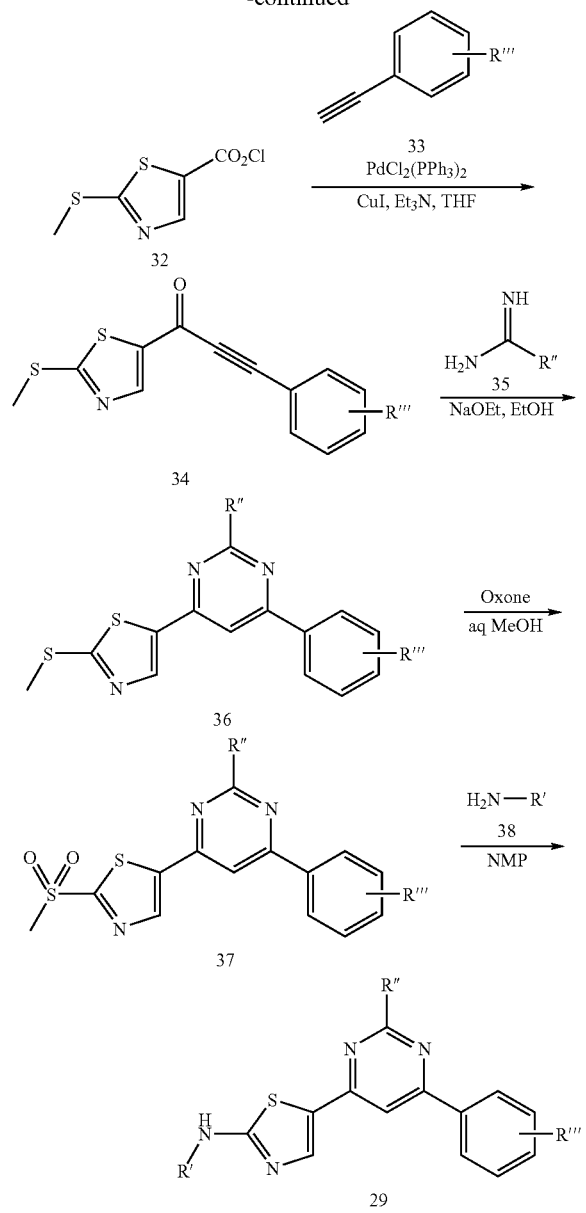

50

SCHEME 6a

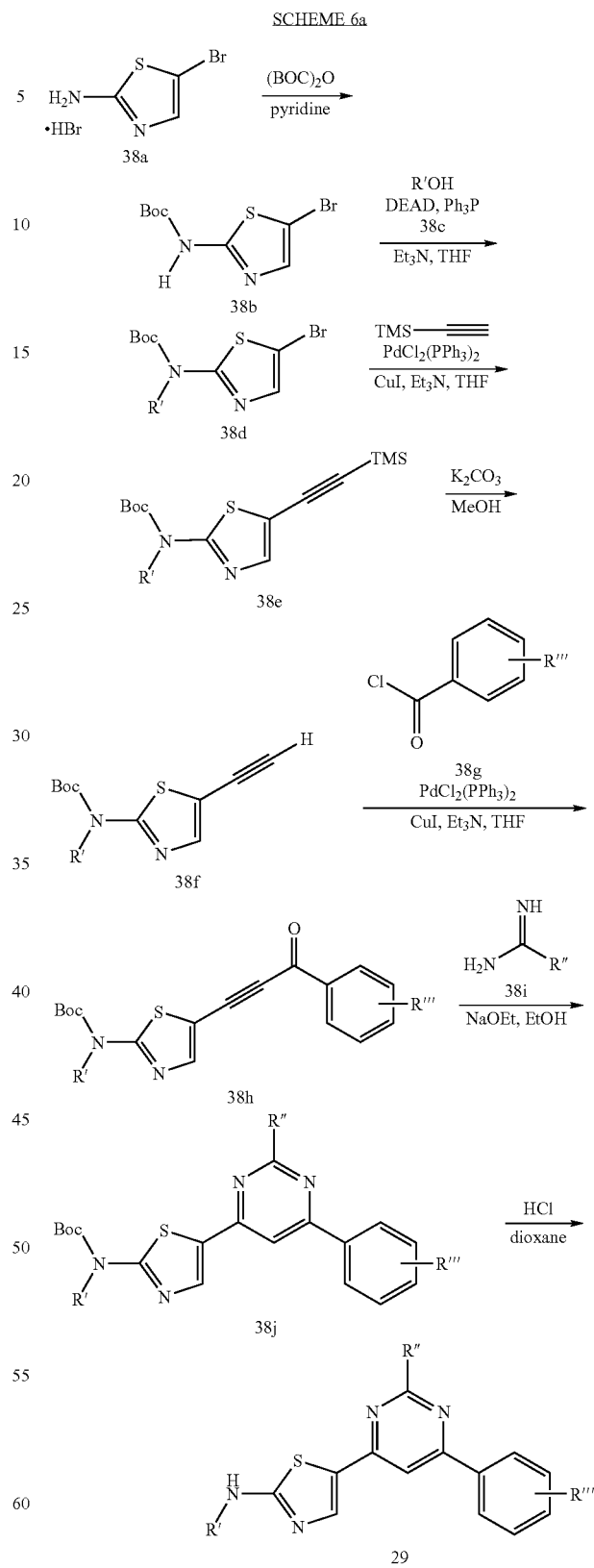

Alternatively, Compound 29 can be prepared from commercially-available Compound 30 as depicted in Scheme 6. Compound 30 can be converted to Compound 31 by reacting with a base, such as n-butyllithium, followed by carboxylation to afford Compound 31. Compound 31 can be reacted with a reagent, such as thionyl chloride, in the presence of a catalyst, such as DMF, in a solvent, such as dichloromethane, to afford Compound 32. Compound 32 can be coupled to Compound 33 in the presence of catalysts, such as $PdCl_2$ $(PPh_3)_4$ and copper iodide, and in the presence of a base, such as triethylamine, in a solvent, such as THF, to afford Compound 34. Compound 34 can be converted to Compound 36 by coupling with Compound 35 in the presence of a base, such as sodium ethoxide, in the presence of a solvent, such as ethanol. Compound 36 can be oxidized in the presence of an oxidant, such as Oxone™ compound, in a solvent, such as aqueous methanol, to afford Compound 37. Finally, Compound 37 can be coupled with amine 38, in the presence of a solvent, such as NMP, to afford Compound 29.

Alternatively, Compound 29 can be prepared from commercially-available Compound 38a as depicted in Scheme 6a. Compound 38a can be converted to Compound 38b by reacting with di-tert-butyl-dicarbonate [(Boc)$_2$O], in a basic solvent, such as pyridine then Compound 38b can be converted to Compound 38d by coupling with alcohol 38c in the presence of diethyl azodicarboxylate (DEAD), triphenylphosphine, and a base, such as triethylamine, in a solvent, such as THF. Compound 38d can be reacted with trimethylsilylacetylene in the presence of catalysts, such as PdCl$_2$(PPh$_3$)$_4$ and copper iodide, and in the presence of a base, such as triethylamine, in a solvent, such as THF, to afford Compound 38e. Disilylation of Compound 38e to afford Compound 38f can be accomplished using a base, such as K$_2$CO$_3$, in the presence of an alcoholic solvent, such as methanol. Compound 38f can be coupled to Compound 38g in the presence of catalysts, such as PdCl$_2$(PPh$_3$)$_4$ and copper iodide, and in the presence of a base, such as triethylamine, in a solvent, such as THF, to afford Compound 38h and Compound 38h can be coupled to Compound 38i in the presence of a base, such as NaOEt, in a solvent, such as ethanol, to afford Compound 38j. Finally, Compound 29 can be prepared from Compound 38j by reacting with an acid, such as hydrogen chloride, in the presence of a solvent, such as dioxane.

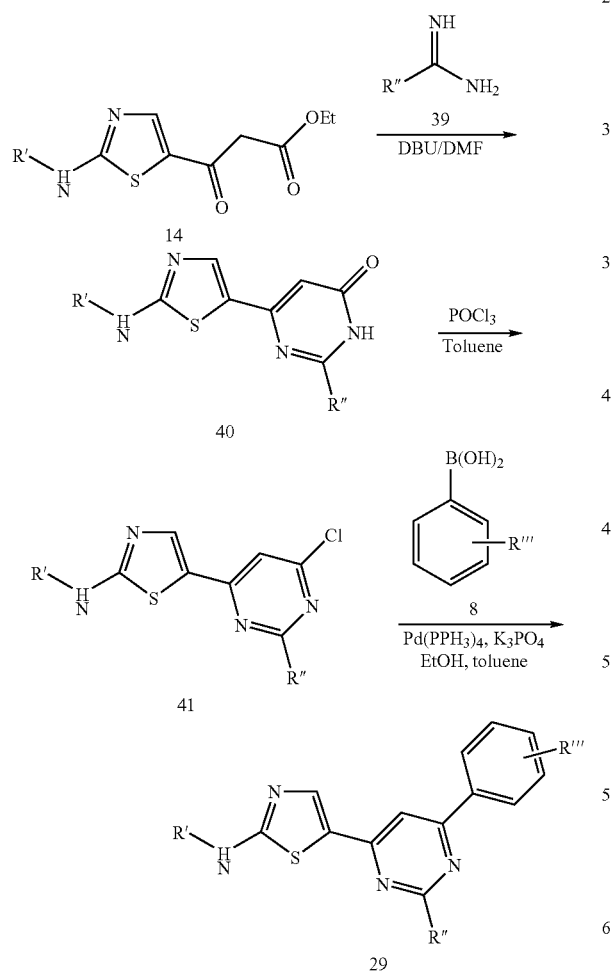

Alternatively, Compound 29 can be prepared from Compound 14 as depicted in Scheme 7. Compound 14 can be converted to Compound 40 by reacting with Compound 39 in the presence of base, such as DBU, in a solvent, such as DMF. Compound 40 can be converted to Compound 41 by reacting with phosphorus oxychloride in the presence of a base, such as Hunig's base, in a solvent, such as toluene. Finally, Compound 41 can be coupled to Compound 8 in the presence of a catalyst, such as Pd(PPh$_3$)$_4$, and in the presence of a base, such as K$_3$PO$_4$, in a solvent, such as toluene, to afford Compound 29.

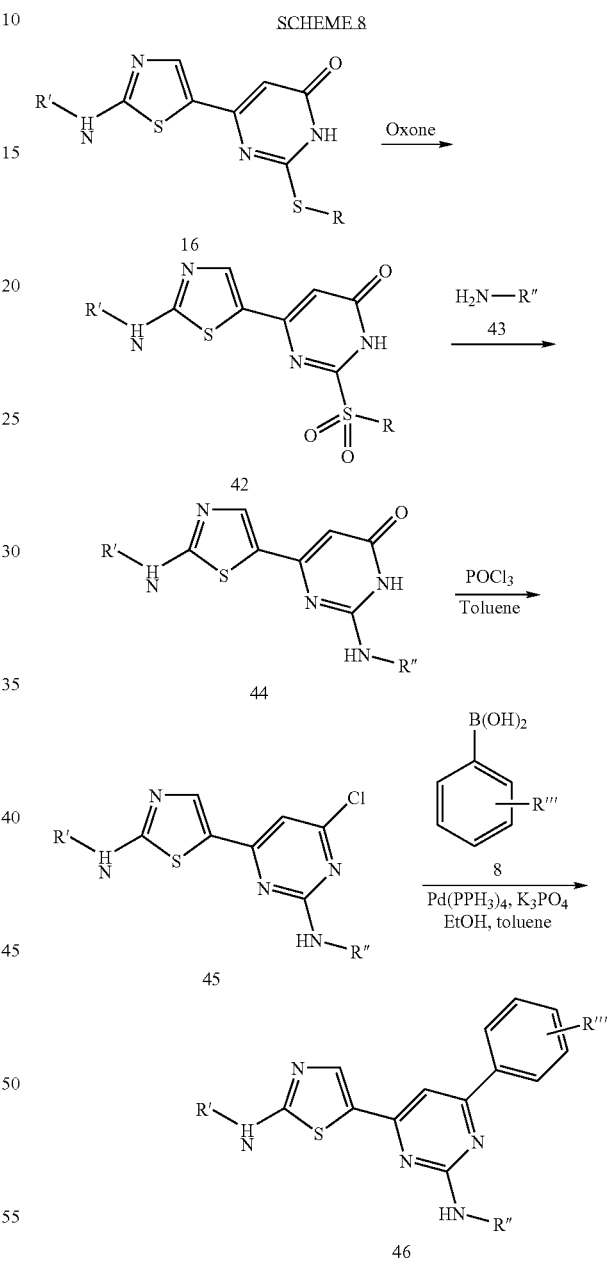

Compound 46 can be prepared from Compound 16 as depicted in Scheme 8. Compound 16 can be oxidized in the presence of an oxidant, such as Oxone™ compound, in a solvent, such as aqueous methanol, to afford Compound 42. Compound 42 can be converted to Compound 44 by reacting with an amine 43 in a solvent, such as ethanol. Compound 44 can be converted to Compound 45 by reacting with phosphorus oxychloride in the presence of a base, such as Hunig's base, in a solvent, such as toluene. Finally, Compound 45 can be converted to Compound 46 by coupling to Compound 8 in the presence of a catalyst, such as Pd(PPh$_3$)$_4$, and in the presence of a base, such as K$_3$PO$_4$, in a solvent, such as toluene.

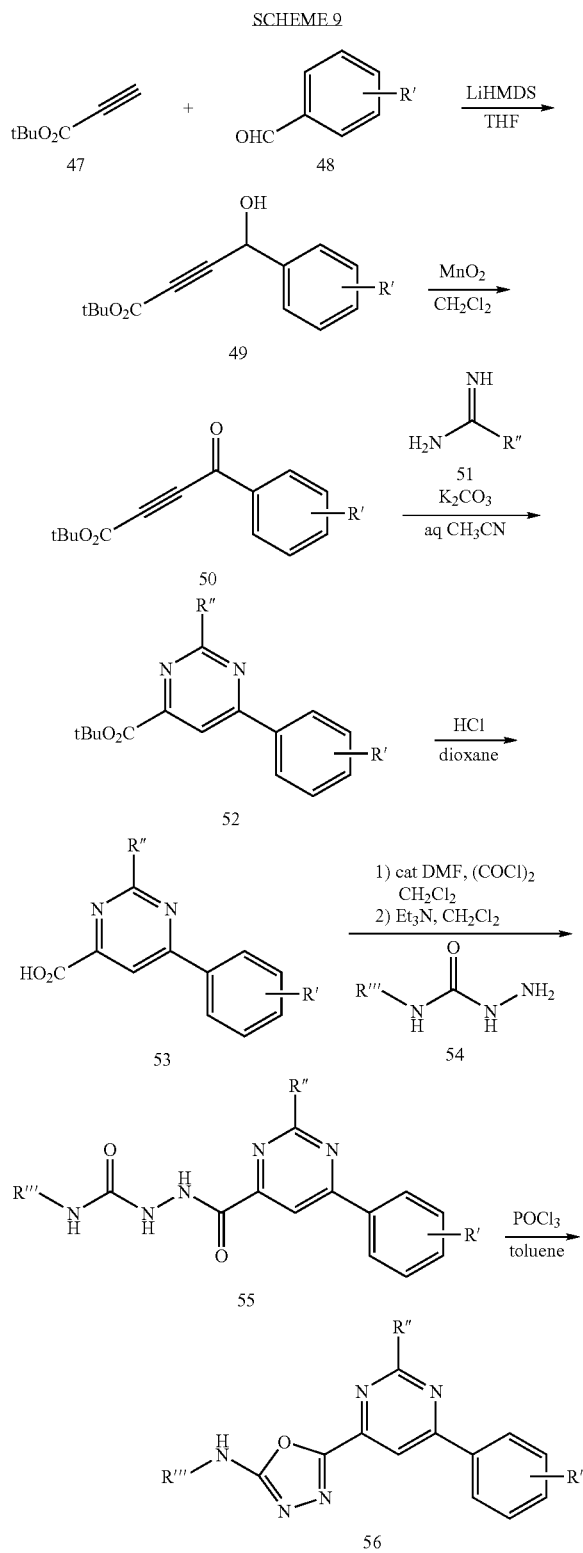

Compound 56 can be prepared from Compounds 47 and 48 as depicted in Scheme 9. Compound 47 can be reacted with Compound 48 in the presence of a base, such as lithium hexamethylsilazide (LiHMDS), in a solvent, such as THF, to afford Compound 49. Compound 49 can be oxidized with an oxidant, such as manganese dioxide, in a solvent, such as dichloromethane, to afford Compound 50. Compound 50 can be reacted with Compound 51 in the presence of a base, such as potassium carbonate, in a solvent, such as aqueous acetonitrile, to afford Compound 52. Compound 52 can be reacted with an acid, such as hydrogen chloride, in a solvent, such as dioxane, to afford Compound 53. Compound 53 can be converted to Compound 55 by (1) reacting with oxalyl chloride in the presence of a catalytic amount of DMF in a solvent, such as dichloromethane, then (2) coupling with Compound 54 in the presence of a base, such as triethylamine, in a solvent, such as dichloromethane, to afford Compound 55. Finally, Compound 55 can be converted to Compound 56 by reacting with a dehydrating reagent, such as phosphorus oxychloride, in a solvent, such as toluene.

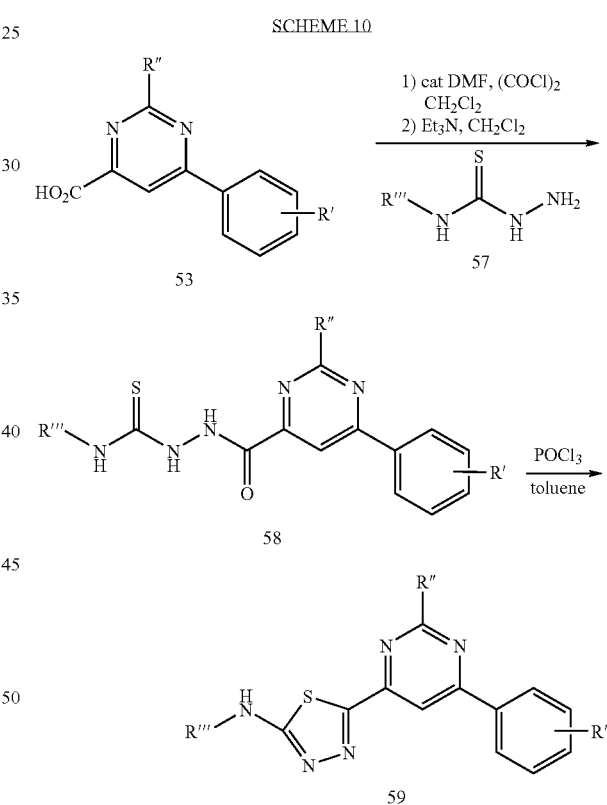

In addition, Compound 59 can be prepared from Compound 53 as depicted in Scheme 10. Compound 53 can be converted to Compound 58 by (1) reacting with oxalyl chloride in the presence of a catalytic amount of DMF in a solvent, such as dichloromethane, then (2) coupling with Compound 57 in the presence of a base, such as triethylamine, in a solvent, such as dichloromethane, to afford Compound 58. Finally, Compound 58 can be converted to Compound 59 by reacting with a dehydrating agent, such as phosphorus oxychloride, in a solvent, such as toluene.

SCHEME 11

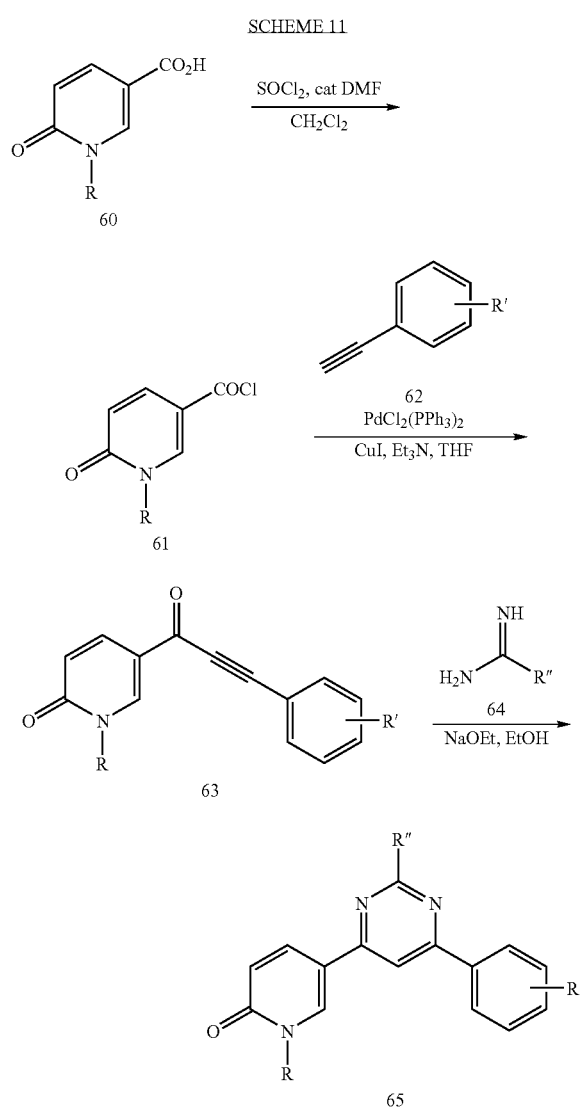

Compound 65 can be prepared from Compound 60 as depicted in Scheme 11. Compound 60 can be reacted with a reagent, such as thionyl chloride, in the presence of a catalyst, such as DMF, in a solvent, such as dichloromethane, to afford Compound 61. Compound 61 can be coupled to Compound 62 in the presence of catalysts, such as PdCl$_2$(PPh$_3$)$_4$ and copper iodide, and in the presence of a base, such as triethylamine, in a solvent, such as THF, to afford Compound 63. Finally, Compound 63 can be converted to Compound 65 by coupling with Compound 64 in the presence of a base, such as sodium ethoxide, in the presence of a solvent, such as ethanol.

SCHEME 12

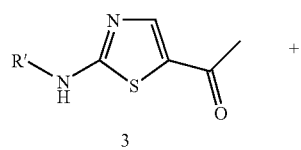

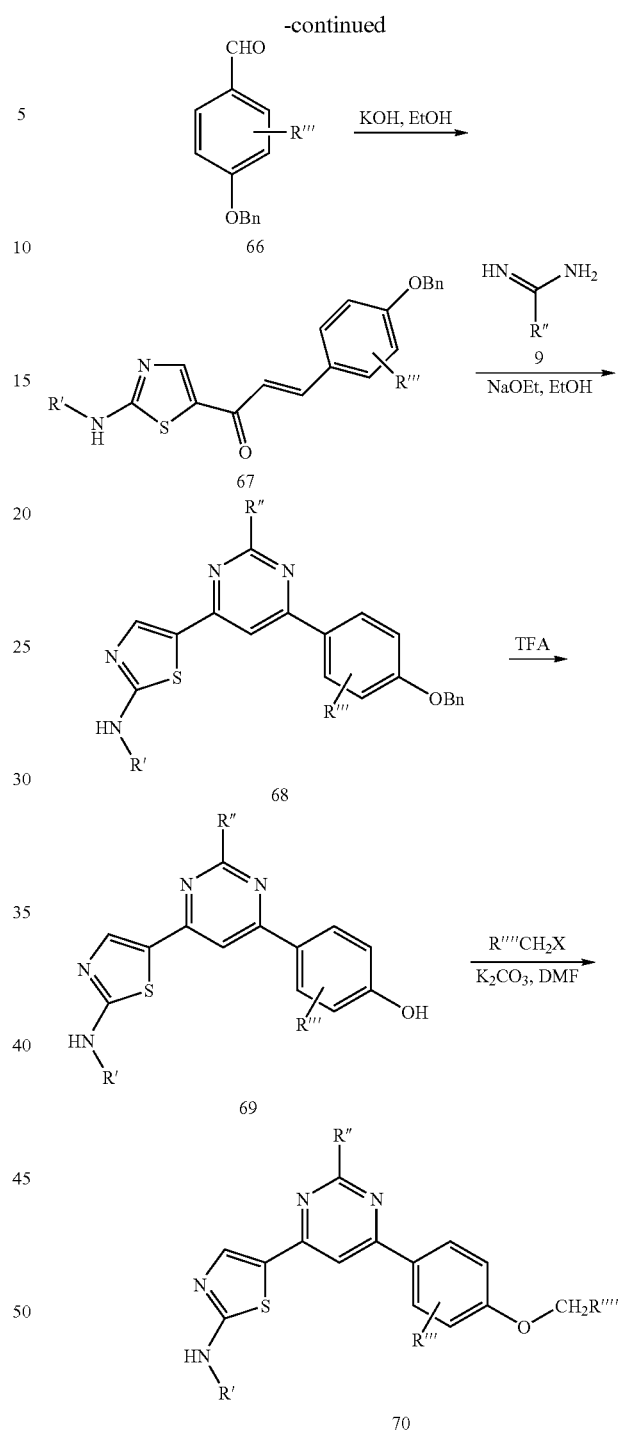

Compound 70 can be prepared from Compound 3 as depicted in Scheme 12. Compound 3 can be reacted with Compound 66, in the presence of a base, such as potassium hydroxide, and a solvent, such as ethanol, to afford Compound 67. Compound 67 can be coupled to Compound 9 to afford Compound 68, in the presence of a base, such as sodium ethoxide, and a solvent, such as ethanol. Compound 68 can be converted to Compound 69 in the presence of an acid, such as TFA. Finally, Compound 69 can be alkylated with a primary alkyl halide, such as 1-iodopropane, a base, such as potassium carbonate, and in a solvent, such as DMF, to yield Compound 70.

SCHEME 13

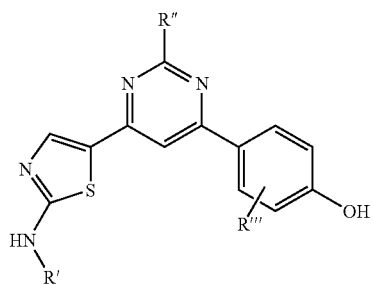

Alternatively, as depicted in Scheme 13, Compound 69 can be alkylated with a branched alkyl halide, such as 3-bromopentane, in the presence of a base, such as sodium hydride, and in a solvent, such as DMF, to yield Compound 71.

SCHEME 14

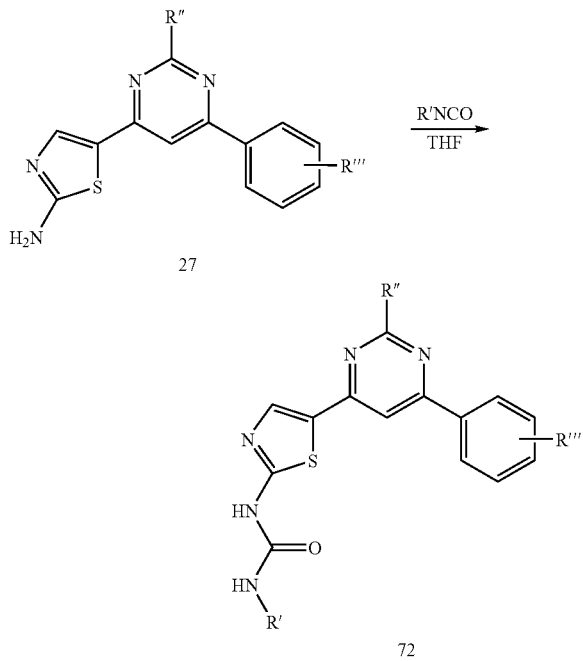

Compound 72 can be prepared from Compound 27 as depicted in Scheme 14. Compound 27 can be reacted with an isocyanate, in the presence of a solvent, such as THF, to yield Compound 72.

SCHEME 15

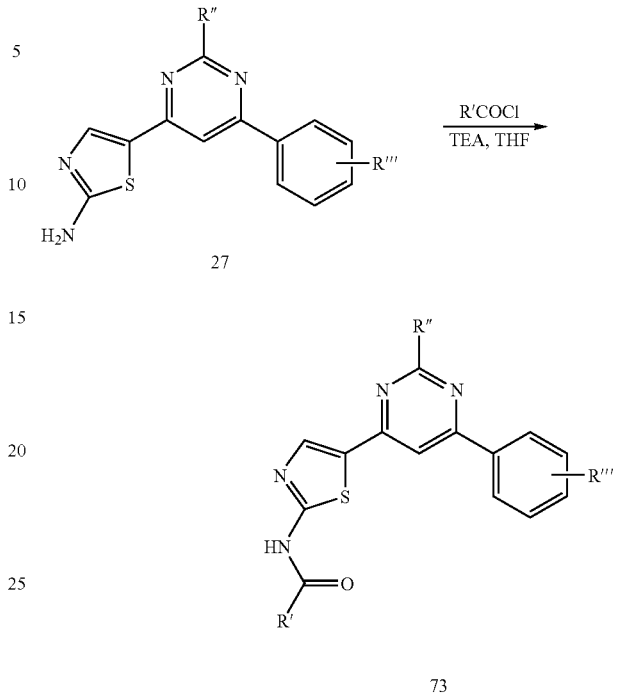

Alternatively, as depicted in Scheme 15, Compound 27 can be reacted with an acid chloride in the presence of a base, such as TEA, and in a solvent, such as THF, to afford Compound 73.

In the following examples, HPLC retention times were determined using the following conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100.

LCMS analyses were performed using the following conditions: Waters Xterra 5 µM 4.6×30 mm column with a binary solvent system where solvent A=10% methanol, 90% water, 0.1% trifluoroacetic acid and solvent B=90% methanol, 10% water, and 0.1% trifluoroacetic acid, flow rate=4 mL/min, linear gradient time=2 min, start % B=0, final % B=100.

Preparative reverse-phase HPLC purifications were performed using the following conditions: Ballistic YMC S5 ODS 20×100 mm column with a binary solvent system where solvent A=10% methanol, 90% water, 0.1% trifluoroacetic acid and solvent B=90% methanol, 10% water, and 0.1% trifluoroacetic acid, flow rate=20 mL/min, linear gradient time=10 min, start % B=20, final % B=100.

Solvent quantities for the above HPLC retention times, HPLC purifications, and LCMS analyses are reported on volume basis.

All reagents were purchased from commercial sources unless otherwise noted. All reactions were performed under an argon atmosphere. Reactions run in aqueous media were run under an ambient atmosphere unless otherwise noted. Yields are reported as mole %.

Example 1

5-(2-(2-fluorophenyl)pyrimidin-4-yl)-N-propylthiazol-2-amine

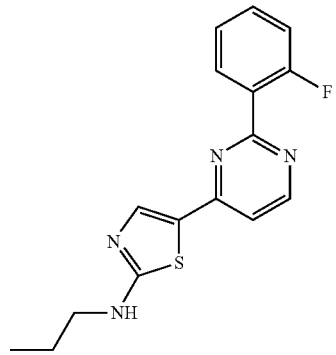

Step 1: Preparation 1

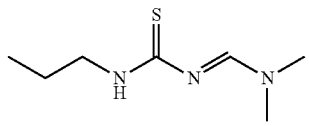

A mixture of n-propylthiourea (4.00 g, 33.8 mmol) and N,N-dimethylformamide dimethyl acetal (5.4 mL, 40.6 mmol) in absolute ethanol (70 mL) was refluxed for 1 h. The solvent was removed in vacuo and the resulting clear oil was dissolved in ethyl acetate (5 mL) and hexanes (100 mL) was added. After standing for 1 h, the solid was collected by filtration and washed with additional hexanes to afford 5.55 g (95%) of Preparation 1 as a white solid. HPLC Ret. time: 1.07 min. LCMS MH+ (m/z) 174.12.

Step 2: Preparation 2

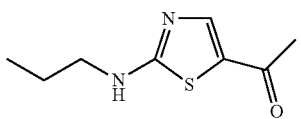

A mixture of Preparation 1 (2.31 g, 13.3 mmol) and chloroacetone (1.27 mL, 15 mmol) in acetonitrile (50 mL) was refluxed for 1 h. The solvent was removed in vacuo and the residue was stirred with saturated aqueous sodium bicarbonate for 10 min. and the resulting solid was collected by vacuum filtration to provide 2.32 g (94%) of Preparation 2 as a tan solid. HPLC Ret. time: 1.57 min. LCMS MH+ (m/z) 185.12. $^1$H NMR: (CD$_3$Cl, 500 MHz) δ 7.74 (s, 1H), 5.99 (br. s, 1H), 3.25 (t, 2H), 2.42 (s, 3H), 1.69 (m, 2H), 0.99 (t, 3H).

Step 3: Preparation 3

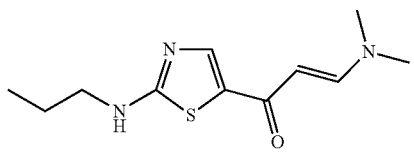

A mixture of Preparation 2 (1.12 g) in N,N-dimethylformamide dimethyl acetal (8 mL) was heated at 100° C. for 4 h. After cooling to rt, ether was added and the mixture was stirred for 30 minutes. The resulting solid was collected by vacuum filtration and washed with ether to give 0.96 g (66%) of Preparation 3 as tan solid. HPLC Ret. time: 1.45 min. LCMS MH+ (m/z) 240.22. $^1$H NMR: (d$_3$-DMSO, 500 MHz) δ 8.14 (t, 1H), 7.77 (s, 1H), 7.47 (d, J=12 Hz, 1H), 3.16 (m, 2H), 3.05 (br. s, 3H), 2.85 (br. s, 3H), 1.56 (m, 2H), 0.90 (t, 3H).

Step 4: Preparation 4

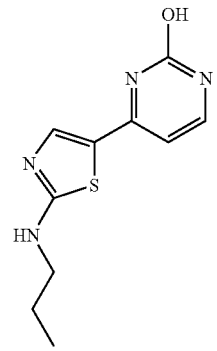

Preparation 3 (800 mg, 3.34 mmol) and sodium hydride (1.1 g, 27 mmol) were mixed together. Urea (3.20 g, 53 mmol) was added and the resulting slurry was sonicated briefly. The mixture was heated at 140° C. under argon for 5 min. After cooling to rt, water was slowly added and the pH was adjusted to a pH of 8 by addition of 1N HCl. The resulting yellow solid was collected by vacuum filtration and was successively washed with water and hexanes to provide 660 mg (84%) of Preparation 4 as a yellow solid. HPLC Ret. time: 1.24 min. LCMS MH+ (m/z) 237.18. $^1$H NMR: (d$_6$-DMSO, 500 MHz) δ 11.2 (br. s, 1H), 8.46 (t, 1H), 7.67 (d, 1H), 6.72 (d, 1H), 3.22 (m, 2H), 1.56 (m, 2H), 0.90 (t, 3H).

Step 5: Preparation 5

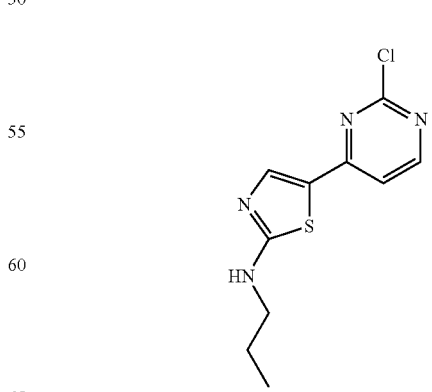

To a slurry of Preparation 4 (180 mg, 0.762 mmol) in toluene (4 mL) at rt was added phosphorus oxychloride (85

µL, 0.914 mmol) followed by the addition of diisopropylethylamine (132 µL, 0.762 mmol). The resulting mixture was heated at 100° C. for 4 h. After cooling to rt, the mixture was diluted with dichloromethane (100 mL) and the solution was poured into a mixture of saturated aqueous sodium bicarbonate (50 mL) and crushed ice (50 mL). The resulting layers were separated and the aqueous layer was extracted with dichloromethane (3×60 mL). The combined extracts were dried over anhyd. sodium sulfate, filtered, and concentrated in vacuo to afford 117 mg (60%) of Preparation 5 as a yellow solid. This material was used directly without any further purification. HPLC Ret. time: 2.56 min. LCMS MH+ (m/z) 255.14.

Step 6: Example 1

A mixture of Preparation 5 (29 mg, 0.114 mmol) and 2-fluorophenyl boronic acid (24 mg, 0.170 mmol) in toluene (0.5 mL) was purged with argon for 15 minutes. Ethanol (50 µL), aqueous potassium carbonate (2M, 120 µL), and tetrakis(triphenylphosphine)palladium(0) (6.5 mg, 0.005 mol) were successively added and the resulting mixture was heated at 110° C. for 2 h. After cooling to rt, the mixture was extracted with ethyl acetate (3×60 mL) and the combined extracts were washed with brine and dried over anhyd. sodium sulfate. Filtration and concentration in vacuo yielded 9.6 mg of a yellow solid. Purification by reverse-phase preparative HPLC afforded fractions containing the desired product. The fractions were concentrated in vacuo to remove the methanol and the resulting aqueous solution was lyophilized to provide 6.4 mg (19%) of a yellow solid as the TFA salt of the title compound. HPLC Ret. time: 2.92 min. LCMS MH+ (m/z) 315.18. $^1$H NMR: (d$_6$-DMSO, 500 MHz) δ 8.62 (d, 1H), 8.12 (s, 1H), 7.94 (t, 1H), 7.65 (d, 1H), 7.45 (m. 1H), 7.24 (m, 1H), 7.15 (m, 1H) 3.30 (t, 2H), 1.65 (m, 2H), 0.94 (t, 3H).

Example 2

5-(2-phenylpyrimidin-4-yl)-N-propylthiazol-2-amine

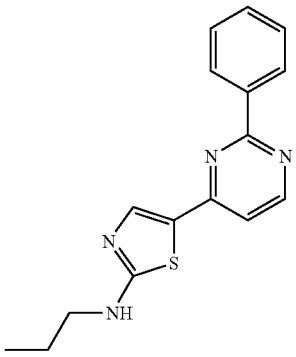

Preparation 3 (25 mg, 0.104 mmol) and benzamidine (14 mg, 0.115 mmol) were refluxed in ethanol (0.40 mL) for 20 h. After cooling to rt, the mixture was purified by reverse-phase preparative HPLC. Fractions containing the product were concentrated in vacuo to remove the methanol and the resulting aqueous solution was lyophilized to provide 14 mg (45%) of a yellow solid as the TFA salt of the title compound. HPLC Ret. time: 3.18 min. LCMS MH+ (m/z) 297.16. $^1$H NMR: (d$_4$-CD$_3$OD, 500 MHz) δ 8.71 (d, 1H), 8.39 (m, 2H), 8.18 (s, 1H), 7.68 (d, 1H), 7.51 (m. 3H), 3.43 (t, 2H), 1.74 (m, 2H), 1.04 (t, 3H).

Examples 3-20

Examples 3-20 listed in Table 1 below were prepared utilizing a similar procedure as described for Example 2.

TABLE 1

| Ex. # | Compound Structure/Name | HPLC and LCMS Data |
|---|---|---|
| 3 | 4-(4-(2-(propylamino)thiazol-5-yl)pyrimidin-2-yl)benzamide | HPLC t$_R$ = 2.37 min<br>LCMS [M + H]+ = 340.15 |
| 4 | 5-(2-(2-chlorophenyl)pyrimidin-4-yl)-N-propylthiazol-2-amine | HPLC t$_R$ = 3.10 min<br>LCMS [M + H]+ = 331.21 |

TABLE 1-continued

| Ex. # | Compound Structure/Name | HPLC and LCMS Data |
|---|---|---|
| 5 | 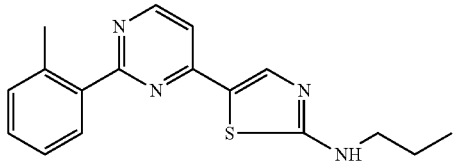<br>N-propyl-5-(2-o-tolylpyrimidin-4-yl)thiazol-2-amine | HPLC $t_R$ = 3.45 min<br>LCMS [M + H]+ = 311.29 |
| 6 | 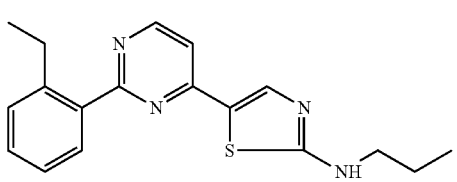<br>5-(2-(2-ethylphenyl)pyrimidin-4-yl)-N-propythiazol-2-amine | HPLC $t_R$ = 3.81 min<br>LCMS [M + H]+ = 325.30 |
| 7 | 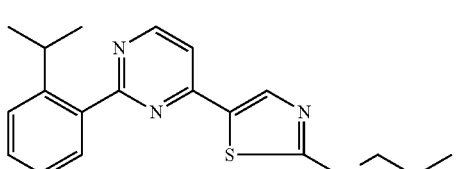<br>5-(2-(2-isopropylphenyl)pyrimidin-4-yl)-N-propylthiazol-2-amine | HPLC $t_R$ = 3.94 min<br>LCMS [M + H]+ = 339.31 |
| 8 | 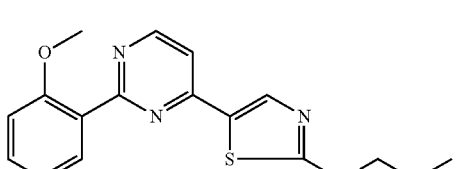<br>5-(2-(2-methoxyphenyl)pyrimidin-4-yl)-N-propylthiazol-2-amine | HPLC $t_R$ = 3.16 min<br>LCMS [M + H]+ = 327.31 |
| 9 | 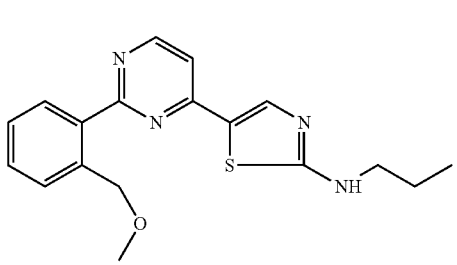<br>5-(2-(2-methoxymethyl)phenyl)pyrimidin-4-yl)-N-propylthiazol-2-amine | HPLC $t_R$ = 3.48 min<br>LCMS [M + H]+ = 341.28 |

TABLE 1-continued

| Ex. # | Compound Structure/Name | HPLC and LCMS Data |
|---|---|---|
| 10 | 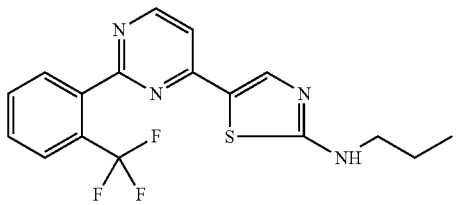<br>N-propyl-5-(2-(2-(trifluoromethyl)phenyl)pyrimidin-4-yl)thiazol-2-amine | HPLC $t_R$ = 3.64 min<br>LCMS [M + H]+ = 365.26 |
| 11 | 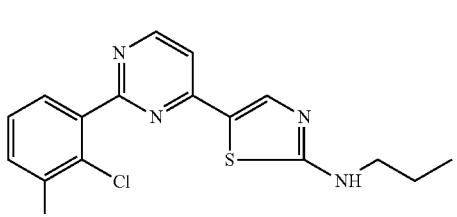<br>5-(2-(2,3-dichlorophenyl)pyrimidin-4-yl)-N-propylthiazol-2-amine | HPLC $t_R$ = 3.96 min<br>LCMS [M + H]+ = 365.19 |
| 12 | 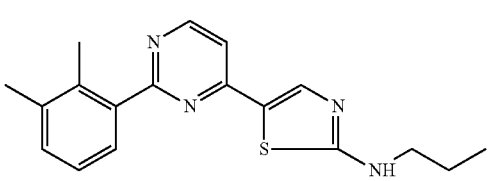<br>5-(2-(2,3-dimethylphenyl)pyrimidin-4-yl)-N-propylthiazol-2-amine | HPLC $t_R$ = 3.75 min<br>LCMS [M + H]+ = 325.33 |
| 13 | 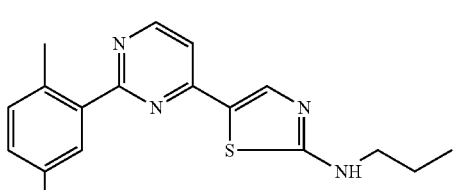<br>5-(2-(2,5-dimethylphenyl)pyrimidin-4-yl)-N-propylthiazol-2-amine | HPLC $t_R$ = 3.87 min<br>LCMS [M + H]+ = 325.33 |
| 14 | 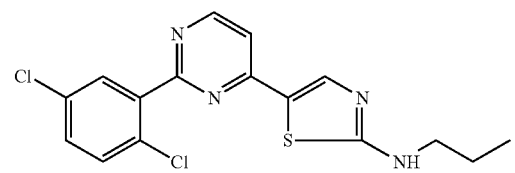<br>5-(2-(2,5-dichlorophenyl)pyrimidin-4-yl)-N-propylthiazol-2-amine | HPLC $t_R$ = 4.08 min<br>LCMS [M + H]+ = 365.19 |

TABLE 1-continued

| Ex. # | Compound Structure/Name | HPLC and LCMS Data |
|---|---|---|
| 15 | 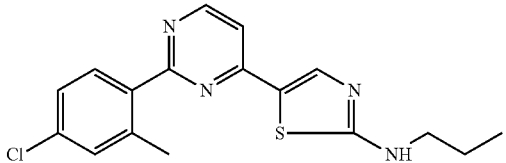<br>5-(2-(4-chloro-2-methylphenyl)pyrimidin-4-yl)-N-propylthiazol-2-amine | HPLC $t_R$ = 4.23 min<br>LCMS [M + H]+ = 345.22 |
| 16 | 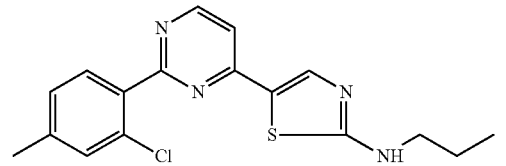<br>5-(2-(2-chloro-4-methylphenyl)pyrimidin-4-yl)-N-propylthiazol-2-amine | HPLC $t_R$ = 3.85 min<br>LCMS [M + H]+ = 345.20 |
| 17 | 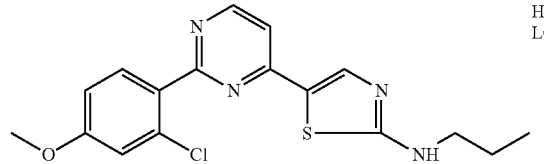<br>5-(2-(2-chloro-4-methoxyphenyl)pyrimidin-4-yl)-N-propylthiazol-2-amine | HPLC tR = 3.68 min<br>LCMS [M + H]+ = 361.19 |
| 18 | 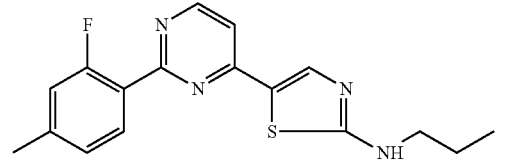<br>5-(2-(2-fluoro-4-methylphenyl)pyrimidin-4-yl)-N-propylthiazol-2-amine | HPLC $t_R$ = 3.75 min<br>LCMS [M + H]+ = 329.26 |
| 19 | 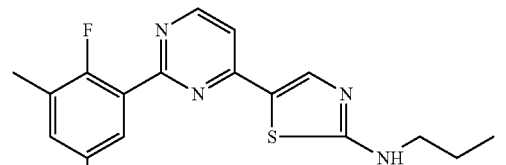<br>5-(2-(5-chloro-2-fluoro-3-methylphenyl)pyrimidin-4-yl)-N-propylthiazol-2-amine | HPLC $t_R$ = 4.26 min<br>LCMS [M + H]+ = 363.25 |

TABLE 1-continued

| Ex. # | Compound Structure/Name | HPLC and LCMS Data |
|---|---|---|
| 20 | 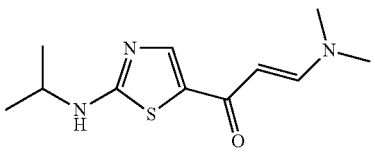<br>5-(2-mesitylpyrimidin-4-yl)-N-propylthiazol-2-amine | HPLC $t_R$ = 3.87 min<br>LCMS [M + H]+ = 339.28 |

Example 23

5-(2-(2-chlorophenyl)pyrimidin-4-yl)-N-isopropylthiazol-2-amine

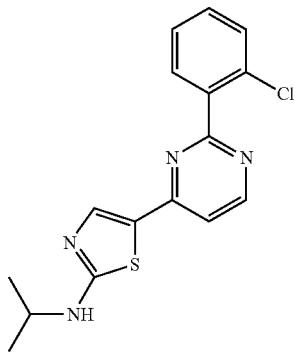

Step 1: Preparation 6

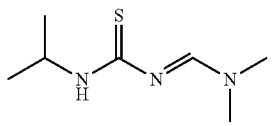

Preparation 6 was prepared from isopropylthiourea using a similar procedure as described in step 1 of Example 1. HPLC Ret. time: 1.04 min. LCMS MH+ (m/z)=174.4.

Step 2: Preparation 7

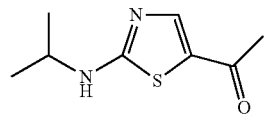

Preparation 7 was prepared from Preparation 6 utilizing a similar procedure as described in step 2 of Example 1. HPLC Ret. time: 1.42 min. LCMS MH+ (m/z)=185.

Step 3: Preparation 8

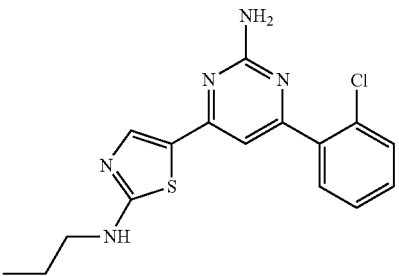

Preparation 8 was prepared from Preparation 7 utilizing a similar procedure as described in step 3 of Example 1. HPLC Ret. time: 1.44 min. LCMS MH+ (m/z)=240.

Step 4: Example 23

The title compound was prepared from Preparation 8 utilizing a similar procedure as described for Example 2. HPLC Ret. time: 3.10 min. LCMS MH+ (m/z)=331.

Example 24

4-(2-chlorophenyl)-6-(2-(propylamino)thiazol-5-yl)pyrimidin-2-amine

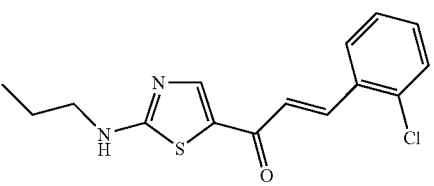

Step 1: Preparation 9

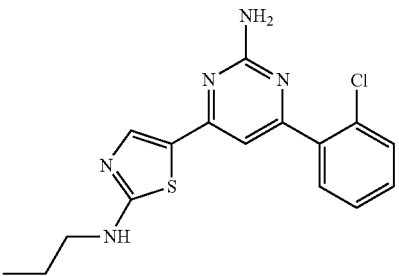

To a suspension of Preparation 2 from Example 1 (310 mg, 1.68 mmol) and 2-chlorobenzaldehyde (0.21 mL, 1.85 mmol) in ethanol (3.5 mL) at 0° C. was added ice-cold aqueous potassium hydroxide solution (50%, 2.5 mL) dropwise. After stirring at rt for 20 h, the resulting mixture was poured into ice-water (50 mL) and the pH was adjusted to 7 by addition of acetic acid. The yellow solid was collected by vacuum filtration, washed with water, and dried in vacuo to provide 330 mg (64%) of Preparation 9 as a yellow solid. HPLC Ret. time:

3.56 min. and 3.83 min. [trans (90%) and cis (10%)]. LCMS MH+ (m/z) 307.08. $^1$H NMR: (d$_3$-CD$_3$Cl, 500 MHz), trans isomer: δ 8.07 (d, J=15.4, 1H), 7.88 (s, 1H), 7.63 (dd, 1H), 7.36 (dd, 1H), 7.25 (m, 2H), 7.17 (d, J=15.4, 1H), 6.13 (br. S, 1H), 3.27 (m, 2H), 1.66 (m, 2H), 0.97 (t, 3H).

Step 2: Example 24

The title compound was prepared from Preparation 9 utilizing a similar procedure as described for Example 2 by replacing benzamidine with guanidine carbonate. HPLC Ret. time: 2.59 min. LCMS MH+ (m/z) 436.12. $^1$H NMR: (d$_4$-CD$_3$OD, 500 MHz) δ 8.29 (s, 1H), 7.63 (m, 1H), 7.60 (m, 1H), 7.52 (m, 1H), 7.36 (s, 1H), 3.38 (t, 2H), 1.70 (m, 2H), 1.00 (t, 3H).

Examples 25-44

Examples 25-44 listed in Table 2 below were prepared as previously described for Example 24.

TABLE 2

| Ex. # | Compound Structure/Name | HPLC and LCMS Data |
| --- | --- | --- |
| 25 | 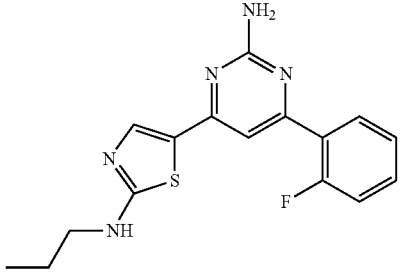<br>4-(2-fluorophenyl)-6-(2-(propylamino)thiazol-5-yl)pyrimidin-2-amine | HPLC t$_R$ = 2.50 min<br>LCMS [M + H]+ = 330.14 |
| 26 | 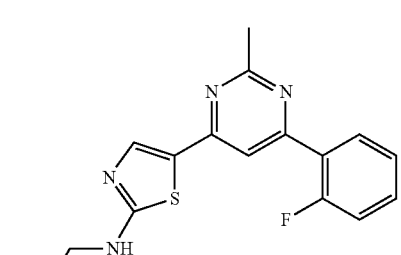<br>5-(6-(2-fluorophenyl)-2-methylpyrimidin-4-yl)-N-propylthiazol-2-amine | HPLC t$_R$ = 3.25 min<br>LCMS [M + H]+ = 329.16 |
| 27 | 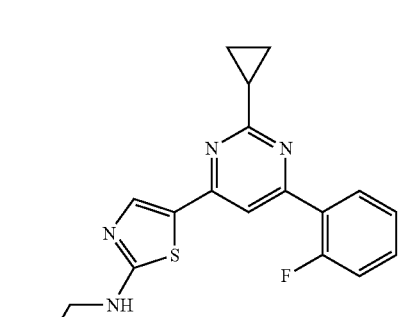<br>5-(2-cyclopropyl-6-(2-fluorophenyl)pyrimidin-4-yl)-N-propylthiazol-2-amine | HPLC t$_R$ = 3.70 min<br>LCMS [M + H]+ = 355.13 |

TABLE 2-continued
| Ex. # | Compound Structure/Name | HPLC and LCMS Data |
|---|---|---|
| 28 | 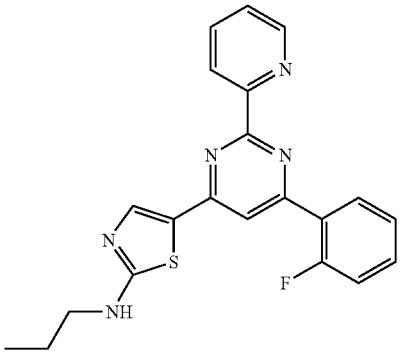<br>5-(6-(2-fluorophenyl)-2-(pyridin-2-yl)pyrimidin-4-yl)-N-propylthiazol-2-amine | HPLC $t_R$ = 3.02 min<br>LCMS [M + H]$^+$ = 392.11 |
| 29 | 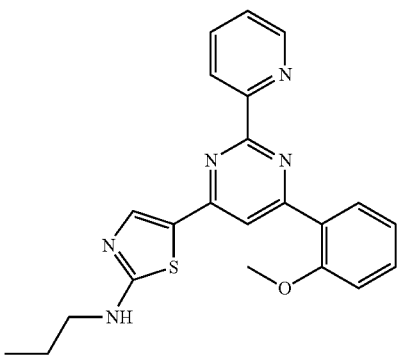<br>5-(6-(2-methoxyphenyl)-2-(pyridin-2-yl)pyrimidin-4-yl)-N-propylthiazol-2-amine | HPLC $t_R$ = 3.20 min<br>LCMS [M + H]$^+$ = 418.16 |
| 30 | 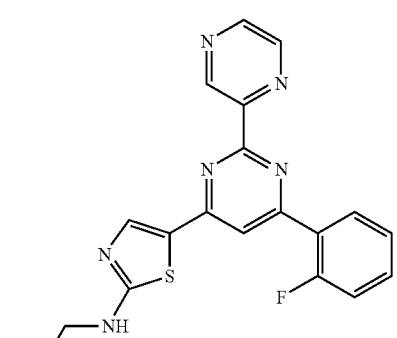<br>5-(6-(2-fluorophenyl)-2-(pyrazin-2-yl)pyrimidin-4-yl)-N-propylthiazol-2-amine | HPLC $t_R$ = 3.46 min<br>LCMS [M + H]$^+$ = 393.12 |

TABLE 2-continued

| Ex. # | Compound Structure/Name | HPLC and LCMS Data |
|---|---|---|
| 31 | 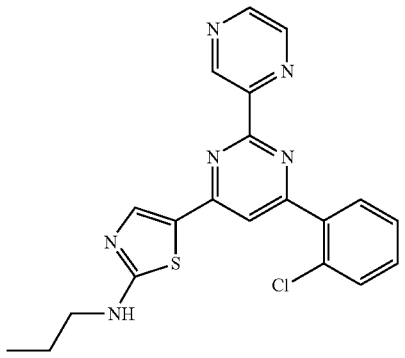<br>5-(6-(2-chlorophenyl)-2-(pyrazin-2-yl)pyrimidin-4-yl)-N-propylthiazol-2-amine | HPLC $t_R$ = 3.48 min<br>LCMS [M + H]$^+$ = 409.09 |
| 32 | 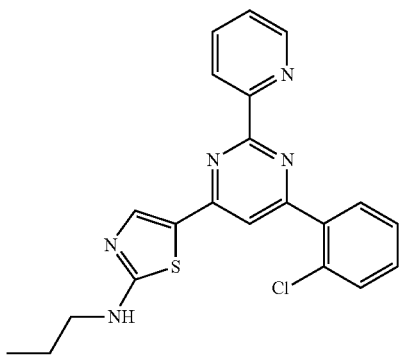<br>5-(6-(2-chlorophenyl)-2-(pyridin-2-yl)pyrimidin-4-yl)-N-propylthiazol-2-amine | HPLC $t_R$ = 3.07 min<br>LCMS [M + H]$^+$ = 408.08 |
| 33 | 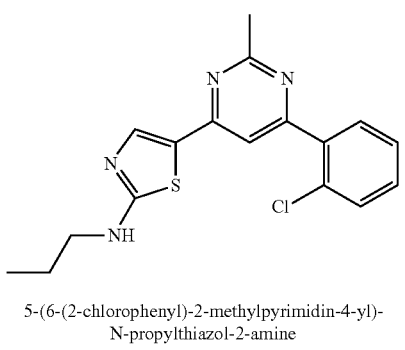<br>5-(6-(2-chlorophenyl)-2-methylpyrimidin-4-yl)-N-propylthiazol-2-amine | HPLC $t_R$ = 3.19 min<br>LCMS [M + H]$^+$ = 345.12 |
| 34 | 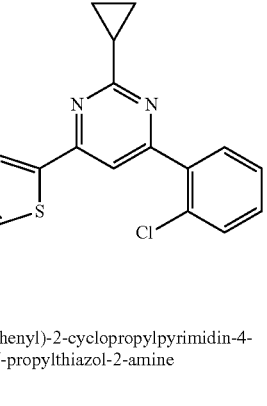<br>5-(6-(2-chlorophenyl)-2-cyclopropylpyrimidin-4-yl)-N-propylthiazol-2-amine | HPLC $t_R$ = 3.61 min<br>LCMS [M + H]$^+$ = 371.12 |

TABLE 2-continued

| Ex. # | Compound Structure/Name | HPLC and LCMS Data |
|---|---|---|
| 35 | 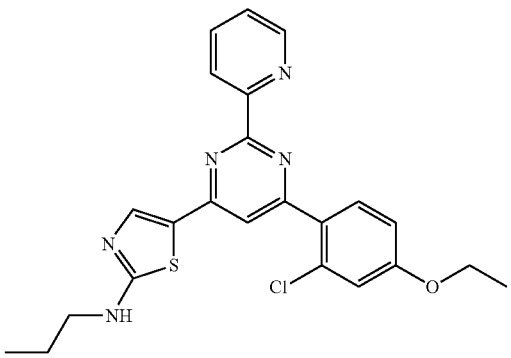<br>5-(6-(2-chloro-4-ethoxyphenyl)-2-(pyridin-2-yl)pyrimidin-4-yl)-N-propylthiazol-2-amine | HPLC $t_R$ = 3.45 min<br>LCMS [M + H]$^+$ = 452.60 |
| 36 | 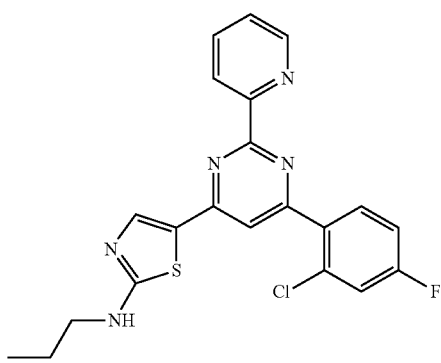<br>5-(6-(2-chloro-4-fluorophenyl)-2-(pyridin-2-yl)pyrimidin-4-yl)-N-propylthiazol-2-amine | HPLC $t_R$ = 3.43 min<br>LCMS [M + H]$^+$ = 426.14 |
| 37 | 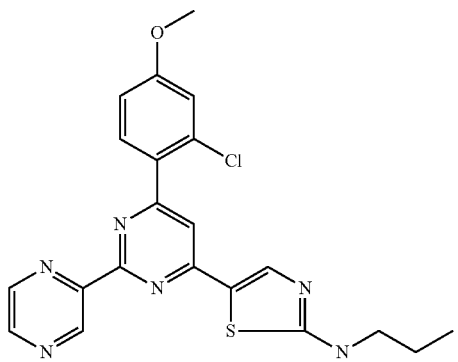<br>5-(6-(2-chloro-4-methoxyphenyl)-2-(pyrazin-2-yl)pyrimidin-4-yl)-N-propylthiazol-2-amine | HPLC $t_R$ = 4.14 min<br>LCMS [M + H]+ = 439.24 |

TABLE 2-continued

| Ex. # | Compound Structure/Name | HPLC and LCMS Data |
|---|---|---|
| 38 | 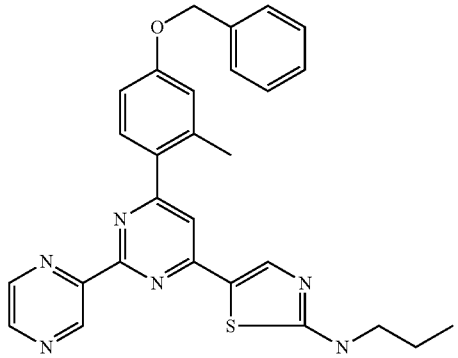<br>5-(6-(4-(benzyloxy)-2-methylphenyl)-2-(pyrazin-2-yl)pyrimidin-4-yl)-N-propylthiazol-2-amine | HPLC $t_R$ = 4.54 min<br>LCMS [M + H]+ = 495.15 |
| 39 | 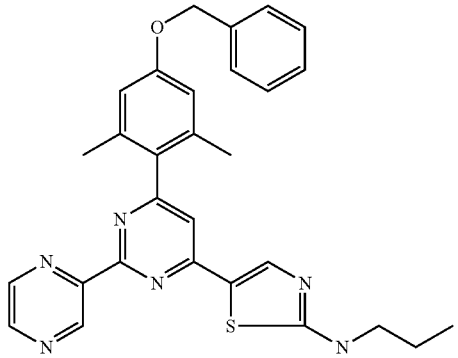<br>5-(6-(4-(benzyloxy)-2,6-dimethylphenyl)-2-(pyrazin-2-yl)pyrimidin-4-yl)-N-propylthiazol-2-amine | HPLC $t_R$ = 4.53 min<br>LCMS [M + H]+ = 509.27 |
| 40 | 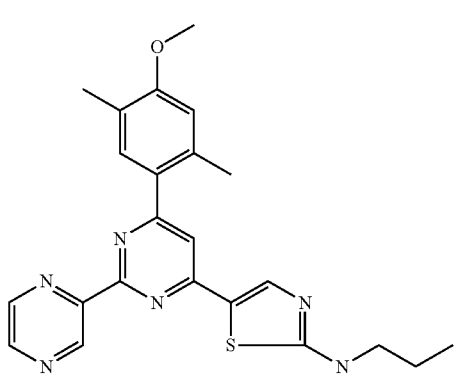<br>5-(6-(4-methoxy-2,5-dimethylphenyl)-2-(pyrazin-2-yl)pyrimidin-4-yl)-N-propylthiazol-2-amine | HPLC $t_R$ = 4.19 min<br>LCMS [M + H]+ = 433.21 |

TABLE 2-continued

| Ex. # | Compound Structure/Name | HPLC and LCMS Data |
|---|---|---|
| 41 | 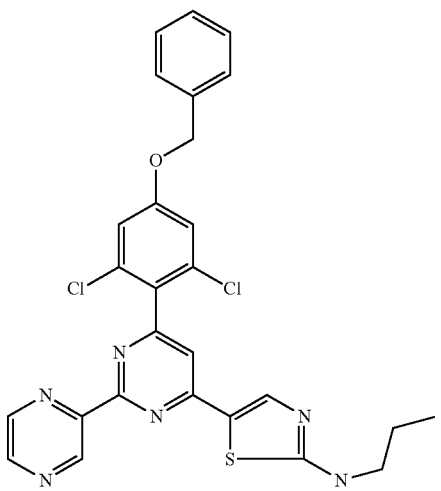<br>5-(6-(4-(benzyloxy)-2,6-dichlorophenyl)-2-(pyrazin-2-yl)pyrimidin-4-yl)-N-propylthiazol-2-amine | HPLC $t_R$ = 4.61 min<br>LCMS [M + H]+ = 549.08 |
| 42 | 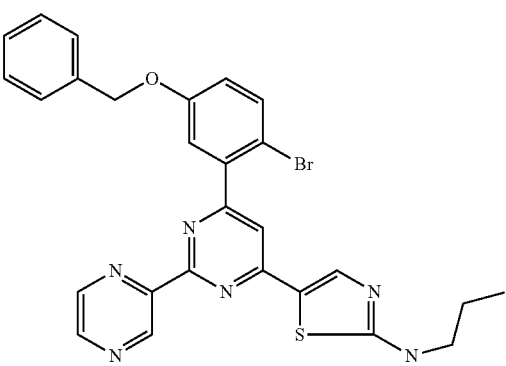<br>5-(6-(5-(benzyloxy)-2-bromophenyl)-2-(pyrazin-2-yl)pyrimidin-4-yl)-N-propylthiazol-2-amine | HPLC $t_R$ = 4.62 min<br>LCMS [M + H]$^+$ = 559.01 |
| 43 | 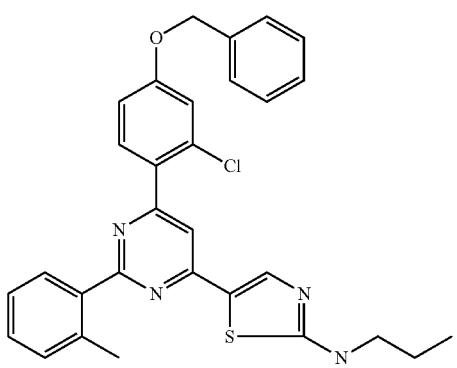<br>5-(6-(4-(benzyloxy)-2-chlorophenyl)-2-o-tolylpyrimidin-4-yl)-N-propylthiazol-2-amine | HPLC $t_R$ = 4.69 min<br>LCMS [M + H]+ = 527.23 |

TABLE 2-continued

| Ex. # | Compound Structure/Name | HPLC and LCMS Data |
|---|---|---|
| 44 | 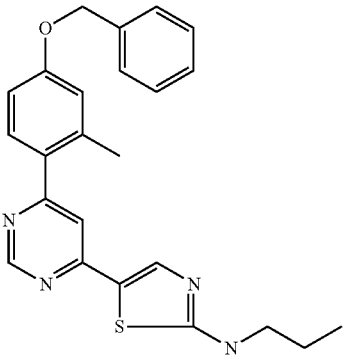<br>5-(6-(4-(benzyloxy)-2-methylphenyl)pyrimidin-4-yl)-N-propylthiazol-2-amine | HPLC $t_R$ = 4.34 min<br>LCMS [M + H]+ = 417.24 |

Example 45

5-(6-(2-chlorophenyl)-2-(pyridin-2-yl)pyrimidin-4-yl)-N-isopropylthiazol-2-amine

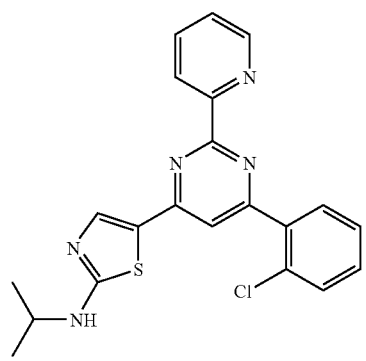

Step 1: Preparation 10

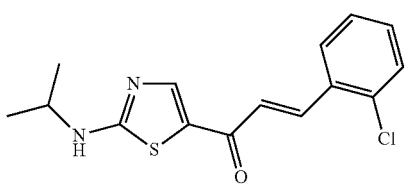

Preparation 10 was prepared from Preparation 7 utilizing a similar procedure as described for Preparation 9 in step 1 of Example 24. HPLC Ret. time: 3.81 min. LCMS MH⁺ (m/z) 307.42.

Step 2: Example 45

The title compound was prepared from Preparation 10 utilizing a similar procedure as described for Example 2 by replacing benzamidine with 2-amidinopyridinium chloride. HPLC Ret. time: 3.24 min. LCMS MH⁺ (m/z) 408.25.

Examples 46-49

Examples 46-49 listed in Table 3 below were prepared from Preparation 10 utilizing similar procedures as previously described for Example 45.

TABLE 3

| Ex. # | Compound Structure/Name | HPLC and LCMS Data |
|---|---|---|
| 46 | <br>5-(6-(2,4-difluorophenyl)-2-(pyridin-2-yl)pyrimidin-4-yl)-N-isopropylthiazol-2-amine | HPLC $t_R$ = 3.15 min<br>LCMS [M + H]⁺ = 410.31 |

TABLE 3-continued

| Ex. # | Compound Structure/Name | HPLC and LCMS Data |
|---|---|---|
| 47 | 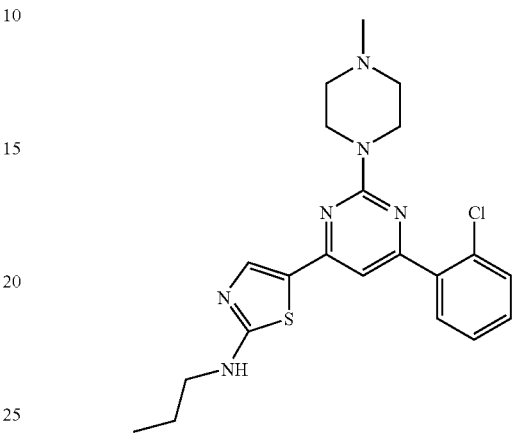<br>5-(6-(2,3-dichlorophenyl)-2-(pyridin-2-yl)pyrimidin-4-yl)-N-isopropylthiazol-2-amine | HPLC $t_R$ = 3.53 min<br>LCMS [M + H]$^+$ = 442.4 |
| 48 | 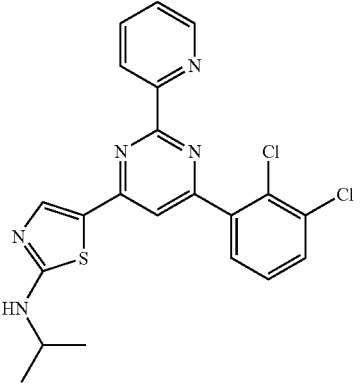<br>(2-(2-amino-6-(2-(isopropylamino)thiazol-5-yl)pyrimidin-4-yl)phenyl)methanol | HPLC $t_R$ = 2.12 min<br>LCMS [M + H]$^+$ = 342.4 |
| 49 | 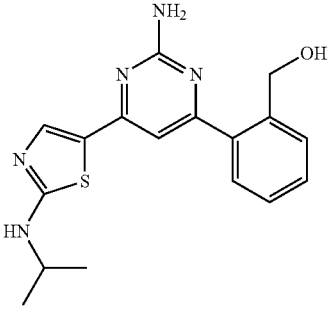<br>5-(6-(2-bromophenyl)-2-(pyridin-2-yl)pyrimidin-4-yl)-N-isopropylthiazol-2-amine | HPLC $t_R$ = 3.17 min<br>LCMS [M + H]$^+$ = 452.14 |

Example 50

5-(6-(2-chlorophenyl)-2-(4-methylpiperazin-1-yl)pyrimidin-4-yl)-N-propylthiazol-2-amine

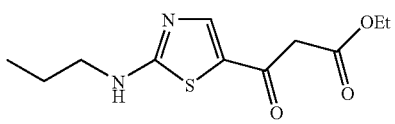

Step 1: Preparation 11

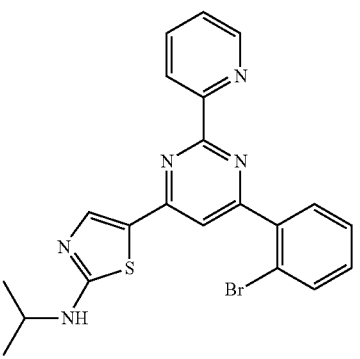

Preparation 11 was prepared from Preparation 1 in Example 1 utilizing a similar procedure as described in step 2 of Example 1 by replacing chloroacetone with ethyl-4-chloroacetate. Yellow solid (95% yield). HPLC Ret. time: 2.33 min. LCMS MH$^+$ (m/z) 257.17. $^1$H NMR: (d$_6$-DMSO, 500 MHz) δ 8.80 (s, 1H), 8.05 (s, 1H), 4.07 (q, 2H), 3.88 (s, 2H), 3.22 (m, 2H), 1.55 (m, 2H), 1.17 (t, 3H), 0.89 (t, 3H).

Step 2: Preparation 12

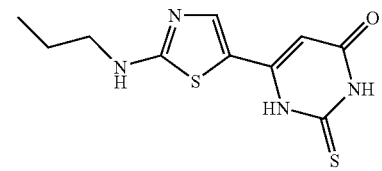

A mixture of Preparation 11 (6.57 g, 25.5 mmol) and thiourea (2.15 g, 28.2 mmol) in xylenes (300 mL) was azeotroped using a Dean-Stark trap over 20 h in the presence of catalytic amount of pyridinium p-toluenesulfonate. The solvent was removed in vacuo and the resulting solid was rinsed with toluene and dried to afford 5.02 g (73%) of Preparation 12 as a brown solid. HPLC Ret. time: 2.03 min. LCMS MH+ (m/z) 269.14.

Step 3: Preparation 13

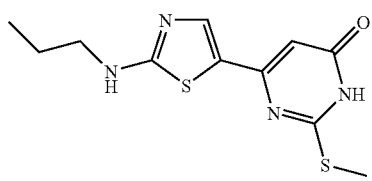

To a slurry of Preparation 12 (1.00 g, 3.73 mmol) and potassium carbonate (0.51 g, 3.73 mmol) in acetone (15 mL) at rt was added iodomethane (0.35 mL, 3.73 mmol) dropwise. After stirring at rt for 30 min., crushed ice was added and the mixture was stirred at rt for 1 h. Acetic acid was added until pH range of 3-4 was reached and the resulting solid was collected by vacuum filtration and dried in vacuo to afford 0.86 g (82%) of Preparation 13 as a light yellow solid. HPLC Ret. time: 2.08 min. LCMS MH+ (m/z) 283. $^1$H NMR: (d$_6$-DMSO, 500 MHz) δ 12.2 (br. s, 1H), 8.09 (t, 1H), 7.78 (s, 1H), 6.05 (br. s, 1H), 3.12 (m, 2H), 2.41 (s, 3H), 1.48 (m, 2H), 1.17 (t, 3H), 0.82 (t, 3H).

Step 4: Preparation 14

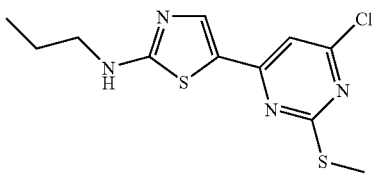

Preparation 14 was prepared from Preparation 13 utilizing a similar procedure as described in step 5 of Example 1. Yellow solid (72% yield). HPLC Ret. time: 3.45 min. LCMS MH+ (m/z) 301.08.

Step 5: Example 51, 5-(6-(2-chlorophenyl)-2-(methylthio)pyrimidin-4-yl)-N-propylthiazol-2-amine

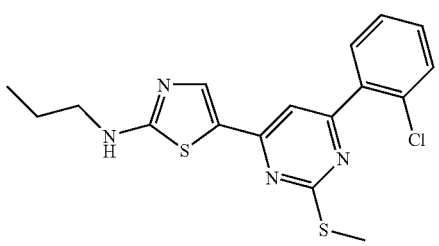

Example 51 was prepared from Preparation 14 utilizing a similar procedure as described in Step 6 of Example 1 by replacing 2-fluorophenyl boronic acid with 2-chlorophenylboronic acid. Light yellow solid (62% yield). HPLC Ret. time: 3.78 min. LCMS MH+ (m/z) 377.01. $^1$H NMR: (d$_6$-DMSO, 500 MHz) δ 8.41 (t, 1H), 8.17 (s, 1H), 7.70 (s, 1H), 7.59 (m, 2H), 7.50 (m, 2H), 3.23 (m, 2H), 2.49 (s, 3H), 1.58 (m, 2H), 1.17 (t, 3H), 0.91 (t, 3H).

Step 6: Example 52

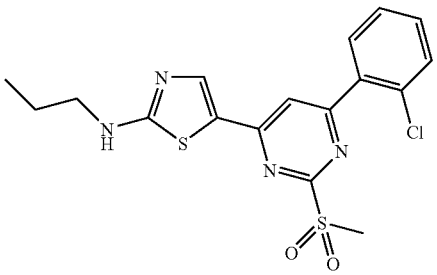

To a slurry of Example 51 (0.49 g, 1.30 mmol) in methanol (10 mL) at 0° C. was added a slurry of Oxone™ compound (3.20 g) in 10 mL of water. After stirring for 5 h at 0° C., the reaction was diluted with water (10 mL) and the solid was collected by filtration and washed with water to afford 0.46 g (87%) of Example 52 as a bright yellow solid. HPLC Ret. time: 3.15 min. LCMS MH+ (m/z) 408.99. $^1$H NMR: (d$_6$-DMSO, 400 MHz) δ 8.70 (t, 1H), 8.42 (s, 1H), 8.28 (s, 1H), 7.70 (m, 1H), 7.65 (m, 1H), 3.42 (s, 3H), 3.28 (m, 2H), 2.49 (s, 3H), 1.58 (m, 2H), 0.96 (t, 3H).

Step 7: Example 50

A solution of Example 52 (30 mg, 0.073 mmol) and 1-methylpiperazine (25 μL, 0.22 mmol) in ethanol (0.3 mL) was heated at 80° C. for 1 h. After cooling to rt, the mixture was purified by reverse-phase preparative HPLC and the fractions containing the product were neutralized by adding saturated aq sodium bicarbonate solution (~1 mL). The fractions were concentrated in vacuo to remove the methanol and the resulting aqueous slurry was filtered by vacuum filtration to collect the solid. Drying in vacuo afforded 18 mg (58%) of the title compound as a yellow solid. HPLC Ret. time: 2.43 min. LCMS MH+ (m/z) 429.23. $^1$H NMR: (d$_6$-DMSO, 500 MHz) δ 8.18 (t, 1H), 7.99 (s, 1H), 7.56 (m, 2H), 7.45 (m, 2H), 7.14 (s, 1H), 3.72 (m, 4H), 3.28 (m, 2H), 2.32 (m, 4H), 2.20 (s, 3H), 1.57 (m, 2H), 0.91 (t, 3H).

Examples 53-64

Examples 53-64 listed in Table 4 below were prepared utilizing a similar procedure as described for Example 50.

TABLE 4

| Ex. # | Compound Structure/Name | HPLC and LCMS Data |
|---|---|---|
| 53 | 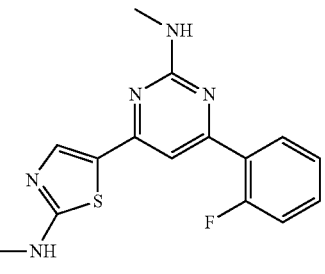<br>4-(2-fluorophenyl)-N-methyl-6-(2-(propylamino)thiazol-5-yl)pyrimidin-2-amine | HPLC $t_R$ = 2.82 min<br>LCMS [M + H]$^+$ = 360.04 |
| 54 | 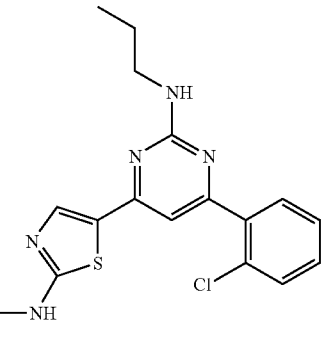<br>4-(2-chlorophenyl)-N-propyl-6-(2-(propylamino)thiazol-5-yl)pyrimidin-2-amine | HPLC $t_R$ = 3.21 min<br>LCMS [M + H]$^+$ = 388.03 |
| 55 | 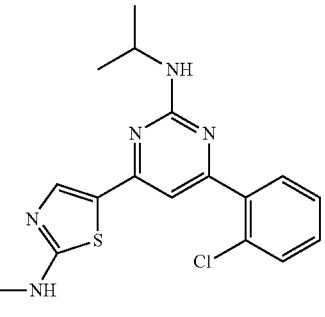<br>4-(2-chlorophenyl)-N-isopropyl-6-(2-(propylamino)thiazol-5-yl)pyrimidin-2-amine | HPLC $t_R$ = 3.19 min<br>LCMS [M + H]$^+$ = 388.03 |
| 56 | 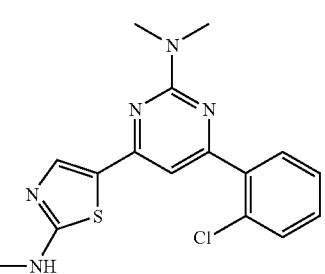<br>4-(2-chlorophenyl)-N,N-dimethyl-6-(2-(propylamino)thiazol-5-yl)pyrimidin-2-amine | HPLC $t_R$ = 3.41 min<br>LCMS [M + H]$^+$ = 374.26 |

TABLE 4-continued

| Ex. # | Compound Structure/Name | HPLC and LCMS Data |
|---|---|---|
| 57 | 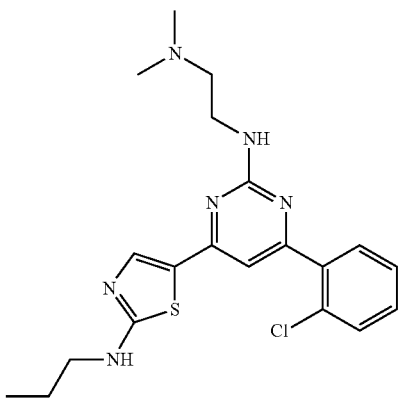<br>4-(2-chlorophenyl)-N-(2-(dimethylamino)ethyl)-6-(2-(propylamino)thiazol-5-yl)pyrimidin-2-amine | HPLC $t_R$ = 2.25 min<br>LCMS $[M + H]^+$ = 417.22 |
| 58 | 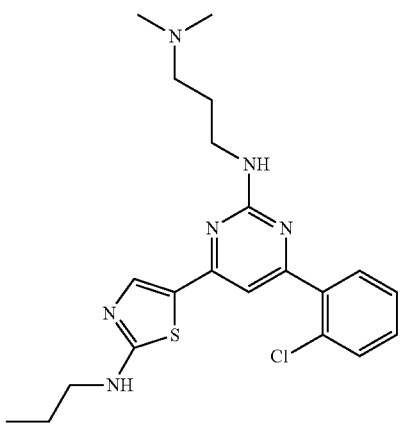<br>4-(2-chlorophenyl)-N-(3-(dimethylamino)propyl)-6-(2-(propylamino)thiazol-5-yl)pyrimidin-2-amine | HPLC $t_R$ = 2.28 min<br>LCMS $[M + H]^+$ = 431.09 |
| 59 | 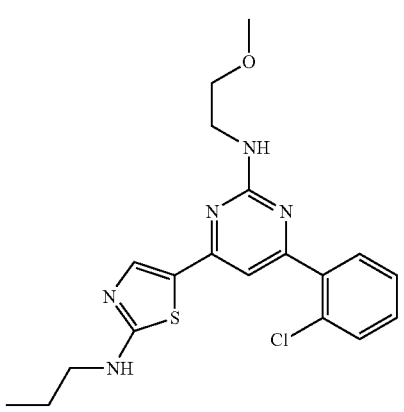<br>4-(2-chlorophenyl)-N-(2-methoxyethyl)-6-(2-(propylamino)thiazol-5-yl)pyrimidin-2-amine | HPLC $t_R$ = 2.94 min<br>LCMS $[M + H]^+$ = 404.24 |

TABLE 4-continued
| Ex. # | Compound Structure/Name | HPLC and LCMS Data |
|---|---|---|
| 60 | 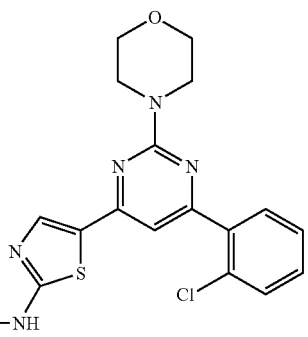 5-(6-(2-chlorophenyl)-2-morpholinopyrimidin-4-yl)-N-propylthiazol-2-amine | HPLC $t_R$ = 3.54 min LCMS $[M + H]^+$ = 416.19 |
| 61 | 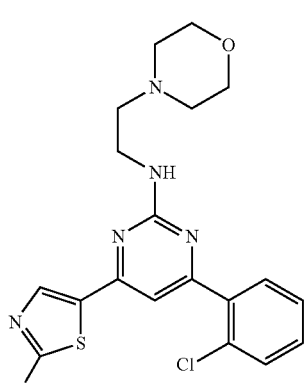 4-(2-chlorophenyl)-N-(2-morpholinoethyl)-6-(2-(propylamino)thiazol-5-yl)pyrimidin-2-amine | HPLC $t_R$ = 2.25 min LCMS $[M + H]^+$ = 459.28 |
| 62 | 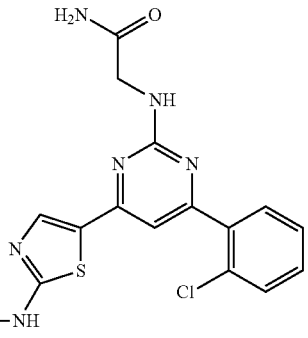 2-(4-(2-chlorophenyl)-6-(2-(propylamino)thiazol-5-yl)pyrimidin-2-ylamino)acetamide | HPLC $t_R$ = 2.48 min LCMS $[M + H]^+$ = 403.04 |

TABLE 4-continued

| Ex. # | Compound Structure/Name | HPLC and LCMS Data |
|---|---|---|
| 63 | 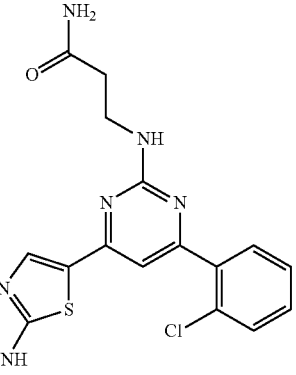  2-(4-(2-chlorophenyl)-6-(2-(propylamino)thiazol-5-yl)pyrimidin-2-ylamino)propionamide | HPLC $t_R$ = 2.57 min  LCMS [M + H]$^+$ = 417.22 |
| 64 | 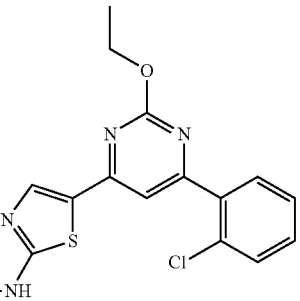  5-(6-(2-chlorophenyl)-2-ethoxypyrimidin-4-yl)-N-propylthiazol-2-amine | HPLC $t_R$ = 3.63 min  LCMS [M + H]$^+$ = 375.07 |

Example 65

4-(2-chlorophenyl)-N-(piperidin-4-yl)-6-(2-(propylamino)thiazol-5-yl)pyrimidin-2-amine

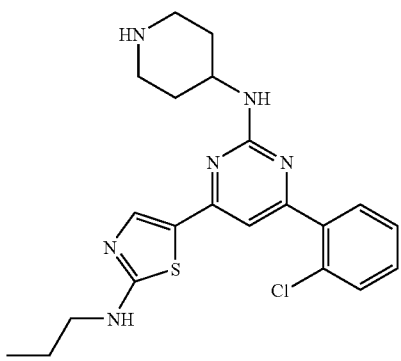

Step 1: Example 66

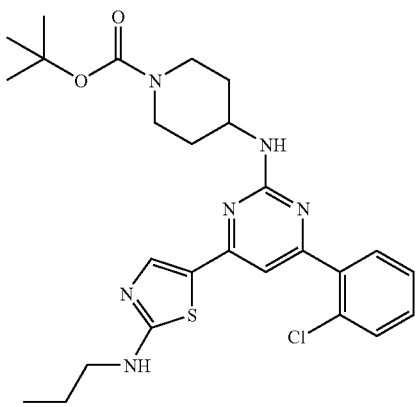

Example 66 was prepared from Example 52 utilizing a similar procedure as described in Step 7 of Example 50 by replacing 1-methylpiperazine with tert-butyl 4-aminopiperidine-1-carboxylate. HPLC Ret. time: 3.78 min.

Step 2: Example 65

To a solution of Example 66 in anhydrous dioxane (0.5 mL) was added a solution of 4N HCl in dioxane (0.5 mL) and the resulting solution was stirred at rt for 20 h. The mixture was diluted with ether (~5 mL) and the solid was collected by vacuum filtration. The solid was purified by reverse-phase preparative HPLC and the fractions containing the product were concentrated in vacuo to remove the methanol. The resulting aqueous slurry was filtered by vacuum filtration to collect the solid. Drying in vacuo afforded 18 mg (57%) of Example 65 of TFA salt as a yellow solid. HPLC Ret. time: 2.37 min. LCMS MH+ (m/z) 429.28. $^1$H NMR (d$_6$-DMSO, 500 MHz): δ 8.51 (m, 1H), 8.44 (m, 1H), 8.25 (m, 1H), 8.04 (s, 1H), 7.56 (m, 2H), 7.46 (m, 2H), 7.15 (s, 1H), 3.98 (m, 1H), 3.30 (m, 2H), 3.24 (m, 2H), 3.01 (m, 2H), 2.07 (m, 2H), 1.72 (m, 2H), 1.60 (m, 2H), 0.91 (t, 3H).

Examples 67-68

Examples 67-68 listed in Table 5 below were prepared according to the general procedure described in Example 38.

TABLE 5

| Ex. # | Compound Structure | HPLC and LCMS Data |
|---|---|---|
| 67 | 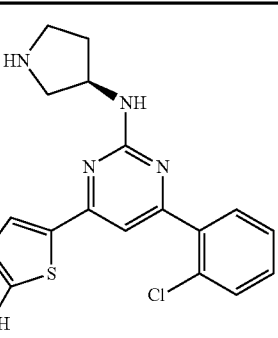 4-(2-chlorophenyl)-6-(2-(propylamino)thiazol-5-yl)-N-((R)-pyrrolidin-3-yl)pyrimidin-2-amine | HPLC t$_R$ = 2.34 min LCMS [M + H]$^+$ = 415.24 |
| 68 | 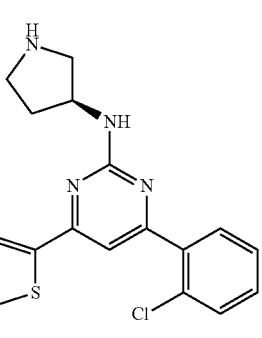 4-(2-chlorophenyl)-6-(2-(propylamino)thiazol-5-yl)-N-((S)-pyrrolidin-3-yl)pyrimidin-2-amine | HPLC t$_R$ = 2.31 min LCMS [M + H]$^+$ = 415.34 |

Example 69

5-(6-(2-chloro-4-fluorophenyl)-2-(4-methylpiperazin-1-yl)pyrimidin-4-yl)-N-isopropylthiazol-2-amine

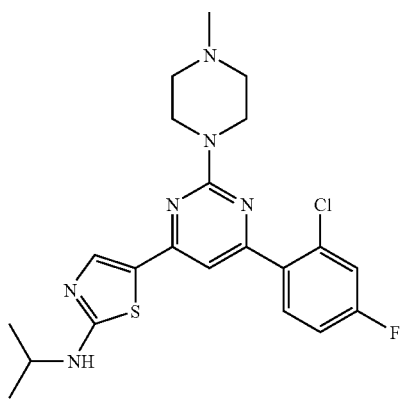

Step 1: Preparation 15

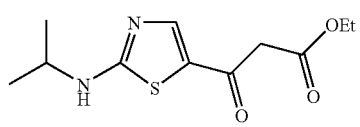

Preparation 15 was prepared from Preparation 6 in Example 23 utilizing a similar procedure as described in step 2 of Example 1 by replacing chloroacetone with ethyl-4-chloroacetate. Yellow solid (95% yield). HPLC Ret. Time: 2.40 min. LCMS MH$^+$ (m/z) 257.48. $^1$H NMR: (d$_6$-CDCl$_3$, 500 MHz) δ 7.79 (s, 1H), 6.33 (br s, 1H), 4.19 (q, 2H), 3.75 (s, 2H), 3.67 (m, 1H), 1.30 (d, 6H), 1.24 (t, 3H).

Step 2: Preparation 16

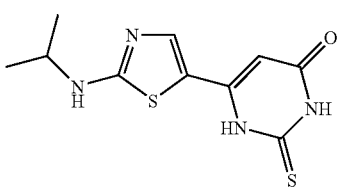

Preparation 16 was prepared from Preparation 15 utilizing a similar procedure as described in step 2 of Example 50. HPLC Ret. time: 2.06 min. LCMS MH$^+$ (m/z) 269.48.

Step 3: Preparation 17

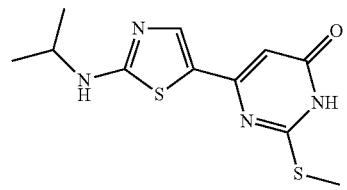

Preparation 17 was prepared from Preparation 16 utilizing a similar procedure as described in step 3 of Example 50. HPLC Ret. time: 2.21 min. LCMS MH$^+$ (m/z) 283.21.

Step 4: Preparation 18

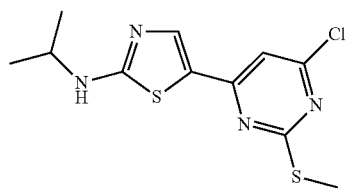

Preparation 18 was prepared from Preparation 17 utilizing a similar procedure as described in step 4 of Example 50. HPLC Ret. Time: 3.55 min. LCMS MH$^+$ (m/z) 301.5.

Step 5: Example 70, 5-(6-(2-chloro-4-fluorophenyl)-2-(methylthio)pyrimidin-4-yl)-N-isopropylthiazol-2-amine

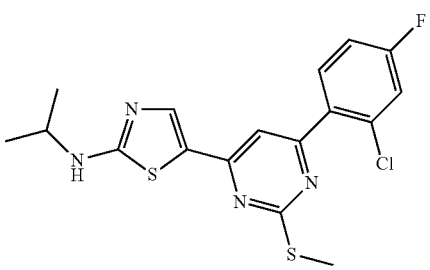

Example 70 was prepared from Preparation 18 utilizing a similar procedure as described in Step 5 of Example 50. Light yellow solid. HPLC Ret. Time: 3.97 min. LCMS MH$^+$ (m/z) 395.49.

Step 6: Example 71, 5-(6-(2-chloro-4-fluorophenyl)-2-(methylsulfonyl)pyrimidin-4-yl)-N-isopropylthiazol-2-amine

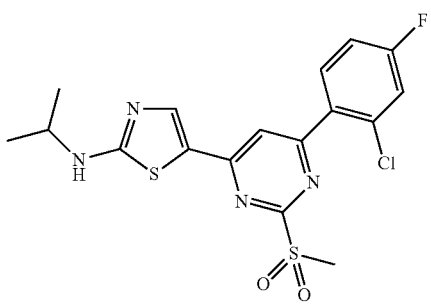

Example 71 was prepared from Example 70 utilizing a similar procedure as described in Step 6 of Example 50. Light yellow solid. HPLC Ret. Time: 3.34 min. LCMS MH+ (m/z) 427.17.

Step 7: Example 69

The title compound was prepared from Example 71 utilizing a similar procedure as described in Step 7 of Example 50. Light yellow solid. HPLC Ret. Time: 2.60 min. LCMS MH+ (m/z) 447.28.

Examples 72-125

Examples 72-125 listed in Table 6 below were prepared according to the general procedure described for Example 71. Non-commercial amines were used in the preparation of Examples 85-87, 102, and 116 and were prepared according to the following literature procedures: 2-amino-N,N-dimethylacetamide and 2-amino-1-morpholinoethanone were prepared as in J. Am. Chem. Soc. 1967, 89(24), 6096-103, 2-aminomethyl-3-fluoropyridine was prepared as in WO2003203922, and morpholine-4-sulfonamide was prepared as in WO2004011443.

TABLE 6

| Ex. # | Compound Structure | HPLC and LCMS Data |
|---|---|---|
| 72 | 4-(2-chloro-4-fluorophenyl)-N-(2-(dimethylamino)ethyl)-6-(2-(isopropylamino)thiazol-5-yl)pyrimidin-2-amine | HPLC $t_R$ = 2.44 min<br>LCMS [M + H]+ = 435.29 |
| 73 | 4-(2-chloro-4-fluorophenyl)-6-(2-(isopropylamino)thiazol-5-yl)-N-(2-morpholinoethyl)pyrimidin-2-amine | HPLC $t_R$ = 2.49 min<br>LCMS [M + H]+ = 477.30 |

TABLE 6-continued

| Ex. # | Compound Structure | HPLC and LCMS Data |
|---|---|---|
| 74 | 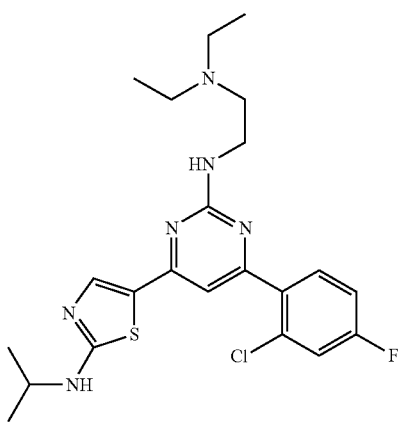<br>4-(2-chloro-4-fluorophenyl)-N-(2-(diethylamino)ethyl)-6-(2-(isopropylamino)thiazol-5-yl)pyrimidin-2-amine | HPLC $t_R$ = 2.57 min<br>LCMS $[M + H]^+$ = 463.27 |
| 75 | 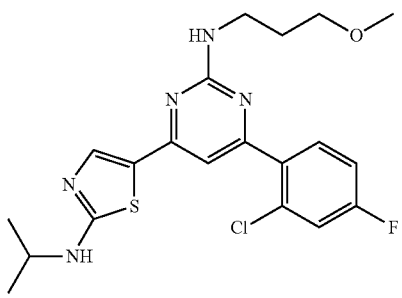<br>4-(2-chloro-4-fluorophenyl)-6-(2-(isopropylamino)thiazol-5-yl)-N-(3-methoxypropyl)pyrimidin-2-amine | HPLC $t_R$ = 3.26 min<br>LCMS $[M + H]^+$ = 436.24 |
| 76 | 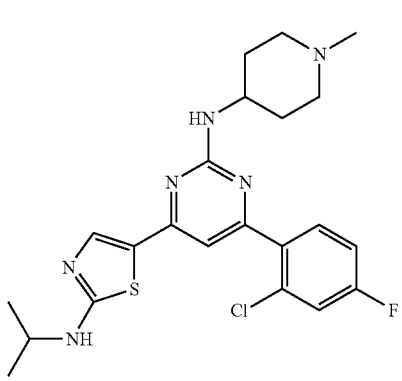<br>4-(2-chloro-4-fluorophenyl)-6-(2-(isopropylamino)thiazol-5-yl)-N-(1-methylpiperidin-4-yl)pyrimidin-2-amine | HPLC $t_R$ = 2.50 min<br>LCMS $[M + H]^+$ = 461.23 |

TABLE 6-continued

| Ex. # | Compound Structure | HPLC and LCMS Data |
|---|---|---|
| 77 | 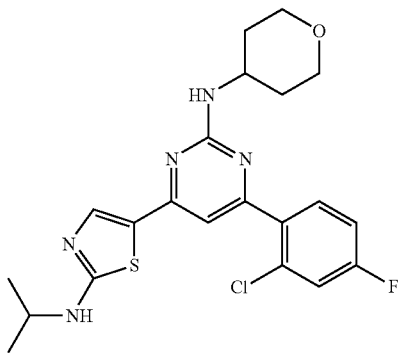<br>4-(2-chloro-4-fluorophenyl)-6-(2-(isopropylamino)thiazol-5-yl)-N-(tetrahydro-2H-pyran-4-yl)pyrimidin-2-amine | HPLC $t_R$ = 3.29 min<br>LCMS [M + H]$^+$ = 448.34 |
| 78 | 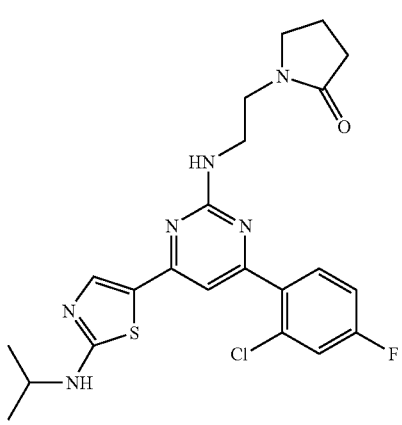<br>1-(2-(4-(2-chloro-4-fluorophenyl)-6-(2-(isopropylamino)thiazol-5-yl)pyrimidin-2-ylamino)ethyl)pyrrolidin-2-one | HPLC $t_R$ = 2.91 min<br>LCMS [M + H]$^+$ = 476.34 |
| 79 | 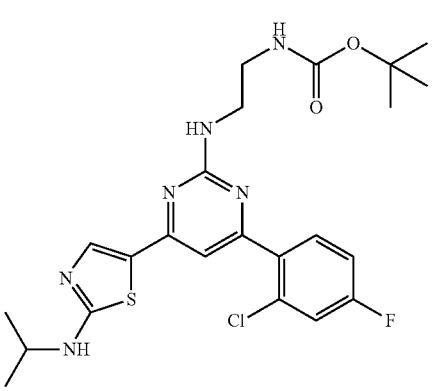<br>tert-butyl 2-(4-(2-chloro-4-fluorophenyl)-6-(2-(isopropylamino)thiazol-5-yl)pyrimidin-2-ylamino)ethylcarbamate | HPLC $t_R$ = 3.62 min<br>LCMS [M + H]$^+$ = 521.32 |

TABLE 6-continued

| Ex. # | Compound Structure | HPLC and LCMS Data |
|---|---|---|
| 80 | 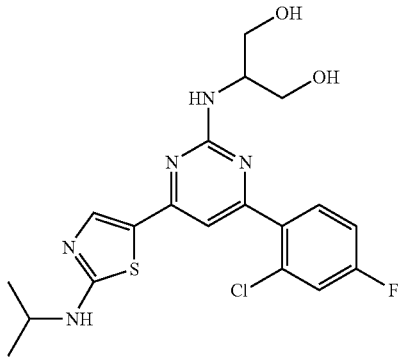<br>2-(4-(2-chloro-4-fluorophenyl)-6-(2-(isopropylamino)thiazol-5-yl)pyrimidin-2-ylamino)propane-1,3-diol | HPLC $t_R$ = 2.69 min<br>LCMS [M + H]$^+$ = 438.18 |
| 81 | 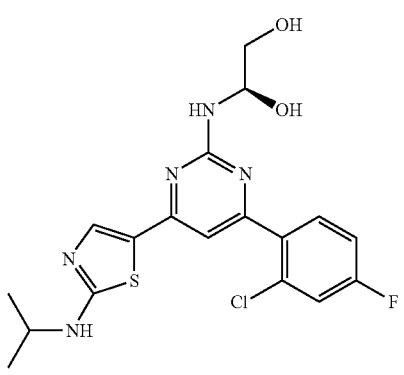<br>(1R)-1-(4-(2-chloro-4-fluorophenyl)-6-(2-(isopropylamino)thiazol-5-yl)pyrimidin-2-ylamino)ethane-1,2-diol | HPLC $t_R$ = 3.02 min<br>LCMS [M + H]$^+$ = 422.37 |
| 82 | <br>(1S)-1-(4-(2-chloro-4-fluorophenyl)-6-(2-(isopropylamino)thiazol-5-yl)pyrimidin-2-ylamino)ethane-1,2-diol | HPLC $t_R$ = 3.02 min<br>LCMS [M + H]$^+$ = 422.37 |
| 83 | 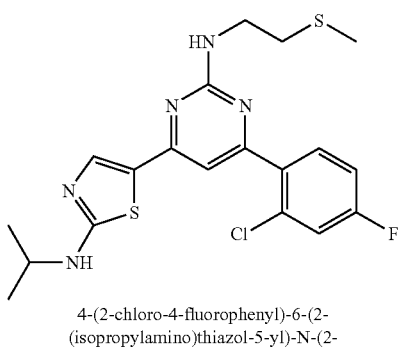<br>4-(2-chloro-4-fluorophenyl)-6-(2-(isopropylamino)thiazol-5-yl)-N-(2-(methylthio)ethyl)pyrimidin-2-amine | HPLC $t_R$ = 3.48 min<br>LCMS [M + H]$^+$ = 438.30 |

TABLE 6-continued

| Ex. # | Compound Structure | HPLC and LCMS Data |
|---|---|---|
| 84 | 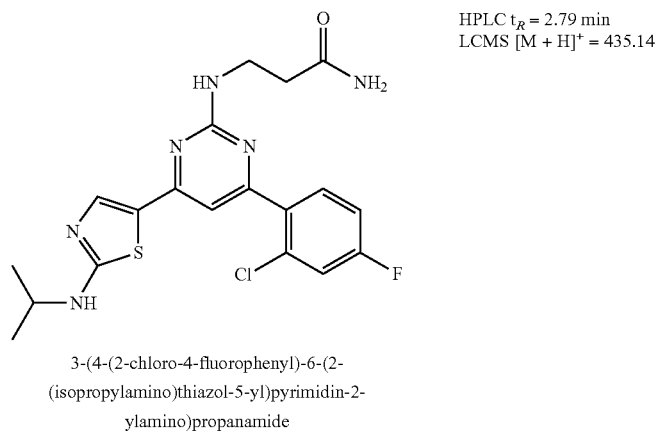<br>3-(4-(2-chloro-4-fluorophenyl)-6-(2-(isopropylamino)thiazol-5-yl)pyrimidin-2-ylamino)propanamide | HPLC $t_R$ = 2.79 min<br>LCMS $[M + H]^+$ = 435.14 |
| 85 | 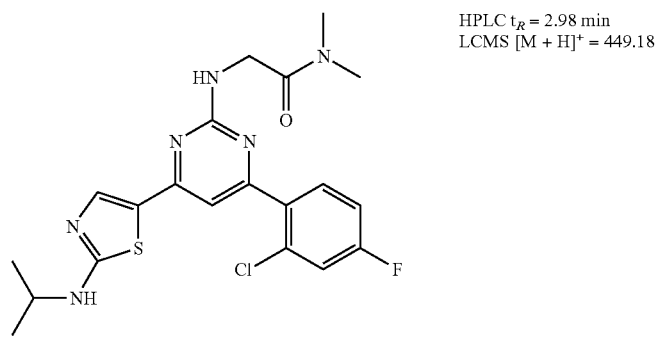<br>2-(4-(2-chloro-4-fluorophenyl)-6-(2-(isopropylamino)thiazol-5-yl)pyrimidin-2-ylamino)-N,N-dimethylacetamide | HPLC $t_R$ = 2.98 min<br>LCMS $[M + H]^+$ = 449.18 |
| 86 | 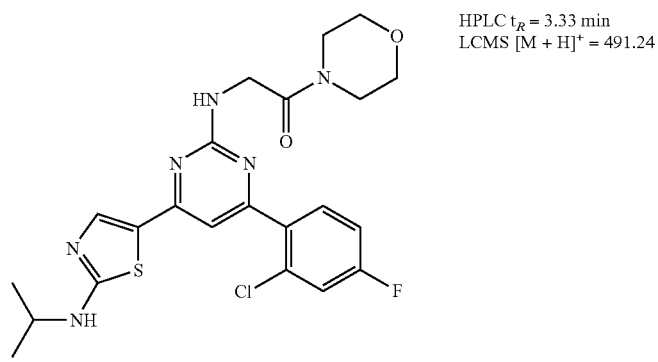<br>2-(4-(2-chloro-4-fluorophenyl)-6-(2-(isopropylamino)thiazol-5-yl)pyrimidin-2-ylamino)-1-morpholinoethanone | HPLC $t_R$ = 3.33 min<br>LCMS $[M + H]^+$ = 491.24 |

TABLE 6-continued

| Ex. # | Compound Structure | HPLC and LCMS Data |
|---|---|---|
| 87 | 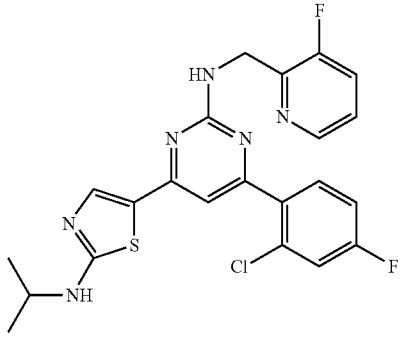<br>4-(2-chloro-4-fluorophenyl)-N-((3-fluoropyridin-2-yl)methyl)-6-(2-(isopropylamino)thiazol-5-yl)pyrimidin-2-amine | HPLC $t_R$ = 2.92 min<br>LCMS [M + H]$^+$ = 473.27 |
| 88 | 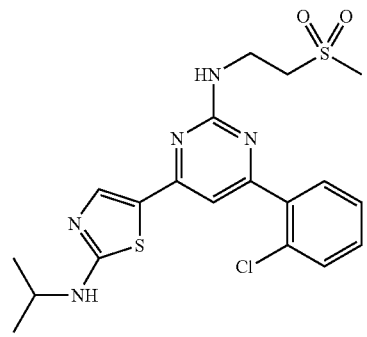<br>4-(2-chlorophenyl)-6-(2-(isopropylamino)thiazol-5-yl)-N-(2-(methylsulfonyl)ethyl)pyrimidin-2-amine | HPLC $t_R$ = 3.09 min<br>LCMS [M + H]$^+$ = 470.35 |
| 89 | 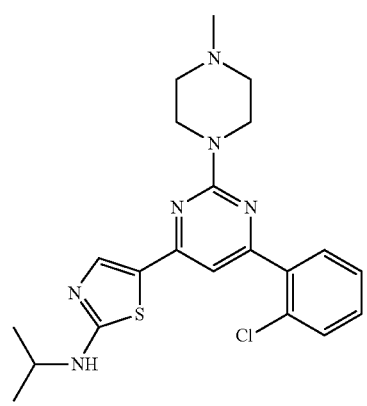<br>5-(6-(2-chlorophenyl)-2-(4-methylpiperazin-1-yl)pyrimidin-4-yl)-N-isopropylthiazol-2-amine | HPLC $t_R$ = 2.39 min<br>LCMS [M + H]$^+$ = 439.34 |

TABLE 6-continued

| Ex. # | Compound Structure | HPLC and LCMS Data |
|---|---|---|
| 90 | 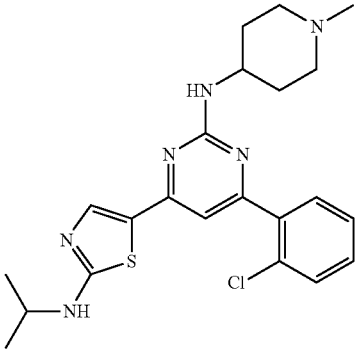<br>4-(2-chlorophenyl)-6-(2-(isopropylamino)thiazol-5-yl)-N-(1-methylpiperidin-4-yl)pyrimidin-2-amine | HPLC $t_R$ = 2.29 min<br>LCMS [M + H]$^+$ = 443.29 |
| 91 | 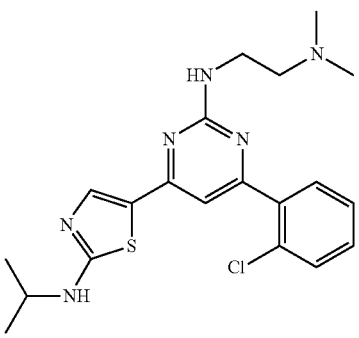<br>4-(2-chlorophenyl)-N-(2-(dimethylamino)ethyl)-6-(2-(isopropylamino)thiazol-5-yl)pyrimidin-2-amine | HPLC $t_R$ = 2.28 min<br>LCMS [M + H]$^+$ = 417.35 |
| 92 | 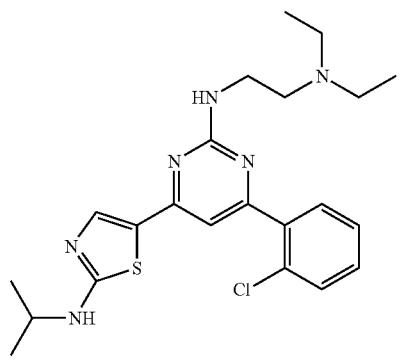<br>4-(2-chlorophenyl)-N-(2-(diethylamino)ethyl)-6-(2-(isopropylamino)thiazol-5-yl)pyrimidin-2-amine | HPLC $t_R$ = 2.41 min<br>LCMS [M + H]$^+$ = 445.34 |

TABLE 6-continued

| Ex. # | Compound Structure | HPLC and LCMS Data |
|---|---|---|
| 93 | 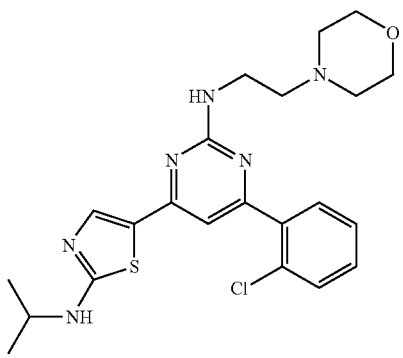<br>4-(2-chlorophenyl)-6-(2-(isopropylamino)thiazol-5-yl)-N-(2-morpholinoethyl)pyrimidin-2-amine | HPLC $t_R$ = 2.27 min<br>LCMS [M + H]$^+$ = 459.31 |
| 94 | 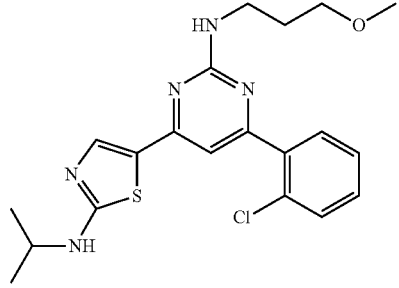<br>4-(2-chlorophenyl)-6-(2-(isopropylamino)thiazol-5-yl)-N-(3-methoxypropyl)pyrimidin-2-amine | HPLC $t_R$ = 3.02 min<br>LCMS [M + H]$^+$ = 418.35 |
| 95 | 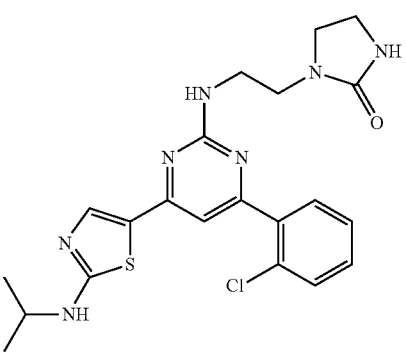<br>1-(2-(4-(2-chlorophenyl)-6-(2-(isopropylamino)thiazol-5-yl)pyrimidin-2-ylamino)ethyl)imidazolidin-2-one | HPLC $t_R$ = 2.69 min<br>LCMS [M + H]$^+$ = 458.32 |
| 96 | 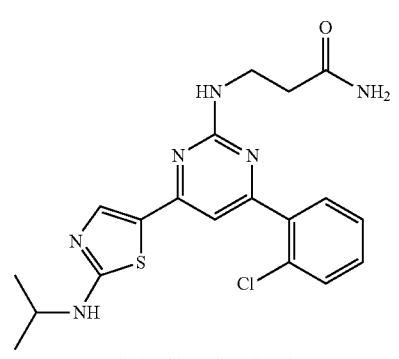<br>3-(4-(2-chlorophenyl)-6-(2-(isopropylamino)thiazol-5-yl)pyrimidin-2-ylamino)propanamide | HPLC $t_R$ = 2.59 min<br>LCMS [M + H]$^+$ = 417.32 |

TABLE 6-continued

| Ex. # | Compound Structure | HPLC and LCMS Data |
|---|---|---|
| 97 | 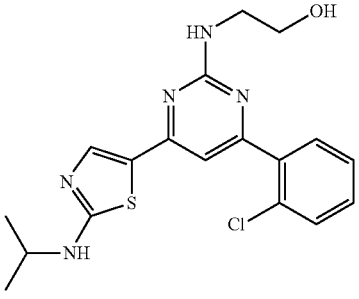<br>2-(4-(2-chlorophenyl)-6-(2-(isopropylamino)thiazol-5-yl)pyrimidin-2-ylamino)ethanol | HPLC $t_R$ = 2.70 min<br>LCMS [M + H]$^+$ = 390.3 |
| 98 | 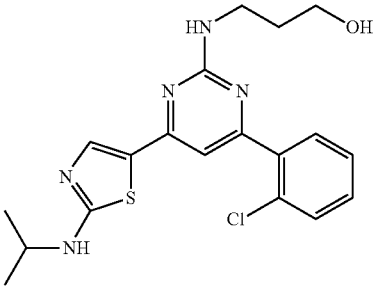<br>3-(4-(2-chlorophenyl)-6-(2-(isopropylamino)thiazol-5-yl)pyrimidin-2-ylamino)propan-1-ol | HPLC $t_R$ = 2.77 min<br>LCMS [M + H]$^+$ = 404.32 |
| 99 | 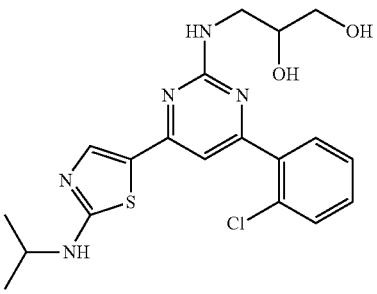<br>3-(4-(2-chlorophenyl)-6-(2-(isopropylamino)thiazol-5-yl)pyrimidin-2-ylamino)propane-1,2-diol | HPLC $t_R$ = 2.58 min<br>LCMS [M + H]$^+$ = 420.30 |
| 100 | 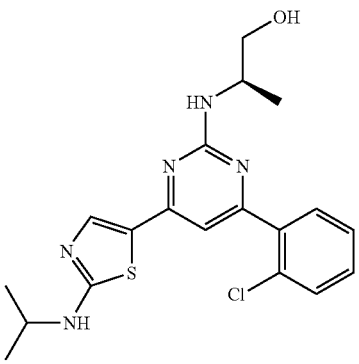<br>(2R)-2-(4-(2-chlorophenyl)-6-(2-(isopropylamino)thiazol-5-yl)pyrimidin-2-ylamino)propan-1-ol | HPLC $t_R$ = 2.83 min<br>LCMS [M + H]$^+$ = 404.31 |

TABLE 6-continued

| Ex. # | Compound Structure | HPLC and LCMS Data |
|---|---|---|
| 101 | 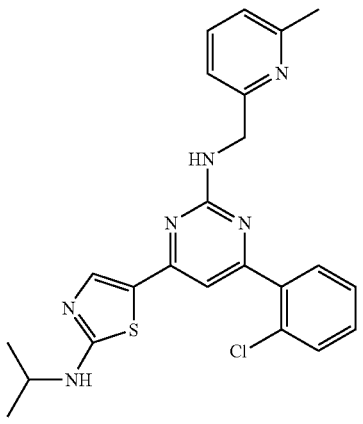<br>4-(2-chlorophenyl)-6-(2-(isopropylamino)thiazol-5-yl)-N-((6-methylpyridin-2-yl)methyl)pyrimidin-2-amine | HPLC $t_R$ = 2.42 min<br>LCMS [M + H]$^+$ = 451.29 |
| 102 | 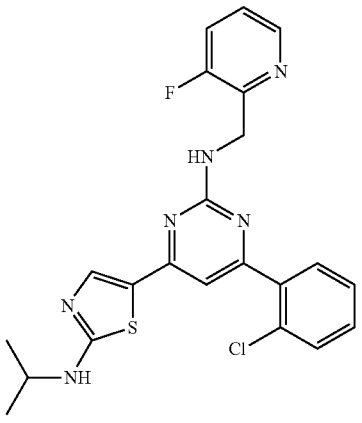<br>4-(2-chlorophenyl)-N-((3-fluoropyridin-2-yl)methyl)-6-(2-(isopropylamino)thiazol-5-yl)pyrimidin-2-amine | HPLC $t_R$ = 3.14 min<br>LCMS [M + H]$^+$ = 455.28 |
| 103 | 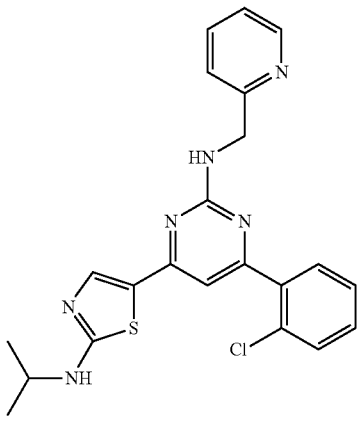<br>4-(2-chlorophenyl)-6-(2-(isopropylamino)thiazol-5-yl)-N-(pyridin-2-ylmethyl)pyrimidin-2-amine | HPLC $t_R$ = 2.42 min<br>LCMS [M + H]$^+$ = 437.32 |

TABLE 6-continued

| Ex. # | Compound Structure | HPLC and LCMS Data |
|---|---|---|
| 104 | 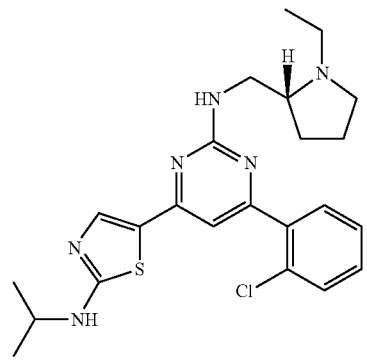<br>4-(2-chlorophenyl)-N-(((R)-1-ethylpyrrolidin-2-yl)methyl)-6-(2-(isopropylamino)thiazol-5-yl)pyrimidin-2-amine | HPLC $t_R$ = 2.46 min<br>LCMS $[M + H]^+$ = 457.35 |
| 105 | 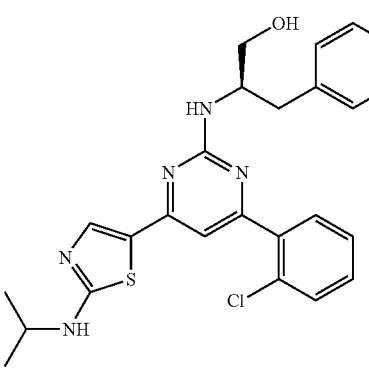<br>(2R)-2-(4-(2-chlorophenyl)-6-(2-(isopropylamino)thiazol-5-yl)pyrimidin-2-ylamino)-3-phenylpropan-1-ol | HPLC $t_R$ = 3.35 min<br>LCMS $[M + H]^+$ = 480.28 |
| 106 | 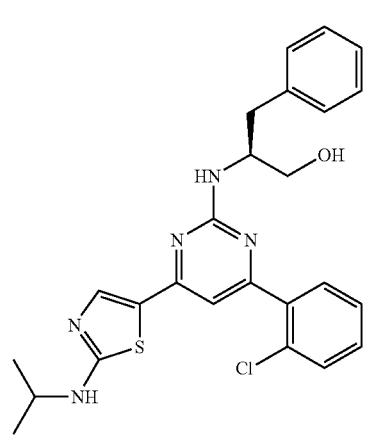<br>(2S)-2-(4-(2-chlorophenyl)-6-(2-(isopropylamino)thiazol-5-yl)pyrimidin-2-ylamino)-3-phenylpropan-1-ol | HPLC $t_R$ = 3.35 min<br>LCMS $[M + H]^+$ = 480.28 |

TABLE 6-continued

| Ex. # | Compound Structure | HPLC and LCMS Data |
|---|---|---|
| 107 | 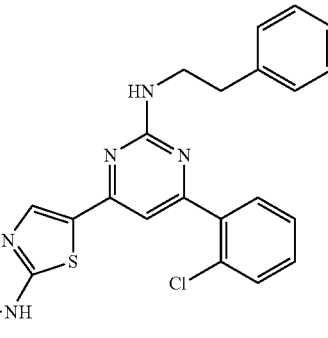<br>4-(2-(4-(2-chlorophenyl)-6-(2-(isopropylamino)thiazol-5-yl)pyrimidin-2-ylamino)ethyl)benzenesulfonamide | HPLC $t_R$ = 2.91 min<br>LCMS [M + H]$^+$ = 529.18 |
| 108 | 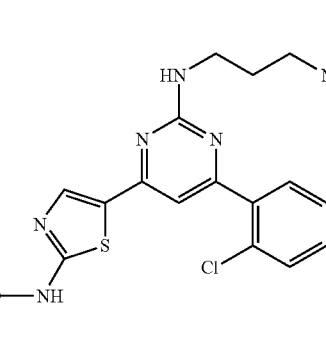<br>1-(3-(4-(2-chlorophenyl)-6-(2-(isopropylamino)thiazol-5-yl)pyrimidin-2-ylamino)propyl)pyrrolidin-2-one | HPLC $t_R$ = 2.89 min<br>LCMS [M + H]$^+$ = 471.28 |
| 109 | 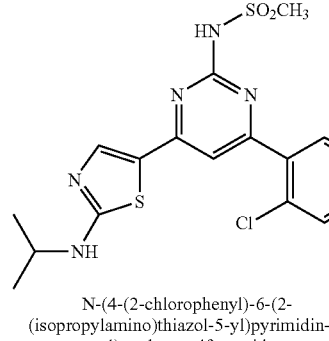<br>N-(4-(2-chlorophenyl)-6-(2-(isopropylamino)thiazol-5-yl)pyrimidin-2-yl)methanesulfonamide | HPLC $t_R$ = 2.97 min<br>LCMS [M + H]$^+$ = 424.24 |
| 110 | 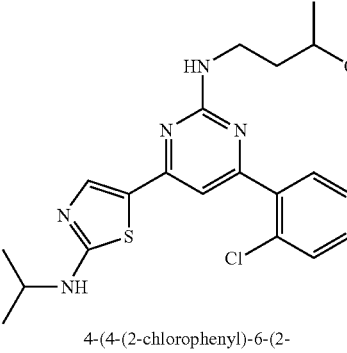<br>4-(4-(2-chlorophenyl)-6-(2-(isopropylamino)thiazol-5-yl)pyrimidin-2-ylamino)butan-2-ol | HPLC $t_R$ = 2.96 min<br>LCMS [M + H]$^+$ = 418.15 |

TABLE 6-continued
| Ex. # | Compound Structure | HPLC and LCMS Data |
|---|---|---|
| 111 | 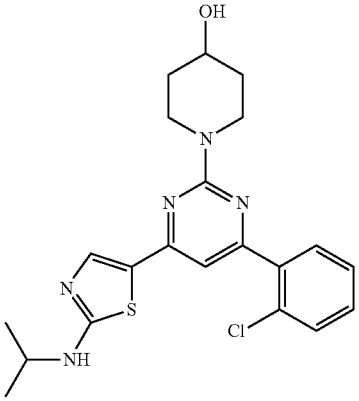<br>1-(4-(2-chlorophenyl)-6-(2-(isopropylamino)thiazol-5-yl)pyrimidin-2-yl)piperidin-4-ol | HPLC $t_R$ = 3.25 min<br>LCMS $[M + H]^+$ = 430.36 |
| 112 | 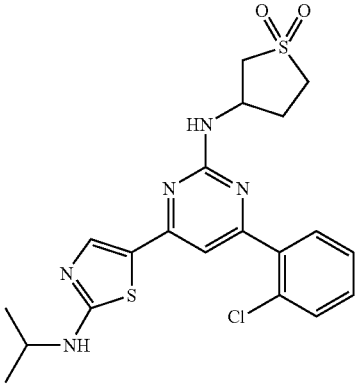 | HPLC $t_R$ = 2.92 min<br>LCMS $[M + H]^+$ = 464.28 |
| 113 | 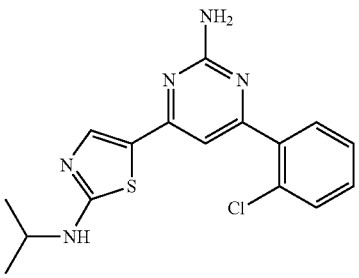<br>4-(2-chlorophenyl)-6-(2-(isopropylamino)thiazol-5-yl)pyrimidin-2-amine | HPLC $t_R$ = 2.60 min<br>LCMS $[M + H]^+$ = 346.39 |

TABLE 6-continued

| Ex. # | Compound Structure | HPLC and LCMS Data |
|---|---|---|
| 114 | 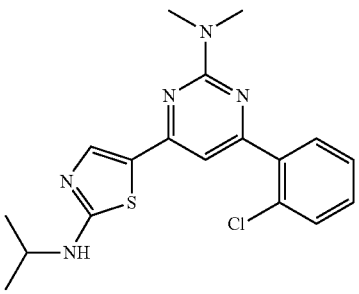<br>4-(2-chlorophenyl)-6-(2-(isopropylamino)thiazol-5-yl)-N,N-dimethylpyrimidin-2-amine | HPLC $t_R$ = 3.42 min<br>LCMS $[M + H]^+$ = 374.40 |
| 115 | 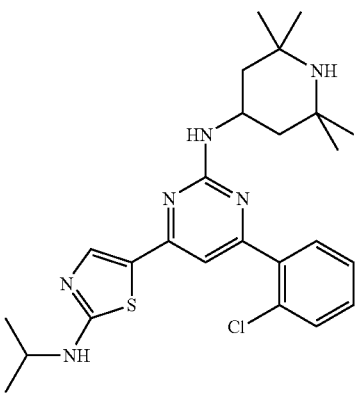<br>4-(2-chlorophenyl)-6-(2-(isopropylamino)thiazol-5-yl)-N-(2,2,6,6-tetramethylpiperidin-4-yl)pyrimidin-2-amine | HPLC $t_R$ = 2.74 min<br>LCMS $[M + H]^+$ = 485.35 |
| 116 | 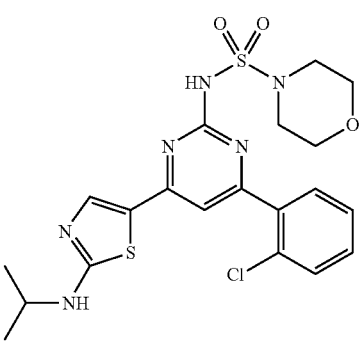<br>N-(4-(2-chlorophenyl)-6-(2-(isopropylamino)thiazol-5-yl)pyrimidin-2-yl)morpholine-4-sulfonamide | HPLC $t_R$ = 3.19 min<br>LCMS $[M + H]^+$ = 495.23 |

TABLE 6-continued

| Ex. # | Compound Structure | HPLC and LCMS Data |
|---|---|---|
| 117 | 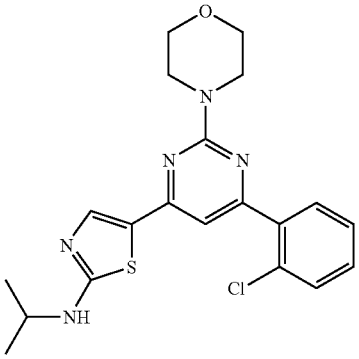<br>5-(6-(2-chlorophenyl)-2-morpholinopyrimidin-4-yl)-N-isopropylthiazol-2-amine | HPLC $t_R$ = 3.55 min<br>LCMS [M + H]$^+$ = 416.37 |
| 118 | 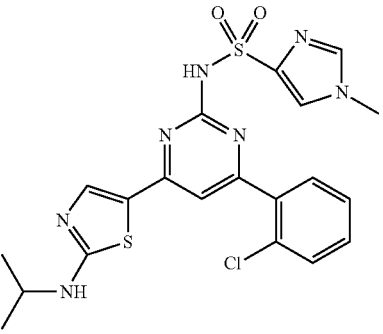<br>N-(4-(2-chlorophenyl)-6-(2-(isopropylamino)thiazol-5-yl)pyrimidin-2-yl)-1-methyl-1H-imidazole-4-sulfonamide | HPLC $t_R$ = 2.74 min<br>LCMS [M + H]$^+$ = 490.24 |
| 120 | 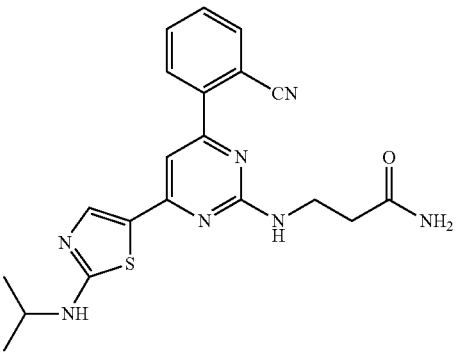<br>3-(4-(2-cyanophenyl)-6-(2-(isopropylamino)thiazol-5-yl)pyrimidin-2-ylamino)propanamide | HPLC $t_R$ = 2.40 min<br>LCMS [M + H]$^+$ = 408.21 |

TABLE 6-continued

| Ex. # | Compound Structure | HPLC and LCMS Data |
|---|---|---|
| 121 | 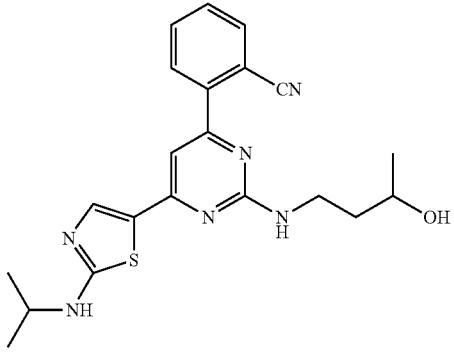<br>2-(2-(3-hydroxybutylamino)-6-(2-(isopropylamino)thiazol-5-yl)pyrimidin-4-yl)benzonitrile | HPLC $t_R$ = 2.77 min<br>LCMS [M + H]$^+$ = 409.24 |
| 122 | 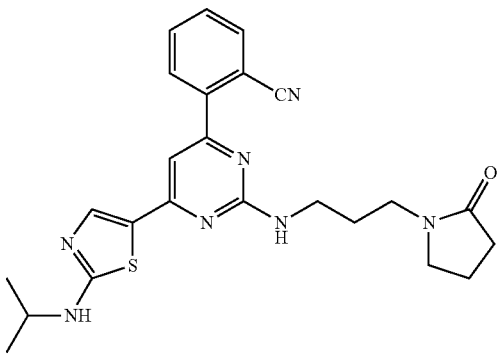<br>2-(6-(2-(isopropylamino)thiazol-5-yl)-2-(3-(2-oxopyrrolidin-1-yl)propylamino)pyrimidin-4-yl)benzonitrile | HPLC $t_R$ = 2.75 min<br>LCMS [M + H]$^+$ = 462.40 |
| 123 | 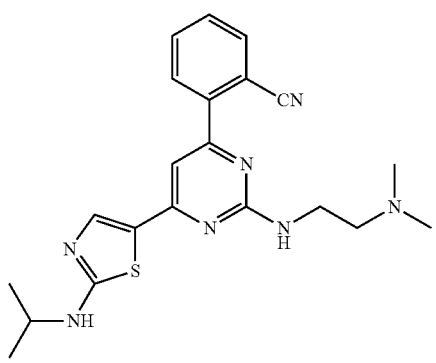<br>2-(2-(2-(dimethylamino)ethylamino)-6-(2-(isopropylamino)thiazol-5-yl)pyrimidin-4-yl)benzonitrile | HPLC $t_R$ = 1.96 min<br>LCMS [M + H]$^+$ = 408.25 |

TABLE 6-continued

| Ex. # | Compound Structure | HPLC and LCMS Data |
|---|---|---|
| 124 | 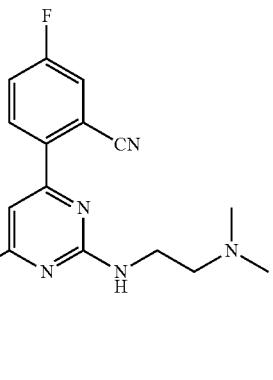<br>2-(2-(2-(dimethylamino)ethylamino)-6-(2-(isopropylamino)thiazol-5-yl)pyrimidin-4-yl)-5-fluorobenzonitrile | HPLC $t_R$ = 2.18 min<br>LCMS $[M + H]^+$ = 426.40 |
| 125 | 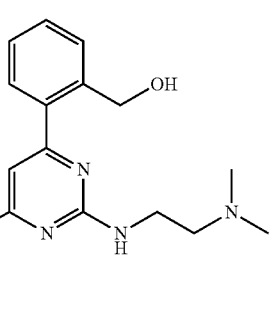<br>(2-(2-(2-(dimethylamino)ethylamino)-6-(2-(isopropylamino)thiazol-5-yl)pyrimidin-4-yl)phenyl)methanol | HPLC $t_R$ = 1.91 min<br>LCMS $[M + H]^+$ = 413.30 |
| 125a | 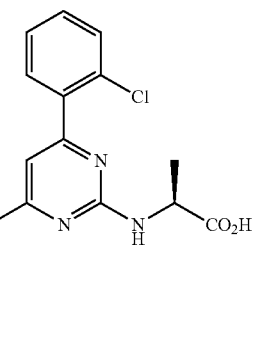<br>(S)-2-(4-(2-chlorophenyl)-6-(2-(isopropylamino)thiazol-5-yl)pyrimidin-2-ylamino)propanoic acid | HPLC $t_R$ = 1.91 min<br>LCMS $[M + H]^+$ = 413.30 |

TABLE 6-continued

| Ex. # | Compound Structure | HPLC and LCMS Data |
|---|---|---|
| 125b | 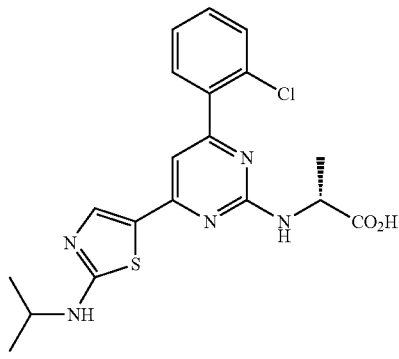<br>(R)-2-(4-(2-chlorophenyl)-6-(2-(isopropylamino)thiazol-5-yl)pyrimidin-2-ylamino)propanoic acid | HPLC $t_R$ = 1.91 min<br>LCMS [M + H]$^+$ = 413.30 |
| 125c | 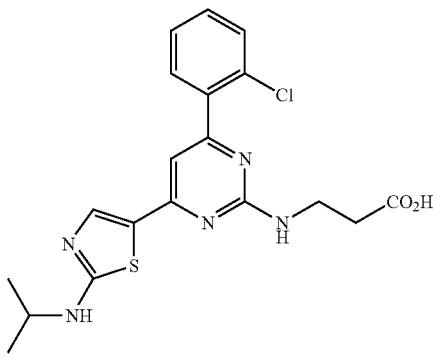<br>3-(4-(2-chlorophenyl)-6-(2-(isopropylamino)thiazol-5-yl)pyrimidin-2-ylamino)propanoic acid | HPLC $t_R$ = 2.74 min<br>LCMS [M + H]$^+$ = 418.16 |
| 125d | 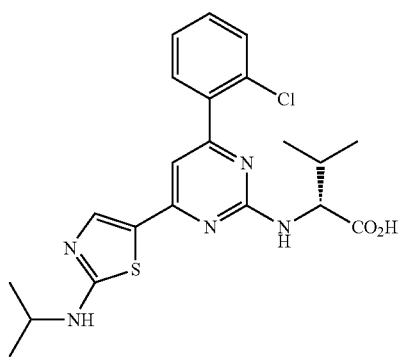<br>(R)-2-(4-(2-chlorophenyl)-6-(2-(isopropylamino)thiazol-5-yl)pyrimidin-2-ylamino)-3-methylbutanoic acid | HPLC $t_R$ = 3.24 min<br>LCMS [M + H]$^+$ = 446.24 |

Example 126

1-(2-(2-(2-(dimethylamino)ethylamino)-6-(2-(isopropylamino)thiazol-5-yl)pyrimidin-4-yl)benzyl)-3-cyclopropylurea

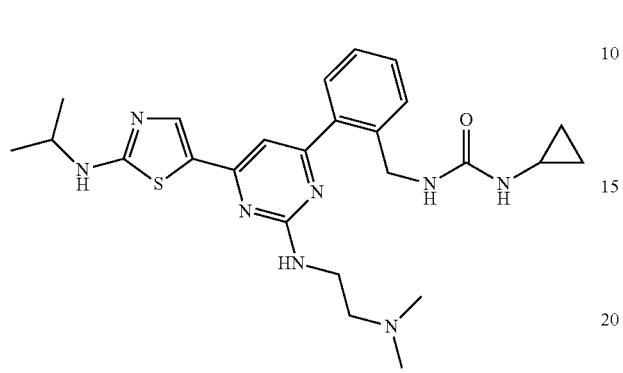

Step 1: Example 127, tert-butyl 2-(6-(2-(isopropylamino)thiazol-5-yl)-2-(methylthio)pyrimidin-4-yl)benzylcarbamate

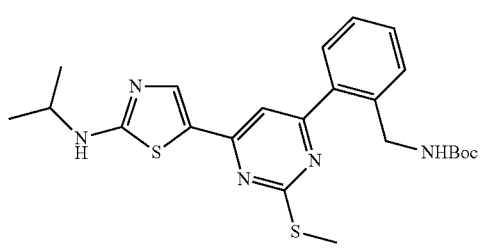

Example 127 was prepared from Preparation 18 utilizing a similar procedure as described in step 5 of Example 50. Yellow solid. HPLC Ret. time: 3.92 min. LCMS MH+ (m/z) 472. $^1$H NMR: (d$_6$-DMSO, 500 MHz) δ 8.26 (d, 1H), 8.18 (s, 1H), 7.65 (s, 1H), 7.46 (m, 2H), 7.39 (m, 2H), 7.25 (br t, 1H), 4.30 (d, 2H), 3.82 (m, 1H), 2.50 (s, 3H), 1.34 (s, 9H), 1.18 (d, 6H).

Step 2: Example 128, tert-butyl 2-(6-(2-(isopropylamino)thiazol-5-yl)-2-(methylsulfonyl)pyrimidin-4-yl)benzylcarbamate

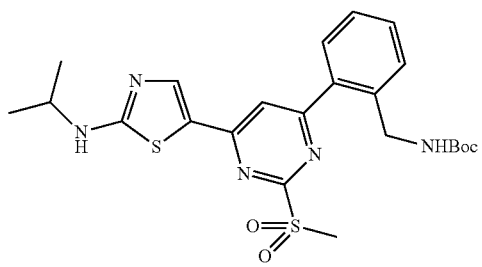

Example 128 was prepared from Example 127 utilizing a similar procedure as described in step 6 of Example 50. Yellow solid. HPLC Ret. time: 3.50 min. LCMS MH+ (m/z) 504.27.

Step 3: Example 129, tert-butyl 2-(2-(2-(dimethylamino)ethylamino)-6-(2-(isopropylamino)thiazol-5-yl)pyrimidin-4-yl)benzylcarbamate

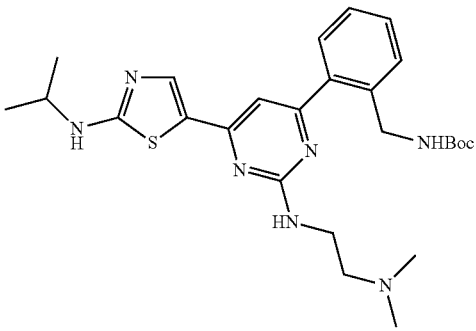

Example 129 was prepared from Example 128 utilizing a similar procedure as described in step 7 of Example 50 and by replacing 1-methylpiperazine with 2-dimethylaminoethylamine. Yellow solid. HPLC Ret. time: 2.56 min. LCMS MH+ (m/z) 512.39.

Step 4: Example 130, 4-(2-(aminomethyl)phenyl)-N-(2-(dimethylamino)ethyl)-6-(2-(isopropylamino)thiazol-5-yl)pyrimidin-2-amine

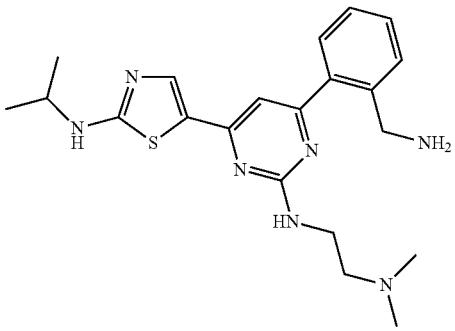

To a solution of Example 129 (85 mg, 0.166 mmol) in anhydrous dioxane (1 mL) was added a solution of 4N HCl in dioxane (2 mL) and the resulting solution was stirred at rt for 20 h. The mixture was diluted with ether (~20 mL) and filtered to collect the bis hydrochloride salt of Example 130 as a yellow solid. HPLC Ret. time: 1.39 min. LCMS MH+ (m/z) 412.33.

Step 5: Example 126

To a slurry of Example 130 (0.10 g, 0.20 mmol) in methylene chloride (1 mL) at 0° C. were successively added p-nitrophenylchloroformate (44 mg, 0.22 mmol) and diisopropylethylamine (0.18 mL, 1.0 mmol) and the resulting mixture was stirred at 0° C. for 30 min. The mixture was concentrated in vacuo and the resulting oil was dissolved in DMF (1 mL) and cyclopropylamine (46 mg, 0.40 mmol) was added. After stirring at rt for 30 min, the mixture was purified by reverse-phase preparative HPLC to afford fractions containing the desired product. These fractions were neutralized by adding saturated sodium bicarbonate (~1 mL) and concentrated in vacuo to remove the methanol. The resulting solid was collected by filtration to afford 17 mg of the title compound as a yellow solid. HPLC Ret. time: 1.98 min. LCMS MH+ (m/z)

495.38. ¹H NMR: (d₆-DMSO, 500 MHz) δ 8.06 (d, 1H), 8.00 (s, 1H), 7.46 (m, 1H), 7.41 (m, 2H), 7.38 (m, 1H), 7.13 (s, 1H), 7.00 (br. s, 1H), 6.28 (br s, 1H), 6.25 (br s, 1H), 4.38 (m, 1H), 3.82 (br m, 1H), 3.47 (m, 2H), 2.70 (br m, 2H), 2.38 (br s, 6H), 1.18 (d, 6H), 0.53 (m, 2H), 0.29 (m, 2H).

Examples 131-133

Examples 131-133 in Table 7 were prepared from Example 130 utilizing a similar procedure as described for Example 126.

TABLE 7

| Ex. # | Compound Structure | HPLC and LCMS Data |
|---|---|---|
| 131 | 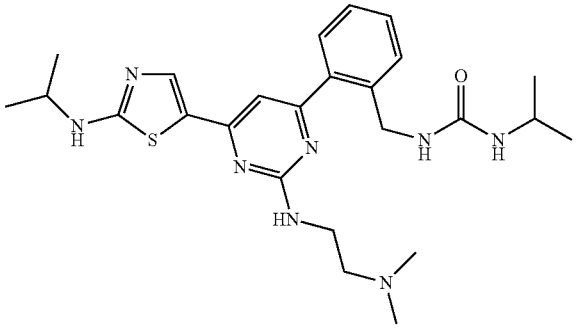<br>1-(2-(2-(2-(dimethylamino)ethylamino)-6-(2-(isopropylamino)thiazol-5-yl)pyrimidin-4-yl)benzyl)-3-isopropylurea | HPLC $t_R$ = 2.09 min<br>LCMS [M + H]⁺ = 497.39 |
| 132 | 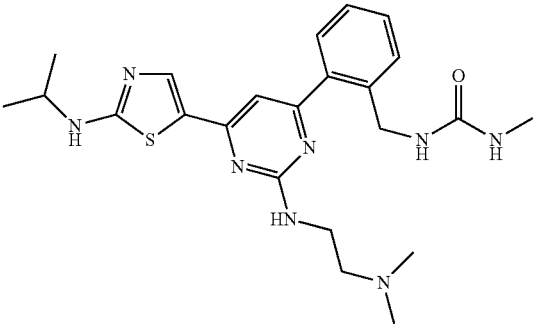<br>1-(2-(2-(2-(dimethylamino)ethylamino)-6-(2-(isopropylamino)thiazol-5-yl)pyrimidin-4-yl)benzyl)-3-methylurea | HPLC $t_R$ = 1.84 min<br>LCMS [M + H]⁺ = 469.28 |
| 133 | 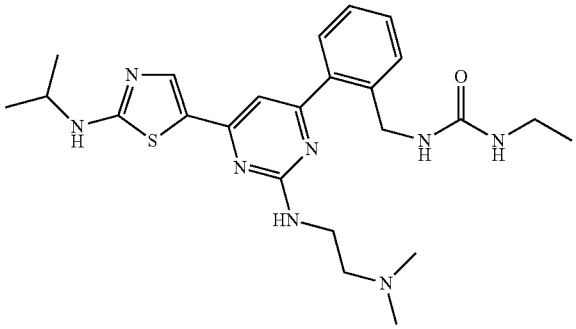<br>1-(2-(2-(2-(dimethylamino)ethylamino)-6-(2-(isopropylamino)thiazol-5-yl)pyrimidin-4-yl)benzyl)-3-ethylurea | HPLC $t_R$ = 1.90 min<br>LCMS [M + H]⁺ = 483.26 |

Alternative Preparation of Example 133

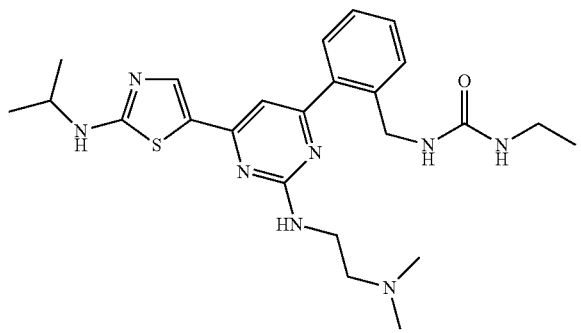

1-(2-(2-(2-(dimethylamino)ethylamino)-6-(2-(iso-propylamino)thiazol-5-yl)pyrimidin-4-yl)benzyl)-3-ethylurea Step 1: Preparation 18a

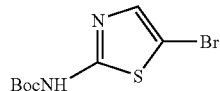

To a slurry of 2-amino-5-bromo-thiazole monohydrobromide (25 g, 96 mmol) in 75 mL of pyridine at rt was added (Boc)$_2$O (23.1 g, 106 mmol) in three portions over 15 min and the resulting mixture was allowed to stir at rt for ~16 h. The mixture was concentrated in vacuo and partitioned between water (200 mL) and ethyl acetate (200 mL). The aqueous layer containing a significant amount of undissolved solids was further extracted with warm ethyl acetate (3×150 mL). The combined organic extracts were then washed with 1 N aq. HCl (3×150 mL), sat'd aq. sodium bicarbonate (2×100 mL), and brine (100 mL), then dried over anhyd sodium sulfate, filtered, and concentrated to afford 16.7 g (62%) of Preparation 18a as a tan solid. HPLC Ret. time: 3.71 min.

Step 2: Preparation 18b

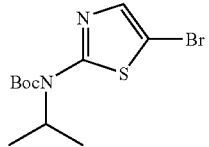

To a solution of Preparation 18a (10 g, 36 mmol), triphenylphosphine (14.1 g, 54 mmol), and isopropanol (4.1 mL, 54 mmol) in THF (75 mL) at rt was slowly added diethyl azodicarboxylate (8.4 mL, 54 mmol) over 10 min causing a slight exothermic reaction. After stirring for 2.5 h at rt, the reaction was concentrated in vacuo to remove the THF and the remaining material was dissolved in ethyl acetate (150 mL). The solution was washed with 1 N aq. HCl (3×100 mL), water (50 mL), and satd. Aq. sodium bicarbonate (50 mL), then dried over anhyd sodium sulfate, filtered, and concentrated in vacuo to afford a thick reddish-brown oil. Approximately 50 mL of ethyl acetate was added causing a precipitate to form from the solution. The solution was filtered to remove the solid and the resulting clear solution was concentrated. To the resulting material was then added diethyl ether (200 mL) and a 20% aq. solution of Oxone was added and the mixture was stirred vigorously at rt for ~16 h. Ethyl acetate (200 mL) was added and the resulting layers were separated. The organic layer was concentrated and the resulting oil was purified by flash chromatography on silica gel using a gradient elution from 5% to 10% ethyl acetate in hexanes as the eluant. Fractions containing the product were collected and concentrated to afford 9.2 g (79%) of a grey solid as Preparation 18b. HPLC Ret. time: 4.20 min.

Step 3: Preparation 18c

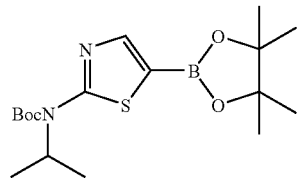

To a solution of Preparation 18c (9.2 g, 28.4 mmol) in THF (140 mL) at −78° C. was added a 2.5 M solution of n-butyllithium in hexanes (12.5 mL, 31.2 mmol) and the resulting orange-colored solution was stirred at −78° C. for 25 min. At this time, 2-isopropoxy-4,4,5,5-tetramethyl-1,3,2-dioxaborolane (6.4 mL, 31.2 mmol) was added and the solution was stirred at −78° C. for an additional 45 min, then warmed to rt over 1 h. The reaction was quenched by a slow dropwise addition of satd aq ammonium chloride (25 mL) then water (50 mL). The mixture was concentrated on a rotary evaporator to remove the THF, then the mixture was extracted with ethyl acetate (2×150 mL). The combined extracts were washed with water (2×50 mL) and brine (50 mL), then dried over anhyd. Sodium sulfate, filtered, and concentrated in vacuo to afford 10.0 g (95%) of a yellow solid as Preparation 18c. HPLC Ret. time: 3.24 min.

Step 4: Preparation 18d

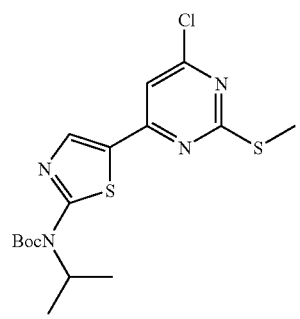

To a solution of Preparation 18c (9.9 g, 24.7 mmol) and 4,6-dichloro-2-(methylthio)-pyrimidine (7.2 g, 37.1 mmol) in toluene (125 mL) was added ethanol (16.7 mL) and 2M aq potassium phosphate solution (25 mL) and the resulting mixture was degassed with argon. At this time, Pd(PPh$_3$)$_4$ (1.4 g, 1.24 mmol) was added and the resulting solution was refluxed for 6 h. After cooling to rt, ethyl acetate (100 mL) was added and the layers were separated. The organic portion was washed with water (50 mL) and brine (50 mL), then dried over anhyd sodium sulfate, filtered, and concentrated in vacuo to afford a thick red oil. This material was purified by flash chromatography on silica gel using a gradient elution from 100% hexanes initially to 5% ethyl acetate in hexanes to elute the product. Concentration in vacuo afforded 7.25 g (73%) of Preparation 18d as a pale yellow solid. HPLC Ret. time: 4.64 min.

Step 5: Example 133a

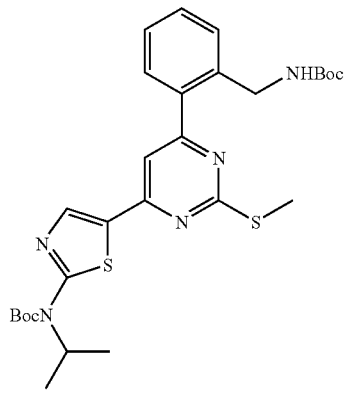

Example 133a was prepared from Preparation 18d and tert-butyl 2-(4,4,5,5-tetramethyl-1,3,2-dioxaborolan-2-yl) benzylcarbamate utilizing a similar procedure as described in Step 4 for Preparation 18d. Afforded Example 133a as an off-white solid (86%). HPLC Ret. time: 4.70 min.

Step 6: Example 133b

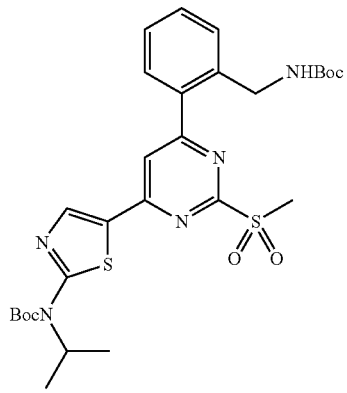

Example 133b was prepared from Example 133a utilizing a similar procedure as described in step 6 of Example 50. Afforded a pale yellow solid (89%). HPLC Ret. time: 4.14 min. LCMS MH$^+$ (m/z) 604.35.

Step 7: Example 133c

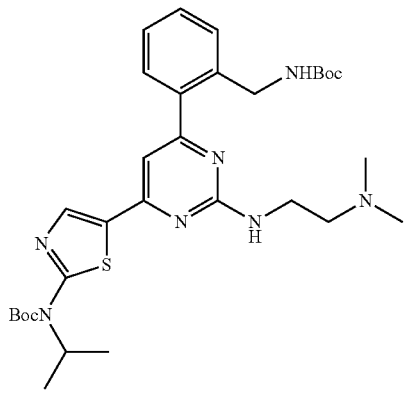

Example 133c was prepared from Example 133b utilizing a similar procedure as described in step 7 of Example 50. Afforded a white solid (66%). HPLC Ret. time: 3.57 min.

Step 8: Example 133d, N1-(4-(2-(aminomethyl)phenyl)-6-(2-(isopropylamino)thiazol-5-yl)pyrimidin-2-yl)-N2,N2-dimethylethane-1,2-diamine

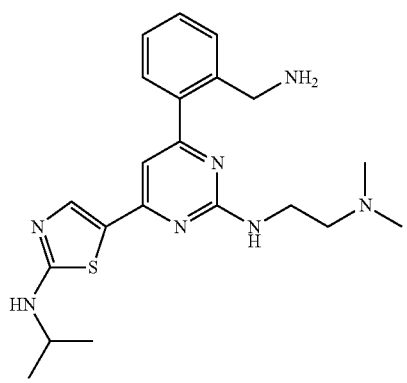

To a solution of Example 133c (0.70 g, 1.14 mmol) in dioxane (3 mL) was added a 4 N solution of HCl in dioxane (3 mL) and the resulting solution was warmed to 50° C. for 4.5 h. Nitrogen was bubbled into the solution to purge the excess HCl then the solution was diluted with diethyl ether (~5 mL). The resulting slurry was briefly sonicated and the solid was collected by vacuum filtration washing with additional diethyl ether (10 mL). The partially hygroscopic solid was dried in vacuo to afford 0.58 g (98%) of yellow powder as the tris-HCl salt of Example 133d. HPLC Ret. time: 1.30 min.

Step 9: Example 133

To a slurry of Example 133d (0.58 g, 1.12 mmol) in dichloromethane (12 mL) at rt was added diisopropylethylamine (0.68 mL, 3.91 mmol) and the resulting mixture was stirred until a clear, homogeneous solution resulted (~5 min). At this time, ethyl isocyanate (97 µL, 1.23 mmol) was added and the mixture was stirred at rt for 30 min then concentrated in vacuo. The resulting oil was purified by flash chromatography on silica gel using a gradient elution beginning with 100% dichloromethane and ending with a 10% of 2 M ammonia in methanol to 90% dichloromethane mixture. Fractions containing the desired product were concentrated to afford an oil which was dissolved in water (5 mL) and extracted with dichloromethane (5×10 mL). The combined extracts were washed with brine, dried over anhyd sodium sulfate, filtered, and concentrated in vacuo to afford 0.31 g (58%) of Example 133 as a pale yellow solid. HPLC Ret. time: 1.90 min. LCMS MH+ (m/z) 483.26.

Example 133e

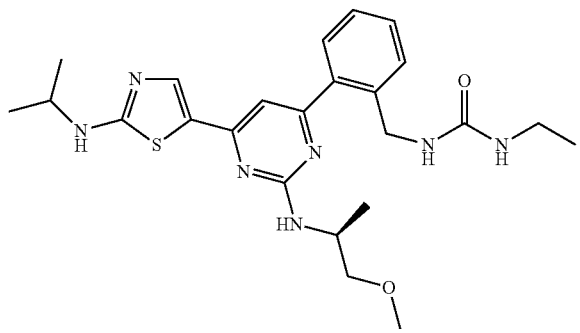

Step 1: Example 133f

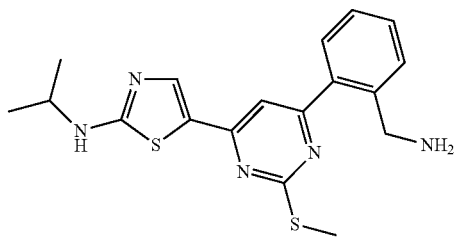

Example 133f was prepared from Example 127 utilizing a similar procedure as described in step 4 of Example 127. Afforded Example 133f as a yellow solid. HPLC Ret. time: 2.32 min. LCMS MH+ (m/z) 372.25.

Step 2: Example 133g

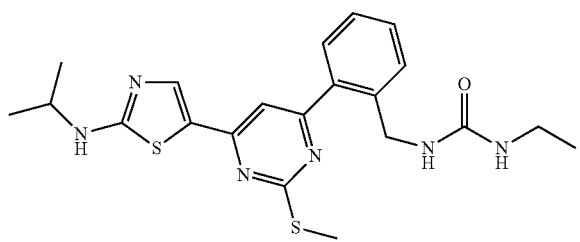

To a slurry of Example 133f (0.11 g, 0.25 mmol) in methylene chloride (1 mL) at rt were successively added ethyl isocyanate (22 µL, 0.28 mmol) and diisopropylethyl-amine (0.16 mL, 0.89 mmol) and the resulting mixture was stirred for 1 h. The mixture was concentrated in vacuo and the resulting mixture was sonicated with water (2 mL). The resulting solid was collected by filtration to afford 170 mg of the title compound as a light yellow solid. HPLC Ret. time: 3.17 min. LCMS MH+ (m/z) 443.31.

Step 3: Example 133h

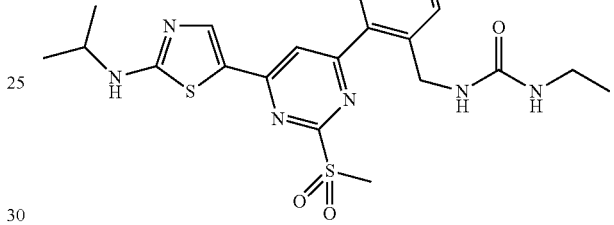

Example 133h was prepared from Example 133g utilizing a similar procedure as described in step 6 of Example 50. Afforded Example 133h as a yellow solid. HPLC Ret. time: 2.81 min. LCMS MH+ (m/z) 475.33.

Step 4: Example 133e

Example 133e was prepared from Example 133h utilizing a similar procedure as described in step 7 of Example 50 and by replacing 1-methylpiperazine with (S)-(+)-2-amino-1-methoxypropane. Afforded Example 133e as a yellow solid. HPLC Ret. time: 2.81 min. LCMS MH+ (m/z) 484.44. $^1$H NMR: (d$_6$-DMSO, 400 MHz) δ 8.00 (s, 1H), 7.94 (s, 1H), 7.42 (m, 2H), 7.38 (m, 1H), 7.30 (m, 1H), 7.04 (s, 1H), 6.78 (d, 1H), 6.14 (br s, 1H), 5.95 (br s, 1H), 4.28 (m, 2H), 4.12 (m, 1H), 3.78 (m, 1H), 3.38 (m, 1H), 3.20 (s, 3H), 2.95 (m, 3H), 1.15 (d, 6H), 1.12 (d, 3H), 0.93 (t, 3H).

Examples 133i-133z

Examples 133i-133z in Table 7a were prepared from Example 133h utilizing a similar procedure as described in Step 7 of Example 50.

TABLE 7a

| Ex. # | Compound Structure | HPLC and LCMS Data |
|---|---|---|
| 133i | 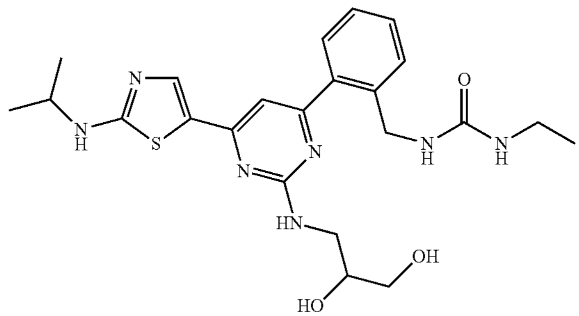 | HPLC $t_R$ = 2.29 min<br>LCMS [M + H]$^+$ = 486.41 |
| 133j | 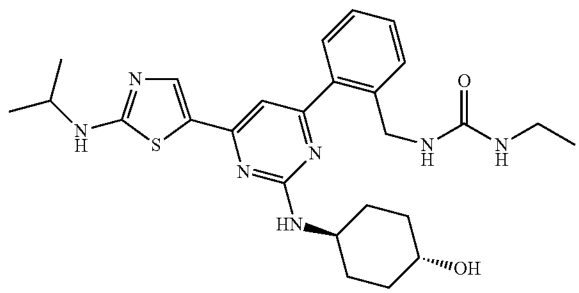 | HPLC $t_R$ = 2.70 min<br>LCMS [M + H]$^+$ = 510.43 |
| 133k | 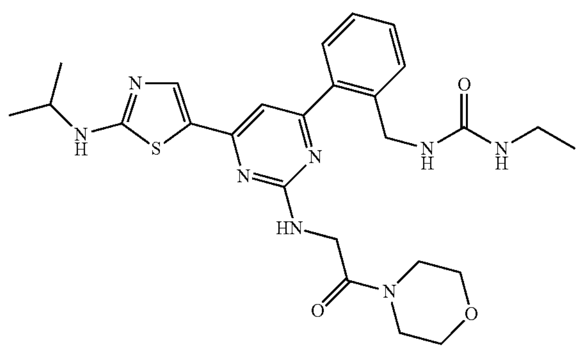 | HPLC $t_R$ = 2.43 min<br>LCMS [M + H]$^+$ = 539.45 |
| 133l | 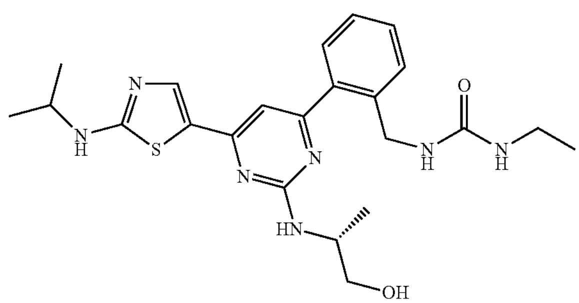 | HPLC $t_R$ = 2.58 min<br>LCMS [M + H]$^+$ = 470.44 |
| 133m | 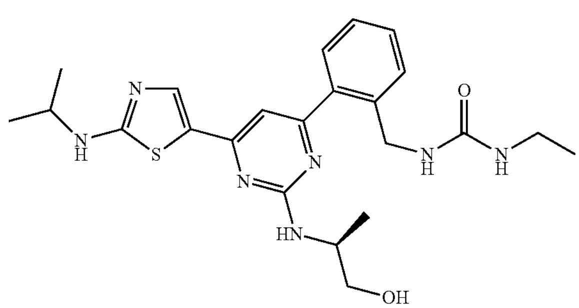 | HPLC $t_R$ = 2.56 min<br>LCMS [M + H]$^+$ = 470.43 |

TABLE 7a-continued

| Ex. # | Compound Structure | HPLC and LCMS Data |
|---|---|---|
| 133n | 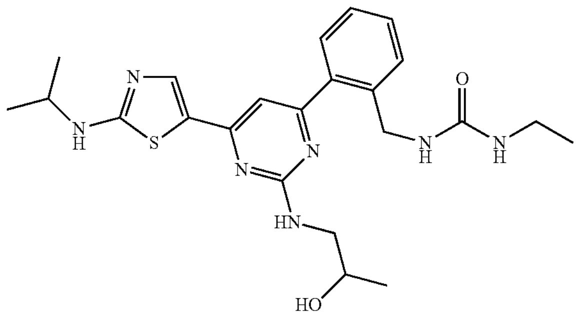 | HPLC $t_R$ = 2.54 min<br>LCMS [M + H]$^+$ = 470.44 |
| 133o | 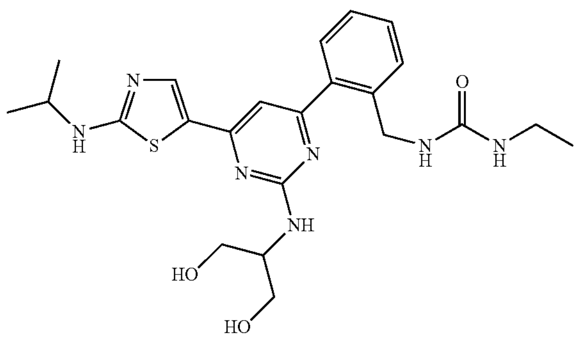 | HPLC $t_R$ = 2.23 min<br>LCMS [M + H]$^+$ = 486.41 |
| 133p | 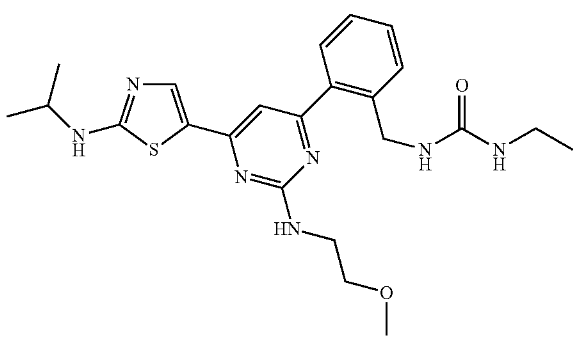 | HPLC $t_R$ = 2.63 min<br>LCMS [M + H]$^+$ = 470.44 |
| 133q | 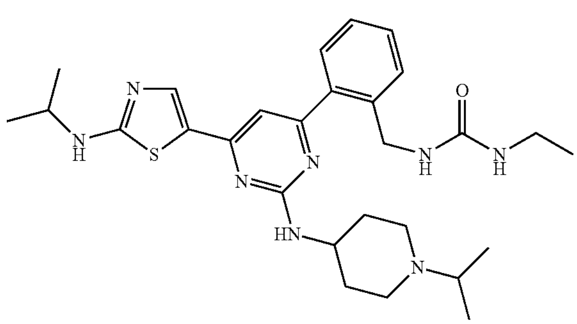 | HPLC $t_R$ = 1.99 min<br>LCMS [M + H]$^+$ = 537.50 |

TABLE 7a-continued

| Ex. # | Compound Structure | HPLC and LCMS Data |
|---|---|---|
| 133r | 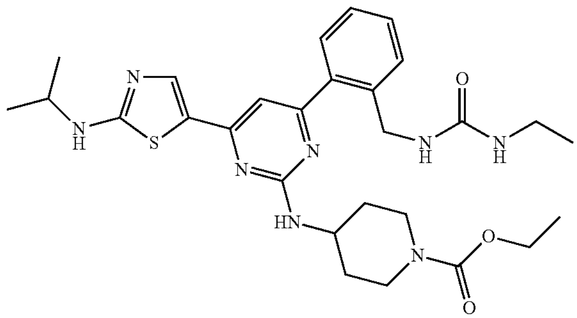 | HPLC $t_R$ = 3.05 min<br>LCMS [M + H]$^+$ = 567.51 |
| 133s | 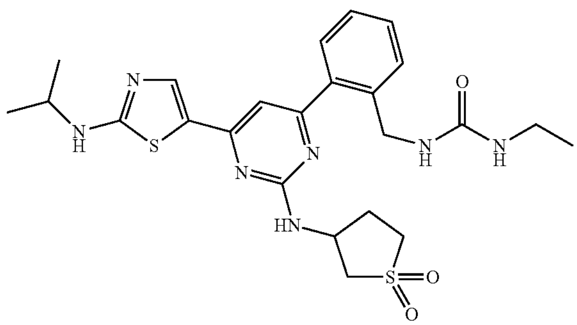 | HPLC $t_R$ = 2.47 min<br>LCMS [M + H]$^+$ = 530.5 |
| 133t | 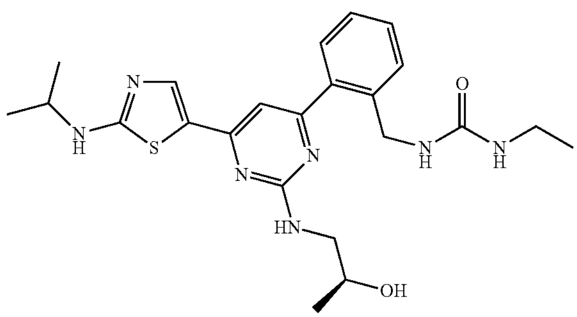 | HPLC $t_R$ = 2.54 min<br>LCMS [M + H]$^+$ = 470.36 |
| 133u | 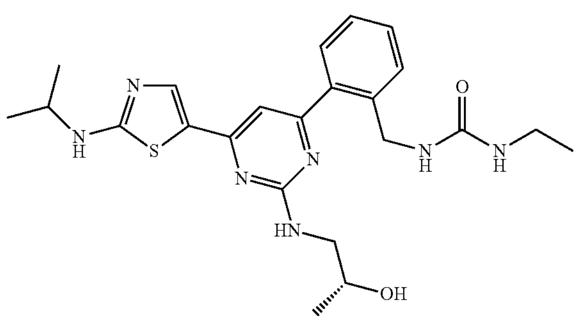 | HPLC $t_R$ = 2.53 min<br>LCMS [M + H]$^+$ = 470.36 |
| 133v | 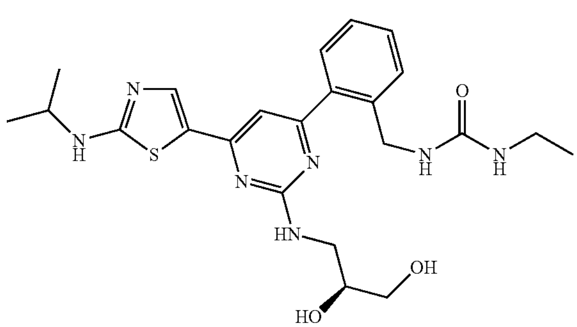 | HPLC $t_R$ = 2.29 min<br>LCMS [M + H]$^+$ = 486.31 |

TABLE 7a-continued

| Ex. # | Compound Structure | HPLC and LCMS Data |
|---|---|---|
| 133w | 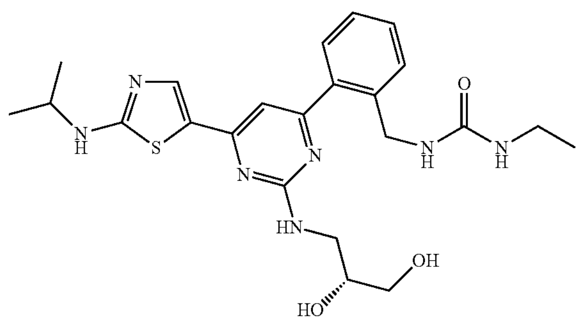 | HPLC $t_R$ = 2.29 min<br>LCMS [M + H]$^+$ = 486.31 |
| 133x | 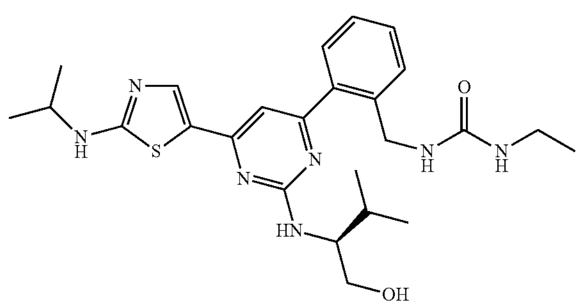 | HPLC $t_R$ = 2.91 min<br>LCMS [M + H]$^+$ = 498.35 |
| 133y | 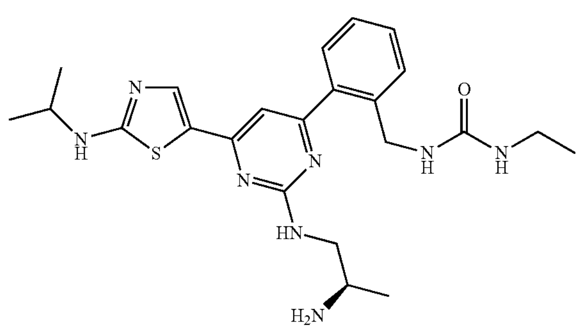 | HPLC $t_R$ = 1.94 min<br>LCMS [M + H]$^+$ = 469.40 |
| 133z | 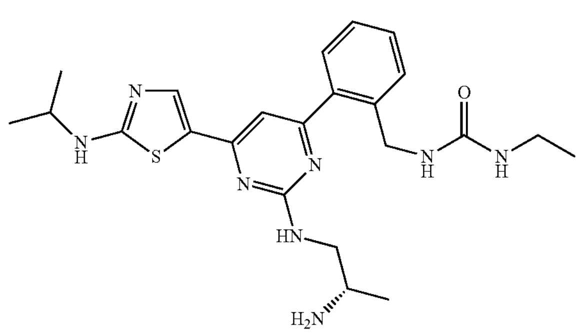 | HPLC $t_R$ = 1.94 min<br>LCMS [M + H]$^+$ = 469.40 |

Example 133za

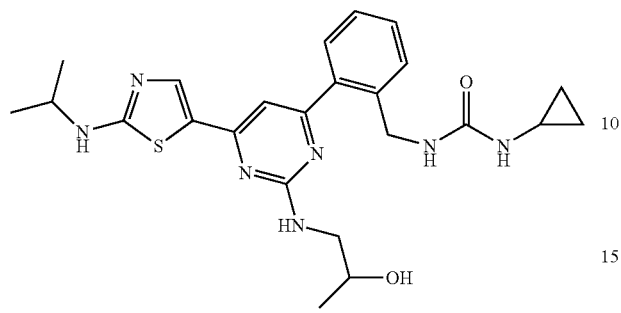

Step 1: Example 133zb

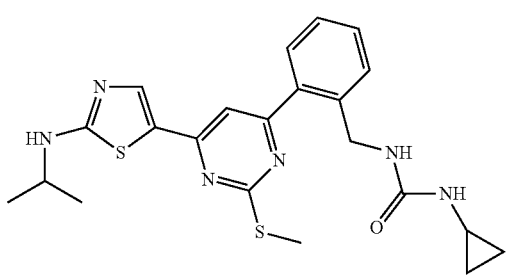

To a slurry of Example 133f (0.62 g, 1.27 mmol) in methylene chloride (4 mL) at 0° C. were successively added diisopropylethylamine (0.1.77 mL, 10 mmol) and CDI (309 mg, 1.90 mmol) and the resulting mixture was stirred at 0° C. for 1 h. Then cyclopropylamine (218 mg, 3.81 mmol) was added and the mixture was allowed to warm to rt overnight. The resulting mixture was diluted with EtOAc (200 mL) and was washed with aq. HCl (0.5 N, 20 mL×2), brine and dried over anhyd. sodium sulfate. Filtration and concentration in vacuo yielded a light yellow solid, which was purified by flash chromatography on silica gel eluting with 10% methanol in ethyl acetate mixture. Concentration in vacuo afforded 506 mg (88%) of Example 133zb as a yellow solid. HPLC Ret. time: 3.35 min. LCMS MH$^+$ (m/z) 455.29.

Step 2: Example 133zc

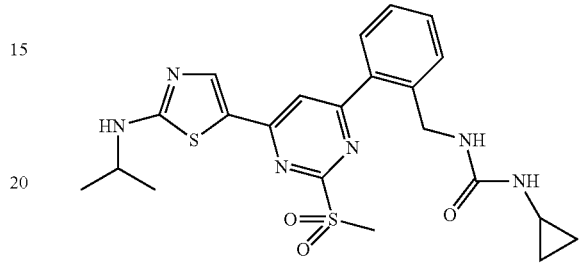

Example 133zc was prepared from Example 133zb using a similar procedure as described in Step 6 of Example 50. HPLC Ret. time: 2.94 min. LCMS MH$^+$ (m/z) 487.23.

Step 3: Example 133za

Example 133za was prepared from Example 133zc using a similar procedure as described in Step 7 of Example 50. HPLC Ret. time: 2.53 min. LCMS MH$^+$ (m/z) 482.23. $^1$H NMR: (d$_6$-DMSO, 400 MHz) δ 7.80 (d, 1H), 7.22 (m, 1H), 7.17 (m, 2H), 7.12 (m, 1H), 6.86 (s, 1H), 6.66 (m, 1H), 6.05 (m, 1H), 4.50 (m, 1H), 4.12 (m, 2H), 3.56 (m, 2H), 2.96 (m, 1H), 2.15 (m, 1H), 0.94 (d, 6H), 0.84 (d, 3H), 0.30 (m 2H), 0.0.06 (m, 2H).

Examples 133zd-133zk

Examples 133zd-133zk in Table 7aa were prepared from Example 133zc utilizing a similar procedure as described in Step 7 of Example 50.

TABLE 7aa

| Ex. # | Compound Structure | HPLC and LCMS Data |
|---|---|---|
| 133zd | 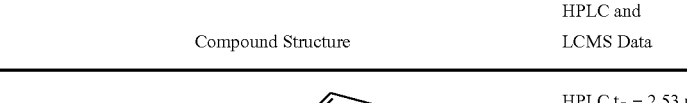 | HPLC t$_R$ = 2.53 min<br>LCMS [M + H]$^+$ = 482.33 |

TABLE 7aa-continued

| Ex. # | Compound Structure | HPLC and LCMS Data |
|---|---|---|
| 133ze | 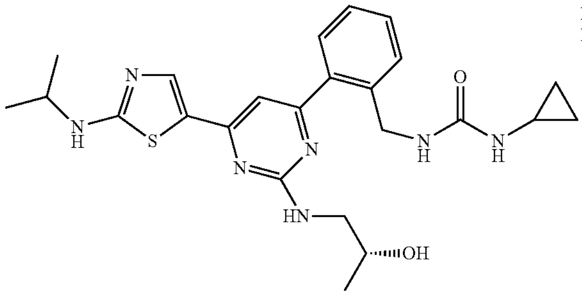 | HPLC $t_R$ = 2.53 min<br>LCMS [M + H]$^+$ = 482.33 |
| 133zf | 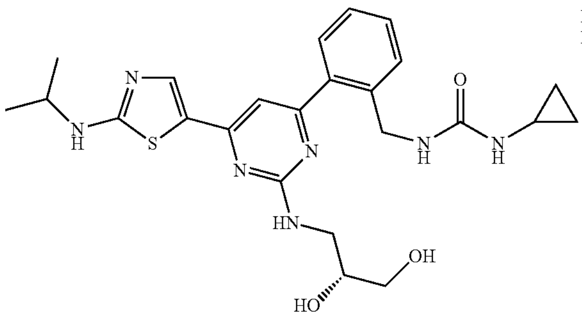 | HPLC $t_R$ = 2.30 min<br>LCMS [M + H]$^+$ = 498.30 |
| 133zg | 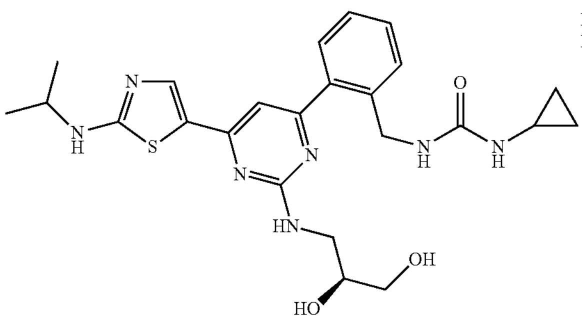 | HPLC $t_R$ = 2.30 min<br>LCMS [M + H]$^+$ = 498.30 |
| 133zh | 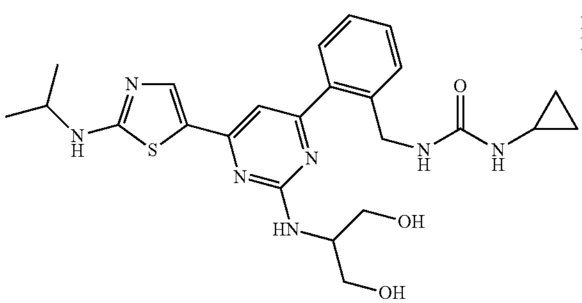 | HPLC $t_R$ = 2.22 min<br>LCMS [M + H]$^+$ = 498.30 |
| 133zi | 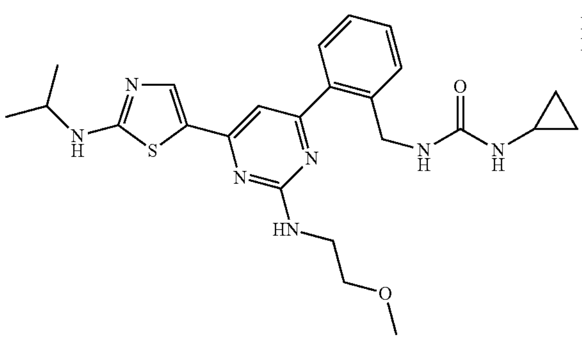 | HPLC $t_R$ = 2.63<br>LCMS [M + H]$^+$ = 482.33 |

TABLE 7aa-continued

| Ex. # | Compound Structure | HPLC and LCMS Data |
|---|---|---|
| 133zj | 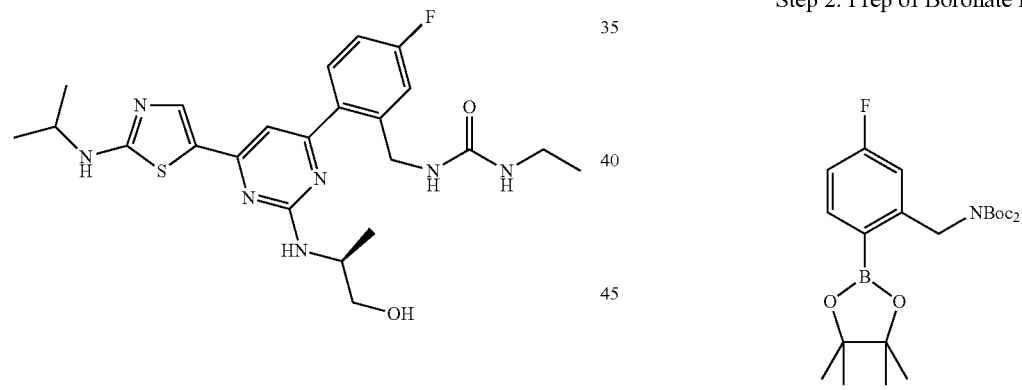 | HPLC $t_R$ = 1.99 min<br>LCMS [M + H]$^+$ = 481.39 |
| 133zk | 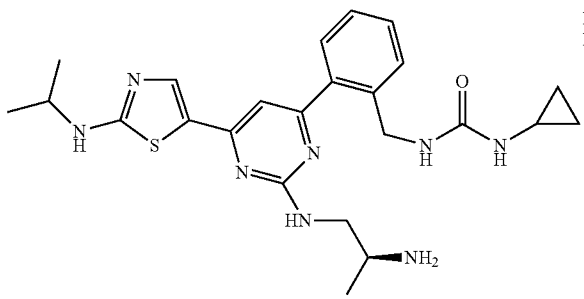 | HPLC $t_R$ = 1.99 min<br>LCMS [M + H]$^+$ = 481.39 |

Example 133aa

Step 1: Prep of Intermediate 1

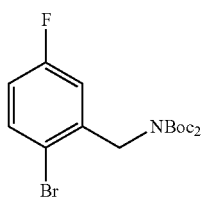

A mixture of 2-bromo-5-fluoro-benzylbromide (2.92 g, 13.4 mmol), di-tert-butyl iminodicarbonate (3.00 g, 11.2 mmol) and cesium carbonate (5.48 g, 16.8 mmol) in DMF (45 mL) was stirred for 18 h. Crushed ice was added and stirred for 3 h. Solid was collected and washed with water, dried in vacuo to afford 4.0 g (89%) of Intermediate 1 as a white solid as title compound. HPLC Ret. time: 4.11 min.

Step 2: Prep of Boronate Ester

A mixture of Intermediate 1 (1.46 g, 3.61 mmol), bis(pinacolato-)diborane (1.06 g, 4.15 mmol), potassium acetate and DMSO (0.18 mL) in a 1,4-dioxane (9 mL) was purged with argon for 15 minutes. [1,1'-bis(diphenylphosphino)ferrocene]dichloropalladium(II) complex with dichloromethane (89 mg, 0.108 mmol) was added and the resulting mixture was heated at 95° C. for 24 h. After cooling to rt, the mixture was extracted with ethyl acetate (3×60 mL) and the combined extracts were washed with brine and dried over anhyd. sodium sulfate. Filtration and concentration in vacuo yielded 1.90 g of a black oil. Purification by ISCO-flash chromatography on silica gel eluting with hexane and ethyl acetate mixture afforded after concentration in vacuo 1.50 g (92%) of the boronate ester as a colorless oil. HPLC Ret. time: 4.33 min.

Step 3: Example 133bb

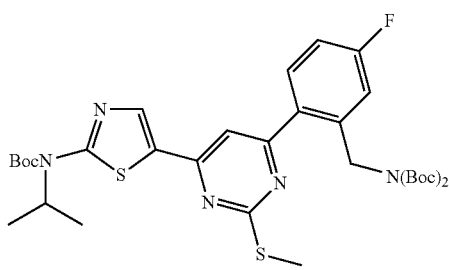

Example 133bb was prepared from Preparation 18d using a similar procedure as described in Step 4 for Preparation 18d.

Step 4: Example 133cc

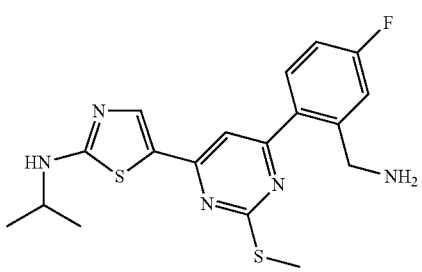

Example 133cc was prepared from Example 133bb utilizing a similar procedure as described in step 8 of Example 133. Afforded the bis-HCl salt of Example 133cc as a yellow solid. HPLC Ret. time: 2.32 min. LCMS MH$^+$ (m/z) 390.27.

Step 5: Example 133dd

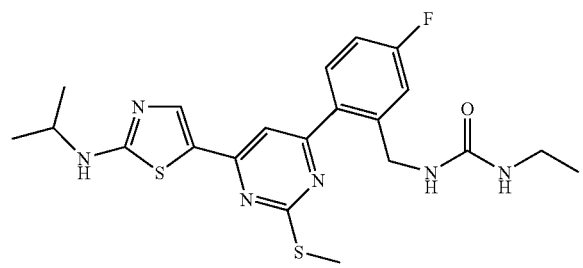

Example 133dd was prepared from Example 133cc using a similar procedure as described in Step 9 of Example 133. HPLC Ret. time: 3.24 min. LCMS MH$^+$ (m/z) 461.25.

Step 6: Example 133ee

Example 133ee was prepared from Example 133dd utilizing a similar procedure as described in step 6 of Example 50. HPLC Ret. time: 2.88 min. LCMS MH$^+$ (m/z) 493.17.

Step 7: Example 133aa

Example 133aa was prepared from Example 133ee utilizing a similar procedure as described in step 7 of Example 50. HPLC $t_R$=2.62 min, LCMS [M+H]$^+$=488.06.

Examples 133ff-133kk

Examples 133ff-133kk in Table 7b were prepared from Example 133 utilizing a similar procedure as described in Step 7 of Example 50.

TABLE 7b

| Ex. # | Compound Structure | HPLC and LCMS Data |
|---|---|---|
| 133ff | 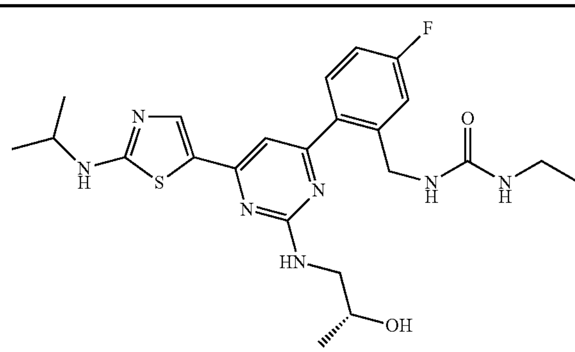 | HPLC $t_R$ = 2.59 min LCMS [M + H]$^+$ = 488.06 |

TABLE 7b-continued

| Ex. # | Compound Structure | HPLC and LCMS Data |
|---|---|---|
| 133gg | 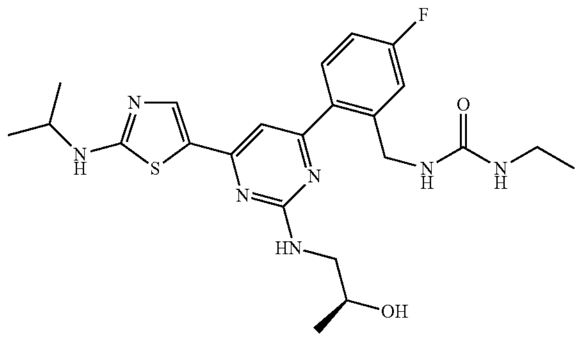 | HPLC $t_R$ = 2.59 min<br>LCMS [M + H]$^+$ = 488.06 |
| 133hh | 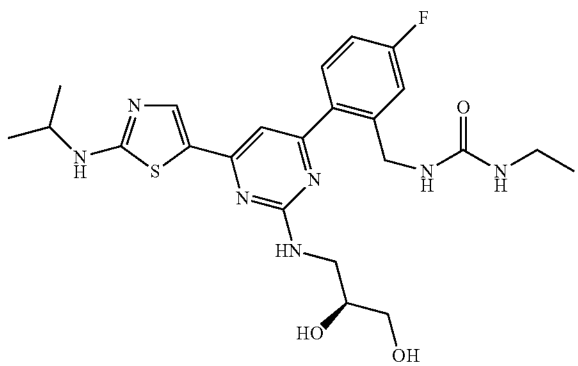 | HPLC $t_R$ = 2.37 min<br>LCMS [M + H]$^+$ = 504.06 |
| 133ii | 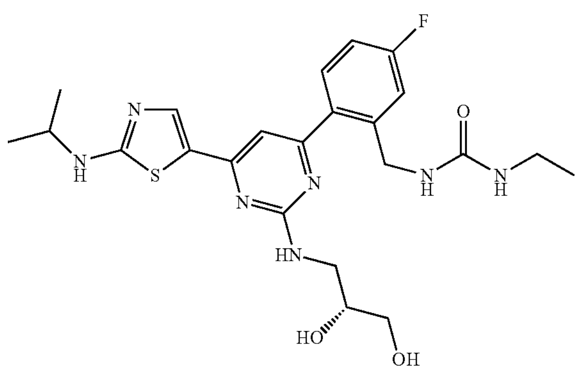 | HPLC $t_R$ = 2.37 min<br>LCMS [M + H]$^+$ = 504.06 |
| 133jj | 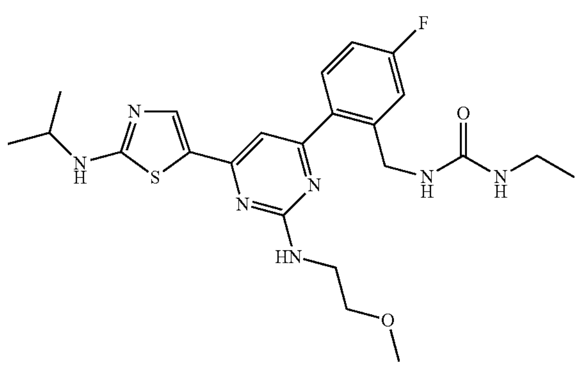 | HPLC $t_R$ = 2.70 min<br>LCMS [M + H]$^+$ = 488.06 |

TABLE 7b-continued

| Ex. # | Compound Structure | HPLC and LCMS Data |
|---|---|---|
| 133kk | 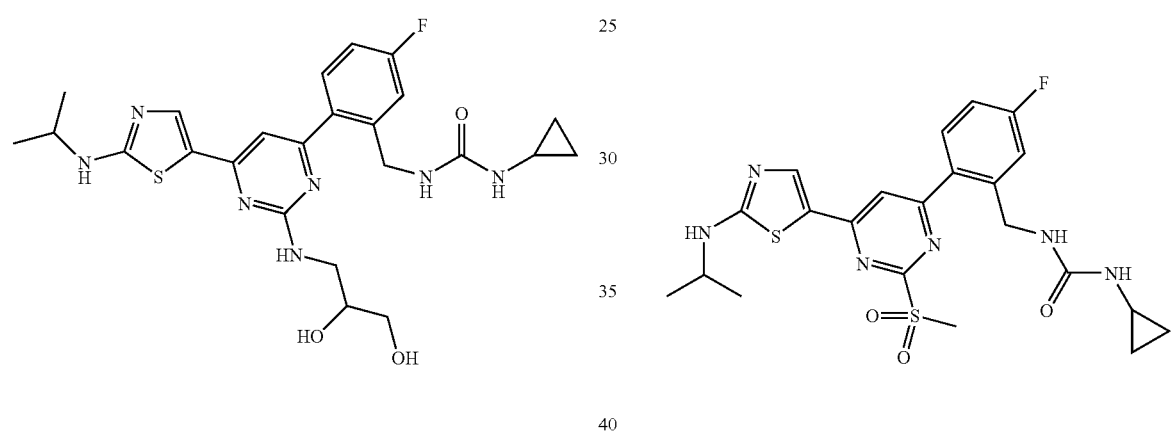 | HPLC $t_R$ = 2.32 min<br>LCMS [M + H]$^+$ = 504.06 |

Example 133ll

Step 1: Example 133 mm

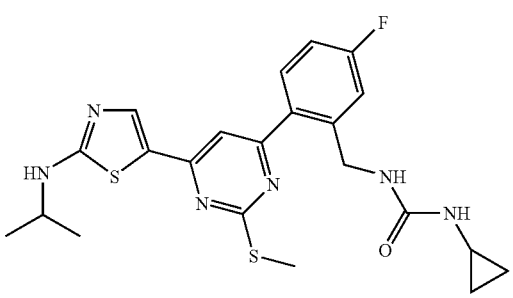

Prepared from Example 133cc.

Step 2: Example 133nn

Example 133nn was prepared from Example 133 mm using a similar procedure as described in Step 6 of Example 50.

Step 3: Example 133ll

Example 133ll was prepared from Example 133nn using a similar procedure as described in Step 7 of Example 50. HPLC $t_R$=2.40 min, LCMS [M+H]$^+$=516.14.

Examples 133oo-133 pp

Examples 133oo-133 pp in Table 7c were prepared from Example 133nn utilizing a similar procedure as described in Step 7 of Example 50.

TABLE 7c

| Ex. # | Compound Structure | HPLC and LCMS Data |
|---|---|---|
| 133oo | 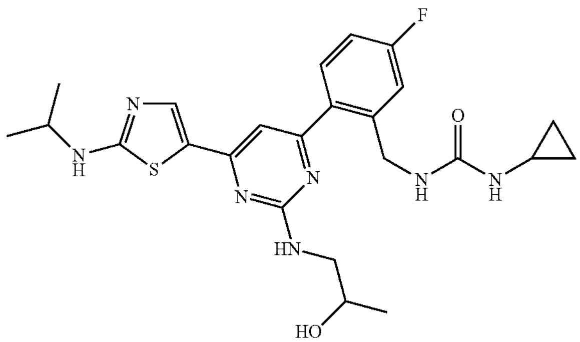 | HPLC $t_R$ = 2.61 min<br>LCMS [M + H]$^+$ = 500.09 |
| 133pp | 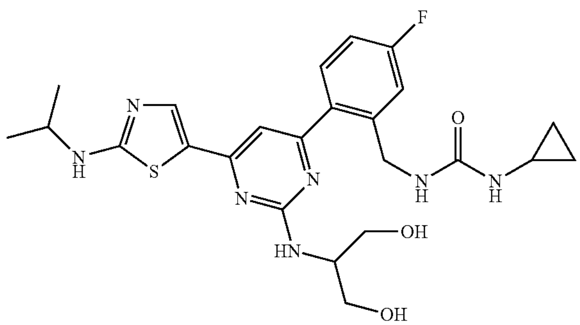 | HPLC $t_R$ = 2.28 min<br>LCMS [M + H]$^+$ = 516.06 |

Example 133qq

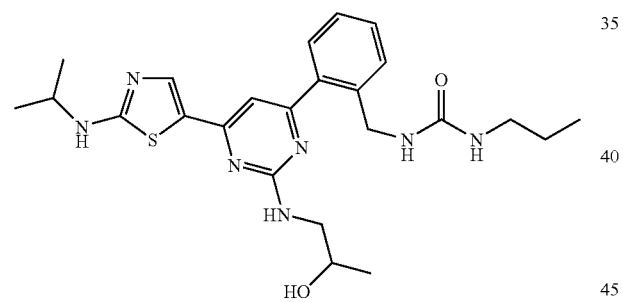

Step 1: Example 133rr

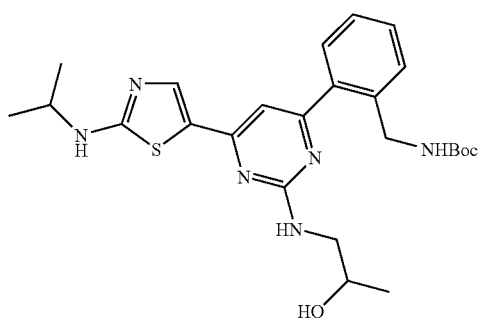

Example 133rr was prepared from Example 127 utilizing a similar procedure as described in step 7 of Example 50 and by replacing 1-methylpiperazine with 1-amino-2-propanol. Afforded Example 133rr as a yellow solid. HPLC Ret. time: 2.89 min. LCMS MH$^+$ (m/z) 499.36.

Step 2: Example 133ss

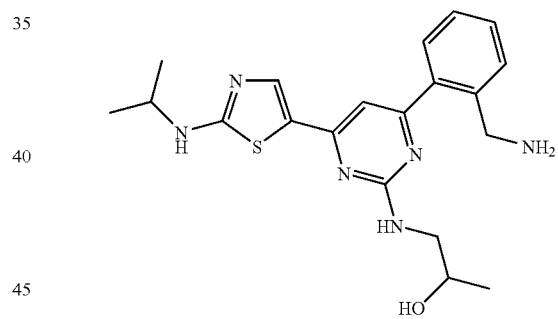

Example 133ss was prepared from Example 133rr utilizing a similar procedure as described in step 4 of Example 127. Afforded Example 133ss as a yellow solid. HPLC Ret. time: 1.93 min. LCMS MH$^+$ (m/z) 399.44.

Step 3: Example 133qq

Example 133qq was prepared from Example 133ss utilizing a similar procedure as described in step 9 of Example 133 and by replacing ethyl isocyanate with n-propyl isocyanate. Afforded Example 133qq as a yellow solid. HPLC Ret. time: 2.68 min. LCMS MH$^+$ (m/z) 484.39. $^1$H NMR: (d$_6$-DMSO, 400 MHz) δ 8.30 (s, 1H), 8.10 (s, 1H), 7.45 (m, 3H), 7.35 (m, 1H), 7.16 (m, 1H), 6.28 (s, 1H), 6.05 (m, 1H), 4.29 (m, 2H), 3.95 (m, 2H), 3.82 (m, 2H), 3.22 (m, 1H), 2.93 (m, 2H), 1.38 (m, 2H), 1.22 (d, 6H), 1.10 (d, 3H), 0.81 (t, 3H).

Examples 133tt-133uu

Examples 133tt and 133uu in Table 7d were prepared from Example 133ss utilizing a similar procedure as described for Step 9 of Example 133.

TABLE 7d

| Ex. # | Compound Structure | HPLC and LCMS Data |
|---|---|---|
| 133tt | 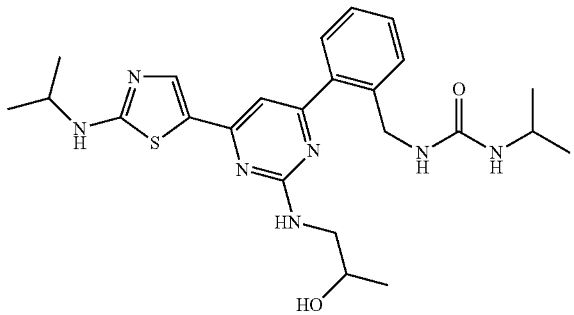 | HPLC $t_R$ = 2.66 min<br>LCMS [M + H]$^+$ = 484.38 |
| 133uu | 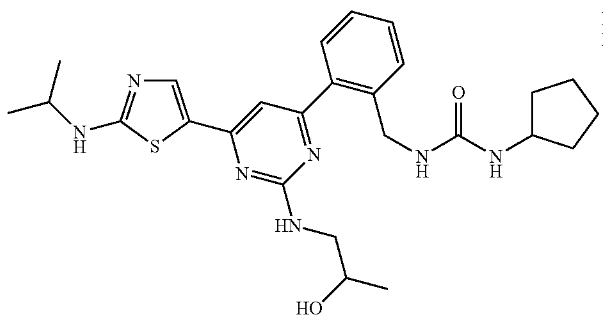 | HPLC $t_R$ = 2.84 min<br>LCMS [M + H]$^+$ = 510.37 |

Example 133vv

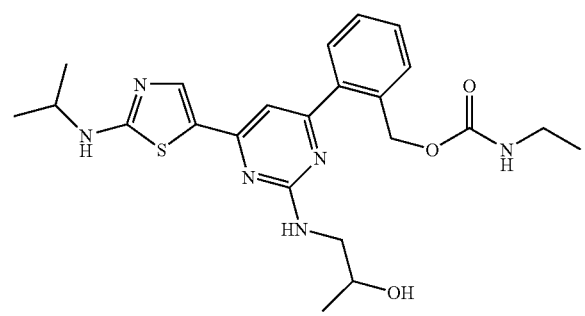

Step 1: Example 133ww

Example 133ww was prepared from Preparation 18 utilizing a similar procedure as described in step 5 of Example 50. Afforded Example 133ww as a yellow solid. HPLC Ret. time: 3.38 min. LCMS MH$^+$ (m/z) 373.18.

Step 2: Example 133xx

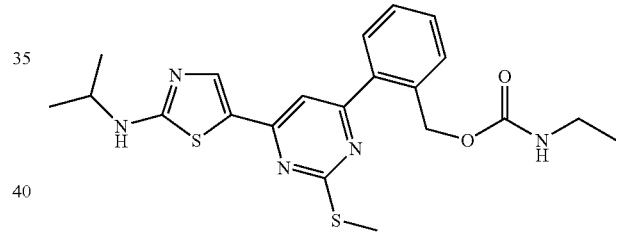

Example 133xx was prepared from Example 133ww utilizing a similar procedure as described in step 9 of Example 133. Afforded Example 133xx as a yellow solid. HPLC Ret. time: 3.40 min. LCMS MH$^+$ (m/z) 443.97. $^1$H NMR: (d$_6$-DMSO, 500 MHz) δ 8.28 (d, 1H), 8.17 (s, 1H), 7.66 (s, 1H), 7.62 (d, 1H), 7.52 (m, 2H), 7.51 (m, 1H), 5.21 (s, 2H), 3.84 (m, 1H), 2.95 (m, 2H), 2.50 (s, 3H), 1.20 (d, 6H), 0.96 (t, 3H).

Step 3: Example 133yy

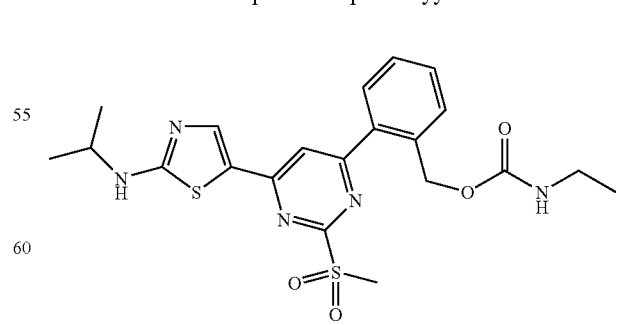

Example 133yy was prepared from Example 133xx utilizing a similar procedure as described in step 6 of Example 50. Afforded Example 133yy as a bright yellow solid. HPLC Ret. time: 2.84 min. LCMS MH$^+$ (m/z) 475.97.

Step 4: Example 133vv

Example 133vv was prepared from Example 133yy utilizing a similar procedure as described in step 7 of Example 50. Afforded Example 133vv as a yellow solid. HPLC Ret. time: 2.59 min. LCMS MH+ (m/z) 471.05. $^1$H NMR: (d$_6$-DMSO, 400 MHz) δ 8.45 (d, 1H), 8.10 (s, 1H), 7.58 (m, 1H), 7.52 (m, 2H), 7.48 (m, 1H), 7.24 (m, 1H), 7.19 (s, 1H), 5.30 (m, 1H), 5.21 (s, 2H), 3.85 (m, 2H), 3.20 (m, 1H), 2.98 (m, 2H), 1.20 (d, 6H), 1.09 (d, 3H), 0.96 (t, 3H).

Example 133zz

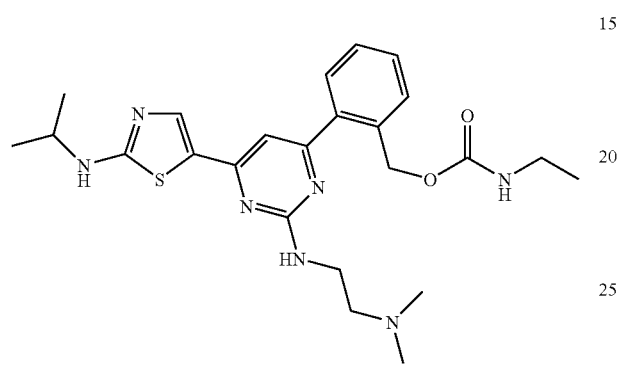

Example 133zz was prepared from Example 133yy utilizing a similar procedure as described in step 9 of Example 133. Afforded Example 133zz as a yellow solid. HPLC Ret. time: 2.06 min. LCMS MH+ (m/z) 483.63.

Example 133aaa

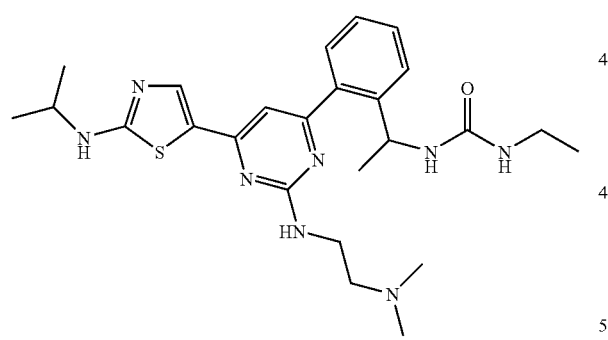

Step 1: Example 133bbb

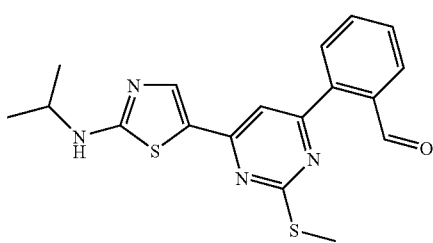

To a solution of Example 133ww (0.20 g, 0.54 mmol) in THF (2 mL) at rt was added MnO$_2$ (0.46 g, 5.4 mmol) in one portion and the resulting mixture was stirred at rt for 16 h. The reaction mixture was filtered through a pad of celite and the filter cake was washed with THF (10 mL×3) and the filtrate was concentrated in vacuo to afford 146 mg of light brown solid as the title compound. HPLC Ret. time: 2.41 min. LCMS MH+ (m/z) 371.16.

Step 2: Example 133ccc

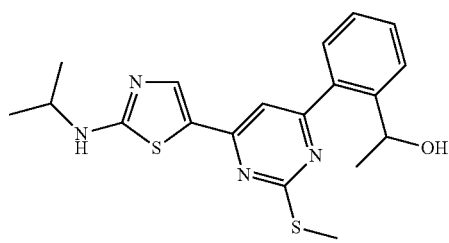

To a solution of MeMgCl (0.6 mL, 3M in THF, 1.8 mmol) in THF (0.5 mL) at 0° C. was added Example 133bbb in THF (2 mL) via cannula. After stirring at 0° C. for 1 h, sat. aq. NH$_4$Cl (5 mL) was added and the mixture was extracted with EtOAc (200 mL). The extracts were washed with brine and dried over anhyd. sodium sulfate. Filtration and concentration in vacuo yielded 196 mg of a brown solid, which was purified by flash chromatography on silica gel eluting with 50% ethyl acetate in hexanes mixture. Concentration in vacuo afforded 140 mg (96%) of Example 133ccc as a yellow foam. HPLC Ret. time: 3.29 min. LCMS MH+ (m/z) 387.15.

Step 3: Example 133ddd

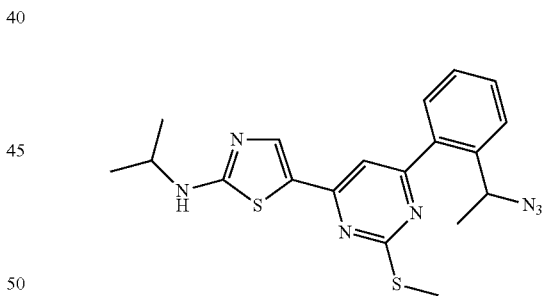

To a solution of Example 133ccc (430 mg, 1.11 mmol) and DPPA (530 μL, 2.45 mmol) in toluene (4.5 mL) at 0° C. was added DBU (366 μL, 2.45 mmol) via syringe. After stirring at 0° C. for 1 h, the mixture was allowed to warm to rt. Ethyl acetate (200 mL) was added and the mixture was washed with water (2×), brine and dried over anhyd. sodium sulfate. Filtration and concentration in vacuo yielded 750 mg of a yellow oil, which was purified by flash chromatography on silica gel eluting with 50% ethyl acetate in hexanes mixture. Concentration in vacuo afforded 150 mg (93%) of Example 133ddd as a yellow solid. HPLC Ret. time: 3.96 min. LCMS MH+ (m/z) 412.16. $^1$H NMR: (d$_6$-DMSO, 400 MHz) δ 8.32 (d, 1H), 8.21 (s, 1H), 7.68 (s, 1H), 7.63 (m, 1H), 7.59 (m, 1H), 7.53 (m, 1H), 7.50 (m, 1H), 5.27 (q, 1H), 3.86 (m, 1H), 2.53 (s, 3H), 1.49 (d, 3H), 1.19 (d, 6H).

Step 4: Example 133eee

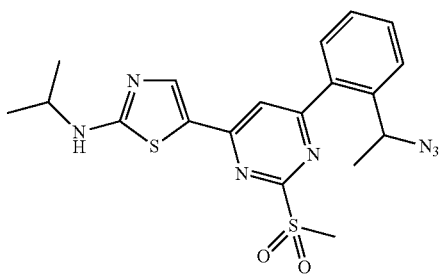

Example 133eee was prepared from Example 133ddd utilizing a similar procedure as described in Step 6 of Example 50. Afforded Example 133eee as a light yellow solid. HPLC Ret. Time: 3.30 min. LCMS MH+ (m/z) 444.2.

Step 5: Example 133fff

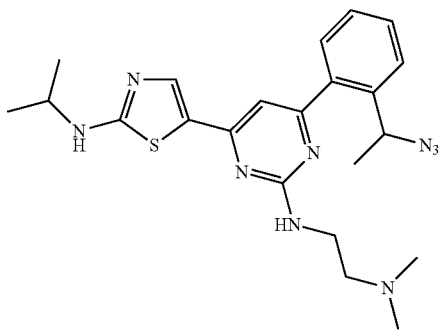

Example 133fff was prepared from Example 133eee utilizing a similar procedure as described in Step 7 of Example 50. Afforded Example 133fff as a light yellow solid. HPLC Ret. Time: 2.48 min. LCMS MH+ (m/z) 452.18.

Step 6: Example 133ggg

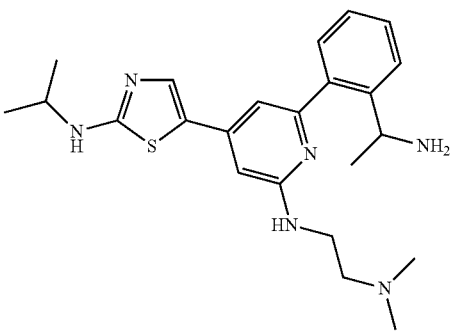

To a solution of Example 133fff (68 mg, 0.15 mmol) in THF (1 mL) and water (20 µL 0.45 mmol) was added triphenylphosphine (59 mg, 0.22 mmol) and the resulting mixture was warmed to 60° C. for 3 h. After cooling to rt, the THF was removed in vacuo and the crude material was purified by reverse-phase preparative HPLC. The fractions containing the product were concentrated to remove the methanol and the resulting aqueous solution was lyophilized to afford 70 mg of Example 133ggg as a yellow solid. HPLC Ret. time: 1.43 min. LCMS MH+ (m/z)=426.25.

Step 7: Example 133aaa

Example 133aaa was prepared from Example 133ggg utilizing a similar procedure as described in the step 9 of Example 133. Afforded Example 133aaa as a light yellow solid. HPLC Ret. Time: 1.97 min. LCMS MH+ (m/z) 497.33. $^1$H NMR: (d$_6$-DMSO, 500 MHz) δ 8.02 (d, 1H), 7.93 (s, 1H), 7.45 (m, 1H), 7.42 (m, 1H), 7.34 (m, 1H), 7.29 (m, 1H), 7.13 (s, 1H), 6.78 (m, 1H), 6.38 (m, 1H), 5.70 (m, 1H), 5.14 (m, 1H), 3.81 (m, 1H), 3.37 (m, 2H), 2.92 (m, 2H), 2.42 (m, 2H), 2.16 (br. s, 6H), 1.28 (m, 3H), 1.18 (d, 6H), 0.91 (t, 3H).

Example 133hhh (S)-1-(1-(2-(2-(2-(dimethylamino)ethylamino)-6-(2-(isopropylamino)thiazol-5-yl)pyrimidin-4-yl)phenyl)ethyl)-3-ethylurea

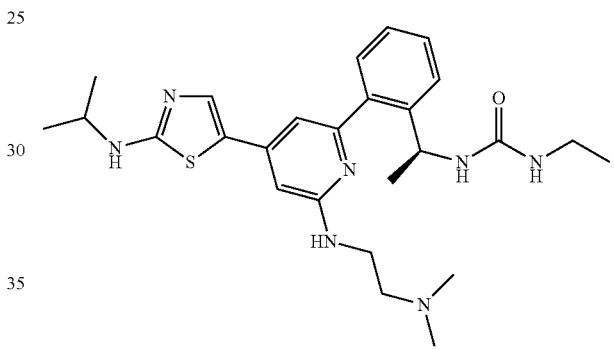

Prepared by chiral chromatography separation of Example 133aaa. Afforded a light yellow powder. HPLC Ret. Time: 1.97 min. LCMS MH+ (m/z) 497.33.

Example 133iii (R)-1-(1-(2-(2-(2-(dimethylamino)ethylamino)-6-(2-(isopropylamino)thiazol-5-yl)pyrimidin-4-yl)phenyl)ethyl)-3-ethylurea

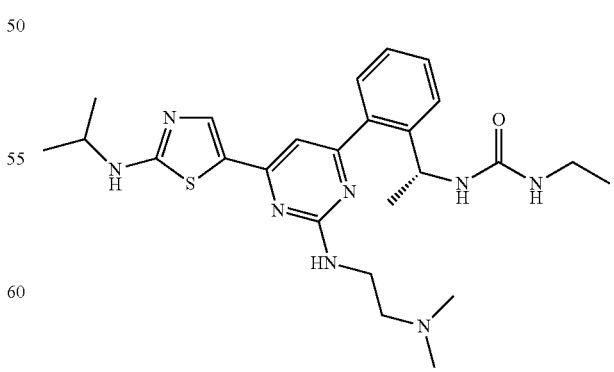

Prepared by chiral chromatography separation of Example 133aaa. Afforded a light yellow powder. HPLC Ret. Time: 1.97 min. LCMS MH+ (m/z) 497.33.

Example 134

5-(6-(2-chlorophenyl)pyrimidin-4-yl)-N-propylthiazol-2-amine

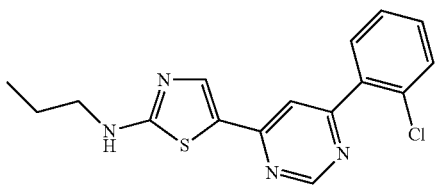

To a solution of Example 52 (0.10 g, 0.25 mmol) in THF (6 mL) at −78° C. was added lithium borohydride (1.6 mL, 1.0M in THF) dropwise and the resulting was stirred at −78° C. for 4 h. The reaction was quenched by a sequential addition of methanol (0.5 mL), 0.2 mL of 6N aqueous sodium hydroxide solution, and water. The resulting mixture was stirred at rt for 4 h and concentrated in vacuo to remove the methanol and THF. The solid was collected by filtration and washed with water. The solid was slurried in methanol and collected by vacuum filtration to afford 59 mg of yellow solid as the title compound. HPLC Ret. time: 3.39 min. LCMS MH$^+$ (m/z) 331.22. $^1$H NMR: (d$_6$-DMSO, 500 MHz) δ 9.00 (s, 1H), 8.38 (t, 1H), 8.17 (s, 1H), 8.01 (s, 1H), 7.62 (m, 2H), 7.50 (m, 2H), 3.23 (m, 2H), 1.57 (m, 2H), 0.91 (m, 3H).

Examples 135-136b

Examples 135-136b in Table 8 were prepared utilizing a similar procedure as described for Example 134.

TABLE 8

| Ex. # | Compound Structure/Name | HPLC and LCMS Data |
|---|---|---|
| 135 | 5-(6-(2-chlorophenyl)pyrimidin-4-yl)-N-isopropylthiazol-2-amine | HPLC t$_R$ = 3.33 min<br>LCMS [M + H]$^+$ = 331.22 |
| 136 | tert-butyl 2-(6-(2-(isopropylamino)thiazol-5-yl)pyrimidin-4-yl)benzylcarbamate | HPLC t$_R$ = 3.47 min<br>LCMS [M + H]$^+$ = 426.28 |
| 136a | 1-ethyl-3-(2-(6-(2-(isopropylamino)thiazol-5-yl)pyrimidin-4-yl)benzyl)urea | HPLC t$_R$ = 2.51 min<br>LCMS [M + H]$^+$ = 397.31 |
| 136b | 1-cyclopropyl-3-(2-(6-(2-(isopropylamino)thiazol-5-yl)pyrimidin-4-yl)benzyl)urea | HPLC t$_R$ = 2.66 min<br>LCMS [M + H]$^+$ = 409.30 |

Example 137

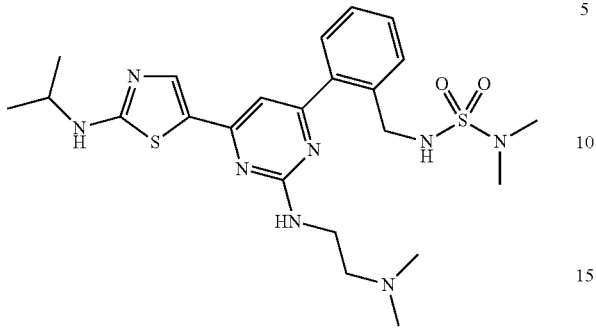

To a slurry of Example 130 (0.025 g, 0.06 mmol) in methylene chloride (1 mL) at rt were successively added dimethylsulfamoyl chloride (11 mg, 0.07 mmol) and triethylamine (0.04 mL, 0.3 mmol) and the resulting mixture was stirred at rt for 4 h. The mixture was concentrated in vacuo. Purification by reverse-phase preparative HPLC afforded fractions containing the desired product. These fractions were neutralized by adding saturated sodium bicarbonate (~1 mL) and concentrated in vacuo to remove the methanol. The resulting aqueous portion was extracted with ethyl acetate (3×10 mL) and the combined extracts were washed with brine (5 mL), dried over anhyd sodium sulfate, filtered, and concentrated in vacuo to afford 13 mg of the title compound as a pale yellow solid. HPLC Ret. time: 1.98 min. LCMS MH$^+$ (m/z) 519.36.

Example 137a

Methyl 2-(2-(2-hydroxypropylamino)-6-(2-(isopropylamino)thiazol-5-yl)pyrimidin-4-yl)benzylcarbamate

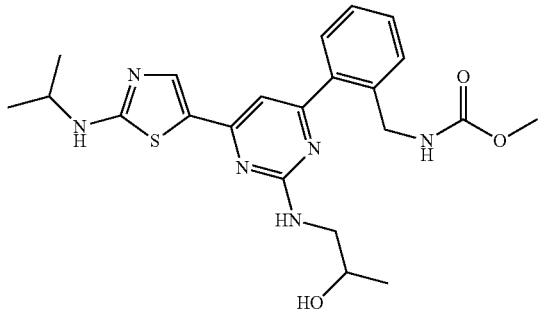

Example 137a was prepared from Example 133ss utilizing a similar procedure as described in the Example 137 by replacing dimethylsulfamoyl chloride with methyl chloroformate. Yellow solid. HPLC Ret. time: 2.46 min. LCMS MH$^+$ (m/z) 457.34. $^1$H NMR: (d$_6$-DMSO, 400 MHz) δ 8.25 (s, 1H), 8.10 (s, 1H), 7.57 (m, 1H), 7.49 (m, 2H), 7.40 (m, 1H), 7.16 (m, 2H), 4.37 (m, 2H), 3.84 (m, 1H), 3.48 (s, 3H), 3.30 (m, 1H), 3.22 (m, 1H), 2.97 (m, 1H), 1.22 (d, 6H), 1.10 (d, 3H).

Examples 137b-137e

Examples 137b-137e in Table 8a were prepared utilizing a similar procedure as described for Example 137a.

TABLE 8a

| Ex. # | Compound Structure/Name | HPLC and LCMS Data |
|---|---|---|
| 137b | | HPLC t$_R$ = 2.64 min<br>LCMS [M + H]$^+$ = 471.31 |
| 137c | | HPLC t$_R$ = 2.46 min<br>LCMS [M + H]$^+$ = 441.29 |

TABLE 8a-continued

| Ex. # | Compound Structure/Name | HPLC and LCMS Data |
|---|---|---|
| 138d | | HPLC $t_R$ = 2.61 min<br>LCMS [M + H]$^+$ = 469.39 |
| 137e | | HPLC $t_R$ = 2.50 min<br>LCMS [M + H]$^+$ = 467.33 |

Example 137f

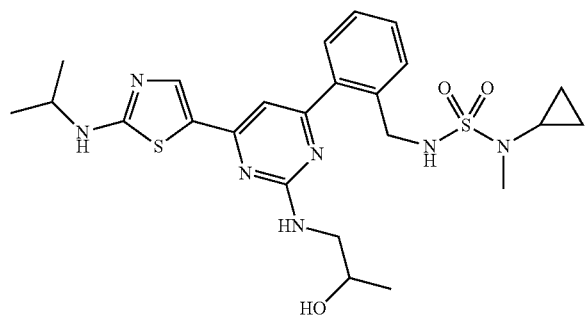

To a solution of chlorosulfonylisocyanate (18 μAl, 0.21 mmol) in dichloroethane (2 mL) at 0° C. were added 2-chloroethanol (15 μAl, 0.21 mmol) and the resulting mixture was stirred at 0° C. for 1.5 h. The resulting clear solution was added to the solution of Example 133ss (100 mg, 0.21 mmol) and triethylamine (150 μL, 1.0 mmol) in dichloroethane (2 mL) at 0° C. via cannula. The resulting mixture was stirred at 0° C. for 1 h and then rt overnight. The reaction was quenched with 0.4N HCl (10 mL) and extracted with dichloromethane (30 mL×2). The combined organic extracts were washed with brine and dried over anhyd. sodium sulfate. Filtration and concentration in vacuo yielded a yellow foam, which was dissolved in acetonitrile (1 mL) and cyclopropylamine was added and heated at 60° C. for 2 h. Purification by reverse-phase preparative HPLC afforded fractions containing the desired product. These fractions were neutralized by adding saturated sodium bicarbonate (~1 mL) and concentrated in vacuo to remove the methanol. The resulting aqueous portion was extracted with ethyl acetate (3×10 mL) and the combined extracts were washed with brine (5 mL), dried over anhyd sodium sulfate, filtered, and concentrated in vacuo to afford 4 mg of the title compound as a pale white solid. HPLC Ret. time: 2.49 min. LCMS MH$^+$ (m/z) 518.38. $^1$H NMR: (d$_6$-DMSO, 400 MHz) δ 8.12 (m, 1H), 8.06 (s, 1H), 7.70 (m, 1H), 7.56 (m, 2H), 7.42 (m, 2H), 7.32 (s, 1H), 7.18 (s, 1H), 7.06 (m, 1H), 4.75 (m, 1H), 4.24 (m, 2H), 3.84 (m, 2H), 3.30 (m, 1H), 2.25 (m, 1H), 1.25 (d, 6H), 1.13 (d, 3H), 0.45 (m, 4H).

Examples 137g-137i

Examples 137g-137i in Table 8b were prepared utilizing a similar procedure as described for Example 137f.

TABLE 8b

| Ex. # | Compound Structure/Name | HPLC and LCMS Data |
|---|---|---|
| 137g | | HPLC $t_R$ = 2.52 min<br>LCMS [M + H]$^+$ = 605.43 |
| 137h | | HPLC $t_R$ = 2.68 min<br>LCMS [M + H]$^+$ = 518.28 |
| 137i | | HPLC $t_R$ = 2.63 min<br>LCMS [M + H]$^+$ = 605.32 |

Example 138

5-(6-(2-chlorophenyl)-2-(pyridin-2-yl)pyrimidin-4-yl)-N-ethylthiazol-2-amine

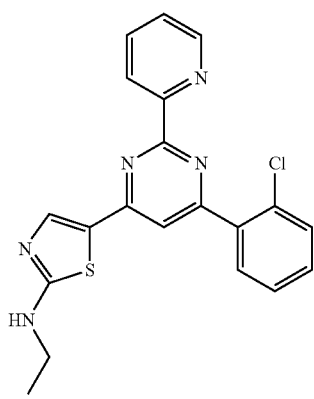

Step 1: Preparation 19

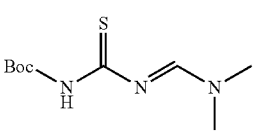

Preparation 19 was prepared from N-tert-butoxycarbonylthiourea utilizing a similar procedure as described in step 1 of Example 1. Clear oil. HPLC Ret. time: 2.72 min. $^1$H NMR: (d$_3$-CD$_3$Cl, 500 MHz): δ 8.71 (s, 1H), 8.20 (s, 1H), 3.20 (s, 3H), 3.15 (s, 3H), 1.49 (s, 9H).

Step 2: Preparation 20

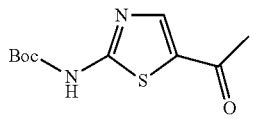

Preparation 20 was prepared from Preparation 19 utilizing a similar procedure as described in step 2 of Example 1. Tan solid (75% yield for two steps). HPLC Ret. time: 2.71 min. LCMS MH+ (m/z) 243.18.

Step 3: Preparation 21

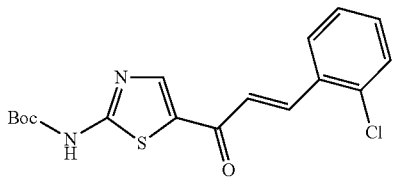

Preparation 21 was prepared from Preparation 20 utilizing a similar procedure as described in Step 1 of Example 24. Near white solid (67% yield). HPLC Ret. time: 3.91 min. LCMS MH+ (m/z) 365.04.

Step 4: Example 139, tert-butyl 5-(6-(2-chlorophenyl)-2-(pyridin-2-yl)pyrimidin-4-yl)thiazol-2-ylcarbamate

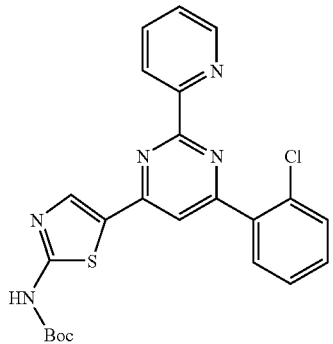

Example 139 was prepared from Preparation 21 utilizing a similar procedure as described for Example 2. Yellow solid (88% yield). HPLC Ret. time: 3.66 min. LCMS MH+ (m/z) 466.05. $^1$H NMR (d$_3$-CD$_3$Cl, 500 MHz); δ 8.91 (m, 1H), 8.68 (m, 1H), 8.22 (s, 1H), 9.94 (m, 2H), 7.89 (s, 1H), 7.42-7.50 (m, 4H), 7.13 (m, 1H), 1.59 (s, 9H).

Step 5: Example 140, 5-(6-(2-chlorophenyl)-2-(pyridin-2-yl)pyrimidin-4-yl)thiazol-2-amine

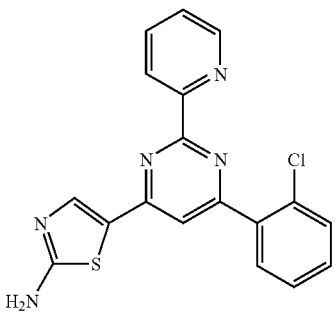

To a solution of Example 139 (112 mg, 0.24 mmol) in anhydrous dioxane (0.5 mL) was added a solution of 4N HCl in dioxane (0.5 mL) and the resulting solution was stirred at rt for 20 h. The mixture was diluted with ether (~50 mL) and the solid was collected by vacuum filtration. The solid was purified by reverse-phase preparative HPLC and the fractions containing the product were neutralized by adding saturated aq sodium bicarbonate solution (~1 mL) and concentrated in vacuo to remove the methanol. The resulting aqueous slurry was filtered by vacuum filtration to collect the solid. Drying in vacuo afforded 42 mg (58%) of Example 140 as a yellow solid. HPLC Ret. time: 2.55 min. LCMS MH+ (m/z) 366.54. $^1$H NMR (d$_6$-DMSO, 500 MHz): δ 8.83 (m, 1H), 8.55 (m, 1H), 8.33 (s, 1H), 8.29 (m, 3H), 8.17 (s, 1H), 7.85 (m, 1H), 7.75 (m, 1H), 7.66 (m, 1H), 7.56 (m, 2H).

Step 6: Example 141, 4-(2-bromothiazol-5-yl)-6-(2-chlorophenyl)-2-(pyridin-2-yl)pyrimidine

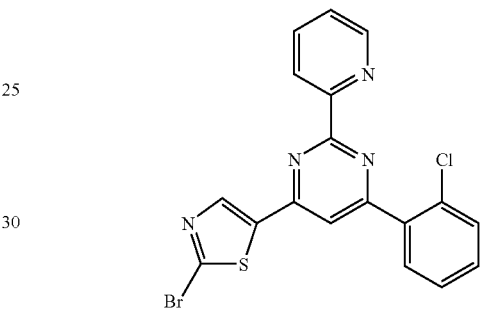

To a slurry of Example 140 (460 mg, 1.26 mmol) and copper(II) bromide (337 mg, 1.51 mmol) in anhydrous acetonitrile (5 mL) at 0° C. was added t-butyl nitrite (0.18 mL, 1.51 mmol) and the resulting solution was stirred at rt for 20 h. The mixture was diluted with ethyl acetate (150 mL) and the organic layer was washed with water (2×50 mL), 0.5N aq. HCl (2×40 mL), water, and brine. The extracts were dried over anhydrous sodium sulfate, filtered, and concentrated in vacuo to give 540 mg (81%) of Example 141 as a yellow solid. HPLC Ret. time: 3.70 min. LCMS MH+ (m/z) 429.44.

Step 7: Example 138

A solution of Example 141 (30 mg, 0.070 mmol) and ethylamine solution (70% in water) (50 μL, 0.35 mmol) in ethanol (0.3 mL) was heated at 80° C. for 20 h. After cooling to rt, the mixture was purified by reverse-phase preparative HPLC and the fractions containing the product were concentrated in vacuo to remove the methanol. The resulting aqueous portion was lyophilized to afford 12.3 mg (28%) of the TFA salt of the title compound as a tan solid. HPLC Ret. time: 3.03 min. LCMS MH+ (m/z) 394.21. $^1$H NMR: (d$_3$-CD$_3$Cl, 500 MHz) δ 11.45 (br s, 1H), 9.23 (s, 1H), 8.75 (m, 1H), 8.22 (m, 1H), 7.94 (s, 1H), 7.88 (m, 2H), 7.76 (m, 1H), 7.50 (m, 1H), 7.43 (m, 2H), 3.39 (m, 2H), 1.40 (t, 3H).

Examples 142-146

Examples 142-146 in Table 9 were prepared utilizing a similar procedure as described for Example 138.

TABLE 9
| Ex. # | Compound Structure/Name | HPLC and LCMS Data |
|---|---|---|
| 142 | 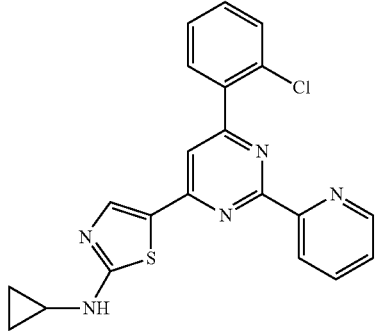<br>5-(6-(2-chlorophenyl)-2-(pyridin-2-yl)pyrimidin-4-yl)-N-cyclopropylthiazol-2-amine | HPLC $t_R$ = 3.19 min<br>LCMS $[M + H]^+$ = 406.20 |
| 143 | 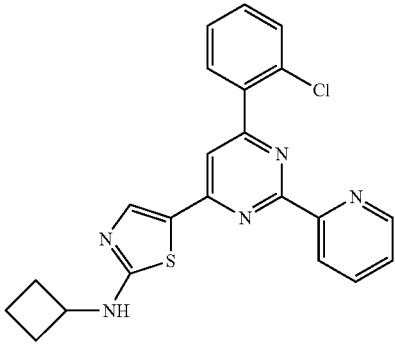<br>5-(6-(2-chlorophenyl)-2-(pyridin-2-yl)pyrimidin-4-yl)-N-cyclobutylthiazol-2-amine | HPLC $t_R$ = 3.38 min<br>LCMS $[M + H]^+$ = 420.10 |
| 144 | 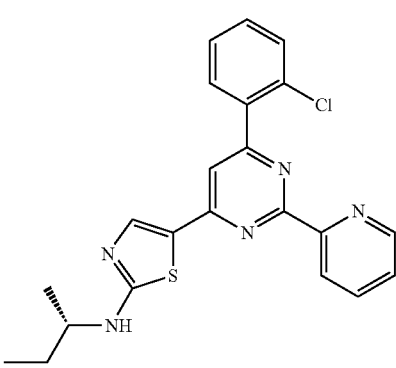<br>N-(S)-sec-butyl-5-(6-(2-chlorophenyl)-2-(pyridin-2-yl)pyrimidin-4-yl)thiazol-2-amine | HPLC $t_R$ = 3.38 min<br>LCMS $[M + H]^+$ = 422.21 |

US 7,923,556 B2

TABLE 9-continued

| Ex. # | Compound Structure/Name | HPLC and LCMS Data |
|---|---|---|
| 145 | 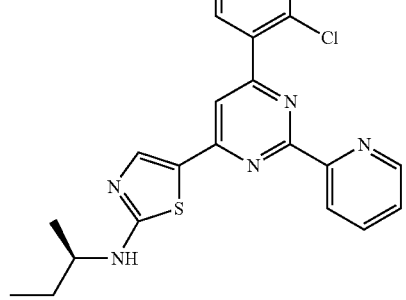<br>N-(R)-sec-butyl-5-(6-(2-chlorophenyl)-2-(pyridin-2-yl)pyrimidin-4-yl)thiazol-2-amine | HPLC $t_R$ = 3.39 min<br>LCMS [M + H]$^+$ = 422.20 |
| 146 | 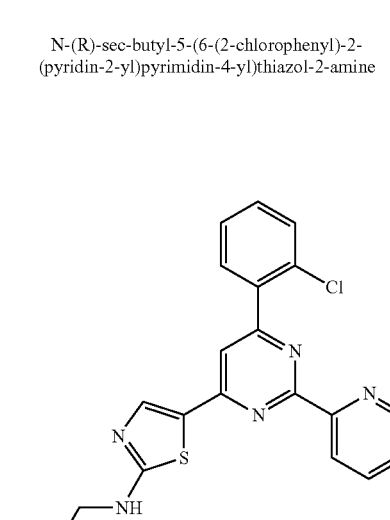<br>5-(6-(2-chlorophenyl)-2-(pyridin-2-yl)pyrimidin-4-yl)-N-(2-fluoroethyl)thiazol-2-amine | HPLC $t_R$ = 3.03 min<br>LCMS [M + H]$^+$ = 412.49 |

Example 147

2-(6-(2-(isopropylamino)thiazol-5-yl)-2-(2-methoxy-ethylamino)pyrimidin-4-yl)benzonitrile Step 1: Preparation 22

Preparation 22 was prepared from Preparation 17 utilizing a similar procedure as described in step 6 of Example 50. Yellow solid (45% yield). HPLC Ret. time: 1.68 min. LCMS MH$^+$ (m/z) 315.16.

Step 2: Preparation 23

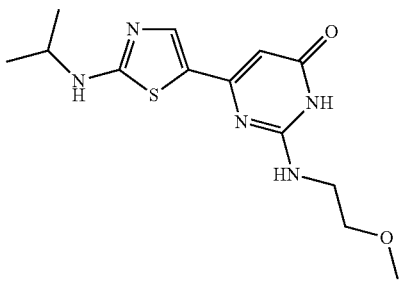

Preparation 23 was prepared from Preparation 22 utilizing a similar procedure as described in step 7 of Example 50 and by replacing 1-methylpiperazine with 2-methoxyethylamine. Grey solid (37% yield). HPLC Ret. time: 2.09 min. LCMS MH+ (m/z) 310.23. $^1$H NMR: ($d_6$-DMSO, 500 MHz) δ 10.40 (br s, 1H), 7.86 (d, 1H), 7.69 (s, 1H), 6.48 (br s, 1H), 5.75 (s, 1H), 3.75 (m, 2H), 3.44 (m, 4H), 3.31 (s, 3H), 1.16 (t, 3H).

Step 3: Preparation 24

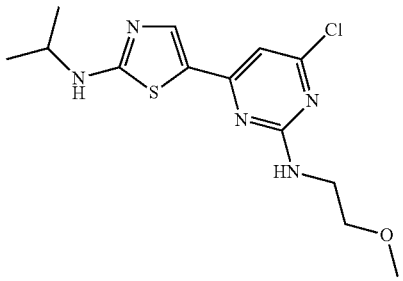

Preparation 24 was prepared from Preparation 23 utilizing a similar procedure as described in step 5 of Example 1. Yellow solid (quantitative). HPLC Ret. time: 2.71 min. LCMS MH+ (m/z) 328.23. This material was used directly without any further purification.

Step 4: Example 148

The title compound was prepared from Preparation 24 utilizing a similar procedure as described in step 6 of Example 1 by substituting 2-fluorophenyl boronic acid with 2-(1,3,2-dioxaborinan-2-yl)benzonitrile and by substituting potassium carbonate with potassium phosphate as the base. Orange solid (30% yield). HPLC Ret. time: 2.81 min. LCMS MH+ (m/z) 395.27. $^1$H NMR: ($d_6$-DMSO, 500 MHz) δ 8.11 (d, 1H), 8.04 (br s, 1H), 7.96 (d, 1H), 7.81 (dd, 1H), 7.67 (dd, 1H), 7.35 (s, 1H), 7.15 (s, 1H), 3.83 (m, 1H), 3.53 (m, 2H), 3.49 (m, sH), 3.25 (s, 3H), 1.18 (d, 3H).

Examples 149-153

Examples 149-153 in Table 10 were prepared utilizing a similar procedure as described for Example 147.

TABLE 10

| Ex. # | Compound Structure/Name | HPLC and LCMS Data |
|---|---|---|
| 149 | 4-(2,5-dichlorophenyl)-6-(2-(isopropylamino)thiazol-5-yl)-N-(2-methoxyethyl)pyrimidin-2-amine | HPLC $t_R$ = 3.45 min<br>LCMS [M + H]+ = 438.19 |
| 150 | 4-(2-chloro-5-(trifluoromethyl)phenyl)-6-(2-(isopropylamino)thiazol-5-yl)-N-(2-methoxyethyl)pyrimidin-2-amine | HPLC $t_R$ = 3.75 min<br>LCMS [M + H]+ = 456.25 |
| 151 | 4-(2-chlorophenyl)-6-(2-(isopropylamino)thiazol-5-yl)-N-(2-methoxyethyl)pyrimidin-2-amine | HPLC $t_R$ = 3.03 min<br>LCMS [M + H]+ = 404.21 |

TABLE 10-continued

| Ex. # | Compound Structure/Name | HPLC and LCMS Data |
|---|---|---|
| 152 | 2-(6-(2-isopropylamino)thiazol-5-yl)-2-(2-methoxyethylamino)pyrimidin-4-yl)phenol | HPLC $t_R$ = 3.15 min<br>LCMS [M + H]$^+$ = 386.25 |
| 153 | 4-(2-aminophenyl)-6-(2-(isopropylamino)thiazol-5-yl)-N-(2-methoxyethyl)pyrimidin-2-amine | HPLC $t_R$ = 2.37 min<br>LCMS [M + H]$^+$ = 385.28 |

Example 154

5-(6-(2-chlorophenyl)-2-(pyridin-2-yl)pyrimidin-4-yl)-N-isopropyl-1,3,4-oxadiazol-2-amine

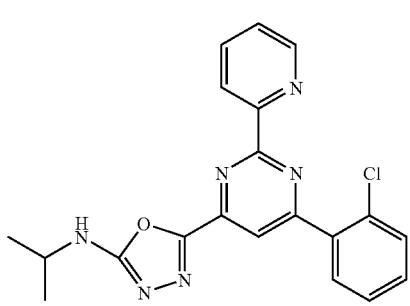

Step 1: Preparation 25

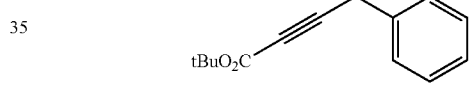

To a 1.0 M solution of lithium bis(trimethylsilyl)amide (0.92 mL, 9.2 mmol) in THF at −78° C. was added a solution of tert-butyl propiolate (0.92 mL, 7.9 mmol) in THF (6 mL) via cannula over 5 minutes and the resulting clear, amber-colored solution was stirred at −78° C. for 20 minutes. At this time, 2-chlorobenzaldehyde (0.89 mL, 7.9 mmol) was slowly added dropwise and the mixture was stirred at −78° C. for an additional 35 min and at rt for 15 min. A saturated aqueous solution of ammonium chloride (6 mL) was added and the mixture was concentrated in vacuo to remove the THF. The mixture was partitioned between methylene chloride (30 mL) and water (10 mL) and the methylene chloride portion was washed with brine (10 mL), dried over anhyd. sodium sulfate, filtered, and concentrated in vacuo to afford 2.1 g of a yellow oil. Purification by flash chromatography on silica gel eluting with 5-10% ethyl acetate in hexanes afforded 1.1 g (52%) of Preparation 25 as a yellow oil. HPLC Ret. time: 3.47 min. $^1$H NMR: (CDCl$_3$, 400 MHz) δ 7.72 (m, 1H), 7.35 (m, 3H), 5.92 (d, 1H), 2.58 (d, 1H), 1.50 (s, 9H).

Step 2: Preparation 26

To a solution of Preparation 25 (1.0 g, 3.8 mmol) in methylene chloride (40 mL) at rt was added manganese dioxide (4.5 g) and the resulting slurry was stirred at rt for 3.5 h. The slurry was filtered through Celite and the filter cake was washed with additional methylene chloride (~150 mL) and the resulting clear filtrate was concentrated in vacuo to afford 0.81 g (82%) Preparation 26 as a yellow oil. This material was used without any further purification. HPLC Ret. time: 3.81 min. $^1$H NMR: (CDCl$_3$, 400 MHz) δ 8.06 (d, 1H), 7.51 (m, 2H), 7.42 (m, 1H), 1.54 (s, 9H).

Step 3: Example 155

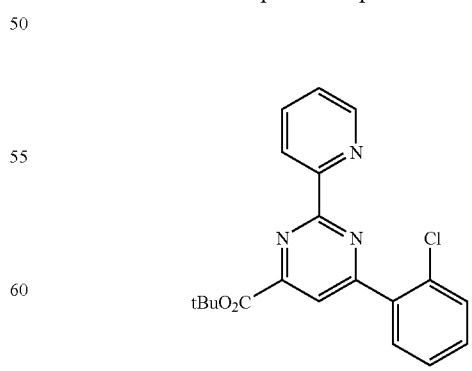

To a mixture of 2-amidinopyridinium hydrochloride (0.51 g, 3.2 mmol) and potassium carbonate (1.48 g, 10.7 mmol) in 25% aqueous acetonitrile (20 mL) at rt was added a solution of Preparation 26 in acetonitrile (20 mL) and the resulting mixture was stirred at rt for 15 h. The mixture was concentrated on a rotary evaporator to remove the acetonitrile and the mixture was partitioned between methylene chloride (30 mL) and water (15 mL). The separated aqueous portion was extracted with additional methylene chloride (2×10 mL) and the combined organic portions were washed with brine (20 mL), dried over anhyd sodium sulfate, filtered, and concentrated in vacuo to initially give a foam which eventually solidified to afford 1.1 g (99%) of Example 155 as a yellow semi-solid. This material was directly used without any further purification. HPLC Ret. time: 3.66 min. $^1$H NMR: (d$_4$-MeOH, 400 MHz) δ 8.77 (m, 1H), 8.69 (d, 1H), 8.33 (s, 1H), 8.08 (t, 1H), 7.91 (m, 1H), 7.63 (m, 2H), 7.56 (m, 2H), 1.70 (s, 9H).

Step 4: Example 156

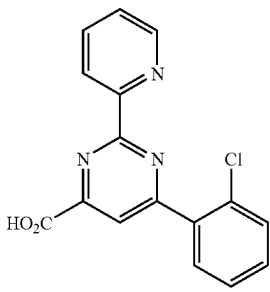

To a solution of Example 155 (1.1 g, 3.0 mmol) in anhydrous dioxane (5 mL) was added a solution of 4N HCl in dioxane (5 mL) and the resulting solution was stirred at rt for 2.5 h. The mixture was diluted with hexanes (~50 mL) and the solid was collected by vacuum filtration. After rinsing the solid with additional hexanes (2×30 mL), the solid was dried in the funnel then in vacuo to afford 0.86 g (91%) of Example 156 as an off-white powder. HPLC Ret. time: 2.52 min. LCMS MH$^+$ (m/z) 312.41. $^1$H NMR: (d$_6$-DMSO, 400 MHz) δ 8.94 (m, 1H), 8.77 (d, 1H), 8.45 (m, 1H), 8.41 (s, 1H), 7.95 (m, 2H), 7.71 (m, 1H), 7.62 (m, 2H).

Step 5: Preparation 27

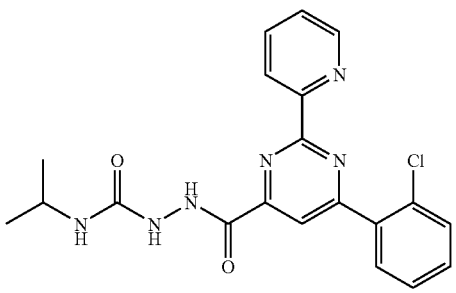

To a slurry of Example 156 (0.10 g, 0.32 mmol) in methylene chloride (2 mL) at rt were successively added oxalyl chloride (66 µL, 0.49 mmol) and DMF (10 µL, 0.01 mmol) and the resulting was stirred at rt for 30 min. The mixture was concentrated in vacuo and the resulting oil was dissolved in methylene chloride (1 mL) and a solution of 4-isopropyl-3-semicarbazide hydrochloride (56 mg, 0.37 mmol) and triethylamine (0.14 mL, 0.98 mmol) in methylene chloride (1 mL) was added dropwise. After stirring at rt for 15 min, the mixture was concentrated in vacuo and the residue was slurried in methanol (3 mL). After sonicating for 30 sec, the resulting solid was collected by vacuum filtration and allowed to dry in vacuo to afford 66 mg (50%) of Preparation 27 as an off-white solid HPLC Ret. time: 2.97 min. LCMS MH$^+$ (m/z) 312.41. $^1$H NMR: (d$_6$-DMSO, 400 MHz) δ 10.75 (s, 1H), 8.96 (d, 1H), 8.84 (d, 1H), 8.30 (s, 1H), 8.15 (t, 1H), 8.03 (s, 1H), 7.85 (m, 1H), 7.71 (m, 2H), 7.62 (m, 2H), 6.39 (d, 1H), 3.76 (m, 1H), 1.08 (d, 6H).

Step 6: Example 157

To a slurry of Preparation 27 (66 mg, 0.15 mmol) in toluene (1.8 mL) at rt was added phosphorus oxychloride (36 µL, 0.45 mmol) and the resulting mixture was heated at 80° C. for 3 h. After cooling to rt, the mixture was diluted with methanol (1 mL) and the solution was concentrated in vacuo to afford a yellow oil. Purification by reverse-phase preparative HPLC afforded fractions containing the desired product. These fractions were neutralized by adding saturated sodium bicarbonate (~1 mL) and concentrated in vacuo to remove the methanol. The resulting aqueous portion was extracted with methylene chloride (3×10 mL) and the combined extracts were washed with brine (5 mL), dried over anhyd sodium sulfate, filtered, and concentrated in vacuo to afford 34 mg (59%) of the title compound as a pale yellow solid. HPLC Ret. time: 3.18 min. LCMS MH$^+$ (m/z) 393.37. $^1$H NMR: (d$_6$-DMSO, 400 MHz) δ 8.87 (m, 1H), 8.53 (d, 1H), 8.38 (d, 1H), 8.11 (m, 1H), 7.94 (m, 1H), 7.76 (m, 1H), 7.65 (m, 3H), 3.90 (m, 1H), 1.31 (d, 6H).

Example 158

5-(6-(2-chlorophenyl)-2-(pyridin-2-yl)pyrimidin-4-yl)-N-isopropyl-1,3,4-thiadiazol-2-amine

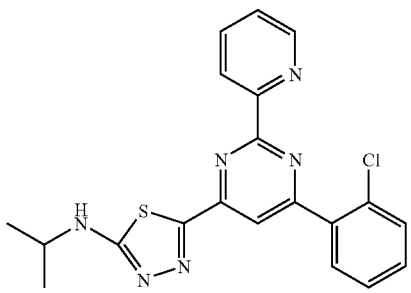

Step 1: Preparation 28

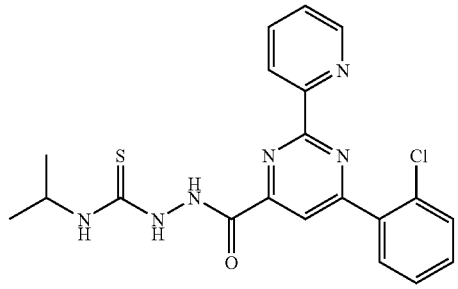

To a slurry of Example 156 (0.10 g, 0.32 mmol) in methylene chloride (2 mL) at rt were successively added oxalyl chloride (66 µL, 0.49 mmol) and DMF (10 µL, 0.01 mmol) and the resulting was stirred at rt for 30 min. The mixture was concentrated in vacuo and the resulting oil was dissolved in methylene chloride (1 mL) and a solution of 4-isopropyl-3-thiosemicarbazide (49 mg, 0.37 mmol) and triethylamine (0.14 mL, 0.98 mmol) in methylene chloride (1 mL) was added dropwise. After stirring at rt for 15 min, After stirring at rt for 15 min, the mixture was concentrated in vacuo and the resulting residue was dissolved in methanol (~2 mL). After stirring for ~16 h, the crystallized solid was collected by vacuum filtration, rinsed with ice-cold methanol (~1 mL), and allowed to dry in vacuo to afford 60 mg (44%) of Preparation 28 as a pale yellow solid. HPLC Ret. time: 3.22 min. LCMS MH$^+$ (m/z) 427.29.

Step 2: Example 158

To a slurry of Preparation 28 (60 mg, 0.14 mmol) in toluene (1.8 mL) at rt was added phosphorus oxychloride (36 µL, 0.45 mmol) and the resulting mixture was heated at 80° C. for 12 h. After cooling to rt, the mixture was diluted with methanol (1 mL) and the solution was concentrated in vacuo to afford a yellow oil. Purification by reverse-phase preparative HPLC afforded fractions containing the desired product. These fractions were neutralized by adding saturated sodium bicarbonate (~1 mL) and concentrated in vacuo to remove the methanol. The resulting solid was collected by vacuum filtration, rinsed with water (~1 mL), and dried in vacuo to afford 23 mg (40%) of the title compound as an off-white solid. HPLC Ret. time: 3.43 min. LCMS MH$^+$ (m/z) 409.25.

Example 159

5-(2-amino-6-(2-chlorophenyl)pyrimidin-4-yl)-1-benzylpyridin-2(1H)-one

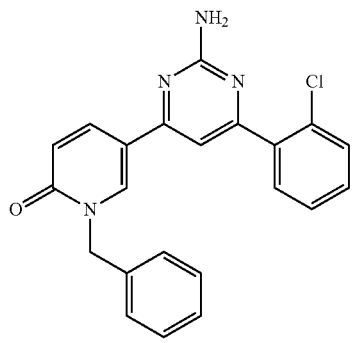

Step 1: Preparation 29

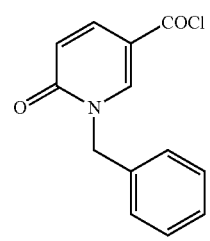

To a slurry of 1-benzyl-6-oxo-1,6-dihydro-3-pyridinecarboxylic acid (0.30 g, 1.3 mmol) in methylene chloride (3 mL) at rt were successively added thionyl chloride (0.12 mL, 1.7 mmol) and DMF (10 µL, 0.01 mmol) and the resulting mixture was refluxed for 50 min. After cooling to rt, the mixture was concentrated in vacuo and the resulting oil was partitioned between methylene chloride (20 mL) and water (10 mL). The layers were separated and the organic portion was washed with brine (3 mL), dried over anhyd sodium sulfate, filtered through Celite, and the resulting clear filtrate was concentrated in vacuo to afford 0.32 g (quant.) of Preparation 31 as a clear oil. This material was used directly without any further purification.

Step 2: Preparation 30

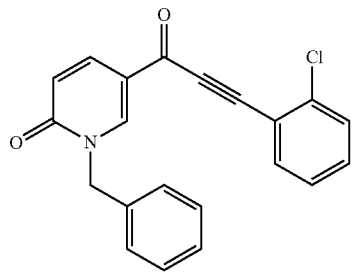

To a solution of PdCl$_2$(PPh$_3$)$_4$ (18 mg, 0.03 mmol), copper iodide (10 mg, 0.05 mmol), and triethylamine (0.18 mL, 1.3 mmol) in anhyd THF (3 mL) at rt was added a solution of Preparation 29 (0.32 mg, 1.3 mmol) and 1-chloro-2-ethynyl benzene (0.16 mL, 1.3 mmol) in anhyd THF (3 mL) via cannula. The resulting solution was stirred at rt for ~16 h then the mixture was concentrated in vacuo and partitioned between ethyl acetate (20 mL) and water (30 mL). The layers were separated and the aqueous portion was extracted with additional ethyl acetate (20 mL). The combined extracts were washed with brine (8 mL), dried over anhyd sodium sulfate, filtered, and concentrated in vacuo to afford 0.42 g of a brown solid. Purification by flash chromatography on silica gel eluting with 100% methylene chloride to remove the nonpolar impurities then eluting with 10% ethyl acetate in methylene chloride mixture to elute the product. Concentration in vacuo afforded 0.32 g (73%) of Preparation 32 as a brown solid. HPLC Ret. time: 3.80 min. LCMS MH$^+$ (m/z) 348.18. $^1$H NMR: (d$_6$-DMSO, 400 MHz) δ 8.86 (d, 1H), 8.01 (dd, 1H), 7.86 (dd, 1H), 6.68 (d, 1H), 7.61 (t, 1H), 7.50 (t, 1H), 7.35 (m, 5H), 6.59 (d, 1H), 5.77 (s, 2H).

Step 3: Example 159

To a mixture of guanidine hydrogen carbonate (0.16 g, 0.86 mmol) and Preparation 30 (0.15 g, 0.43 mmol) in ethanol (3 mL) at rt was added sodium ethoxide (0.18 g, 1.7 mmol) and the resulting mixture was heated at reflux for 9 h. At this time, water (3 mL) was slowly added dropwise to the mixture while at reflux and the resulting solution was allowed to slowly cool to rt overnight. The resulting solid was collected by vacuum filtration and washed with water (2 mL) then dried in vacuo to afford 0.15 g (90%) of the title compound as a medium brown solid. HPLC Ret. time: 3.18 min. LCMS MH$^+$ (m/z) 389.21.

Example 160

4-(2-chlorophenyl)-6-(2-(cyclopentylamino)thiazol-5-yl)pyrimidin-2-amine

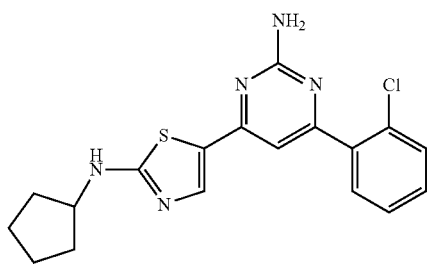

Step 1: Preparation 31

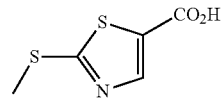

To a solution of 2-thiomethylthiazole (3.0 g, 23 mmol) in anhyd THF at −78° C. was slowly added a 2.5 M solution of n-butyl lithium in hexanes (9.2 mL, 23 mmol) and the resulting solution was stirred at −78° C. for 15 min then at −40° C. for 1.25 h giving a deep red solution. This solution was cooled to −78° C. and $CO_2$ was bubbled directly into the mixture for ~3 min. After warming to rt, the cloudy mixture was diluted with hexanes (~100 mL) and the solid was collected by vacuum filtration. The solid was then dissolved in water (~50 mL) and was acidified by adding 1 N aq HCl until pH range of 1-2 was reached. The resulting solid was collected by vacuum filtration and dried in vacuo to afford 3.6 g (90%) of Preparation 31 as a white powder. HPLC Ret. time: 1.95 min. LCMS MH[+] (m/z) 176.00. $^1$H NMR: (d6-DMSO, 400 MHz) δ 13.50 (s, 1H), 8.23 (s, 1H), 2.80 (s, 3H).

Step 2: Preparation 32

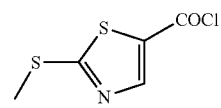

To a solution of Preparation 31 (0.55 g, 3.1 mmol) in methylene chloride (6 mL) at rt were successively added thionyl chloride (0.3 mL, 4.1 mmol) and DMF (3 μL, 0.31 mmol) and the resulting mixture was heated at reflux until a clear solution resulted (~2 h). The mixture was cooled to rt and concentrated in vacuo to afford 0.6 g (quant.) of Preparation 32 as a pale yellow solid. This material was used directly without any further purification.

Step 3: Preparation 33

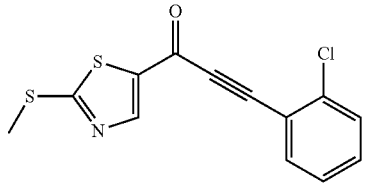

To a solution of $PdCl_2(PPh_3)_4$ (44 mg, 0.06 mmol), copper iodide (24 mg, 0.13 mmol), and triethylamine (0.44 mL, 3.1 mmol) in anhyd THF (9 mL) at rt was added a solution of Preparation 32 (0.6 mg, 3.1 mmol) and 1-chloro-2-ethynyl benzene (0.38 mL, 3.1 mmol) in anhyd THF (5 mL) via cannula. The resulting solution was stirred at rt for 2 h then the mixture was diluted with hexanes (~20 mL) and filtered to remove the solids. The resulting filtrate was decanted away from solids that had precipitated upon filtration and the resulting clear filtrate was concentrated in vacuo to afford 0.95 g of a brown solid. Purification by flash chromatography on silica gel using 60% methylene chloride in hexanes afforded after concentration in vacuo 0.54 g (58%) of Preparation 33 as a pale yellow solid. HPLC Ret. time: 4.00 min. LCMS MH[+] (m/z) 294.12.

Step 4: Example 161, 4-(2-chlorophenyl)-6-(2-(methylthio)thiazol-5-yl)pyrimidin-2-amine

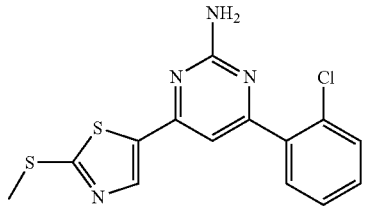

To a mixture of guanidine hydrogen carbonate (0.59 g, 3.3 mmol) and Preparation 33 (0.48 g, 1.6 mmol) in ethanol (20 mL) at rt was added sodium ethoxide (0.44 g, 6.5 mmol) and the resulting mixture was heated at reflux for 6 h. At this time, water (25 mL) was slowly added dropwise to the mixture while at reflux and the resulting solution was allowed to slowly cool to rt overnight. The resulting solid was collected by vacuum filtration and washed with ice-cold ethanol then dried in vacuo to afford 0.27 g (51%) of Example 161 as a pale tan colored solid. HPLC Ret. time: 3.30 min. LCMS MH[+] (m/z) 335.15. $^1$H NMR: (d6-DMSO, 400 MHz) δ 8.54 (s, 1H), 7.57 (m, 2H), 7.49 (m, 2H), 7.33 (s, 1H), 6.92 (m, 2H), 2.75 (s, 3H).

Step 5: Example 162, 4-(2-chlorophenyl)-6-(2-(methylsulfonyl)thiazol-5-yl)pyrimidin-2-amine

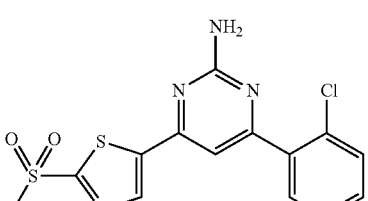

To a solution of Example 161 (0.27 g, 0.80 mmol) in methanol (7 mL) was slowly added a slurry of Oxone™ compound (1.9 g) in 4 mL of water. After stirring for 3 h, the reaction was diluted with ethyl acetate (~80 mL) and the solution was decanted away from the solids. The solution was washed with water (3×20 mL), brine (20 mL), then dried over anhyd sodium sulfate, filtered, and concentrated in vacuo to afford 0.32 g of a bright yellow solid. Purification by flash chromatography on silica gel using a gradient elution of 10-20% ethyl acetate in hexanes afforded after concentration in vacuo 0.22 g (75%) of Example 162 as a pale yellow solid. HPLC Ret. time: 2.94 min. LCMS MH$^+$ (m/z) 367.13.

Step 6: Example 160

A solution of Example 162 (30 mg, 0.08 mmol) and cyclopentylamine (81 μL, 0.8 mmol) in NMP (0.3 mL) was heated at 150° C. in a microwave reactor for 30 min. After cooling to rt, the mixture was purified by reverse-phase preparative HPLC and the fractions containing the product were neutralized by adding saturated aq sodium bicarbonate solution (~1 mL) and concentrated in vacuo to remove the methanol. The resulting aqueous slurry was filtered by vacuum filtration to collect the solid. Dried in vacuo to afford 23 mg (50%) of the title compound as an off-white solid. HPLC Ret. time: 3.00 min. LCMS MH$^+$ (m/z) 372.20. $^1$H NMR: (d$_6$-DMSO, 400 MHz) δ 8.20 (d, 1H), 7.97 (s, 1H), 7.54 (m, 2H), 7.45 (m, 2H), 7.09 (s, 1H), 6.65 (s, 2H), 3.95 (m, 1H), 1.94 (m, 2H), 1.68 (m, 2H), 1.56 (m, 4H).

Examples 163-168

Examples 163-168 in Table 11 were prepared utilizing a similar procedure as described for Example 160.

TABLE 11

| Ex. # | Compound Structure/Name | HPLC and LCMS Data |
|---|---|---|
| 163 | 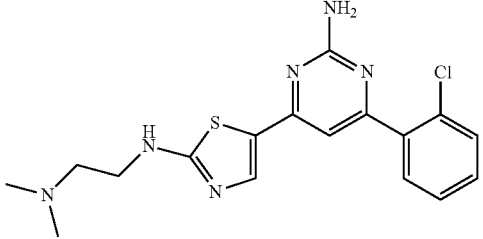<br>4-(2-chlorophenyl)-6-(2-(2-(dimethylamino)ethylamino)thiazol-5-yl)pyrimidin-2-amine | HPLC t$_R$ = 1.61 min<br>LCMS [M + H]$^+$ = 375.23 |
| 164 | 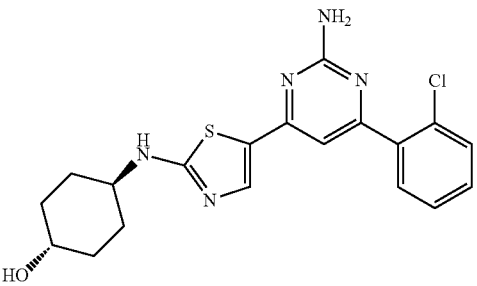<br>(1R,4R)-4-(5-(2-amino-6-(2-chlorophenyl)pyrimidin-4-yl)thiazol-2-ylamino)cyclohexanol | HPLC t$_R$ = 2.39 min<br>LCMS [M + H]$^+$ = 402.25 |
| 165 | 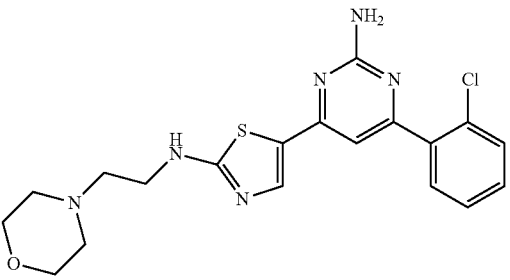<br>4-(2-chlorophenyl)-6-(2-(2-morpholinoethylamino)thiazol-5-yl)pyrimidin-2-amine | HPLC t$_R$ = 1.64 min<br>LCMS [M + H]$^+$ = 417.26 |

TABLE 11-continued

| Ex. # | Compound Structure/Name | HPLC and LCMS Data |
|---|---|---|
| 166 | 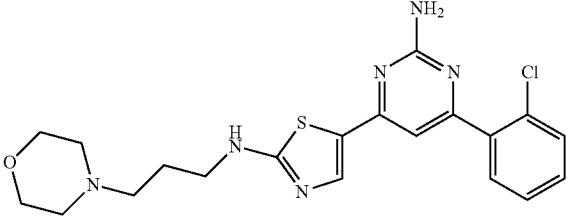<br>4-(2-chlorophenyl)-6-(2-(3-morpholinopropylamino)thiazol-5-yl)pyrimidin-2-amine | HPLC $t_R$ = 1.67 min<br>LCMS [M + H]$^+$ = 431.27 |
| 167 | 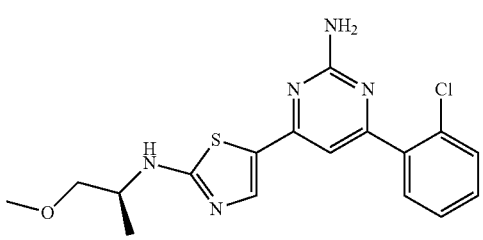<br>4-(2-chlorophenyl)-6-(2-((S)-1-methoxypropan-2-ylamino)thiazol-5-yl)pyrimidin-2-amine | HPLC $t_R$ = 2.62 min<br>LCMS [M + H]$^+$ = 376.24 |
| 168 | 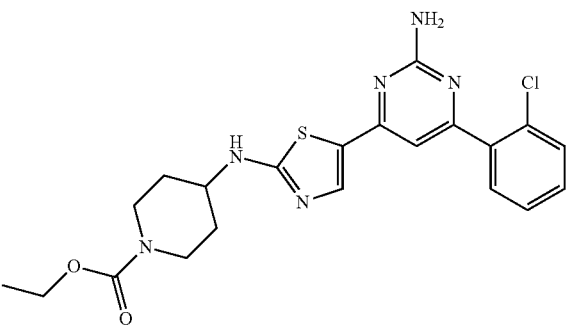<br>ethyl 4-(5-(2-amino-6-(2-chlorophenyl)pyrimidin-4-yl)thiazol-2-ylamino)piperidine-1-carboxylate | HPLC $t_R$ = 2.96 min<br>LCMS [M + H]$^+$ = 459.30 |

Example 168a

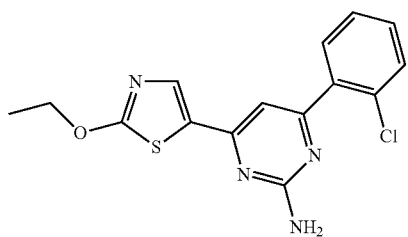

The title compound was prepared from example 162 utilizing a similar procedure as described in step 6 of Example 162 by substituting cyclopentylamine with sodium ethoxide and by substituting NMP with ethanol as the solvent. Yellow solid (35% yield). HPLC Ret. time: 3.27 min. LCMS MH$^+$ (m/z) 330.2. $^1$H NMR: (d$_6$-DMSO, 400 MHz) δ 8.16 (s, 1H), 7.60 (m, 2H), 7.50 (m, 2H), 7.30 (s, 1H), 6.96 (br. s, 2H), 4.48 (q, 2H), 1.39 (t, 3H).

Examples 168b-168c

Examples 168b-168c in Table 11a were prepared utilizing a similar procedure as described for Example 168a.

TABLE 11a

| Ex. # | Compound Structure/Name | HPLC and LCMS Data |
|---|---|---|
| 168b | 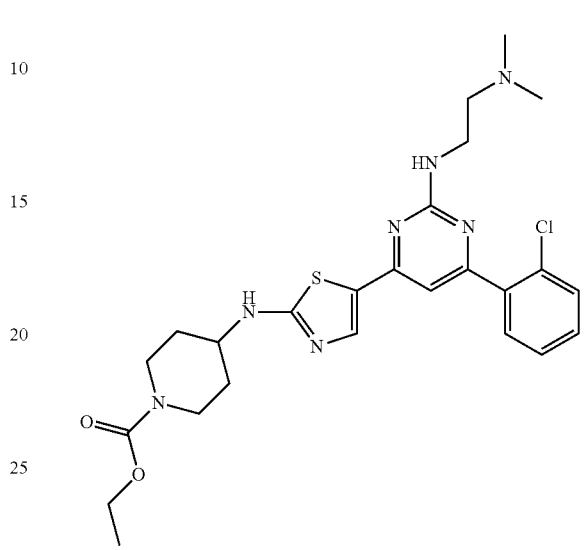 | HPLC $t_R$ = 2.22 min<br>LCMS [M + H]$^+$ = 305.19 |
| 168c | | HPLC $t_R$ = 3.48 min<br>LCMS [M + H]$^+$ = 347.22 |

Example 169

4-(2-chlorophenyl)-6-(2-(piperidin-4-ylamino)thiazol-5-yl)pyrimidin-2-amine

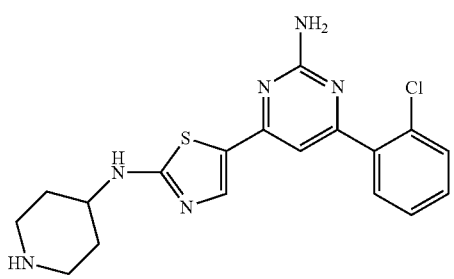

A solution of Example 162 (40 mg, 0.11 mmol) and tert-butyl-4-amino-piperidine-1-carboxylate (0.11 g, 0.55 mmol) in NMP (0.2 mL) was heated to 160° C. in a microwave reactor for 3 h. After cooling to rt, water (10 mL) was added and the resulting solid was collected by vacuum filtration. The solid was dissolved in methanol (0.5 mL) and a few drops of 6 N aq HCl was added. After stirring at rt for 3 h, the mixture was purified by reverse-phase preparative HPLC and the fractions containing the product were concentrated to remove the methanol and the resulting aqueous solution was lyophilized to afford 15 mg of Example 169 as a yellow solid. HPLC Ret. time: 1.68 min. LCMS MH$^+$ (m/z)=387.20.

Example 170

Ethyl 4-(5-(6-(2-chlorophenyl)-2-(2-(dimethylamino)ethylamino)pyrimidin-4-yl)thiazol-2-ylamino)piperidine-1-carboxylate Step 1: Preparation 34

To a slurry of 2-amino-5-bromothiazole mono hydrobromide (25 g, 96 mmol) in pyridine at rt was added di-tert-butyl dicarbonate (25 g, 114 mmol) in three portions over 15 minutes and the resulting mixture was stirred at rt for 16 h. The solvent was removed in vacuo and the solids were slurried in water (~250 mL) and extracted with warm ethyl acetate (3×100 mL). The combined extracts were washed with sequentially with 1N aq HCl (6×75 mL) and brine (75 mL), then dried over anhyd. sodium sulfate, filtered, and concentrated in vacuo to afford 19.9 g (74%) of Preparation 34 as a light tan solid. $^1$H NMR: (CDCl$_3$, 400 MHz): δ 11.56 (br s, 1H), 7.24 (s, 1H), 1.58 (s, 9H).

Step 2: Preparation 35

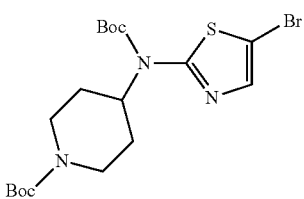

To a solution of Preparation 34 (0.34 g, 1.2 mmol), 4-tert-butyl-1-hydroxy piperidinecarboxylate (0.31 g, 1.5 mmol), and triphenylphosphine (0.40 g, 1.5 mmol) in THF (3 mL) at rt was added dropwise diethyl azodicarboxylate (0.24 mL, 1.5 mmol). After stirring for 1 h at rt, the solvent was removed in vacuo and the material was purified by flash chromatography on silica gel using a gradient elution (100% dichloromethane to 30% ethyl acetate in dichloromethane) to afford after concentration in vacuo 0.48 g (86%) of Preparation 35 as a pale yellow semi-solid. ¹H NMR: (CDCl₃, 400 MHz): δ 7.31 (s, 1H), 5.06 (m, 1H), 4.20 (m, 2H), 2.80 (m, 2H), 2.27 (m, 2H), 1.71 (m, 2H), 1.56 (s, 9H), 1.46 (s, 9H).

Step 3: Preparation 36

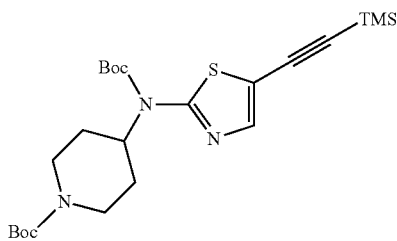

To a solution of Preparation 35 (1.0 g, 3.11 mmol) in triethylamine (3 mL) were added DMF (0.6 mL) and copper iodide (59 mg, 0.31 mmol) and the resulting mixture was degassed by bubbling argon through the reaction mixture for 2-3 minutes. At this time, trimethylsilylacetylene (0.66 mL, 4.67 mmol) and PdCl₂(PPh₃)₄ (0.11 g, 0.16 mmol) were added and the mixture was heated at 80° C. for 3 h then cooled to rt and diluted with ethyl acetate (~70 mL). The mixture was filtered to remove the insoluble solids and the clear filtrate was diluted with hexanes (~40 mL) and washed with 1 N aq HCl (3×40 mL), saturated aq sodium bicarbonate (20 mL), and brine (20 mL). Concentration afforded an oil that was purified by flash chromatography on silica gel eluting with 40% dichloromethane in hexanes mixture. Concentration in vacuo afforded 0.91 g (86%) of Preparation 36 as a yellow oil. ¹H NMR: (d₄-MeOH, 400 MHz): δ 7.30 (s, 1H), 4.92 (m, 1H), 3.97 (m, 2H), 2.63 (m, 2H), 2.10 (m, 2H), 1.48 (m, 2H), 1.35 (s, 9H), 1.24 (s, 9H), 0.00 (s, 9H).

Step 4: Preparation 37

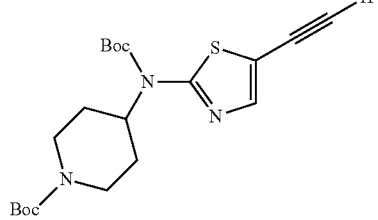

To a solution of Preparation 36 (0.31 g, 0.65 mmol) in methanol (3.5 mL) was added K₂CO₃ (45 mg, 0.33 mmol) and the mixture was stirred at rt for 1 h. The mixture was concentrated in vacuo and to the residue was added water (~10 mL) and the mixture was extracted with ethyl acetate (3×15 mL). The combined extracts were washed with brine, dried over sodium sulfate, filtered, and concentrated in vacuo to afford 234 mg (89%) of Preparation 37 as a pale yellow oil. ¹H NMR: (CDCl₃, 400 MHz): δ 7.56 (s, 1H), 5.10 (m, 1H), 4.20 (m, 2H), 3.35 (s, 1H), 2.80 (m, 2H), 2.30 (m, 2H), 1.73 (m, 2H), 1.57 (s, 9H), 1.47 (s, 9H).

Step 5: Preparation 38

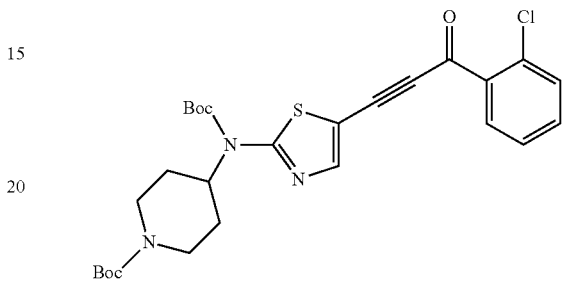

To a mixture of PdCl₂(PPh₃)₄ (8 mg, 11 μmol), copper iodide (4 mg, 22 μmol), and triethylamine (79 μL, 0.56 mmol) in THF (~1 mL) was added a solution of Preparation 37 (0.23 g, 0.56 mmol) and 2-chlorobenzoyl chloride (72 μL, 0.56 mmol) in THF (~2 mL) and the resulting mixture was stirred at rt for 20 minutes. The mixture was concentrated in vacuo and water was added and the product was extracted with ethyl acetate (3×20 mL). The combined extracts were washed with 1 N aq HCl (2×10 mL), water (10 mL), and brine (10 mL), then concentrated. The resulting residue was purified by flash chromatography on silica gel using a gradient elution of 100% dichloromethane to 5% ethyl acetate in dichloromethane mixtures. Concentration in vacuo afforded 0.22 g (71%) of Preparation 38 as a yellow solid. ¹H NMR: (CDCl₃, 400 MHz): δ 8.01 (d, 1H), 7.86 (s, 1H), 7.48 (m, 2H), 7.41 (m, 1H), 5.20 (m, 1H), 4.25 (m, 2H), 2.84 (m, 2H), 2.35 (m, 2H), 1.73 (m, 2H), 1.57 (s, 9H), 1.47 (s, 9H).

Step 6: Preparation 39

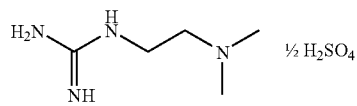

A mixture of N,N-dimethylethylenediamine (4.1 mL, 37.4 mmol) and S-methyl-thiuronium sulfate (5.2 g, 37.4 mmol) in ethanol (100 mL) was heated at reflux for 18 h then cooled to rt. The solution was concentrated in vacuo and the resulting semi-solid was slurried in diethyl ether (~100 mL) and sonicated to break up the aggregates. The diethyl ether was decanted away from the solid and the solid was dried in vacuo to afford 6.5 g (97%) of Preparation 39 as a hygroscopic, off-white powder. ¹H NMR: (d₆-DMSO, 400 MHz): δ 7.80 (br s, 5H), 3.14 (m, 2H), 2.38 (t, 2H), 2.19 (s, 6H).

Step 7: Example 171

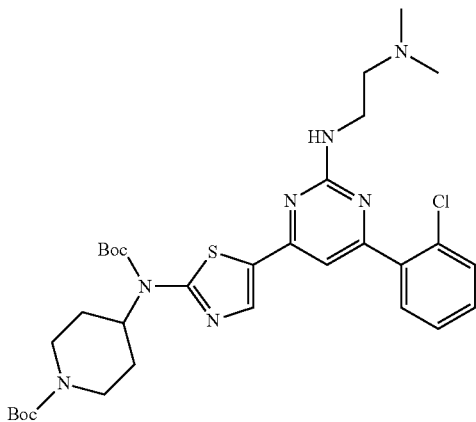

To a slurry of Preparation 38 (0.20 g, 0.38 mmol) and Preparation 39 (0.14 g, 0.75 mmol) in ethanol (3 mL) at rt was added sodium ethoxide (0.10 g, 1.5 mmol) and the resulting mixture was heated at reflux for 30 minutes then cooled to rt. The solvent was removed in vacuo and ethyl acetate (20 mL) was added and the mixture was washed with water (3×10 mL) and brine (10 mL), then dried over anhyd. sodium sulfate, filtered, and concentrated in vacuo to afford 235 mg (95%) of Example 171 as a yellow solid. This material was used without any further purification. $^1$H NMR: (CDCl$_3$, 400 MHz): δ 7.99 (d, 1H), 7.60 (m, 1H), 7.48 (m, 1H), 7.35 (m, 2H), 7.09 (s, 1H), 5.71 (m, 1H), 5.20 (m, 1H), 4.30 (br m, 2H), 3.56 (m, 2H), 2.80 (br m, 2H), 2.53 (t, 2H), 2.30 (m, 2H), 2.28 (s, 6H), 1.76 (m, 2H), 1.59 (s, 9H), 1.47 (s, 9H).

Step 8: Example 172, 4-(2-chlorophenyl)-N-(2-(dimethylamino)ethyl)-6-(2-(piperidin-4-ylamino)thiazol-5-yl)pyrimidin-2-amine

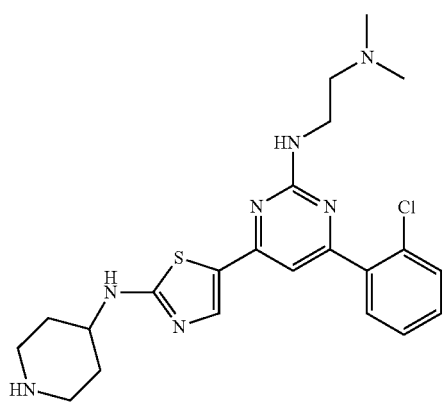

Example 171 (225 mg, 0.34 mmol) was dissolved in trifluoroacetic acid (~3 mL) and the resulting solution was stirred at rt for 30 minutes. The mixture was concentrated in vacuo and the resulting oil was dissolved in methanol (~3 mL) and reconcentrated. This was repeated one more time, then the material was dissolved in dichloromethane (~3 mL) and concentrated in vacuo to afford 275 mg (quant) of the bis-trifluoroacetic acid salt of Example 172 as a yellow semi-solid. The neutral form of Example 172 was obtained by reverse-phase preparative HPLC of a portion of this material. Collected HPLC fractions containing the product were concentrated in vacuo to remove the methanol and the resulting aqueous portion was neutralized by adding sat'd. aq sodium bicarbonate solution. Product was extracted with methylene chloride and extracts were dried over anhyd sodium sulfate, filtered, and concentrated in vacuo to afford 4 mg of the Example 172 as a pale yellow solid. HPLC Ret. time: 1.62 min. LCMS MH$^+$ (m/z)=458.24. $^1$H NMR: (CDCl$_3$, 400 MHz): δ 7.99 (d, 1H), 7.60 (m, 1H), 7.48 (m, 1H), 7.35 (m, 2H), 7.09 (s, 1H), 5.71 (m, 1H), 5.20 (m, 1H), 4.30 (br m, 2H), 3.56 (m, 2H), 2.80 (br m, 2H), 2.53 (t, 2H), 2.30 (m, 2H), 2.28 (s, 6H), 1.76 (m, 2H), 1.59 (s, 9H), 1.47 (s, 9H).

Step 9: Example 170

To a solution of Example 170 (75 mg, 95 μmol) in THF (0.65 mL) at rt were successively added triethylamine (66 μL, 0.47 mmol) and ethyl chloroformate (11 μL, 113 μmol) and the mixture was stirred at rt for 16 h. The solvent was removed in vacuo and the product was purified by reverse-phase preparative HPLC. Collected HPLC fractions containing the product were concentrated in vacuo to remove the methanol and the resulting aqueous portion was neutralized by adding sat'd. aq sodium bicarbonate solution. Product was extracted with methylene chloride and extracts were dried over anhyd sodium sulfate, filtered, and concentrated in vacuo to afford 15 mg of the title compound as a pale yellow solid. HPLC Ret. time: 2.89 min. LCMS MH$^+$ (m/z)=530.28. $^1$H NMR: (CDCl$_3$, 400 MHz): δ 7.74 (s, 1H), 7.53 (m, 1H), 7.40 (m, 1H), 7.27 (m, 2H), 6.96 (s, 1H), 5.60 (m, 1H), 5.29 (m, 1H), 4.08 (m, 4H), 3.60 (m, 1H), 3.53 (m, 2H), 2.93 (m, 2H), 2.56 (m, 2H), 2.26 (s, 6H), 2.07 (m, 2H), 1.43 (m, 2H), 1.20 (t, 3H).

Example 173

4-(2-chlorophenyl)-N-(2-(dimethylamino)ethyl)-6-(2-(1-(ethylsulfonyl)piperidin-4-ylamino)thiazol-5-yl)pyrimidin-2-amine

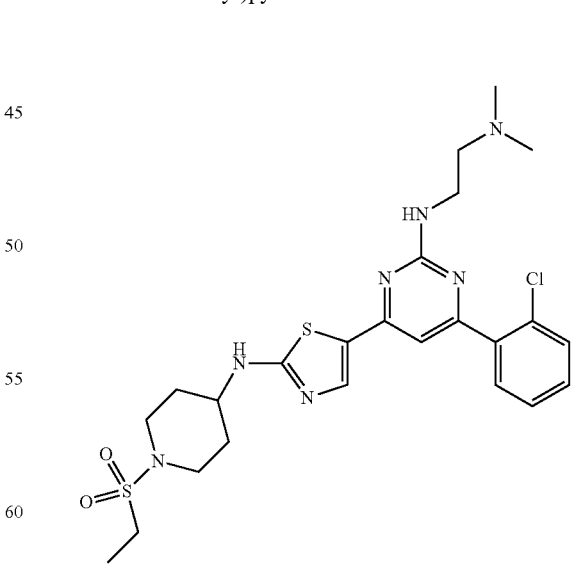

The title compound was prepared from Example 172 as described in Step 9 of Example 170 by using ethanesulfonyl chloride in place of ethyl chloroformate. Pale yellow solid. HPLC Ret. time: 2.55 min. LCMS MH$^+$ (m/z)=550.26. $^1$H NMR: (CDCl₃, 400 MHz): δ 7.73 (d, 1H), 7.58 (m, 1H), 7.44 (m, 1H), 7.33 (m, 2H), 7.01 (s, 1H), 5.65 (br s, 1H), 5.40 (br s, 1H), 3.80 (d, 2H), 3.70 (m, 1H), 3.60 (m, 2H), 2.95 (m, 4H), 2.67 (m, 2H), 2.36 (s, 6H), 2.21 (d, 2H), 1.63 (m, 2H), 1.36 (t, 3H).

Example 174

N-(5-(6-(2-chlorophenyl)pyrimidin-4-yl)thiazol-2-yl)-1-(ethylsulfonyl)piperidin-4-amine

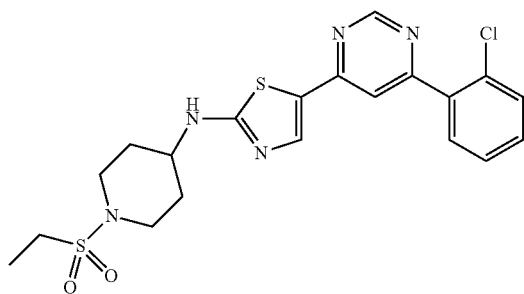

Step 1: Example 175

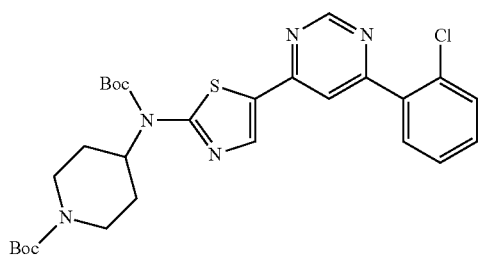

Example 175 was prepared from Preparation 38 as described in Step 7 of Example 170 by using formamidine acetate in place of Preparation 39. Isolated as a pale yellow solid in 92% yield. HPLC Ret. time: 4.61 min. LCMS MH⁺ (m/z)=572.26.

Step 2: Example 176, N-(5-(6-(2-chlorophenyl)pyrimidin-4-yl)thiazol-2-yl)piperidin-4-amine

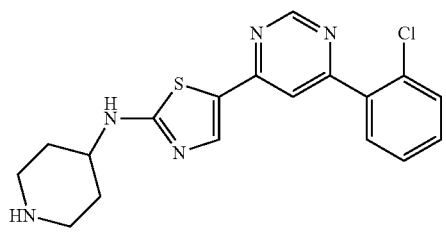

Example 176 was prepared from Example 175 as described in step 8 of Example 170. HPLC Ret. time: 2.13 min. LCMS MH⁺ (m/z)=372.33. Isolated as a yellow solid in 64% yield.

Step 3: Example 174

The title compound was prepared from Example 176 as described in step 9 of Example 170 by using ethanesulfonyl chloride in place of ethyl chloroformate. Isolated as a yellow solid. HPLC Ret. time: 3.31 min. LCMS MH⁺ (m/z)=464.19.

Example 176a

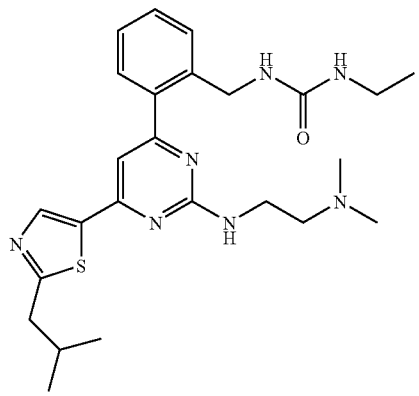

1-(2-(2-(2-(dimethylamino)ethylamino)-6-(2-isobutylthiazol-5-yl)pyrimidin-4-yl)benzyl)-3-ethylurea Step 1: Preparation 39

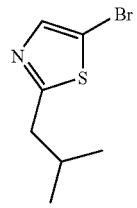

To a solution of 2-isobutylthiazole (1 g, 7.1 mmol) in DMF (30 mL) was added N-bromosuccinimide (1.3 g, 7.1 mmol) and the resulting mixture was stirred at rt for 3.5 h. The reaction was diluted with water (100 mL) and extracted with ethyl acetate (3×30 mL) and the combined extracts were washed with water (3×25 mL) then brine (25 mL) and dried over anhyd sodium sulfate. Filtration and concentration of the solution followed by purification of the resulting oil by flash chromatography on silica gel using 100% dichloromethane as the eluant afforded fractions containing the product. Concentration of these fractions in vacuo afforded 0.93 g (60%) of Preparation 39 as an orange oil. HPLC Ret. time: 3.46 min.

Step 2: Preparation 40

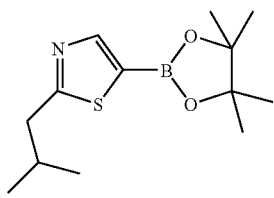

Preparation 40 was prepared from Preparation 39 utilizing a similar procedure as described in Step 3 for Preparation 18c. Afforded Preparation 40 as an orange oil (93%). HPLC Ret. time: 1.72 min.

Step 3: Preparation 41

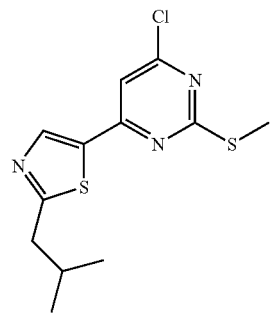

Preparation 41 was prepared from Preparation 40 utilizing a similar procedure as described in Step 4 for Preparation 18d. Afforded Preparation 41 as a yellow solid (52%). HPLC Ret. time: 4.12 min.

Step 4: Example 176b, tert-butyl 2-(6-(2-isobutylthiazol-5-yl)-2-(methylthio)pyrimidin-4-yl)benzylcarbamate

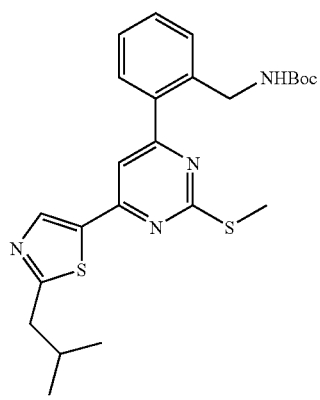

Example 176b was prepared from Preparation 41 using a similar procedure as described in Step 4 for Preparation 18d. Afforded Example 176b as a yellow solid (88%).

Step 5: Example 176c, (2-(6-(2-isobutylthiazol-5-yl)-2-(methylthio)pyrimidin-4-yl)phenyl)methanamine

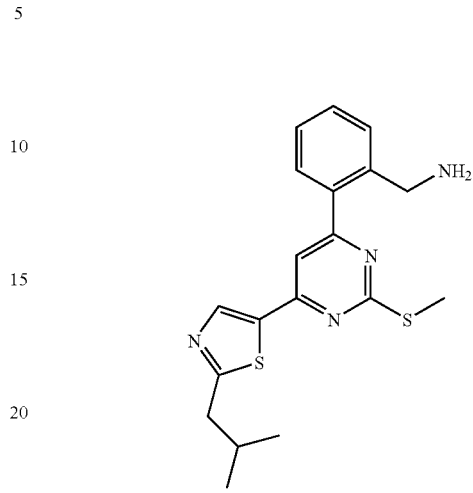

Example 176c was prepared from Example 176b using a similar procedure as described in Step 4 for Example 130. Afforded the bis-HCl salt of Example 176c as a pale tan-colored solid (quant.).

Step 6: Example 176d, 1-ethyl-3-(2-(6-(2-isobutylthiazol-5-yl)-2-(methylthio)pyrimidin-4-yl)benzyl)urea

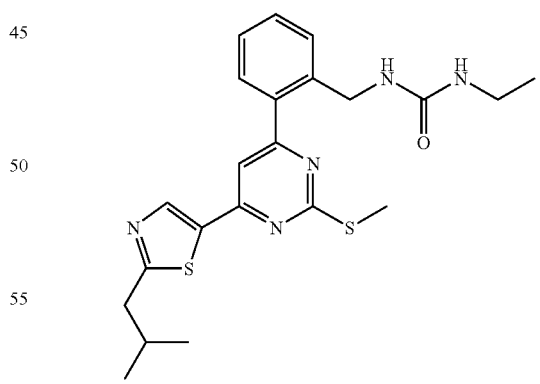

Example 176d was prepared from Example 176c using a similar procedure as described in Step 9 for Example 133. Afforded Example 176d as a light tan solid (80%). HPLC Ret. time: 3.95 min. LCMS MH$^+$ (m/z) 441.95.

Step 7: Example 176e, 1-ethyl-3-(2-(6-(2-isobutylthiazol-5-yl)-2-(methylsulfonyl)pyrimidin-4-yl)benzyl)urea

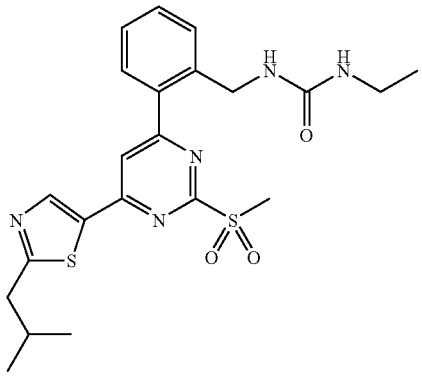

Example 176e was prepared from Example 176d using a similar procedure as described in Step 6 of Example 50. Afforded Example 176e as a yellow solid (97%). HPLC Ret. time: 3.27 min.

Step 8: Example 176a

Example 176a was prepared from Example 176e using a similar procedure as described in Step 7 of Example 50. Afforded Example 176a as an off-white solid. HPLC Ret. time: 2.71 min. LCMS MH$^+$ (m/z) 482.00.

Example 177

5-(6-(2,6-dichloro-4-propoxyphenyl)-2-(pyrazin-2-yl)pyrimidin-4-yl)-N-propylthiazol-2-amine

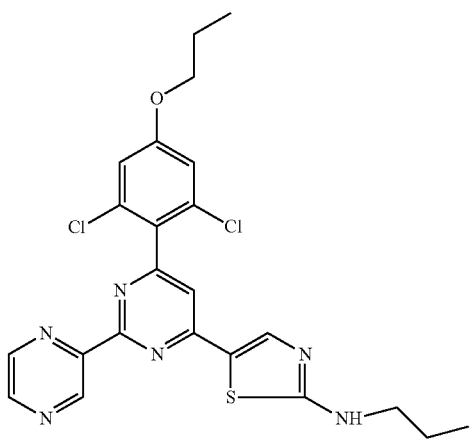

Step 1: Example 178, 5-(6-(2,6-dichloro-4-methoxyphenyl)-2-(pyrazin-2-yl)pyrimidin-4-yl)-N-propylthiazol-2-amine

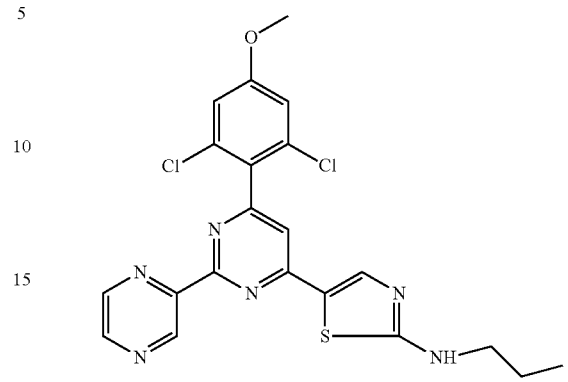

Example 178 was prepared by utilizing a similar procedure as described for Example 45. HPLC Ret. time: 4.14 min. LCMS MH$^+$ (m/z)=473.06. $^1$H NMR: (CDCl$_3$, 400 MHz): δ 9.80 (d, 1H), 8.83 (d, 1H), 8.71 (d, 1H), 7.96 (s, 1H), 7.48 (s, 1H), 7.01 (s, 2H), 6.50 (brs, 1H), 3.88 (s, 3H), 3.40 (m, 2H), 1.81 (m, 2H), 1.09 (t, 3H).

Step 2: Example 179, 3,5-dichloro-4-(6-(2-(propylamino)thiazol-5-yl)-2-(pyrazin-2-yl)pyrimidin-4-yl)phenol

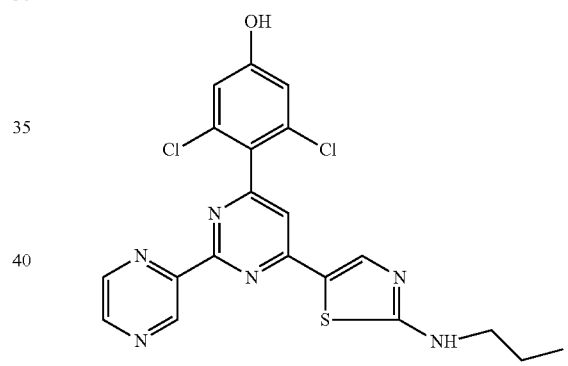

To a slurry of Example 178 (430 mg, 0.91 mmol) in anhydrous dichloroethane (10 ml) was added 1.0 M of boron tribromide in dichloroethane (9.10 ml, 9.1 mmol) at rt. under nitrogen atmosphere. After stirring at rt for 18 hr, diluted with water (20 ml) and saturated sodium bicarbonate (20 ml). The resulted reaction mixture was stirred at rt. for 1 hr and brown solid was collected by vacuum filtration, and dried in vacuo to yield 420 mg (84.5%) light brown solid. HPLC Ret. time: 3.83 min. LCMS MH$^+$ (m/z)=459.04. $^1$H NMR: (DMSO-d$_6$, 400 MHz): δ 10.80 (s, 1H), 9.56 (d, 1H), 8.90 (d, 1H), 8.59 (t, 1H), 8.38 (s, 1H), 8.01 (s, 1H), 7.11 (s, 2H), 6.50 (brs, 1H), 3.37 (m, 2H), 1.70 (m, 2H), 1.02 (t, 3H).

Step 3: Example 177

To a solution of Example 179 (20.0 mg, 0.044 mmol) in DMF (0.2 ml) was added 1-iodopropane (5.1 ul, 0.05 mmol) and potassium carbonate (18.2 mg, 0.13 mmol). After stirred at rt for 18 hr, reaction mixture was diluted with water (2 ml), extracted with methylene (3×1 ml). The combined extracts was dried over anhydrous magnesium sulfate, filtered, and concentrated in vacuo. The residue was then purified by reverse-phase preparative HPLC and the fraction containing the product was concentrated in vacuo and diluted with 1.0 N aqueous hydrochloric acid (1-2 ml), and lyophilized to yield 13.0 mg (59%) yellow solid. HPLC Ret. time: 4.54 min. LCMS MH⁺ (m/z)=501.07. $^1$H NMR: (CDCl$_3$, 400 MHz): δ 9.70 (d, 1H), 8.73 (d, 1H), 8.61 (d, 1H), 7.88 (s, 1H), 7.39 (s, 1H), 6.91 (s, 2H), 6.17 (brs, 1H), 3.89 (t, 2H), 3.29 (m, 2H), 1.74 (m, 4H), 1.00 (m, 6H).

Examples 180-215

Examples 180-215 listed in Table 12 below were prepared utilizing a similar procedure as described for Example 177.

TABLE 12

| Ex. # | Compound Structure/Name | HPLC and LCMS Data |
|---|---|---|
| 180 | 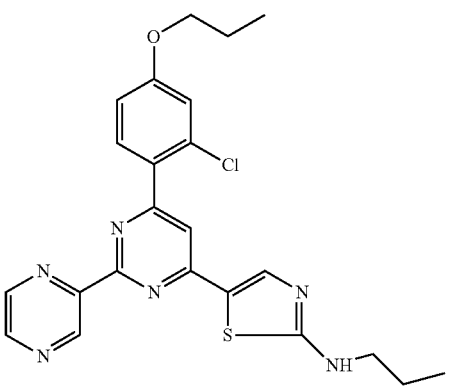<br>5-(6-(2-chloro-4-propoxyphenyl)-2-(pyrazin-2-yl)pyrimidin-4-yl)-N-propylthiazol-2-amine | HPLC $t_R$ = 4.59 min<br>LCMS [M + H]⁺ = 467.21 |
| 181 | 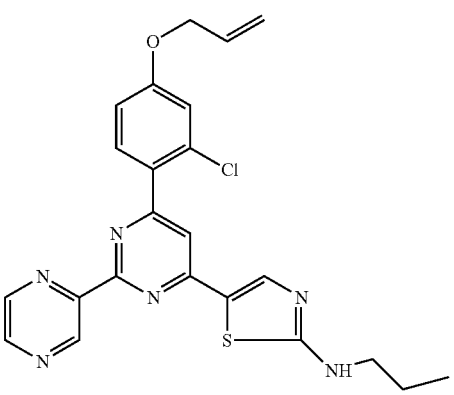<br>5-(6-(4-(allyloxy)-2-chlorophenyl)-2-(pyrazin-2-yl)pyrimidin-4-yl)-N-propylthiazol-2-amine | HPLC $t_R$ = 4.40 min<br>LCMS [M + H]+ = 465.27 |
| 182 | 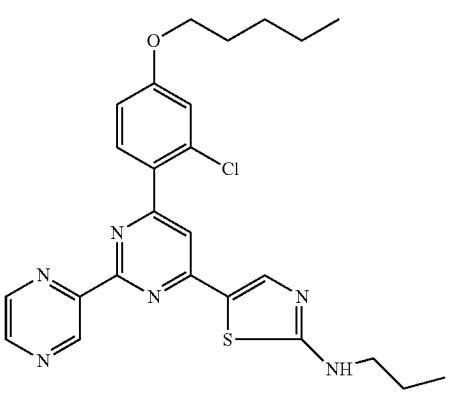<br>5-(6-(2-chloro-4-(pentyloxy)phenyl)-2-(pyrazin-2-yl)pyrimidin-4-yl)-N-propylthiazol-2-amine | HPLC $t_R$ = 4.43 min*<br>LCMS [M + H]⁺ = 495.231 |

TABLE 12-continued

| Ex. # | Compound Structure/Name | HPLC and LCMS Data |
|---|---|---|
| 183 | 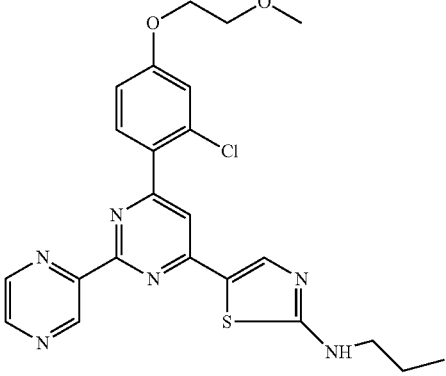<br>5-(6-(2-chloro-4-(2-methoxyethoxy)phenyl)-2-(pyrazin-2-yl)pyrimidin-4-yl)-N-propylthiazol-2-amine | HPLC $t_R$ = 4.01 min<br>LCMS [M + H]$^+$ = 483.20 |
| 184 | 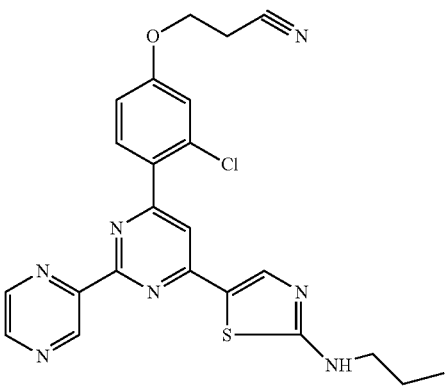<br>3-(3-chloro-4-(6-(2-(propylamino)thiazol-5-yl)-2-(pyrazin-2-yl)pyrimidin-4-yl)phenoxy)propanenitrile | HPLC $t_R$ = 4.05 min<br>LCMS [M + H]$^+$ = 478.19 |
| 185 | 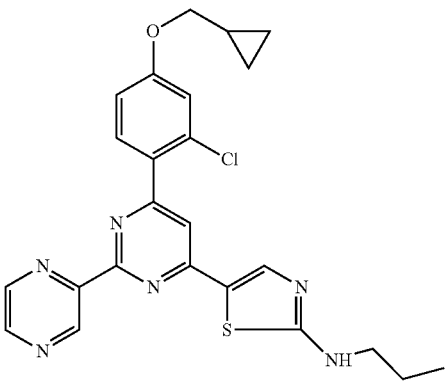<br>5-(6-(2-chloro-4-(cyclopropylmethoxy)phenyl)-2-(pyrazin-2-yl)pyrimidin-4-yl)-N-propylthiazol-2-amine | HPLC $t_R$ = 4.54 min<br>LCMS [M + H]$^+$ = 479.21 |

TABLE 12-continued

| Ex. # | Compound Structure/Name | HPLC and LCMS Data |
|---|---|---|
| 186 | 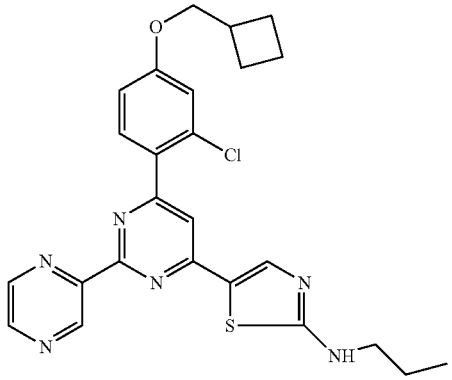<br>5-(6-(2-chloro-4-(cyclobutylmethoxy)phenyl)-2-(pyrazin-2-yl)pyrimidin-4-yl)-N-propylthiazol-2-amine | HPLC $t_R$ = 3.79 min<br>LCMS [M + H]$^+$ = 493.2 |
| 187 | 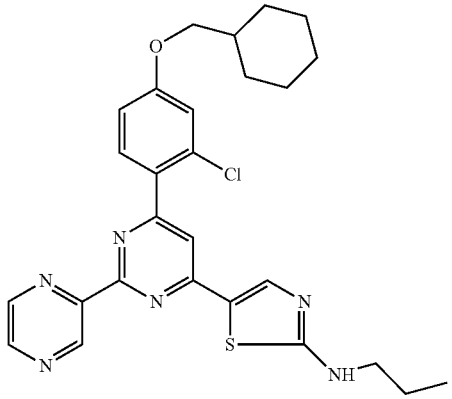<br>5-(6-(2-chloro-4-(cyclohexylmethoxy)phenyl)-2-(pyrazin-2-yl)pyrimidin-4-yl)-N-propylthiazol-2-amine | HPLC $t_R$ = 4.33 min*<br>LCMS [M + H]$^+$ = 521.23 |
| 188 | 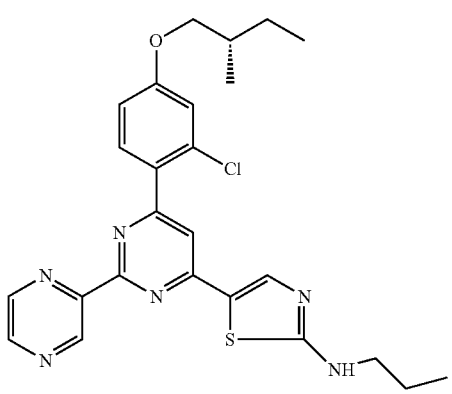<br>5-(6-(2-chloro-4-((S)-2-methylbutoxy)phenyl)-2-(pyrazin-2-yl)pyrimidin-4-yl)-N-propylthiazol-2-amine | HPLC $t_R$ = 4.91 min<br>LCMS [M + H]$^+$ = 495.25 |

TABLE 12-continued

| Ex. # | Compound Structure/Name | HPLC and LCMS Data |
|---|---|---|
| 189 | 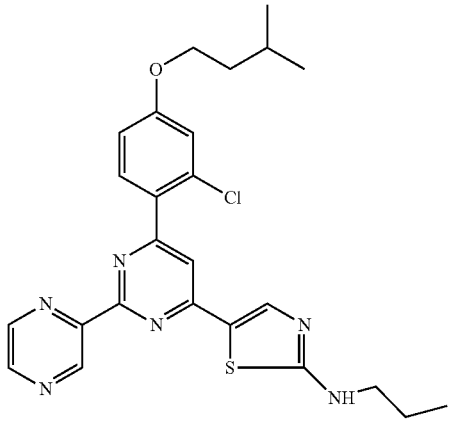<br>5-(6-(2-chloro-4-(isopentyloxy)phenyl)-2-(pyrazin-2-yl)pyrimidin-4-yl)-N-propylthiazol-2-amine | HPLC $t_R$ = 4.52 min<br>LCMS $[M + H]^+$ = 495.25 |
| 190 | 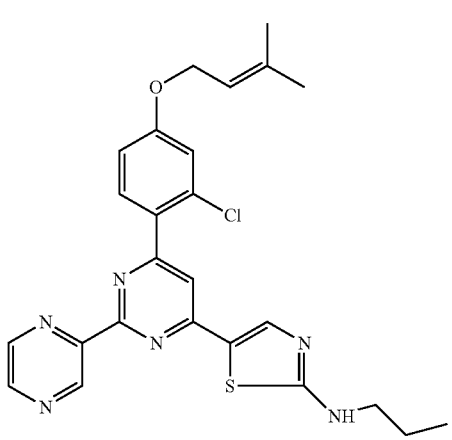<br>5-(6-(2-chloro-4-(3-methylbut-2-enyloxy)phenyl)-2-(pyrazin-2-yl)pyrimidin-4-yl)-N-propylthiazol-2-amine | HPLC $t_R$ = 4.76 min<br>LCMS $[M + H]^+$ = 493.21 |
| 191 | 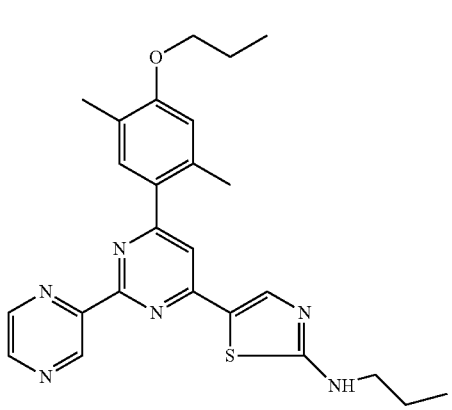<br>5-(6-(2,5-dimethyl-4-propoxyphenyl)-2-(pyrazin-2-yl)pyrimidin-4-yl)-N-propylthiazol-2-amine | HPLC $t_R$ = 4.61 min<br>LCMS $[M + H]^+$ = 461.18 |

TABLE 12-continued

| Ex. # | Compound Structure/Name | HPLC and LCMS Data |
|---|---|---|
| 192 | 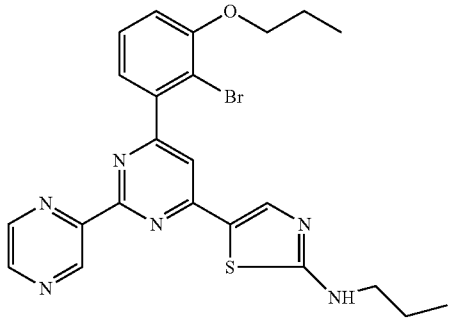\\ 5-(6-(2-bromo-3-propoxyphenyl)-2-(pyrazin-2-yl)pyrimidin-4-yl)-N-propylthiazol-2-amine | HPLC $t_R$ = 4.37 min<br>LCMS [M + H]$^+$ = 511.04 |
| 193 | 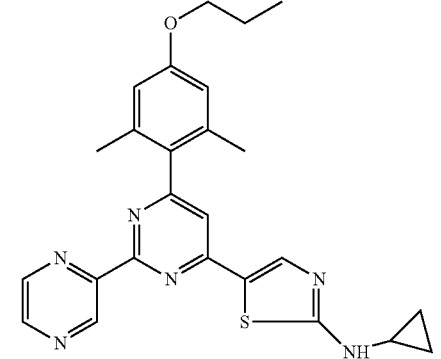<br>N-cyclopropyl-5-(6-(2,6-dimethyl-4-propoxyphenyl)-2-(pyrazin-2-yl)pyrimidin-4-yl)thiazol-2-amine | HPLC $t_R$ = 4.32 min<br>LCMS [M + H]$^+$ = 459.18 |
| 194 | 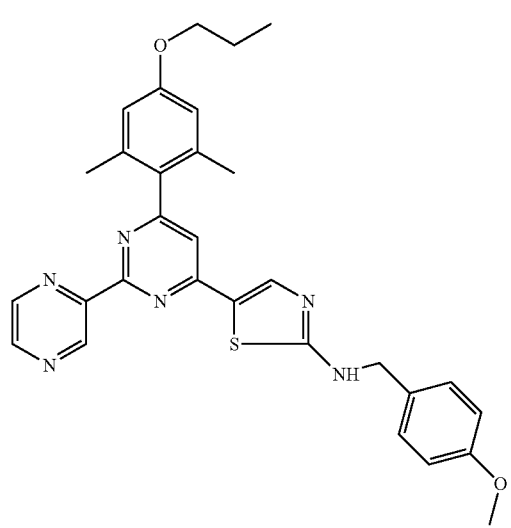<br>N-(4-methoxybenzyl)-5-(6-(2,6-dimethyl-4-propoxyphenyl)-2-(pyrazin-2-yl)pyrimidin-4-yl)thiazol-2-amine | HPLC $t_R$ = 4.57 min<br>LCMS [M + H]$^+$ = 539.22 |

TABLE 12-continued

| Ex. # | Compound Structure/Name | HPLC and LCMS Data |
|---|---|---|
| 195 | 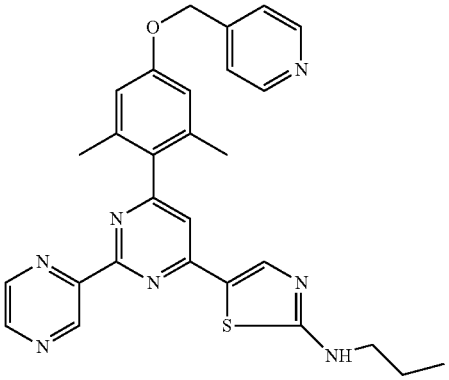<br>5-(6-(2,6-dimethyl-4-(pyridin-4-ylmethoxy)phenyl)-2-(pyrazin-2-yl)pyrimidin-4-yl-N-propylthiazol-2-amine | HPLC $t_R$ = 3.26 min<br>LCMS [M + H]$^+$ = 510.19 |
| 196 | 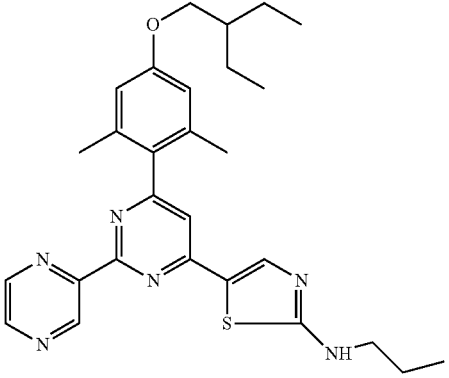<br>5-(6-(4-(2-ethylbutoxy)-2,6-dimethylphenyl)-2-(pyrazin-2-yl)pyrimidin-4-yl)-N-propylthiazol-2-amine | HPLC $t_R$ = 4.84 min<br>LCMS [M + H]$^+$ = 503.23 |
| 197 | 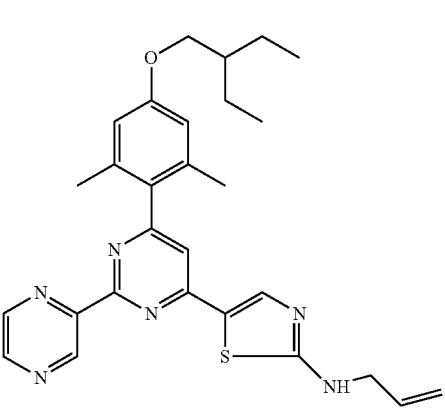<br>N-allyl-5-(6-(4-(2-ethylbutoxy)-2,6-dimethylphenyl)-2-(pyrazin-2-yl)pyrimidin-4-yl)thiazol-2-amine | HPLC $t_R$ = 4.88 min<br>LCMS [M + H]$^+$ = 501.26 |

TABLE 12-continued

| Ex. # | Compound Structure/Name | HPLC and LCMS Data |
|---|---|---|
| 198 | 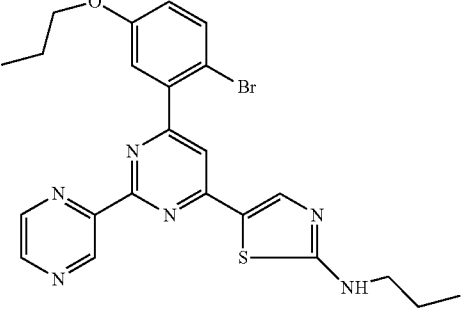<br>5-(6-(2-bromo-5-propoxyphenyl)-2-(pyrazin-2-yl)pyrimidin-4-yl)-N-propylthiazol-2-amine | HPLC $t_R$ = 4.53 min<br>LCMS [M + H]$^+$ = 511.04 |
| 199 | 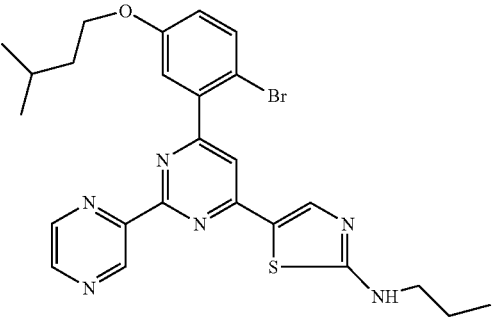<br>5-(6-(2-bromo-5-(isopentyloxy)phenyl)-2-(pyrazin-2-yl)pyrimidin-4-yl)-N-propylthiazol-2-amine | HPLC $t_R$ = 4.80 min<br>LCMS [M + H]+ = 539.00 |
| 200 | 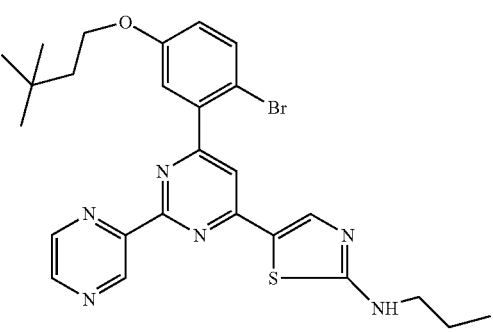<br>5-(6-(2-bromo-5-(3,3-dimethylbutoxy)phenyl)-2-(pyrazin-2-yl)pyrimidin-4-yl)-N-propylthiazol-2-amine | HPLC $t_R$ = 4.90 min<br>LCMS [M + H]+ = 553.11 |

TABLE 12-continued

| Ex. # | Compound Structure/Name | HPLC and LCMS Data |
|---|---|---|
| 201 | 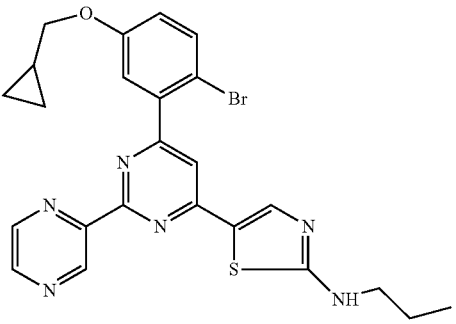<br>5-(6-(2-bromo-5-(cyclopropylmethoxy)phenyl)-2-(pyrazin-2-yl)pyrimidin-4-yl)-N-propylthiazol-2-amine | HPLC $t_R$ = 4.47 min<br>LCMS [M + H]+ = 523.15 |
| 202 | 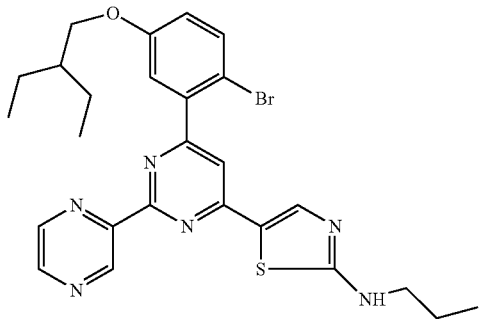<br>5-(6-(2-bromo-5-(2-ethylbutoxy)phenyl)-2-(pyrazin-2-yl)pyrimidin-4-yl)-N-propylthiazol-2-amine | HPLC $t_R$ = 4.94 min<br>LCMS [M + H]+ = 553.17 |
| 203 | 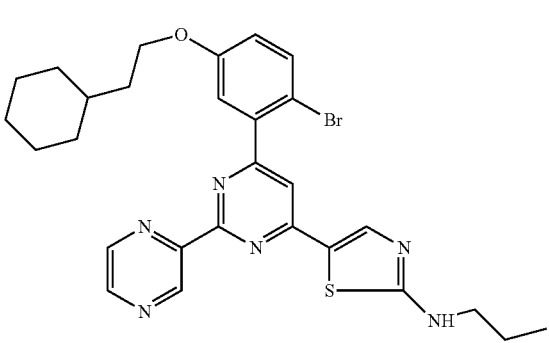<br>5-(6-(2-bromo-5-(2-cyclohexylethoxy)phenyl)-2-(pyrazin-2-yl)pyrimidin-4-yl)-N-propylthiazol-2-amine | HPLC $t_R$ = 5.01 min<br>LCMS [M + H]+ = 553.11 |

TABLE 12-continued

| Ex. # | Compound Structure/Name | HPLC and LCMS Data |
|---|---|---|
| 204 | 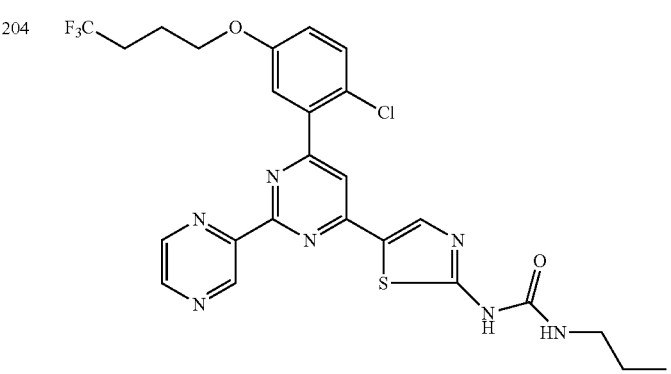<br>1-(5-(6-(2-chloro-5-(4,4,4-trifluorobutoxy)phenyl)-2-(pyrazin-2-yl)pyrimidin-4-yl)thiazol-2-yl)-3-propylurea | HPLC $t_R$ = 4.53 min<br>LCMS [M + H]$^+$ = 535.10 |
| 205 | 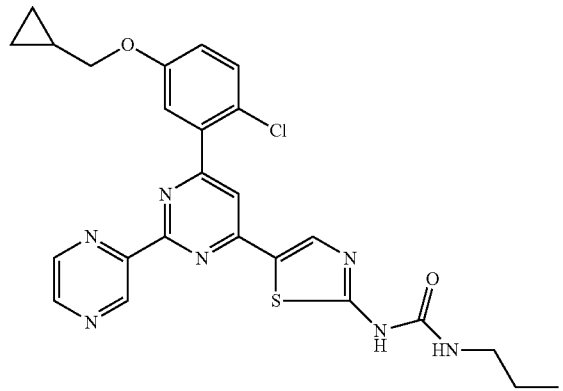<br>1-(5-(6-(2-chloro-5-(cyclopropylmethoxy)phenyl)-2-(pyrazin-2-yl)pyrimidin-4-yl)thiazol-2-yl)-3-propylurea | HPLC $t_R$ = 4.46 min<br>LCMS [M + H]$^+$ = 479.16 |
| 206 | 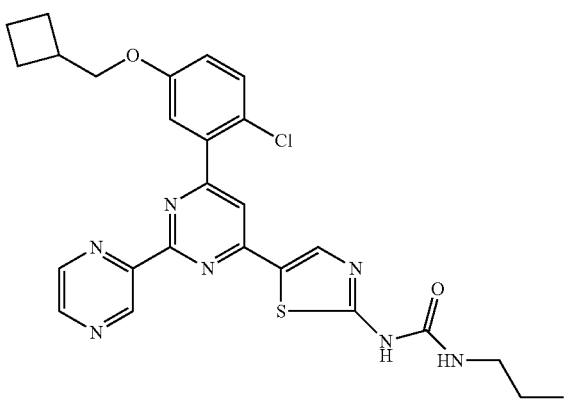<br>1-(5-(6-(2-chloro-5-(cyclobutylmethoxy)phenyl)-2-(pyrazin-2-yl)pyrimidin-4-yl)thiazol-2-yl)-3-propylurea | HPLC $t_R$ = 4.73 min<br>LCMS [M + H]$^+$ = 493.15 |

TABLE 12-continued

| Ex. # | Compound Structure/Name | HPLC and LCMS Data |
|---|---|---|
| 207 | 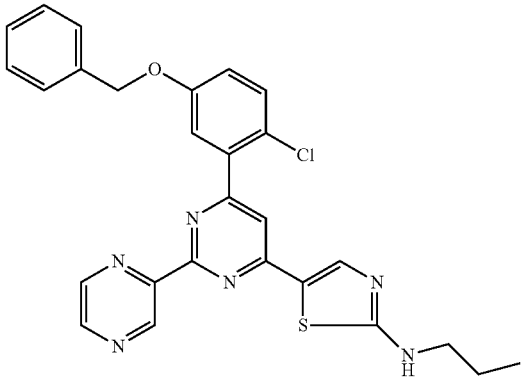<br>5-(6-(5-(benzyloxy)-2-chlorophenyl)-2-(pyrazin-2-yl)pyrimidin-4-yl)-N-propylthiazol-2-amine | HPLC $t_R$ = 4.60 min<br>LCMS [M + H]$^+$ = 515.15 |
| 208 | 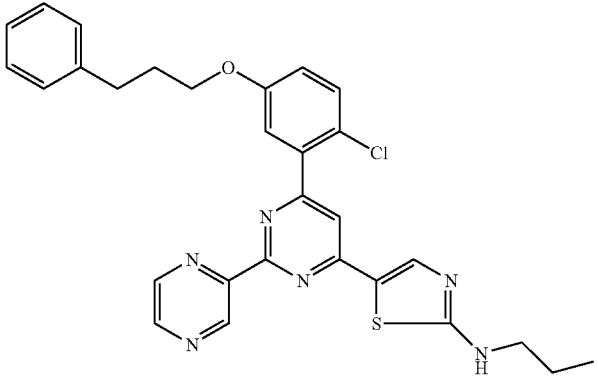<br>5-(6-(2-chloro-5-(3-phenylpropoxy)phenyl)-2-(pyrazin-2-yl)pyrimidin-4-yl)-N-propylthiazol-2-amine | HPLC $t_R$ = 4.84 min<br>LCMS [M + H]$^+$ = 543.17 |
| 209 | 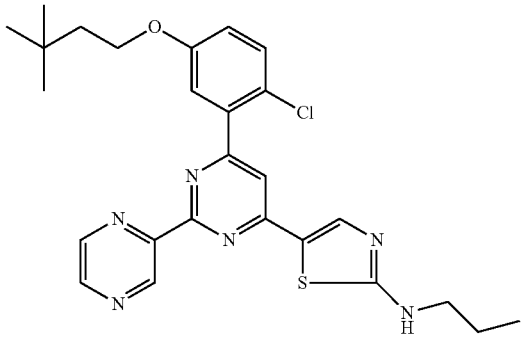<br>5-(6-(2-chloro-5-(3,3-dimethylbutoxy)phenyl)-2-(pyrazin-2-yl)pyrimidin-4-yl)-N-propylthiazol-2-amine | HPLC $t_R$ = 4.90 min<br>LCMS [M + H]$^+$ = 509.17 |

TABLE 12-continued

| Ex. # | Compound Structure/Name | HPLC and LCMS Data |
|---|---|---|
| 210 | 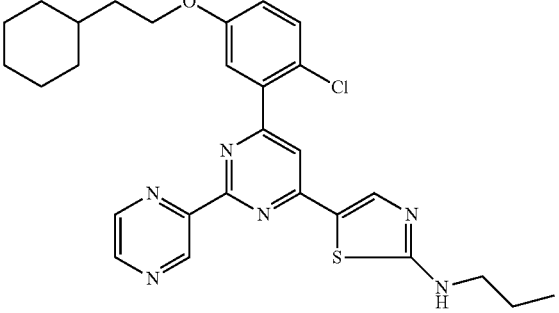<br>5-(6-(2-chloro-5-(2-cyclohexylethoxy)phenyl)-<br>2-(pyrazin-2-yl)pyrimidin-4-yl)-N-<br>propylthiazol-2-amine | HPLC $t_R$ = 5.18 min<br>LCMS [M + H]$^+$ = 535.21 |
| 211 | 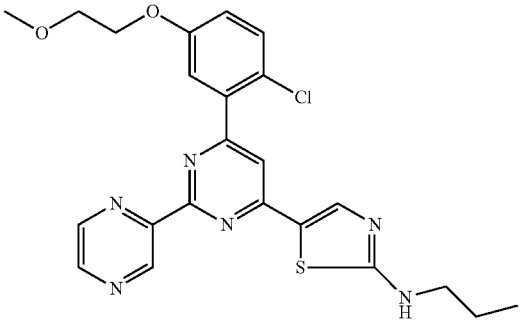<br>5-(6-(2-chloro-5-(2-methoxyethoxy)phenyl)-2-<br>(pyrazin-2-yl)pyrimidin-4-yl)-N-propylthiazol-<br>2-amine | HPLC $t_R$ = 4.01 min<br>LCMS [M + H]$^+$ = 483.13 |
| 212 | 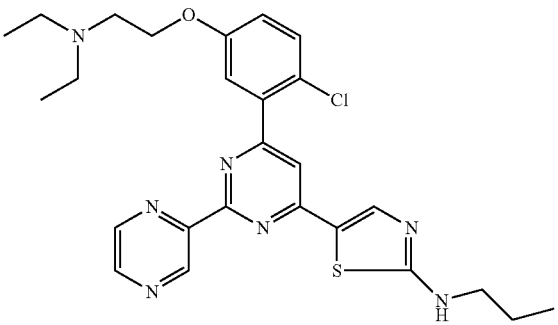<br>5-(6-(2-chloro-5-(2-<br>(diethylamino)ethoxy)phenyl)-2-(pyrazin-2-<br>yl)pyrimidin-4-yl)-N-propylthiazol-2-amine | HPLC $t_R$ = 3.32 min<br>LCMS [M + H]$^+$ = 524.21 |

TABLE 12-continued

| Ex. # | Compound Structure/Name | HPLC and LCMS Data |
|---|---|---|
| 213 | 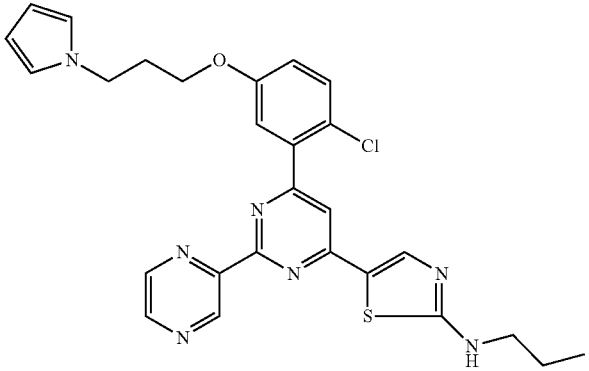<br>5-(6-(5-(3-(1H-pyrrol-1-yl)propoxy)-2-chlorophenyl)-2-(pyrazin-2-yl)pyrimidin-4-yl)-N-propylthiazol-2-amine | HPLC $t_R$ = 4.49 min<br>LCMS [M + H]$^+$ = 532.15 |
| 214 | 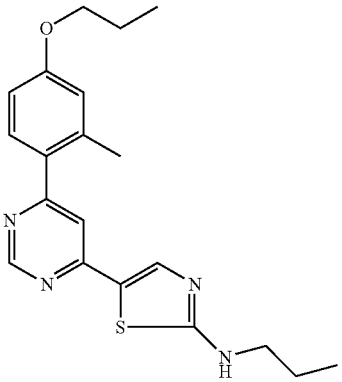<br>5-(6-(2-methyl-4-propoxyphenyl)pyrimidin-4-yl)-N-propylthiazol-2-amine | HPLC $t_R$ = 4.19 min<br>LCMS [M + H]+ = 369.26 |
| 215 | 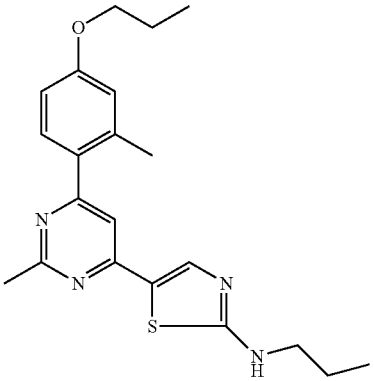<br>5-(2-methyl-6-(2-methyl-4-propoxyphenyl)pyrimidin-4-yl)-N-propylthiazol-2-amine | HPLC $t_R$ = 4.01 min<br>LCMS [M + H]$^+$ = 383.28 |

Example 216

5-(6-(2,6-dimethyl-4-(pentan-3-yloxy)phenyl)-2-(pyrazin-2-yl)pyrimidin-4-yl)-N-propylthiazol-2-amine

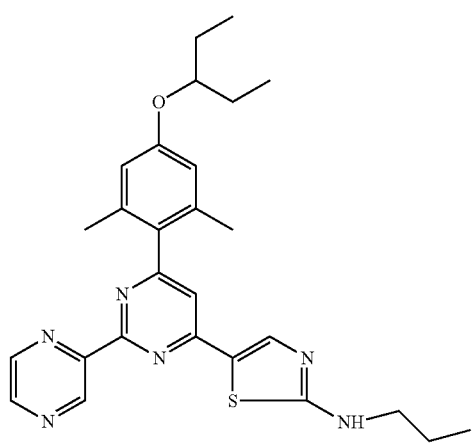

Step 1: Example 217, 5-(6-(4-(benzyloxy)-2,6-dimethylphenyl)-2-(pyrazin-2-yl)pyrimidin-4-yl)-N-propylthiazol-2-amine

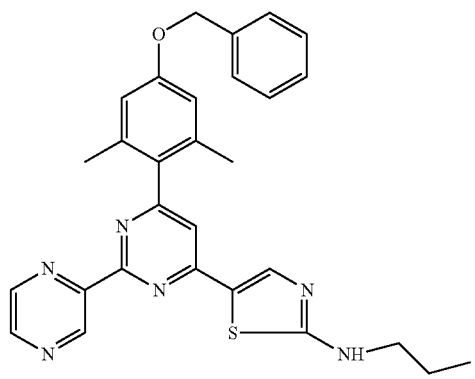

Example 217 was prepared by utilizing a similar procedure as described for Example 45. HPLC Ret. time: 4.53 min. LCMS MH+ (m/z)=509.27. $^1$H NMR: (CDCl$_3$, 500 MHz): δ 9.73 (d, 1H), 8.76 (d, 1H), 8.65 (d, 1H), 7.89 (s, 1H), 7.38 (m, 5H), 7.24 (s, 1H), 6.74 (s, 2H), 5.08 (s, 2H), 3.34 (m, 2H), 2.14 (s, 6H), 1.74 (m, 2H), 1.04 (t, 3H).

Step 2: Example 218, 3,5-dimethyl-4-(6-(2-(propylamino)thiazol-5-yl)-2-(pyrazin-2-yl)pyrimidin-4-yl)phenol

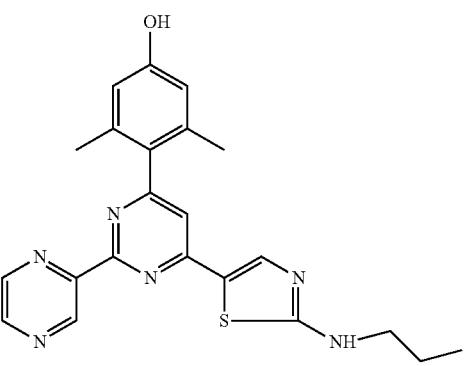

Example 217 (1.6 g, 3.15 mmol) was stirred in TFA (5 ml) at 60° C. for 4 hr. After cooling to rt, the TFA was removed in vacuo and resulting residue was then with aqueous sodium bicarbonate for 1 hr. The resulting solid, Example 218, was collected by vacuum filtration to yield 1.15 g (87%) pale brown solid. HPLC Ret. time: 3.47 min. LCMS MH+ (m/z)=419.19. $^1$H NMR: (CDCl$_3$, 400 MHz): δ 9.63 (d, 1H), 8.64 (d, 1H), 8.65 (d, 1H), 7.74 (s, 1H), 7.23 (s, 1H), 6.45 (s, 2H), 3.23 (m, 2H), 1.96 (s, 6H), 1.65 (m, 2H), 0.92 (t, 3H).

Step 3: Example 216

To a solution of Example 218 (20.0 mg, 0.09 mmol) in anhydrous DMF (0.2 ml) was added NaH (5.4 mg, 0.14 mmol) at 0° C. under nitrogen atmosphere, after 2 min, the reaction mixture was further treated with 3-bromopentane (0.12 ml, 0.9 mmol) and resulting reaction solution was stirred at rt for 20 h. The mixture was diluted with water (2.0 ml) and extracted with methylene chloride (3×2 ml). The combined extracts was dried over anhydrous magnesium sulfate, filtered, and concentrated in vacuo. The solid was purified by reverse-phase preparative HPLC and the fraction containing the product was concentrated in vacuo and diluted with 1.0 N aqueous hydrochloric acid (1-2 ml), and lyophilized to yield 8.0 mg (17%) of the titled compound as a yellow solid. HPLC Ret. time: 4.65 min. LCMS MH+ (m/z)=489.21. $^1$H NMR: (CDCl$_3$, 400 MHz): δ 9.69 (d, 1H), 8.71 (d, 1H), 8.60 (d, 1H), 7.84 (s, 1H), 7.32 (s, 1H), 6.60 (s, 2H), 5.78 (brs, 1H), 4.09 (m, 1H), 3.29 (m, 2H), 2.08 (s, 6H), 1.71 (m, 2H), 1.62 (m, 4H), 0.98 (t, 3H), 0.90 (t, 6H).

Examples 219-241

Examples 219-241 listed in Table 13 below were prepared utilizing a similar procedure as described for Example 216.

TABLE 13

| Ex. # | Compound Structure/Name | HPLC and LCMS Data |
|---|---|---|
| 219 | 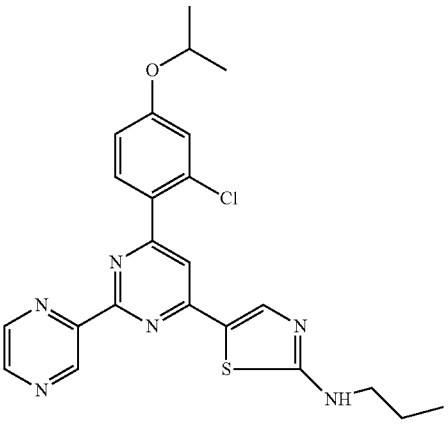<br>5-(6-(2-chloro-4-isopropoxyphenyl)-2-(pyrazin-2-yl)pyrimidin-4-yl)-N-propylthiazol-2-amine | HPLC $t_R$ = 4.46 min<br>LCMS [M + H]$^+$ = 501.02 |
| 220 | 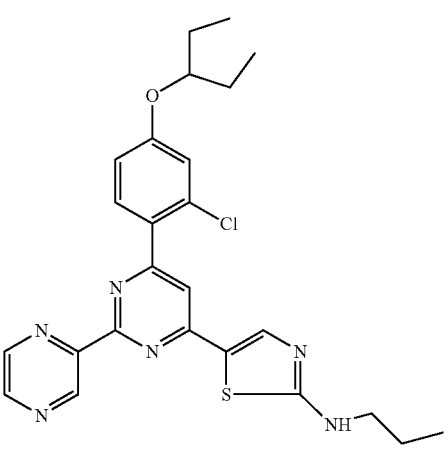<br>5-(6-(2-chloro-4-(pentan-3-yloxy)phenyl)-2-(pyrazin-2-yl)pyrimidin-4-yl)-N-propylthiazol-2-amine | HPLC $t_R$ = 4.89 min<br>LCMS [M + H]$^+$ = 495.25 |
| 221 | 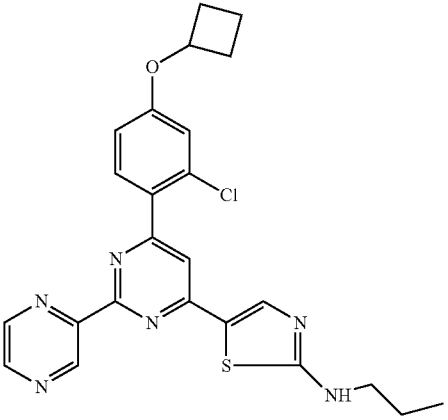<br>5-(6-(2-chloro-4-cyclobutoxyphenyl)-2-(pyrazin-2-yl)pyrimidin-4-yl)-N-propylthiazol-2-amine | HPLC $t_R$ = 4.66 min<br>LCMS [M + H]$^+$ = 479.22 |

TABLE 13-continued
| Ex. # | Compound Structure/Name | HPLC and LCMS Data |
|---|---|---|
| 222 | 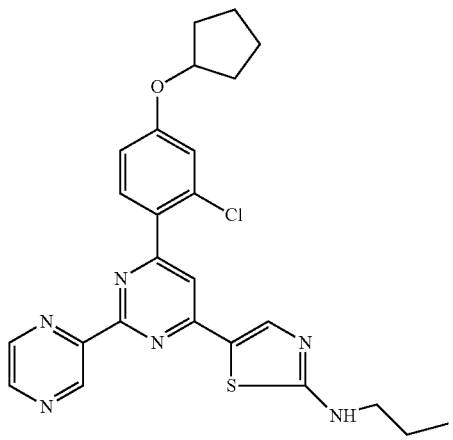<br>5-(6-(2-chloro-4-(cyclopentyloxy)phenyl)-2-(pyrazin-2-yl)pyrimidin-4-yl)-N-propylthiazol-2-amine | HPLC $t_R$ = 4.91 min<br>LCMS [M + H]$^+$ = 493.22 |
| 223 | 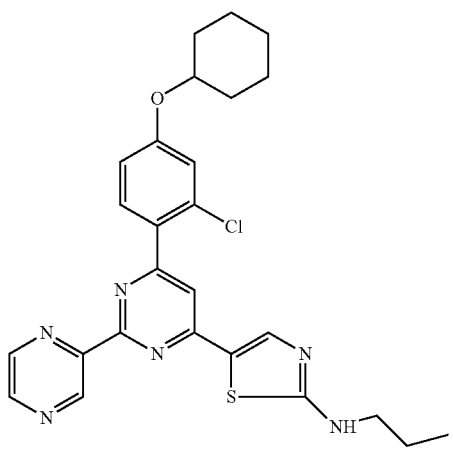<br>5-(6-(2-chloro-4-(cyclohexyloxy)phenyl)-2-(pyrazin-2-yl)pyrimidin-4-yl)-N-propylthiazol-2-amine | HPLC $t_R$ = 4.89 min<br>LCMS [M + H]$^+$ = 507.17 |

TABLE 13-continued
| Ex. # | Compound Structure/Name | HPLC and LCMS Data |
|---|---|---|
| 224 | 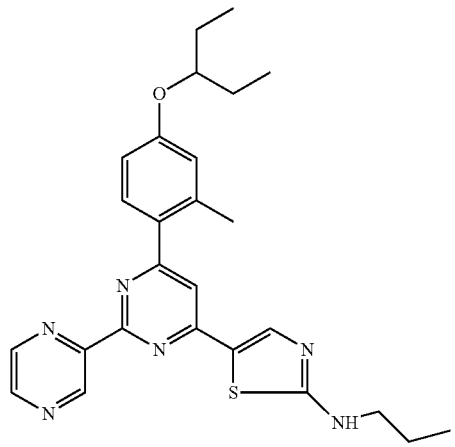<br>5-(6-(2-methyl-4-(pentan-3-yloxy)phenyl)-2-(pyrazin-2-yl)pyrimidin-4-yl)-N-propylthiazol-2-amine | HPLC $t_R$ = 4.65 min<br>LCMS [M + H]$^+$ = 475.20 |
| 225 | 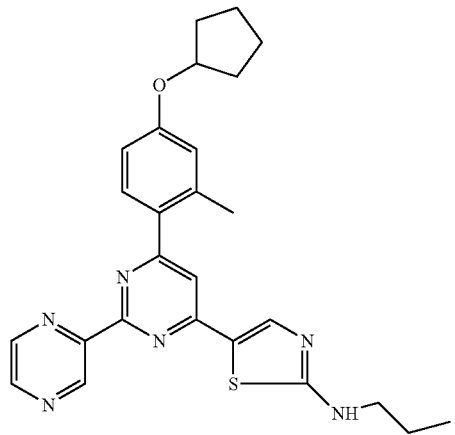<br>-(6-(4-(cyclopentyloxy)-2-methylphenyl)-2-(pyrazin-2-yl)pyrimidin-4-yl)-N-propylthiazol-2-amine | HPLC $t_R$ = 4.62 min<br>LCMS [M + H]$^+$ = 473.19 |

TABLE 13-continued
| Ex. # | Compound Structure/Name | HPLC and LCMS Data |
|---|---|---|
| 226 | 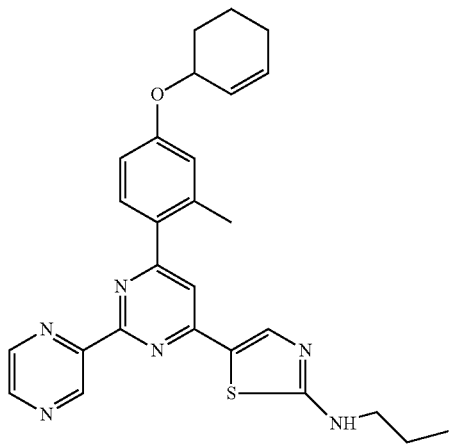<br>5-(6-(4-cyclohex-2-enyloxy)-2-methylphenyl)-2-(pyrazin-2-yl)pyrimidin-4-yl)-N-propylthiazol-2-amine | HPLC tR = 4.60 min<br>LCMS [M + H]+ = 485.21 |
| 227 | 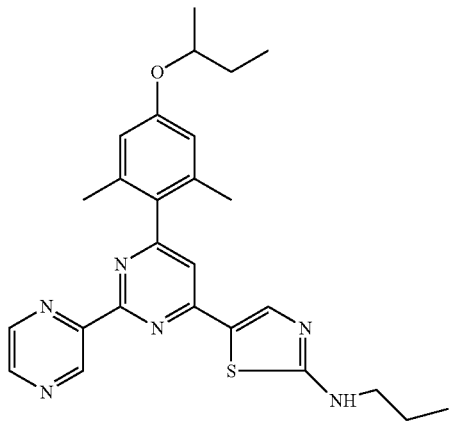<br>5-(6-(4-sec-butoxy-2,6-dimethylphenyl)-2-(pyrazin-2-yl)pyrimidin-4-yl)-N-propylthiazol-2-amine | HPLC tR = 4.48 min<br>LCMS [M + H]+ = 475.20 |

TABLE 13-continued

| Ex. # | Compound Structure/Name | HPLC and LCMS Data |
|---|---|---|
| 228 | 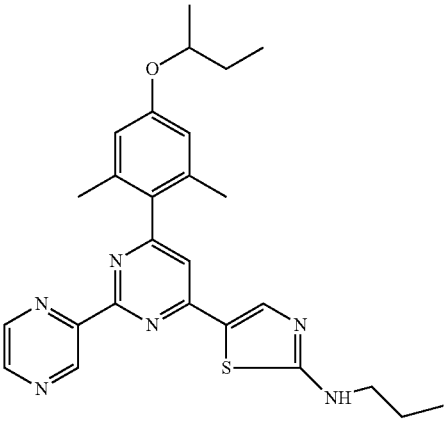<br>5-(6-(4-(cyclohex-2-enyloxy)-2,6-dimethylphenyl)-2-(pyrazin-2-yl)pyrimidin-4-yl)-N-propylthiazol-2-amine | HPLC tR = 4.56 min<br>LCMS [M + H]+ = 499.16 |
| 229 | 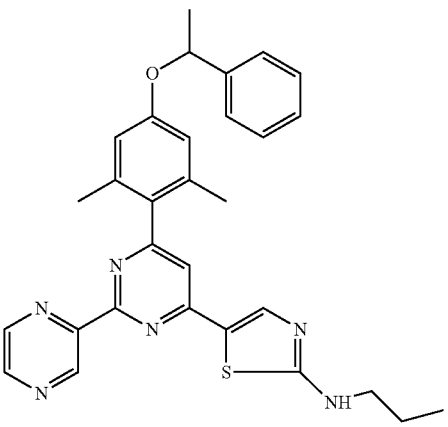<br>5-(6-(2,6-dimethyl-4-(1-phenylethoxy)phenyl)-2-(pyrazin-2-yl)pyrimidin-4-yl)-N-propylthiazol-2-amine | HPLC tR = 4.55 min<br>LCMS [M + H]+ = 523.19 |
| 230 | 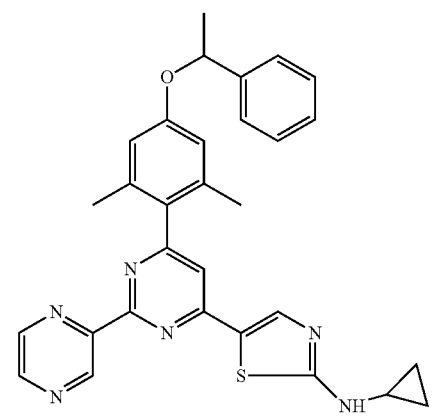<br>N-cyclopropyl-5-(6-(4-isopropoxy-2,6-dimethylphenyl)-2-(pyrazin-2-yl)pyrimidin-4-yl)thiazol-2-amine | HPLC tR = 4.20 min<br>LCMS [M + H]+ = 459.18 |

TABLE 13-continued

| Ex. # | Compound Structure/Name | HPLC and LCMS Data |
|---|---|---|
| 231 | 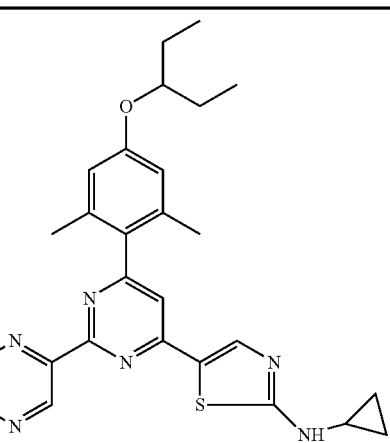<br>N-cyclopropyl-5-(6-(2,6-dimethyl-4-(pentan-3-yloxy)phenyl)-2-(pyrazin-2-yl)pyrimidin-4-yl)thiazol-2-amine | HPLC tR = 4.58 min<br>LCMS [M + H]+ = 487.14 |
| 232 | 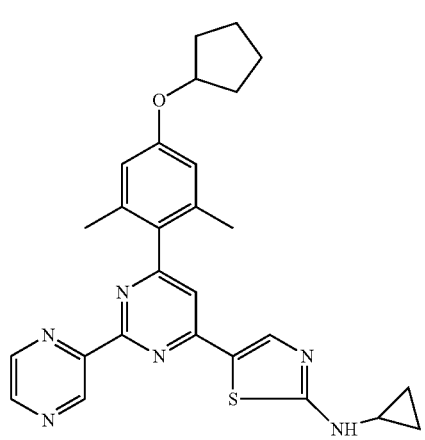<br>5-(6-(4-(cyclopentyloxy)-2,6-dimethylphenyl)-2-(pyrazin-2-yl)pyrimidin-4-yl)-N-cyclopropylthiazol-2-amine | HPLC tR = 4.53 min<br>LCMS [M + H]+ = 485.14 |
| 233 | 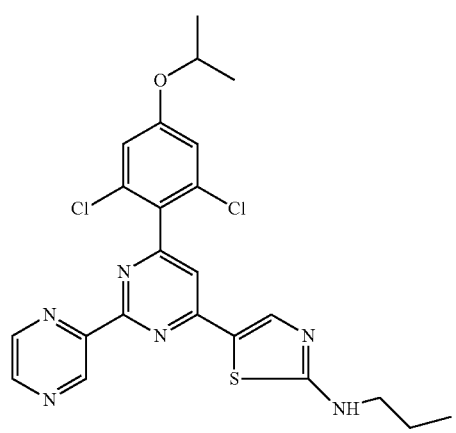<br>5-(6-(2,6-dichloro-4-isopropoxyphenyl)-2-(pyrazin-2-yl)pyrimidin-4-yl)-N-propylthiazol-2-amine | HPLC tR = 4.46 min<br>LCMS [M + H]+ = 501.02 |

TABLE 13-continued
| Ex. # | Compound Structure/Name | HPLC and LCMS Data |
|---|---|---|
| 234 | 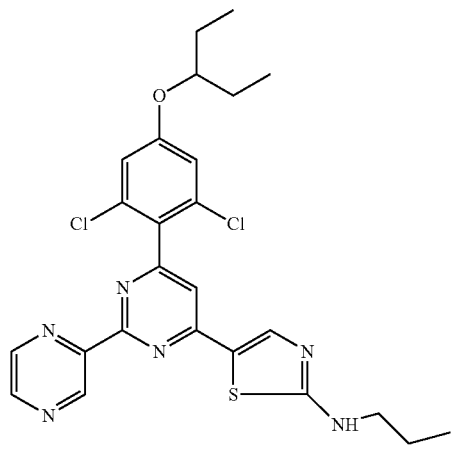<br>5-(6-(2,6-dichloro-4-(pentan-3-yloxy)phenyl)-2-(pyrazin-2-yl)pyrimidin-4-yl)-N-propylthiazol-2-amine | HPLC tR = 4.76 min<br>LCMS [M + H]+ = 529.05 |
| 235 | 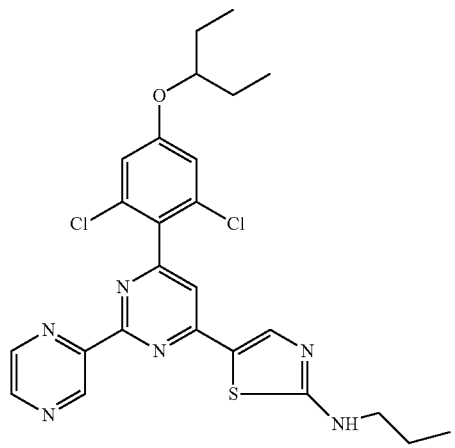<br>5-(6-(2,6-dichloro-4-(cyclopentyloxy)phenyl)-2-(pyrazin-2-yl)pyrimidin-4-yl)-N-propylthiazol-2-amine | HPLC tR = 4.71 min<br>LCMS [M + H]+ = 527.05 |

TABLE 13-continued

| Ex. # | Compound Structure/Name | HPLC and LCMS Data |
|---|---|---|
| 236 | 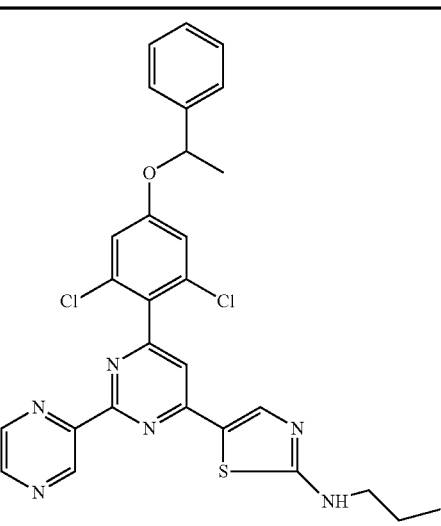<br>5-(6-(2,6-dichloro-4-(1-phenylethoxy)phenyl)-2-(pyrazin-2-yl)pyrimidin-4-yl)-N-propylthiazol-2-amine | HPLC tR = 4.64 min<br>LCMS [M + H]+ = 563.02 |
| 237 | 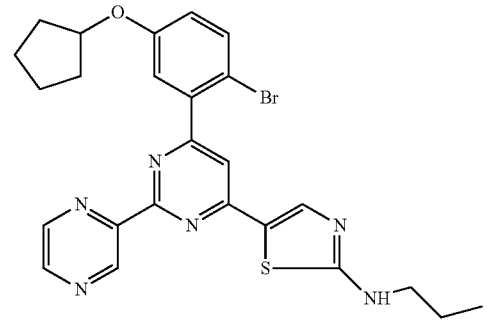<br>5-(6-(2-bromo-5-(cyclopentyloxy)phenyl)-2-(pyrazin-2-yl)pyrimidin-4-yl)-N-propylthiazol-2-amine | HPLC tR = 4.70 min<br>LCMS [M + H]+ = 537.07 |
| 238 | 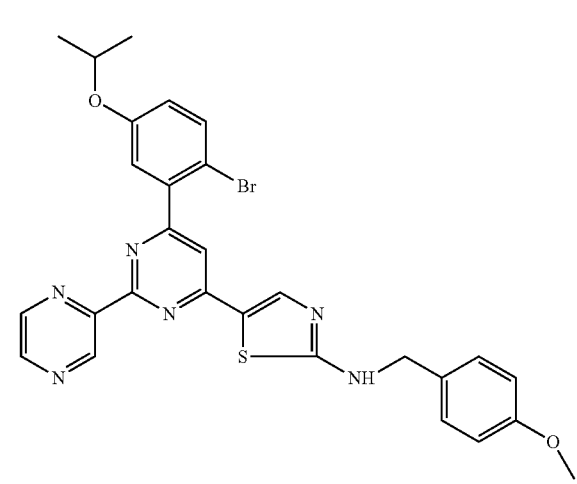<br>N-(4-methoxybenzyl)-5-(6-(2-bromo-5-isopropoxyphenyl)-2-(pyrazin-2-yl)pyrimidin-4-yl)thiazol-2-amine | HPLC tR = 4.63 min<br>LCMS [M + H]+ = 588.97 |

TABLE 13-continued

| Ex. # | Compound Structure/Name | HPLC and LCMS Data |
|---|---|---|
| 239 | 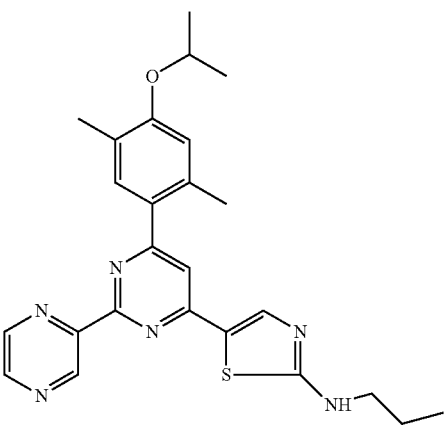<br>5-(6-(4-isopropoxy-2,5-dimethylphenyl)-2-(pyrazin-2-yl)pyrimidin-4-yl)-N-propylthiazol-2-amine | HPLC tR = 4.48 min<br>LCMS [M + H]+ = 461.19 |
| 240 | 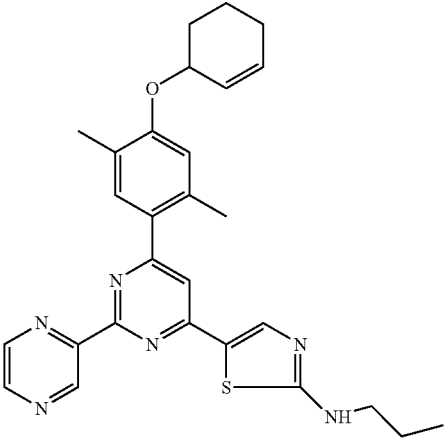<br>5-(6-(4-(cyclohex-2-enyloxy)-2,5-dimethylphenyl)-2-(pyrazin-2-yl)pyrimidin-4-yl)-N-propylthiazol-2-amine | HPLC tR = 4.76 min<br>LCMS [M + H]+ = 499.16 |
| 241 | 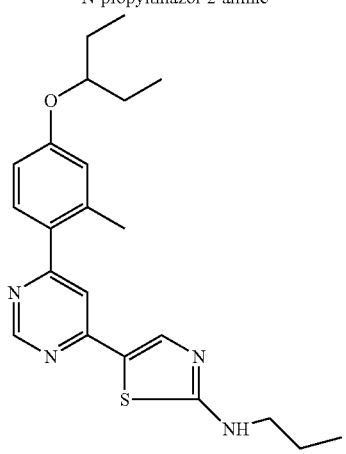<br>5-(6-(2-methyl-4-(pentan-3-yloxy)phenyl)pyrimidin-4-yl)-N-propylthiazol-2-amine | HPLC t$_R$ = 4.47 min<br>LCMS [M + H]+ = 397.27 |

Examples 242-247

Examples 242-247 listed in Table 14 below were prepared utilizing a similar procedure as described in step 2 of Example 206.

TABLE 14

| Ex. # | Compound Structure/Name | HPLC and LCMS Data |
|---|---|---|
| 242 | 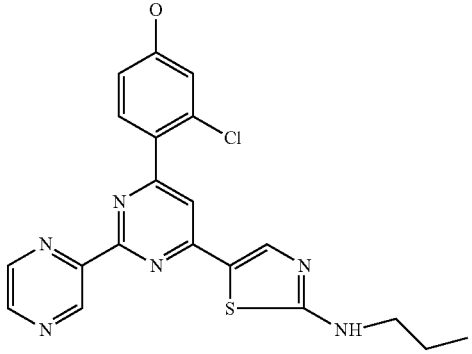<br>3-chloro-4-(6-(2-(propylamino)thiazol-5-yl)-2-(pyrazin-2-yl)pyrimidin-4-yl)phenol | HPLC $t_R$ = 3.73 min<br>LCMS [M + H]+ = 425.25 |
| 243 | 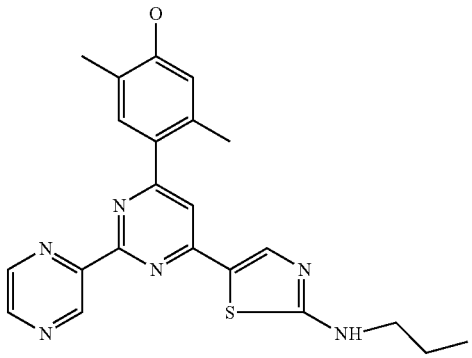<br>2,5-dimethyl-4-(6-(2-(propylamino)thiazol-5-yl)-2-(pyrazin-2-yl)pyrimidin-4-yl)phenol | HPLC $t_R$ = 3.68 min<br>LCMS [M + H]+ = 419.19 |
| 244 | 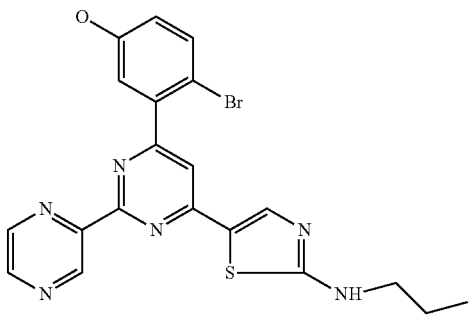<br>4-bromo-3-(6-(2-(propylamino)thiazol-5-yl)-2-(pyrazin-2-yl)pyrimidin-4-yl)phenol | HPLC $t_R$ = 3.82 min<br>LCMS [M + H]+ = 469.05 |

TABLE 14-continued

| Ex. # | Compound Structure/Name | HPLC and LCMS Data |
|---|---|---|
| 245 | 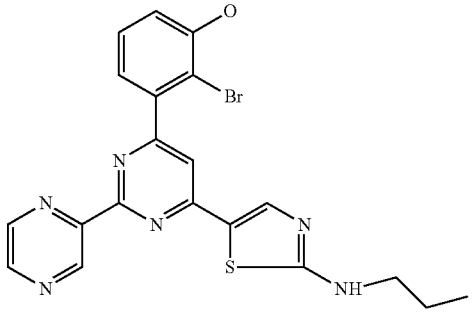<br>2-bromo-3-(6-(2-(propylamino)thiazol-5-yl)-2-(pyrazin-2-yl)pyrimidin-4-yl)phenol | HPLC $t_R$ = 3.53 min<br>LCMS [M + H]+ = 468.99 |
| 246 | 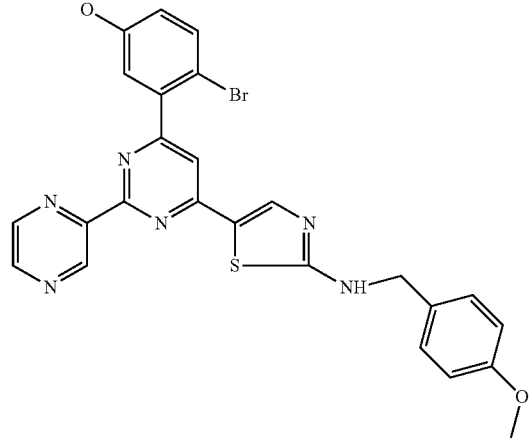<br>3-(6-(2-(4-methoxybenzylamino)thiazol-5-yl)-2-(pyrazin-2-yl)pyrimidin-4-yl)-4-bromophenol | HPLC $t_R$ = 4.11 min<br>LCMS [M + H]+ = 546.94 |
| 247 | 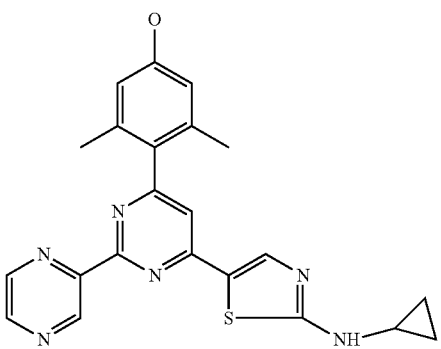<br>4-(6-(2-(cyclopropylamino)thiazol-5-yl)-2-(pyrazin-2-yl)pyrimidin-4-yl)-3,5-dimethylphenol | HPLC $t_R$ = 3.36 min<br>LCMS [M + H]+ = 417.23 |

Example 248

N-(5-(6-(2,6-dimethyl-4-propoxyphenyl)-2-(pyrazin-2-yl)pyrimidin-4-yl)thiazol-2-yl)acetamide

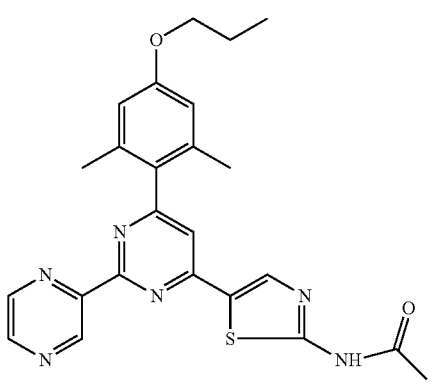

Step 1: Example 249, N-(4-methoxybenzyl)-5-(6-(2,6-dimethyl-4-propoxyphenyl)-2-(pyrazin-2-yl)pyrimidin-4-yl)thiazol-2-amine

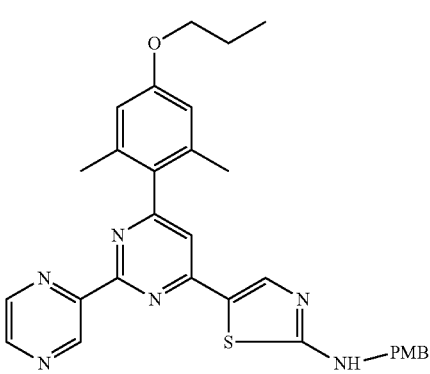

Example 249 was prepared by utilizing a similar procedure as described for Example 45. HPLC Ret. time: 4.57 min. LCMS MH$^+$ (m/z)=539.22. $^1$H NMR: (CDCl$_3$, 400 MHz): δ 9.67 (d, 1H), 8.71 (d, 1H), 8.60 (d, 1H), 7.63 (s, 1H), 7.27 (d, 2H), 7.25 (s, 1H), 7.09 (brs, 1H) 6.85 (d, 2H), 6.61 (s, 2H), 4.42 (s, 2H), 3.88 (t, 2H), 3.69 (s, 3H), 2.09 (s, 6H), 1.75 (m, 2H), 0.98 (t, 3H).

Step 2: Example 250, 5-(6-(2,6-dimethyl-4-propoxyphenyl)-2-(pyrazin-2-yl)pyrimidin-4-yl)thiazol-2-amine

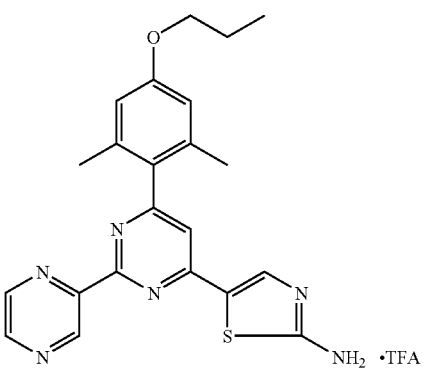

Example 249 (300.0 mg, 0.56 mmol) was stirred in TFA (5 ml) at 60° C. for 24 hr. After cooling to rt, the TFA was removed in vacuo and resulting residue was then with aqueous sodium bicarbonate for 1 hr. The resulting solid, Example 250, was collected by vacuum filtration to yield 200.0 mg (85%) pale brown solid. HPLC Ret. time: 3.82 min. LCMS MH$^+$ (m/z)=419.25. $^1$H NMR: (CDCl$_3$, 400 MHz): δ 9.76 (d, 1H), 9.34 (brs, 2H), 8.86 (d, 1H), 8.77 (d, 1H), 7.88 (s, 1H), 7.46 (s, 1H), 6.72 (s, 2H), 3.95 (t, 2H), 2.14 (s, 6H), 1.83 (m, 2H), 1.07 (t, 3H).

Step 3: Example 248

To a slurry of Example 250 (25.0 mg, 0.06 mmol) in THF (0.2 ml), was added TEA (16.7 ul, 0.12 mmol) and acetyl chloride (8.5 ul, 0.12 mmol). After stirring at rt for 10 min, the reaction mixture was diluted with water (2 ml). A light yellow solid was collected by vacuum filtration, and dried to afford 17.0 mg (62%) of Example 250 as a solid. HPLC Ret. time: 4.34 min. LCMS MH$^+$ (m/z)=461.27. $^1$H NMR: (CDCl$_3$, 400 MHz): δ 13.72 (s, 1H), 9.73 (d, 1H), 8.80 (d, 1H), 8.71 (d, 1H), 8.11 (s, 1H), 7.49 (s, 1H), 6.64 (s, 2H), 3.89 (t, 2H), 2.42 (s, 3H), 2.09 (s, 6H), 1.75 (m, 2H), 0.99 (t, 3H).

Examples 251-262

Examples 251-262 listed in Table 15 below were prepared utilizing a similar procedure as described for Example 248.

TABLE 15

| Ex. # | Compound Structure/Name | HPLC and LCMS Data |
|---|---|---|
| 251 | 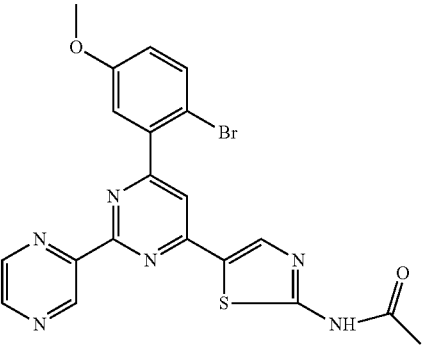<br>N-(5-(6-(2-bromo-5-methoxyphenyl)-2-(pyrazin-2-yl)pyrimidin-4-yl)thiazol-2-yl)acetamide | HPLC $t_R$ = 4.08 min<br>LCMS [M + H]$^+$ = 482.94 |
| 252 | 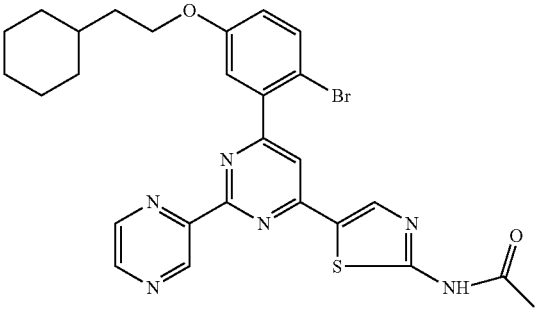<br>N-(5-(6-(2-bromo-5-(2-cyclohexylethoxy)phenyl)-2-(pyrazin-2-yl)pyrimidin-4-yl)thiazol-2-yl)acetamide | HPLC $t_R$ = 5.10 min<br>LCMS [M + H]$^+$ = 579.20 |
| 253 | 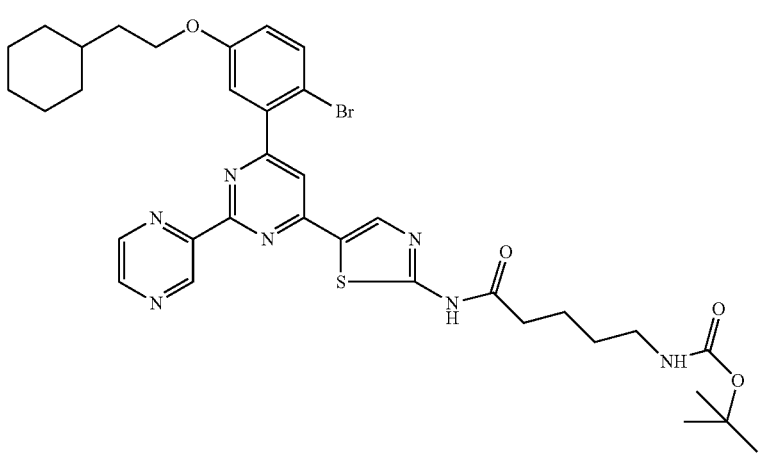<br>tert-butyl 5-(5-(6-(2-bromo-5-(2-cyclohexylethoxy)phenyl)-2-(pyrazin-2-yl)pyrimidin-4-yl)thiazol-2-ylamino)-5-oxopentylcarbamate | HPLC $t_R$ = 5.57 min<br>LCMS [M + H]$^+$ = 736.31, 738.32 |

TABLE 15-continued

| Ex. # | Compound Structure/Name | HPLC and LCMS Data |
|---|---|---|
| 254 | 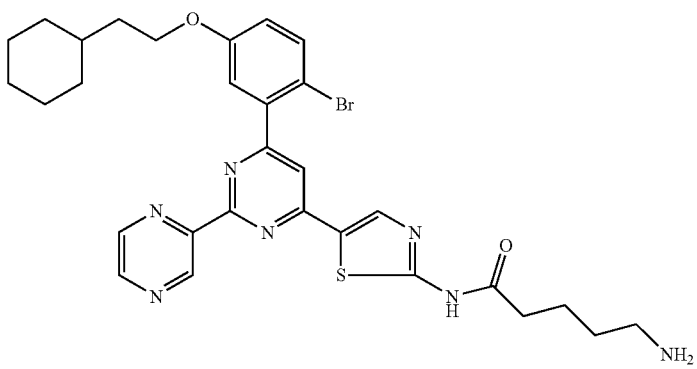  5-amino-N-(5-(6-(2-bromo-5-(2-cyclohexylethoxy)phenyl)-2-(pyrazin-2-yl)pyrimidin-4-yl)thiazol-2-yl)pentanamide | HPLC $t_R$ = 4.61 min<br>LCMS [M + H]$^+$ = 636.26, 638.26 |
| 255 | 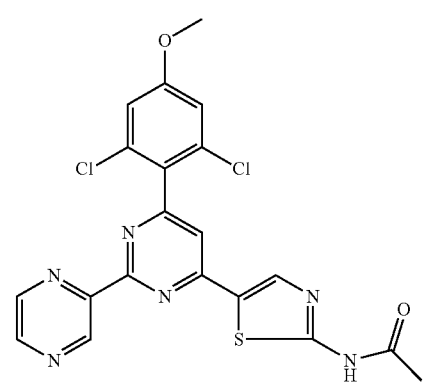  N-(5-(6-(4-methoxy-2,6-dimethylphenyl)-2-(pyrazin-2-yl)pyrimidin-4-yl)thiazol-2-yl)acetamide | HPLC $t_R$ = 4.02 min<br>LCMS [M + H]$^+$ = 473.04 |
| 256 | 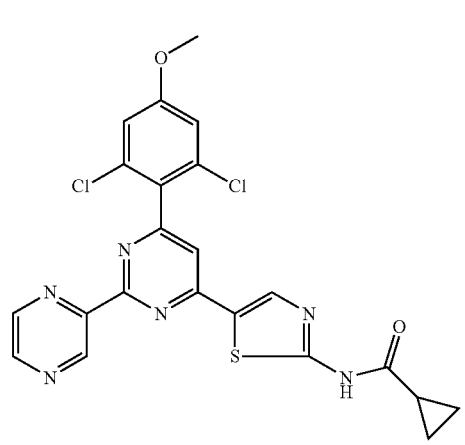  N-(5-(6-(2,6-dichloro-4-methoxyphenyl)-2-(pyrazin-2-yl)pyrimidin-4-yl)thiazol-2-yl)cyclopropanecarboxamide | HPLC $t_R$ = 4.26 min<br>LCMS [M + H]$^+$ = 499.09 |

TABLE 15-continued

| Ex. # | Compound Structure/Name | HPLC and LCMS Data |
|---|---|---|
| 257 | 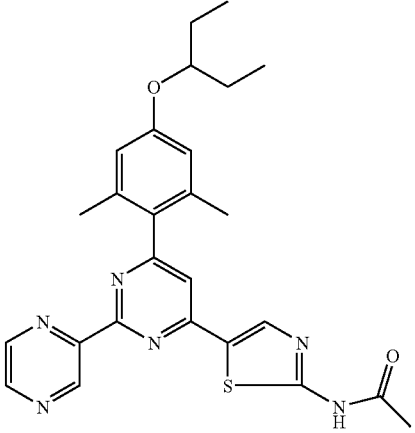<br>N-(5-(6-(2,6-dichloro-4-methoxyphenyl)-2-(pyrazin-2-yl)pyrimidin-4-yl)thiazol-2-yl)cyclopropanecarboxamide | HPLC $t_R$ = 4.58 min<br>LCMS [M + H]$^+$ = 489.28 |
| 258 | 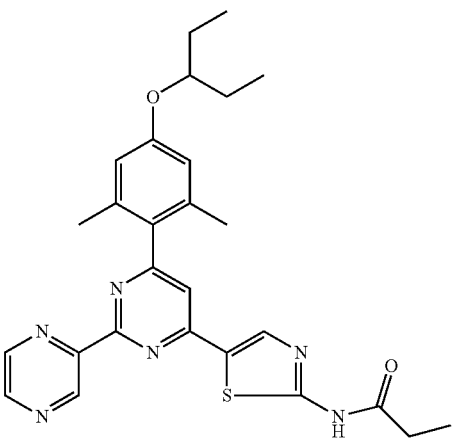<br>N-(5-(6-(2,6-dimethyl-4-(pentan-3-yloxy)phenyl)-2-(pyrazin-2-yl)pyrimidin-4-yl)thiazol-2-yl)propionamide | HPLC $t_R$ = 4.67 min<br>LCMS [M + H]$^+$ = 503.26 |
| 259 | 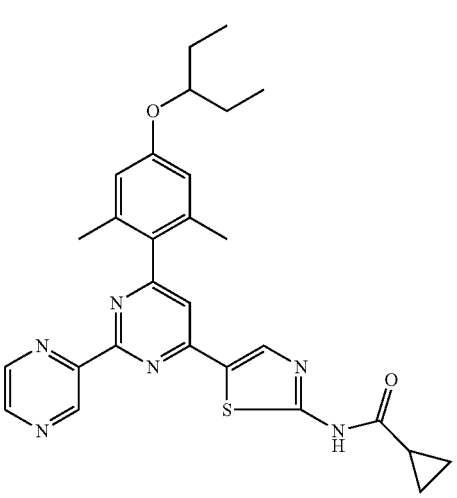<br>N-(5-(6-(2,6-dimethyl-4-(pentan-3-yloxy)phenyl)-2-(pyrazin-2-yl)pyrimidin-4-yl)thiazol-2-yl)cyclopropanecarboxamide | HPLC $t_R$ = 4.59 min<br>LCMS [M + H]$^+$ = 515.25 |

TABLE 15-continued

| Ex. # | Compound Structure/Name | HPLC and LCMS Data |
|---|---|---|
| 260 | 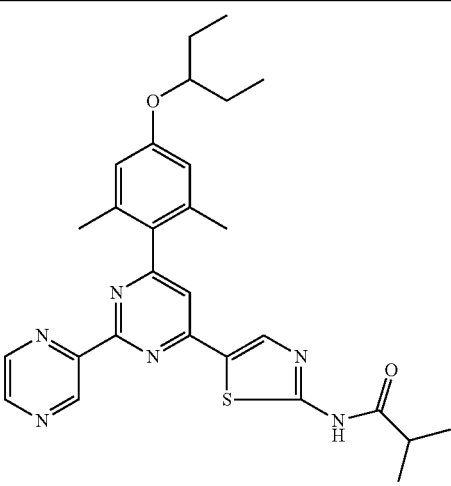<br>N-(5-(6-(2,6-dimethyl-4-(pentan-3-yloxy)phenyl)-2-(pyrazin-2-yl)pyrimidin-4-yl)thiazol-2-yl)isobutyramide | HPLC $t_R$ = 4.75 min<br>LCMS [M + H]$^+$ = 517.30 |
| 261 | 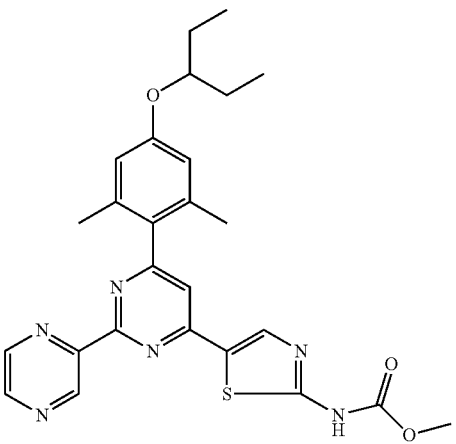<br>N-(5-(6-(2,6-dimethyl-4-(pentan-3-yloxy)phenyl)-2-(pyrazin-2-yl)pyrimidin-4-yl)thiazol-2-yl)-2-methoxyacetamide | HPLC $t_R$ = 4.59 min<br>LCMS [M + H]$^+$ = 519.27 |
| 262 | 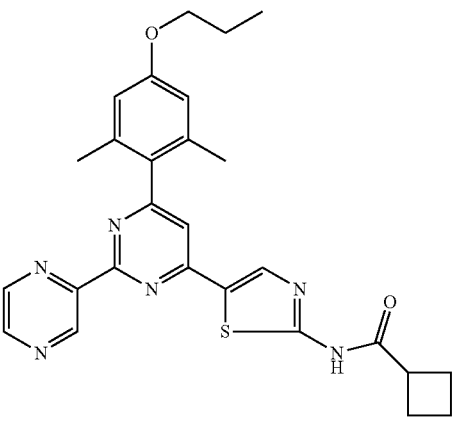<br>N-(5-(6-(2,6-dimethyl-4-propoxyphenyl)-2-(pyrazin-2-yl)pyrimidin-4-yl)thiazol-2-yl)cyclobutanecarboxamide | HPLC $t_R$ = 4.61 min<br>LCMS [M + H]$^+$ = 501.23 |

Example 263

1-allyl-3-(5-(6-(2,6-dimethyl-4-(pentan-3-yloxy)phenyl)-2-(pyrazin-2-yl)pyrimidin-4-yl)thiazol-2-yl)urea

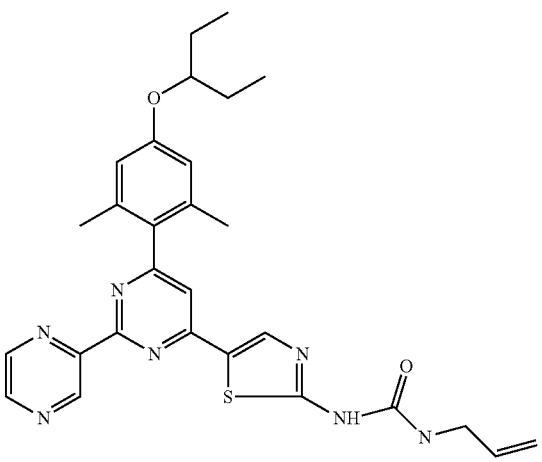

Step 1: Example 264, 5-(6-(2,6-dimethyl-4-(pentan-3-yloxy)phenyl)-2-(pyrazin-2-yl)pyrimidin-4-yl)thiazol-2-amine

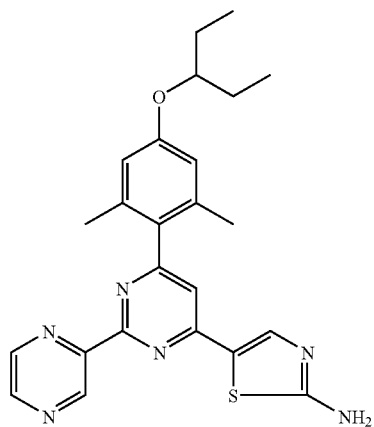

Example 264 was prepared by utilizing a similar procedure as described in step 5 of Example 138. HPLC Ret. time: 4.15 min. LCMS MH$^+$ (m/z)=447.31. $^1$H NMR: (CDCl$_3$, 400 MHz): δ 9.74 (d, 1H), 9.64 (brs, 2H), 8.75 (d, 1H), 8.71 (d, 1H), 7.97 (s, 1H), 7.52 (s, 1H), 6.66 (s, 2H), 4.16 (m, 1H), 1.67 (m, 4H), 0.96 (t, 6H).

Step 2: Example 263

To a slurry of Example 264 (20.0 mg, 0.056 mmol) in THF (0.2 ml) was added TEA (8.5 ul, 0.062 mmol) and isopropylisocyanate (0.05 ml, 0.5 mmol). After stirred at rt. for 60 hr, the solvent was removed in vacuo. The oil residue was purified by reverse-phase preparative HPLC and the fraction containing the product was concentrated in vacuo and diluted with 1.0 N aqueous hydrochloric acid (1-2 ml), and lyophilized to yield 18.5 mg (58.4%) yellow solid. HPLC Ret. time: 4.66 min. LCMS MH$^+$ (m/z)=530.24. $^1$H NMR: (CDCl$_3$, 400 MHz): δ 9.78 (d, 1H), 8.76 (d, 1H), 8.19 (brs, 1H), 7.52 (m, 2H), 6.69 (s, 2H), 5.91 (m, 1H), 5.32 (m, 1H), 5.21 (m, 1H), 4.17 (m, 1H), 4.01 (d, 2H), 2.15 (s, 6H), 1.70 (m, 4H), 0.98 (t, 6H).

Examples 265-305

Examples 265-305 listed in Table 16 below were prepared utilizing a similar procedure as described for Example 263.

TABLE 16

| Ex. # | Compound Structure/Name | HPLC and LCMS Data |
|---|---|---|
| 265 | 1-(5-(6-(2-bromo-5-methoxyphenyl)-2-(pyrazin-2-yl)pyrimidin-4-yl)thiazol-2-yl)-3-methylurea | HPLC t$_R$ = 4.03 min<br>LCMS [M + H]$^+$ = 497.93 |

TABLE 16-continued

| Ex. # | Compound Structure/Name | HPLC and LCMS Data |
|---|---|---|
| 267 | 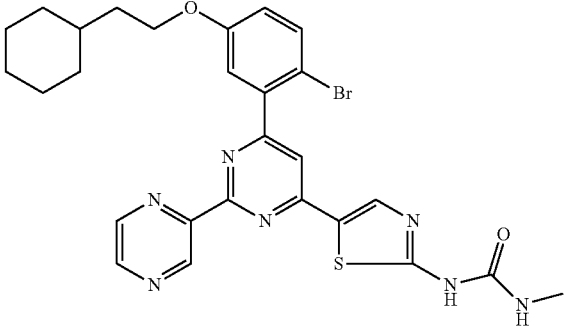<br>1-(5-(6-(2-bromo-5-(2-cyclohexylethoxy)phenyl)-2-(pyrazin-2-yl)pyrimidin-4-yl)thiazol-2-yl)-3-methylurea | HPLC $t_R$ = 5.03 min<br>LCMS [M + H]$^+$ = 594.15 |
| 268 | 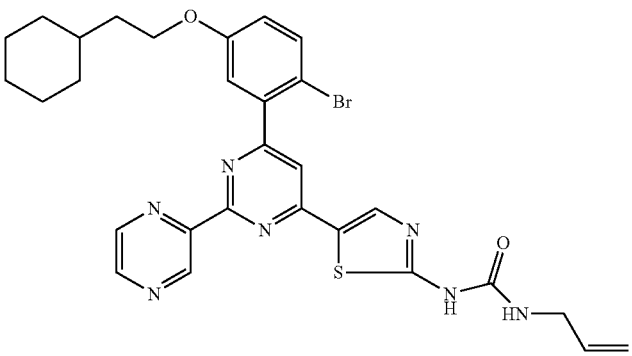<br>1-allyl-3-(5-(6-(2-bromo-5-(2-cyclohexylethoxy)phenyl)-2-(pyrazin-2-yl)pyrimidin-4-yl)thiazol-2-yl)urea | HPLC $t_R$ = 5.20 min<br>LCMS [M + H]$^+$ = 620.20, 622.20 |
| 269 | 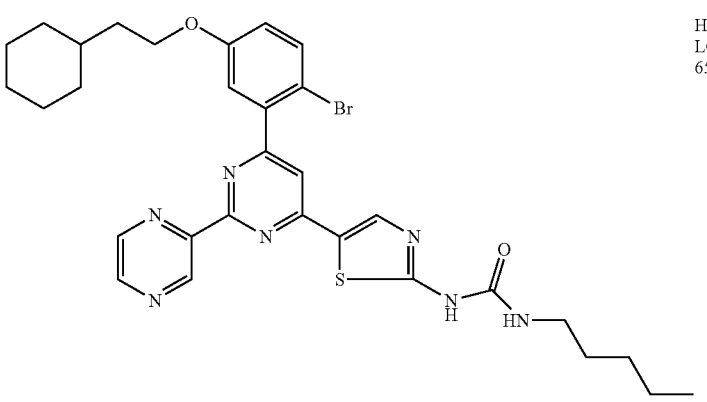<br>1-(5-(6-(2-bromo-5-(2-cyclohexylethoxy)phenyl)-2-(pyrazin-2-yl)pyrimidin-4-yl)thiazol-2-yl)-3-pentylurea | HPLC $t_R$ = 5.71 min<br>LCMS [M + H]$^+$ = 650.24, 652.24 |

TABLE 16-continued

| Ex. # | Compound Structure/Name | HPLC and LCMS Data |
|---|---|---|
| 270 | 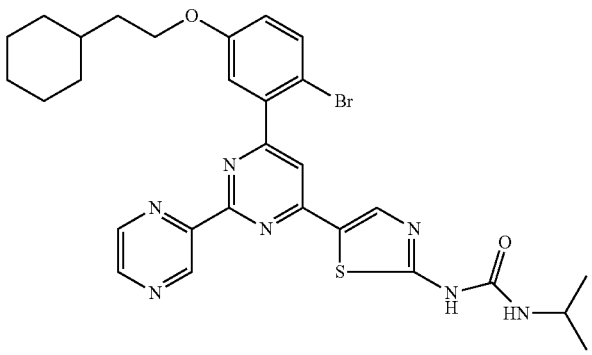<br>1-(5-(6-(2-bromo-5-(2-cyclohexylethoxy)phenyl)-2-(pyrazin-2-yl)pyrimidin-4-yl)thiazol-2-yl)-3-isopropylurea | HPLC $t_R$ = 5.26 min<br>LCMS [M + H]$^+$ = 622.16, 624.16 |
| 271 | 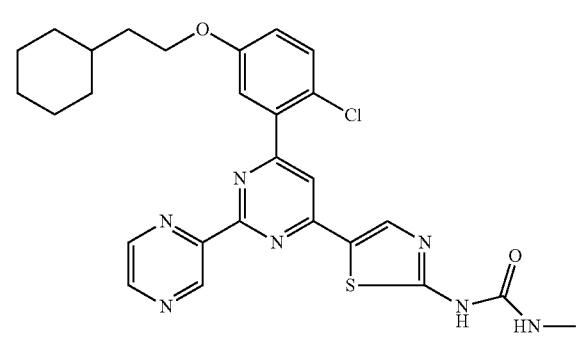<br>1-(5-(6-(2-chloro-5-(2-cyclohexylethoxy)phenyl)-2-(pyrazin-2-yl)pyrimidin-4-yl)thiazol-2-yl)-3-methylurea | HPLC $t_R$ = 5.53 min<br>LCMS [M + H]$^+$ = 550.26 |
| 272 | 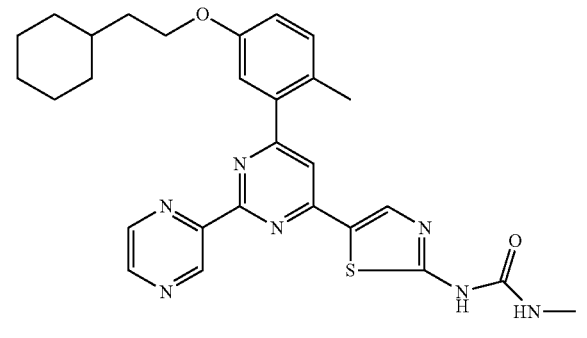<br>1-(5-(6-(5-(2-cyclohexylethoxy)-2-methylphenyl)-2-(pyrazin-2-yl)pyrimidin-4-yl)thiazol-2-yl)-3-methylurea | HPLC $t_R$ = 5.04 min<br>LCMS [M + H]$^+$ = 530.23 |
| 273 | 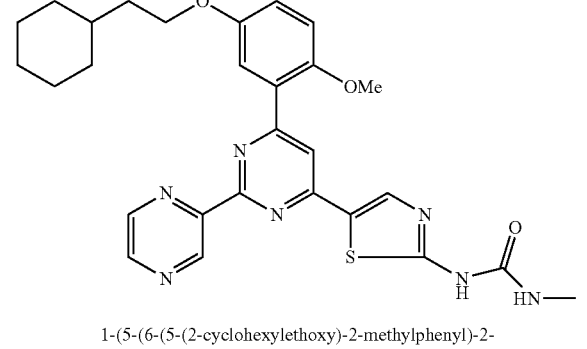<br>1-(5-(6-(5-(2-cyclohexylethoxy)-2-methylphenyl)-2-(pyrazin-2-yl)pyrimidin-4-yl)thiazol-2-yl)-3-methylurea | HPLC $t_R$ = 4.76 min<br>LCMS [M + H]$^+$ = 546.26 |

TABLE 16-continued

| Ex. # | Compound Structure/Name | HPLC and LCMS Data |
|---|---|---|
| 274 | 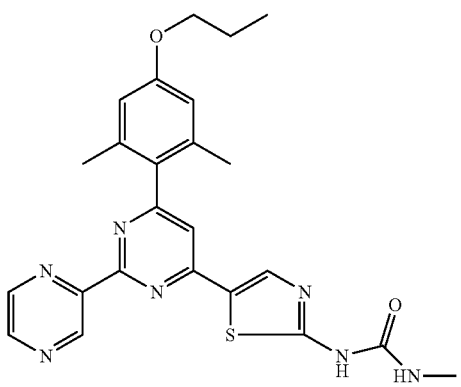<br>1-(5-(6-(2,6-dimethyl-4-propoxyphenyl)-2-(pyrazin-2-yl)pyrimidin-4-yl)thiazol-2-yl)-3-methylurea | HPLC $t_R$ = 4.29 min<br>LCMS $[M + H]^+$ = 476.22 |
| 275 | 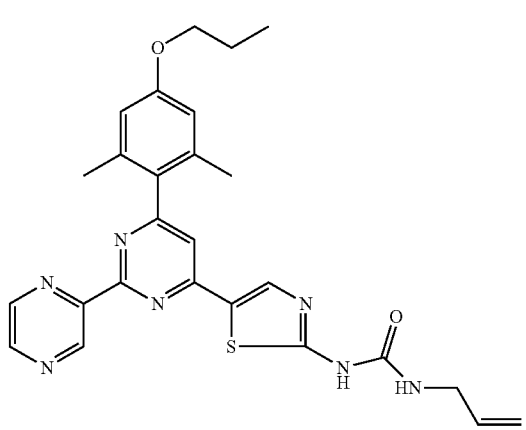<br>1-allyl-3-(5-(6-(2,6-dimethyl-4-propoxyphenyl)-2-(pyrazin-2-yl)pyrimidin-4-yl)thiazol-2-yl)urea | HPLC $t_R$ = 4.43 min<br>LCMS $[M + H]^+$ = 502.26 |
| 276 | 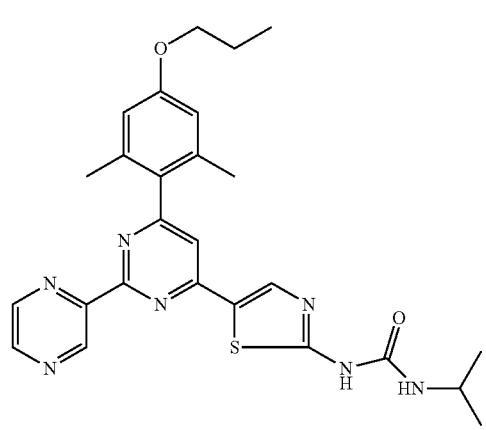<br>1-(5-(6-(2,6-dimethyl-4-propoxyphenyl)-2-(pyrazin-2-yl)pyrimidin-4-yl)thiazol-2-yl)-3-isopropylurea | HPLC $t_R$ = 4.49 min<br>LCMS $[M + H]^+$ = 504.27 |

TABLE 16-continued

| Ex. # | Compound Structure/Name | HPLC and LCMS Data |
|---|---|---|
| 277 | 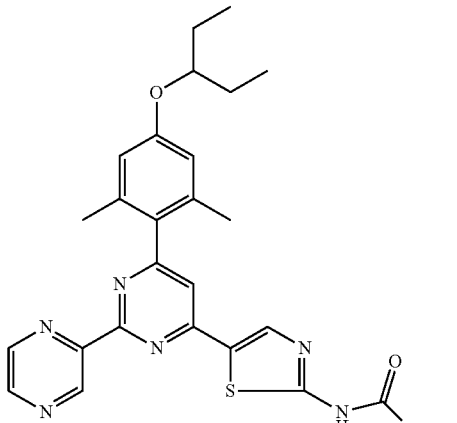<br>1-(5-(6-(2,6-dimethyl-4-(pentan-3-yloxy)phenyl)-2-(pyrazin-2-yl)pyrimidin-4-yl)thiazol-2-yl)-3-methylurea | HPLC $t_R$ = 4.52 min<br>LCMS [M + H]$^+$ = 504.28 |
| 278 | 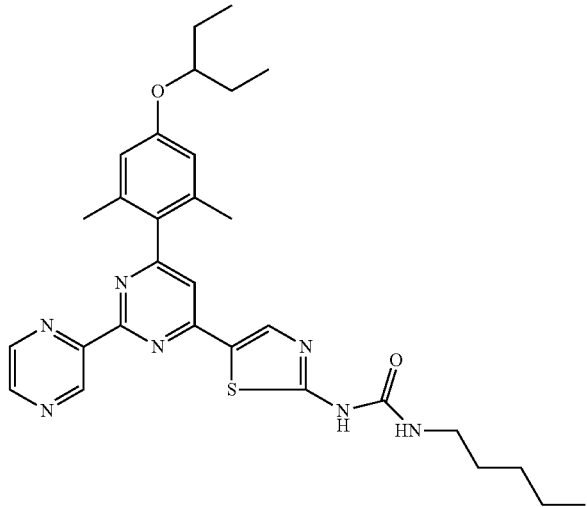<br>1-(5-(6-(2,6-dimethyl-4-(pentan-3-yloxy)phenyl)-2-(pyrazin-2-yl)pyrimidin-4-yl)thiazol-2-yl)-3-pentylurea | HPLC $t_R$ = 4.92 min<br>LCMS [M + H]$^+$ = 560.29 |
| 279 | 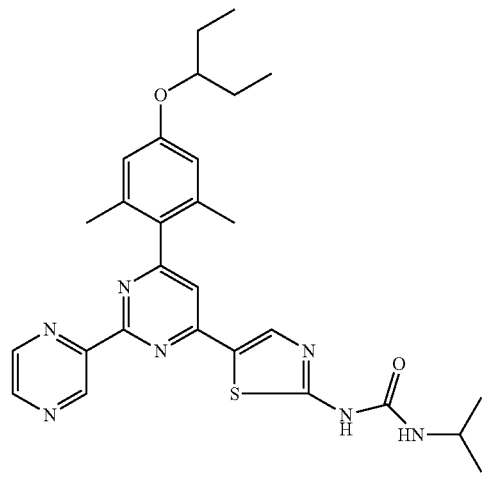<br>1-(5-(6-(2,6-dimethyl-4-(pentan-3-yloxy)phenyl)-2-(pyrazin-2-yl)pyrimidin-4-yl)thiazol-2-yl)-3-isopropylurea | HPLC $t_R$ = 4.70 min<br>LCMS [M + H]$^+$ = 532.28 |

… TABLE 16-continued
| Ex. # | Compound Structure/Name | HPLC and LCMS Data |
|---|---|---|
| 280 | 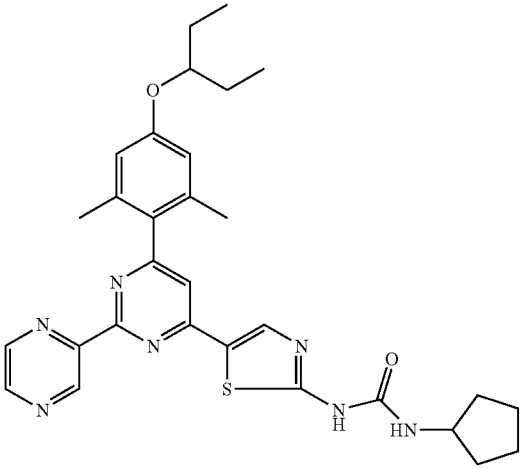<br>1-cyclopentyl-3-(5-(6-(2,6-dimethyl-4-(pentan-3-yloxy)phenyl)-2-(pyrazin-2-yl)pyrimidin-4-yl)thiazol-2-yl)urea | HPLC $t_R$ = 4.83 min<br>LCMS [M + H]$^+$ = 558.28 |
| 281 | 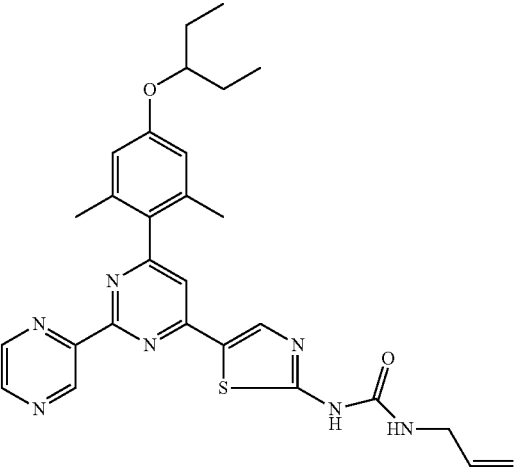<br>1-allyl-3-(5-(6-(2,6-dimethyl-4-(pentan-3-yloxy)phenyl)-2-(pyrazin-2-yl)pyrimidin-4-yl)thiazol-2-yl)urea | HPLC $t_R$ = 4.66 min<br>LCMS [M + H]$^+$ = 530.24 |

TABLE 16-continued
| Ex. # | Compound Structure/Name | HPLC and LCMS Data |
|---|---|---|
| 282 | 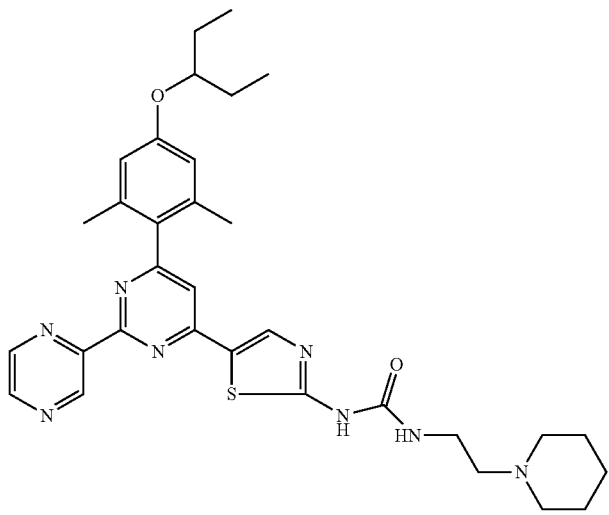<br>1-(5-(6-(2,6-dimethyl-4-(pentan-3-yloxy)phenyl)-2-(pyrazin-2-yl)pyrimidin-4-yl)thiazol-2-yl)-3-(2-(piperidin-1-yl)ethyl)urea | HPLC $t_R$ = 4.03 min<br>LCMS [M + H]$^+$ = 601.38 |
| 283 | 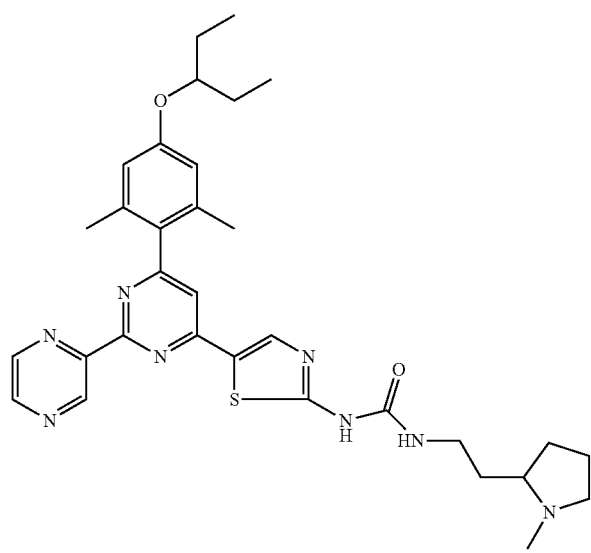<br>1-(5-(6-(2,6-dimethyl-4-(pentan-3-yloxy)phenyl)-2-(pyrazin-2-yl)pyrimidin-4-yl)thiazol-2-yl)-3-(2-(1-methylpyrrolidin-2-yl)ethyl)urea | HPLC $t_R$ = 4.04 min<br>LCMS [M + H]$^+$ = 601.38 |

TABLE 16-continued
| Ex. # | Compound Structure/Name | HPLC and LCMS Data |
|---|---|---|
| 284 | 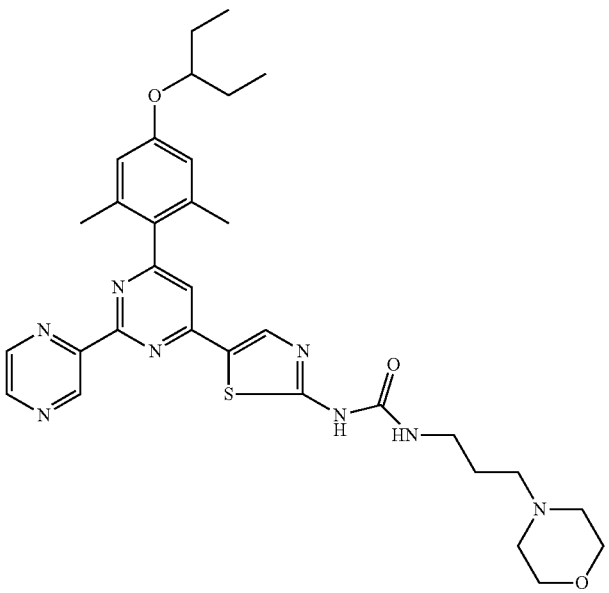<br>1-(5-(6-(2,6-dimethyl-4-(pentan-3-yloxy)phenyl)-2-(pyrazin-2-yl)pyrimidin-4-yl)thiazol-2-yl)-3-(3-morpholinopropyl)urea | HPLC $t_R$ = 4.01 min<br>LCMS [M + H]$^+$ = 617.35 |
| 285 | 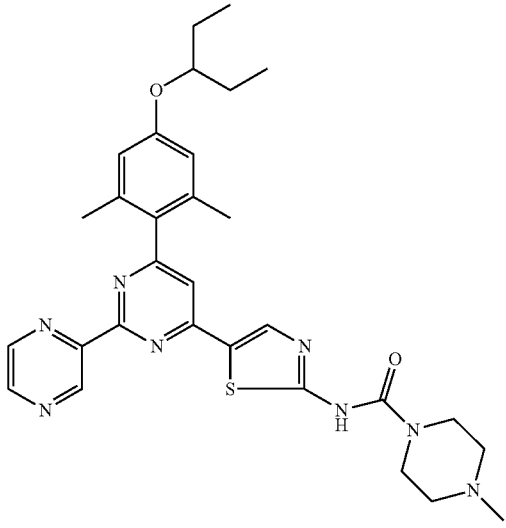<br>N-(5-(6-(2,6-dimethyl-4-(pentan-3-yloxy)phenyl)-2-(pyrazin-2-yl)pyrimidin-4-yl)thiazol-2-yl)-4-methylpiperazine-1-carboxamide | HPLC $t_R$ = 3.95 min<br>LCMS [M + H]$^+$ = 573.35 |

TABLE 16-continued

| Ex. # | Compound Structure/Name | HPLC and LCMS Data |
|---|---|---|
| 286 | 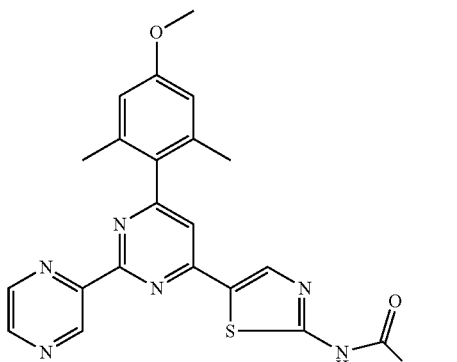<br>1-(5-(6-(4-methoxy-2,6-dimethylphenyl)-2-(pyrazin-2-yl)pyrimidin-4-yl)thiazol-2-yl)-3-methylurea | HPLC $t_R$ = 3.88 min<br>LCMS [M + H]$^+$ = 448.25 |
| 287 | 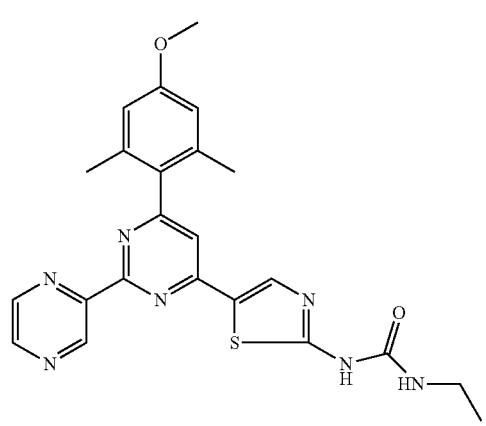<br>1-ethyl-3-(5-(6-(4-methoxy-2,6-dimethylphenyl)-2-(pyrazin-2-yl)pyrimidin-4-yl)thiazol-2-yl)urea | HPLC $t_R$ = 4.06 min<br>LCMS [M + H]$^+$ = 462.31 |
| 288 | 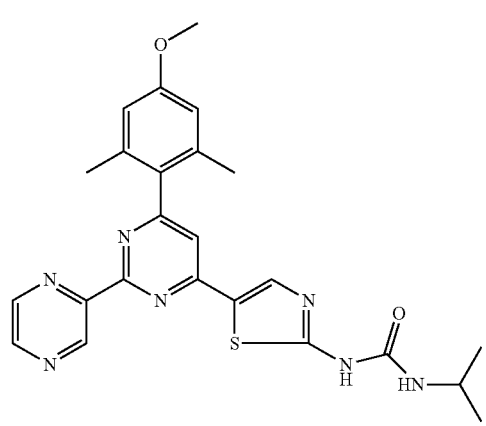<br>1-isopropyl-3-(5-(6-(4-methoxy-2,6-dimethylphenyl)-2-(pyrazin-2-yl)pyrimidin-4-yl)thiazol-2-yl)urea | HPLC $t_R$ = 4.19 min<br>LCMS [M + H]$^+$ = 476.26 |

TABLE 16-continued

| Ex. # | Compound Structure/Name | HPLC and LCMS Data |
|---|---|---|
| 289 | 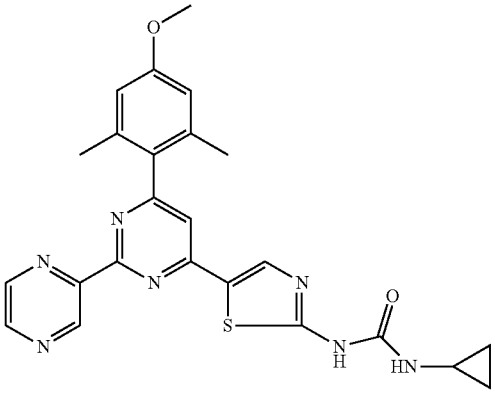<br>1-cyclopropyl-3-(5-(6-(4-methoxy-2,6-dimethylphenyl)-2-(pyrazin-2-yl)pyrimidin-4-yl)thiazol-2-yl)urea | HPLC $t_R$ = 4.18 min<br>LCMS [M + H]$^+$ = 474.22 |
| 290 | 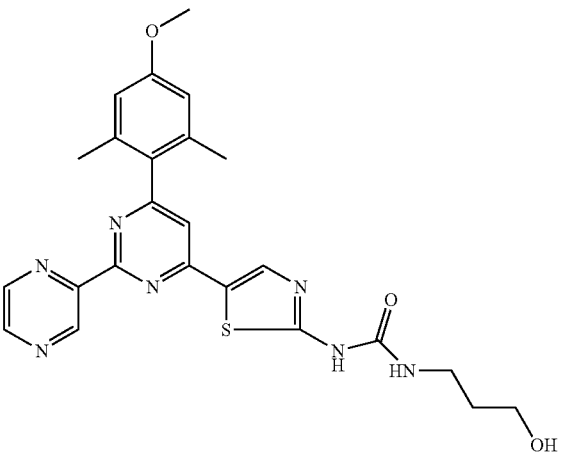<br>1-(3-hydroxypropyl)-3-(5-(6-(4-methoxy-2,6-dimethylphenyl)-2-(pyrazin-2-yl)pyrimidin-4-yl)thiazol-2-yl)urea | HPLC $t_R$ = 3.91 min<br>LCMS [M + H]$^+$ = 492.30 |
| 291 | 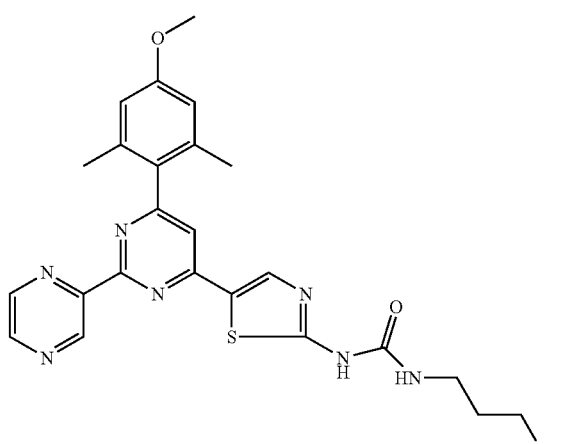<br>1-(5-(6-(4-methoxy-2,6-dimethylphenyl)-2-(pyrazin-2-yl)pyrimidin-4-yl)thiazol-2-yl)-3-(3-(methylamino)propyl)urea | HPLC $t_R$ = 3.43 min<br>LCMS [M + H]$^+$ = 505.21 |

TABLE 16-continued

| Ex. # | Compound Structure/Name | HPLC and LCMS Data |
|---|---|---|
| 292 | 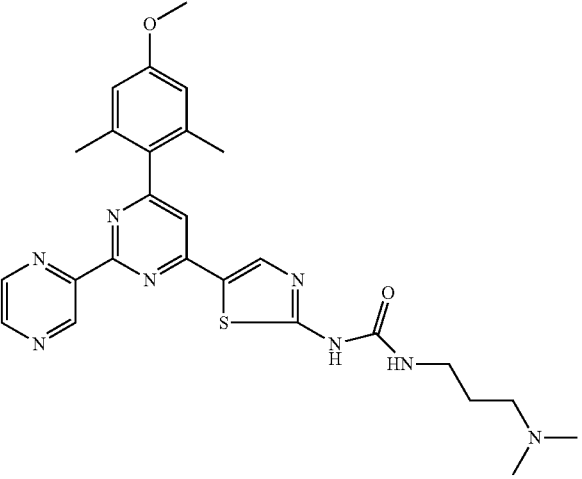<br>1-(3-(dimethylamino)propyl)-3-(5-(6-(4-methoxy-2,6-dimethylphenyl)-2-(pyrazin-2-yl)pyrimidin-4-yl)thiazol-2-yl)urea | HPLC $t_R$ = 3.45 min<br>LCMS [M + H]$^+$ = 519.28 |
| 293 | 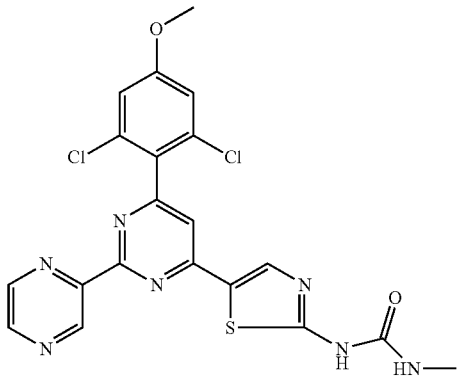<br>1-(5-(6-(2,6-dichloro-4-methoxyphenyl)-2-(pyrazin-2-yl)pyrimidin-4-yl)thiazol-2-yl)-3-methylurea | HPLC $t_R$ = 3.98 min<br>LCMS [M + H]$^+$ = 488.05 |
| 294 | 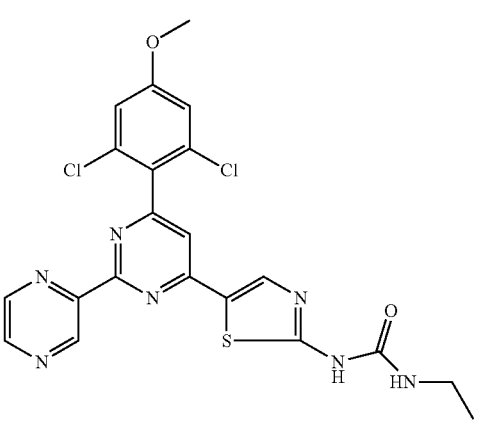<br>1-(5-(6-(2,6-dichloro-4-methoxyphenyl)-2-(pyrazin-2-yl)pyrimidin-4-yl)thiazol-2-yl)-3-ethylurea | HPLC $t_R$ = 4.13 min<br>LCMS [M + H]$^+$ = 502.06 |

TABLE 16-continued

| Ex. # | Compound Structure/Name | HPLC and LCMS Data |
|---|---|---|
| 295 | 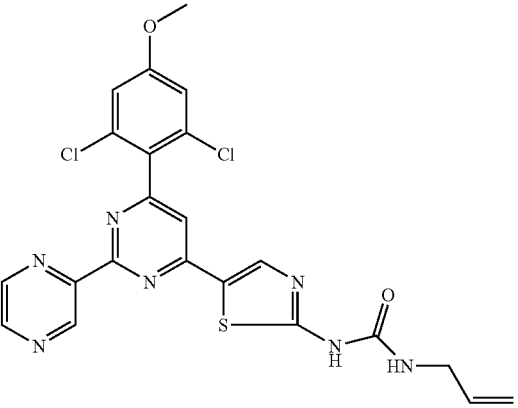<br>1-allyl-3-(5-(6-(2,6-dichloro-4-methoxyphenyl)-2-(pyrazin-2-yl)pyrimidin-4-yl)thiazol-2-yl)ureaethylurea | HPLC $t_R$ = 4.19 min<br>LCMS [M + H]$^+$ = 514.08 |
| 296 | 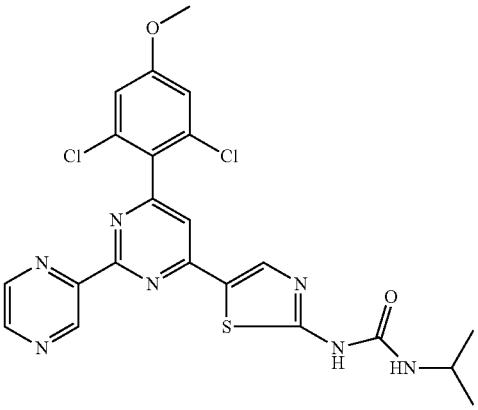<br>11-(5-(6-(2,6-dichloro-4-methoxyphenyl)-2-(pyrazin-2-yl)pyrimidin-4-yl)thiazol-2-yl)-3-isopropylurea | HPLC $t_R$ = 4.26 min<br>LCMS [M + H]$^+$ = 516.04 |
| 297 | 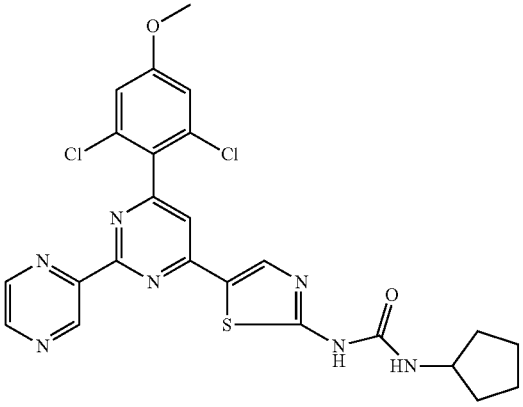<br>1-cyclopentyl-3-(5-(6-(2,6-dichloro-4-methoxyphenyl)-2-(pyrazin-2-yl)pyrimidin-4-yl)thiazol-2-yl)urea | HPLC $t_R$ = 4.45 min<br>LCMS [M + H]$^+$ = 542.06 |

TABLE 16-continued

| Ex. # | Compound Structure/Name | HPLC and LCMS Data |
|---|---|---|
| 298 | 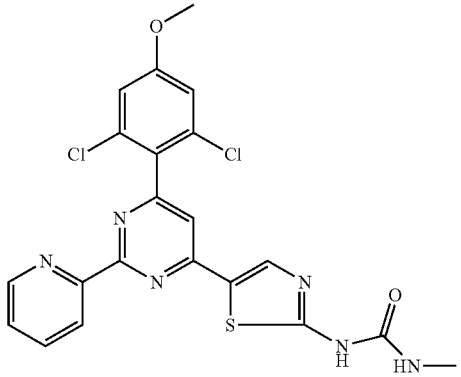<br>1-(5-(6-(2,6-dichloro-4-methoxyphenyl)-2-(pyridin-2-yl)pyrimidin-4-yl)thiazol-2-yl)-3-methylurea | HPLC $t_R$ = 3.60 min<br>LCMS $[M + H]^+$ = 487.13 |
| 299 | 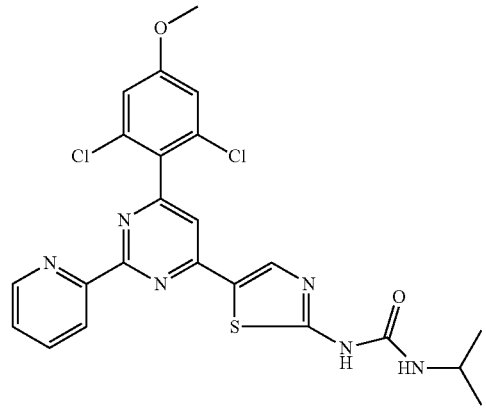<br>1-(5-(6-(2,6-dichloro-4-methoxyphenyl)-2-(pyridin-2-yl)pyrimidin-4-yl)thiazol-2-yl)-3-isopropylurea | HPLC $t_R$ = 3.90 min<br>LCMS $[M + H]^+$ = 515.18 |
| 300 | 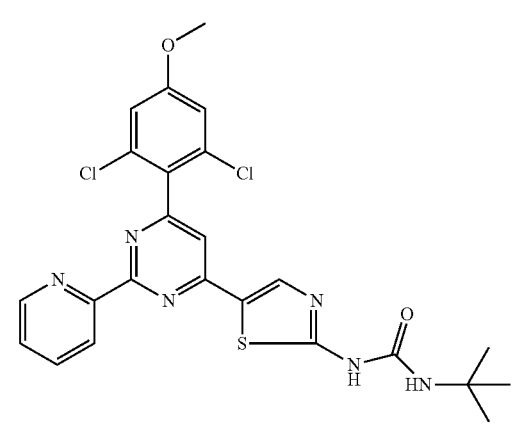<br>1-tert-butyl-3-(5-(6-(2,6-dichloro-4-methoxyphenyl)-2-(pyridin-2-yl)pyrimidin-4-yl)thiazol-2-yl)urea | HPLC $t_R$ = 4.08 min<br>LCMS $[M + H]^+$ = 529.20 |

TABLE 16-continued

| Ex. # | Compound Structure/Name | HPLC and LCMS Data |
|---|---|---|
| 301 | 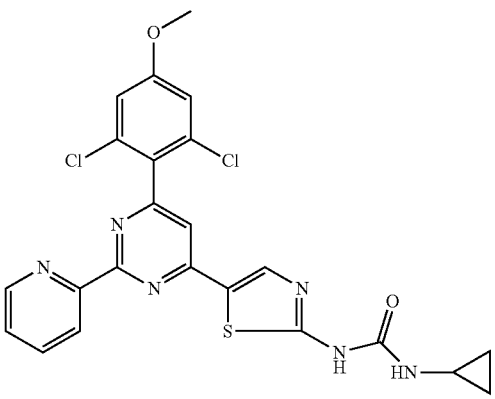<br>1-cyclopropyl-3-(5-(6-(2,6-dichloro-4-methoxyphenyl)-2-(pyridin-2-yl)pyrimidin-4-yl)thiazol-2-yl)urea | HPLC $t_R$ = 4.76 min<br>LCMS [M + H]$^+$ = 513.20 |
| 302 | 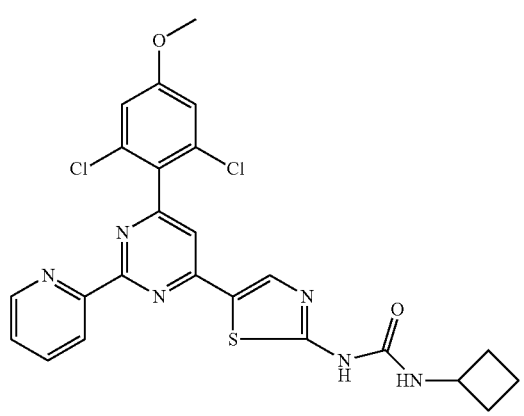<br>1-cyclobutyl-3-(5-(6-(2,6-dichloro-4-methoxyphenyl)-2-(pyridin-2-yl)pyrimidin-4-yl)thiazol-2-yl)urea | HPLC $t_R$ = 3.97 min<br>LCMS [M + H]$^+$ = 527.20 |
| 303 | 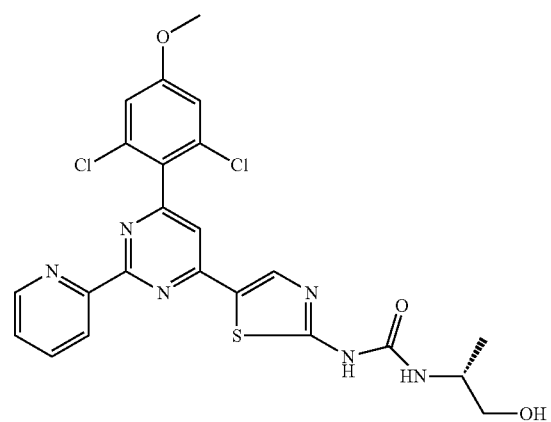<br>(R)-1-(5-(6-(2,6-dichloro-4-methoxyphenyl)-2-(pyridin-2-yl)pyrimidin-4-yl)thiazol-2-yl)-3-(1-hydroxypropan-2-yl)urea | HPLC $t_R$ = 3.62 min<br>LCMS [M + H]$^+$ = 531.20 |

TABLE 16-continued

| Ex. # | Compound Structure/Name | HPLC and LCMS Data |
|---|---|---|
| 304 | 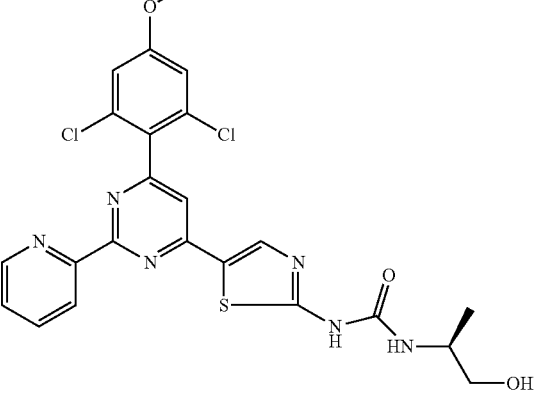<br>(S)-1-(5-(6-(2,6-dichloro-4-methoxyphenyl)-2-(pyridin-2-yl)pyrimidin-4-yl)thiazol-2-yl)-3-(1-hydroxypropan-2-yl)urea | HPLC $t_R$ = 3.60 min<br>LCMS [M + H]$^+$ = 531.20 |
| 305 | 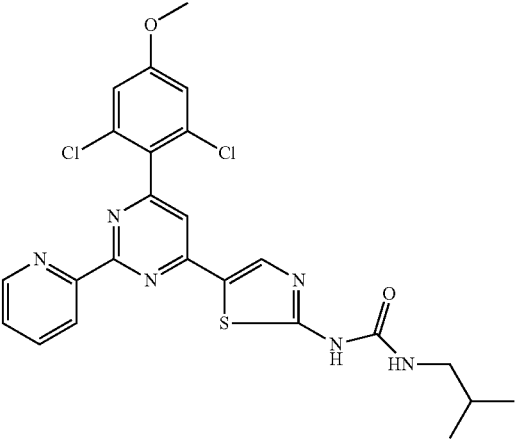<br>1-(5-(6-(2,6-dichloro-4-methoxyphenyl)-2-(pyridin-2-yl)pyrimidin-4-yl)thiazol-2-yl)-3-isobutylurea | HPLC $t_R$ = 4.08 min<br>LCMS [M + H]$^+$ = 529.20 |

Example 306

Methyl 5-(6-(2,6-dimethyl-4-(pentan-3-yloxy)phenyl)-2-(pyrazin-2-yl)pyrimidin-4-yl)thiazol-2-ylcarbamate

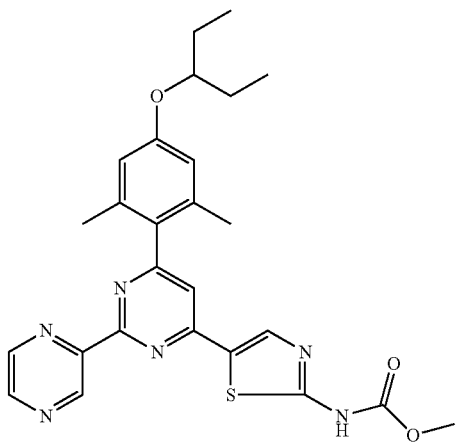

To a slurry of Example 264 (25.0 mg, 0.056 mmol) in THF (0.2 ml) was added TEA (8.5 ul, 0.062 mmol) and methyl chloroformate (0.0052 ml, 0.067 mmol). After stirred at rt. for 1 hr, the solvent was removed in vacuo. The oil residue was purified by reverse-phase preparative HPLC and the fraction containing the product was concentrated in vacuo and diluted with 1.0 N aqueous hydrochloric acid (1-2 ml), and lyophilized to yield 18.5 mg (58.4%) yellow solid. HPLC Ret. time: 4.64 min. LCMS MH$^+$ (m/z)=505.23. $^1$H NMR: (CDCl$_3$, 400 MHz): δ 9.80 (d, 1H), 8.82 (d, 1H), 8.74 (s, 1H), 8.16 (s, 1H), 7.54 (s, 1H), 6.69 (s, 2H), 4.17 (m, 1H), 3.96 (s, 3H), 2.15 (s, 6H), 1.70 (m, 4H), 0.98 (t, 6H).

Examples 307-315

Examples 307-315 listed in Table 18 below were prepared from Example 264 according to the general procedure described in Example 306

TABLE 17

| Ex. # | Compound Structure/Name | HPLC and LCMS Data |
|---|---|---|
| 307 | 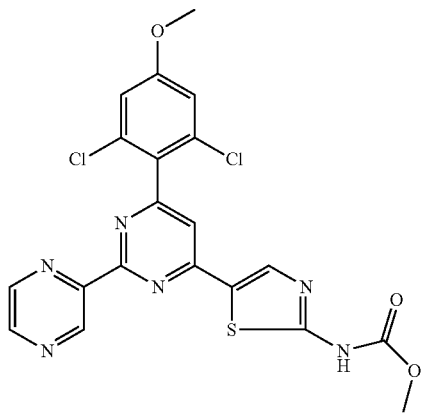<br>methyl 5-(6-(2,6-dichloro-4-methoxyphenyl)-2-(pyrazin-2-yl)pyrimidin-4-yl)thiazol-2-ylcarbamate | HPLC $t_R$ = 4.14 min<br>LCMS [M + H]$^+$ = 489.01 |
| 308 | 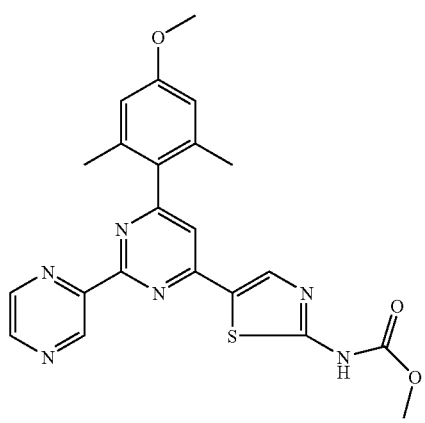<br>methyl 5-(6-(4-methoxy-2,6-dimethylphenyl)-2-(pyrazin-2-yl)pyrimidin-4-yl)thiazol-2-ylcarbamate | HPLC $t_R$ = 4.04 min<br>LCMS [M + H]$^+$ = 449.26 |
| 309 | 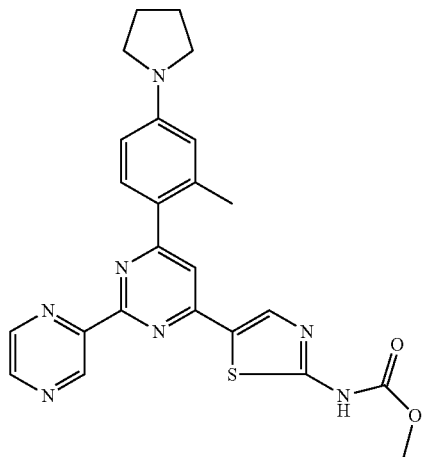<br>methyl 5-(6-(2-methyl-4-(pyrrolidin-1-yl)phenyl)-2-(pyrazin-2-yl)pyrimidin-4-yl)thiazol-2-ylcarbamate | HPLC $t_R$ = 4.43 min<br>LCMS [M + H]$^+$ = 474.15 |

TABLE 17-continued

| Ex. # | Compound Structure/Name | HPLC and LCMS Data |
|---|---|---|
| 310 | 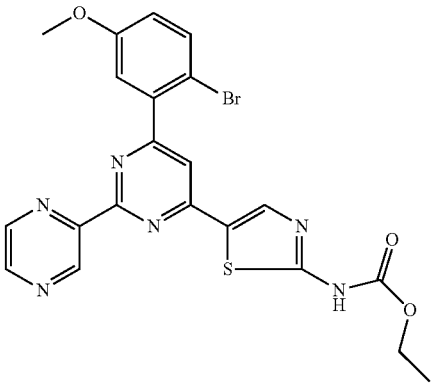<br>ethyl 5-(6-(2-bromo-5-methoxyphenyl)-2-(pyrazin-2-yl)pyrimidin-4-yl)thiazol-2-ylcarbamate | HPLC $t_R$ = 4.36 min<br>LCMS $[M + H]^+$ = 512.90, 514.90 |
| 311 | 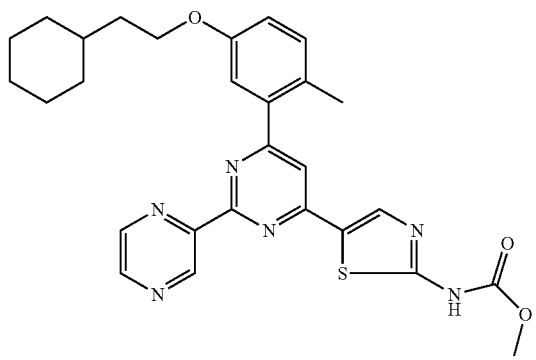<br>methyl 5-(6-(5-(2-cyclohexylethoxy)-2-methylphenyl)-2-(pyrazin-2-yl)pyrimidin-4-yl)thiazol-2-ylcarbamate | HPLC $t_R$ = 5.12 min<br>LCMS $[M + H]^+$ = 531.23 |
| 312 | 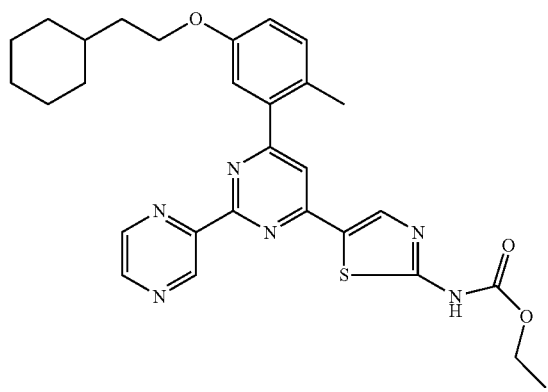<br>ethyl 5-(6-(5-(2-cyclohexylethoxy)-2-methylphenyl)-2-(pyrazin-2-yl)pyrimidin-4-yl)thiazol-2-ylcarbamate | HPLC $t_R$ = 5.36 min<br>LCMS $[M + H]^+$ = 545.23 |

TABLE 17-continued

| Ex. # | Compound Structure/Name | HPLC and LCMS Data |
|---|---|---|
| 313 | 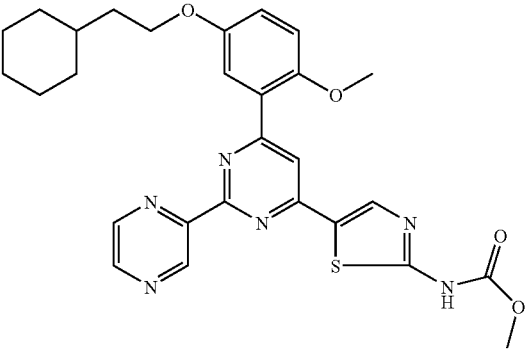<br>methyl 5-(6-(5-(2-cyclohexylethoxy)-2-methoxyphenyl)-2-(pyrazin-2-yl)pyrimidin-4-yl)thiazol-2-ylcarbamate | HPLC $t_R$ = 4.58 min<br>LCMS [M + H]$^+$ = 547.27 |
| 314 | 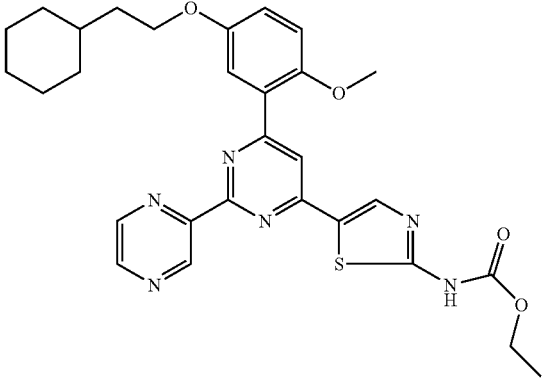<br>ethyl 5-(6-(5-(2-cyclohexylethoxy)-2-methoxyphenyl)-2-(pyrazin-2-yl)pyrimidin-4-yl)thiazol-2-ylcarbamate | HPLC $t_R$ = 5.29 min<br>LCMS [M + H]$^+$ = 561.28 |
| 315 | 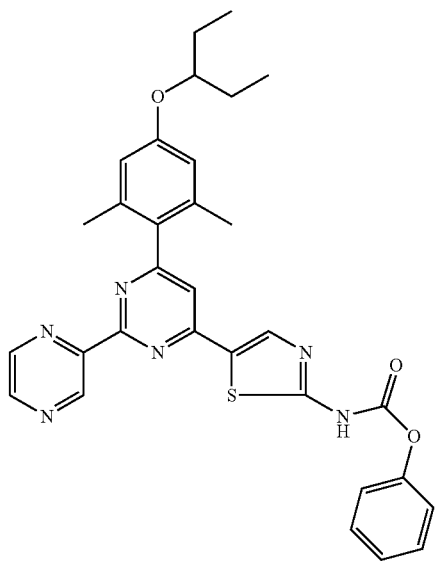<br>phenyl 5-(6-(2,6-dimethyl-4-(pentan-3-yloxy)phenyl)-2-(pyrazin-2-yl)pyrimidin-4-yl)thiazol-2-ylcarbamate | HPLC $t_R$ = 4.85 min<br>LCMS [M + H]$^+$ = 567.26 |

Examples 316-317

Examples 316-317 listed in Table 18 below were prepared from Example 71 according to the general procedure described in Example 65.

TABLE 18

| Ex. # | Compound Structure/Name | HPLC and LCMS Data |
|---|---|---|
| 316 | 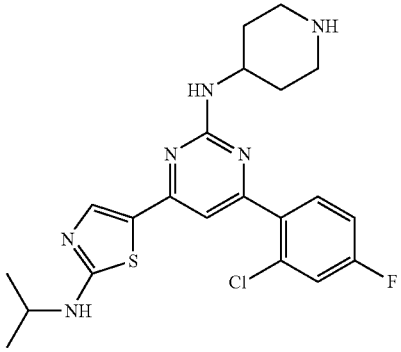<br>4-(2-chloro-4-fluorophenyl)-6-(2-isopropylamino)<br>thiazol-5-yl)-N-(piperidin-4-yl)pyrimidin-2-amine | HPLC $t_R$ = 2.50 min<br>LCMS [M + H]$^+$ = 447.17 |
| 317 | 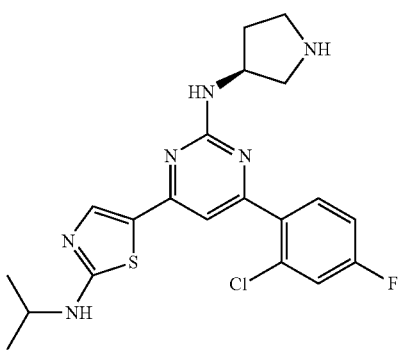<br>4-(2-chloro-4-fluorophenyl)-6-(2-isopropylamino)<br>thiazol-5-yl)-N-((S)-pyrrolidin-3-yl)pyrimidin-2-amine | HPLC $t_R$ = 2.55 min<br>LCMS [M + H]$^+$ = 433.13 |

Example 318

4-(2-chlorophenyl)-6-(2-(isopropylamino)thiazol-5-yl)pyrimidin-2-ol

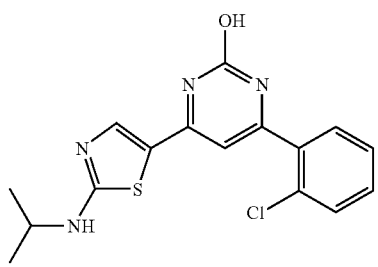

Example 318 was prepared from 5-(6-(2-chlorophenyl)-2-(methylsulfonyl)pyrimidin-4-yl)-N-isopropylthiazol-2-amine utilizing a similar procedure as described in Example 50 by substituting 1-methylpiperazine with 1N NaOH aqueous solution. Yellow solid. HPLC Ret. time: 2.55 min. LCMS MH$^+$ (m/z) 347.20. $^1$H NMR: (d$_6$-DMSO, 500 MHz) δ 11.58 (br, 1H), 8.41 (d, 1H), 8.12 (s, 1H), 7.60 (m, 1H), 7.55 (m, 2H), 7.48 (m, 1H), 6.86 (br. s, 1H), 3.86 (m, 1H), 1.18 (d, 6H).

Example 319-333

Examples 319-333 listed in Table 19 below were prepared as previously described for Example 24.

TABLE 19

| Ex. # | Compound Structure/Name | HPLC and LCMS Data |
|---|---|---|
| 319 | 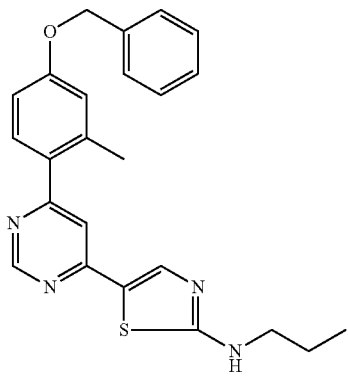<br>5-(6-(4-(benzyloxy)-2-methylphenyl)pyrimidin-4-yl)-N-propylthiazol-2-amine | HPLC $t_R$ = 4.34 min<br>LCMS [M + H]$^+$ = 417.24 |
| 320 | 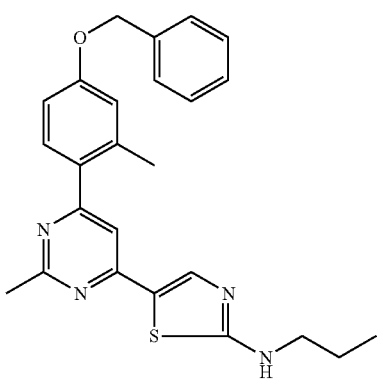<br>5-(6-(4-(benzyloxy)-2-methylphenyl)-2-methylpyrimidin-4-yl)-N-propylthiazol-2-amine | HPLC $t_R$ = 4.19 min<br>LCMS [M + H]$^+$ = 431.22 |
| 321 | 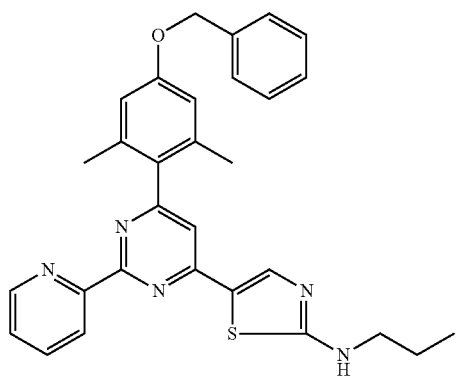<br>5-(6-(4-(benzyloxy)-2,6-dimethylphenyl)-2-(pyridin-2-yl)pyrimidin-4-yl)-N-propylthiazol-2-amine | HPLC $t_R$ = 4.64 min<br>LCMS [M + H]$^+$ = 508.22 |

TABLE 19-continued

| Ex. # | Compound Structure/Name | HPLC and LCMS Data |
|---|---|---|
| 322 | 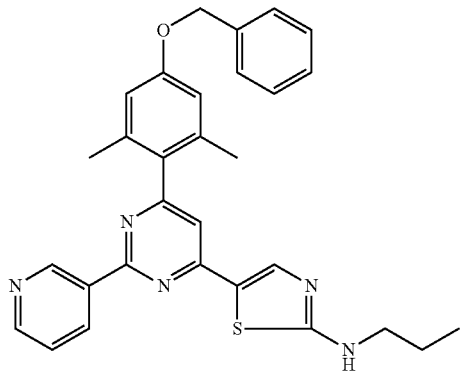<br>5-(6-(4-(benzyloxy)-2,6-dimethylphenyl)-2-(pyridin-3-yl)pyrimidin-4-yl)-N-propylthiazol-2-amine | HPLC $t_R$ = 4.48 min<br>LCMS [M + H]$^+$ = 508.23 |
| 323 | 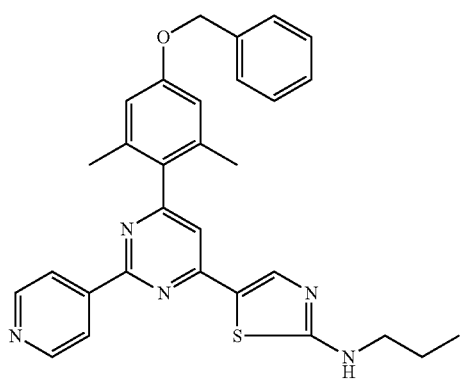<br>5-(6-(4-(benzyloxy)-2,6-dimethylphenyl)-2-(pyridin-4-yl)pyrimidin-4-yl)-N-propylthiazol-2-amine | HPLC $t_R$ = 4.43 min<br>LCMS [M + H]$^+$ = 508.24 |
| 324 | 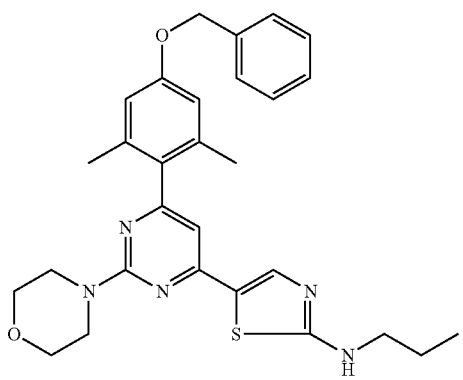<br>5-(6-(4-(benzyloxy)-2,6-dimethylphenyl)-2-morpholinopyrimidin-4-yl)-N-propylthiazol-2-amine | HPLC $t_R$ = 4.42 min<br>LCMS [M + H]$^+$ = 516.27 |

| Ex. # | Compound Structure/Name | HPLC and LCMS Data |
|---|---|---|
| 325 | 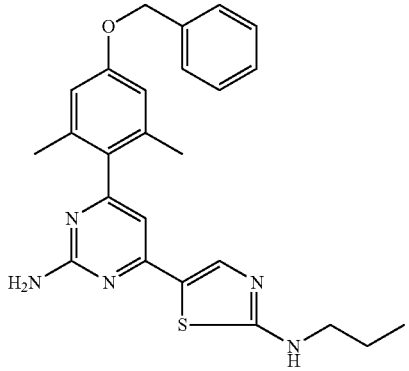<br>5-(2-amino-6-(4-(benzyloxy)-2,6-dimethylphenyl)pyrimidin-4-yl)-N-propylthiazol-2-amine | HPLC $t_R$ = 3.88 min<br>LCMS [M + H]$^+$ = 446.32 |
| 326 | 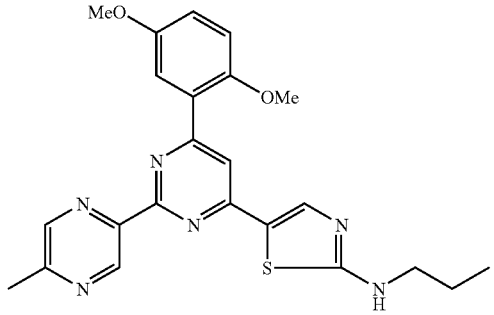<br>5-(6-(2,5-dimethoxyphenyl)-2-(5-methylpyrazin-2-yl)pyrimidin-4-yl)-N-propylthiazol-2-amine | HPLC $t_R$ = 4.04 min<br>LCMS [M + H]$^+$ = 449.23 |
| 327 | 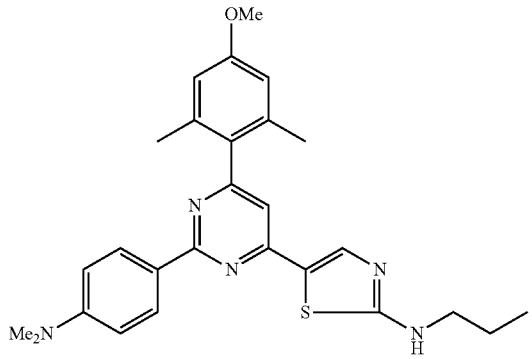<br>5-(2-(4-(dimethylamino)phenyl)-6-(4-methoxy-2,6-dimethylphenyl)pyrimidin-4-yl)-N-propylthiazol-2-amine | HPLC $t_R$ = 4.22 min<br>LCMS [M + H]$^+$ = 474.44 |

TABLE 19-continued

| Ex. # | Compound Structure/Name | HPLC and LCMS Data |
|---|---|---|
| 328 | 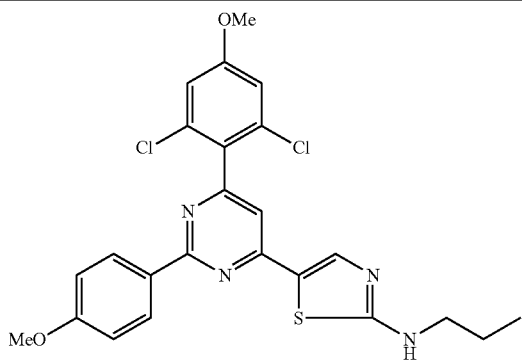<br>5-(6-(2,6-dichloro-4-methoxyphenyl)-2-(4-methoxyphenyl)pyrimidin-4-yl)-N-propylthiazol-2-amine | HPLC $t_R$ = 4.59 min<br>LCMS [M + H]$^+$ = 501.22 |
| 329 | 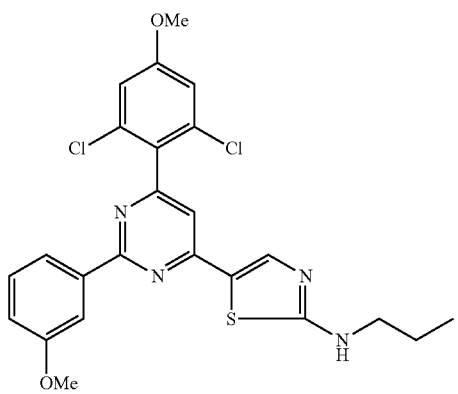<br>5-(6-(2,6-dichloro-4-methoxyphenyl)-2-(3-methoxyphenyl)pyrimidin-4-yl)-N-propylthiazol-2-amine | HPLC $t_R$ = 4.62 min<br>LCMS [M + H]$^+$ = 501.22 |
| 330 | 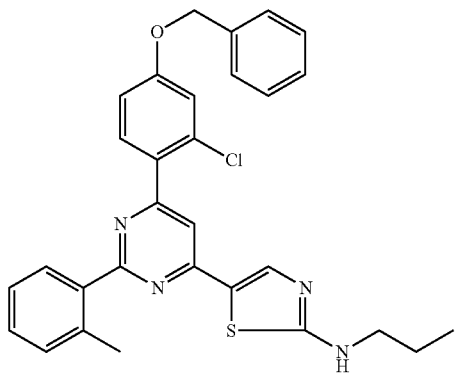<br>5-(6-(4-(benzyloxy)-2-chlorophenyl)-2-o-tolylpyrimidin-4-yl)-N-propylthiazol-2-amine | HPLC $t_R$ = 4.69 min<br>LCMS [M + H]$^+$ = 527.23 |

TABLE 19-continued

| Ex. # | Compound Structure/Name | HPLC and LCMS Data |
|---|---|---|
| 331 | 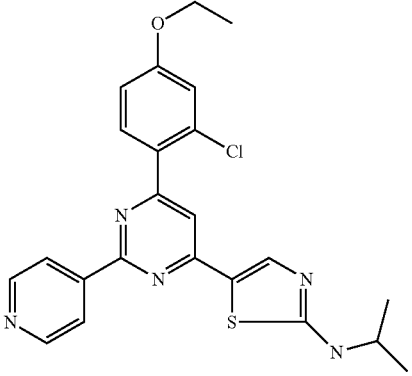 | HPLC $t_R$ = 3.30 min<br>LCMS [M + H]$^+$ = 452.10 |
| 332 | 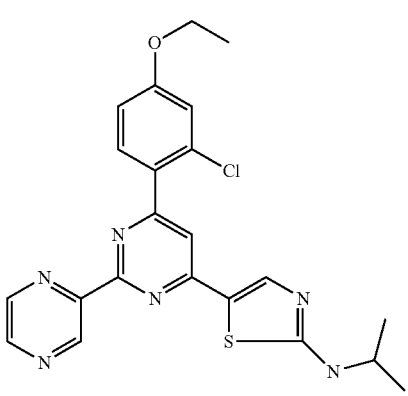 | HPLC $t_R$ = 3.52 min<br>LCMS [M + H]$^+$ = 453.09 |
| 333 | 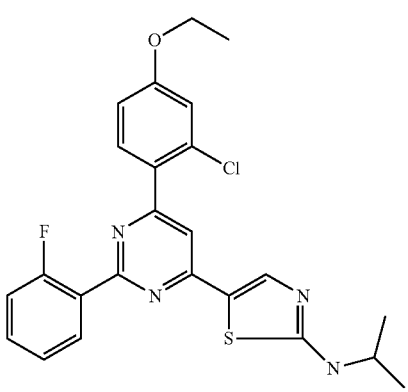 | HPLC $t_R$ = 3.90 min<br>LCMS [M + H]$^+$ = 469.09 |

What is claimed is:

1. A compound of formula (I)

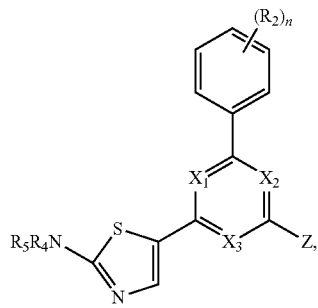

or a pharmaceutically acceptable salt thereof, an enantiomer thereof or a diastereomer thereof, wherein:
  two of $X_1$, $X_2$, and $X_3$ are N, and the remaining one of $X_1$, $X_2$, and $X_3$ is —$CR_1$;
  $R_1$ is hydrogen;
  n is zero, 1, 2, or 3;
  each $R_2$ is independently $C_1$-$C_8$ alkyl, substituted $C_1$-$C_8$ alkyl, cycloalkyl, substituted cycloalkyl, alkenyl, substituted alkenyl, alkynyl, substituted alkynyl, —$OR_4$, —$SR_4$, —$CO_2R_4$, —$C(=O)NR_4R_5$, —$NR_4R_5$, —$S(=O)R_6$, —$SO_2R_6$, —$SO_2NR_4R_5$, —$NR_4SO_2NR_5R_6$, —$NR_4SO_2R_6$, —$NR_4C(=O)R_5$, —$NR_4CO_2R_5$, —$NR_4C(=O)NR_5R_6$, halogen, cyano, aryl, substituted aryl, heterocyclo, and/or substituted heterocyclo;
  each $R_4$ is independently hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, and/or substituted heterocyclo;

each $R_5$ is independently hydrogen, $C_1$-$C_8$ alkyl, substituted $C_1$-$C_8$ alkyl, cycloalkyl, and/or substituted cycloalkyl;

wherein when $R_4$ and $R_5$ are alkyl and/or substituted alkyl and are bonded to the same atom, $R_4$ and $R_5$ can be optionally linked together to form a four-, five-, or six-membered ring heterocyclo or substituted heterocyclo;

each $R_6$ is independently $C_{1-8}$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, and/or substituted heterocyclo;

wherein when $R_5$ and $R_6$ are alkyl and/or substituted alkyl and are bonded to the same atom, $R_5$ and $R_6$ can be optionally linked together to form a four-, five-, or six-membered ring heterocyclo or substituted heterocyclo;

Z is hydrogen, $C_1$-$C_8$ alkyl, $C_1$-$C_8$ substituted alkyl, cycloalkyl, substituted cycloalkyl, —$OR_7$, —$SR_7$, —$CO_2R_7$, —$C(=O)NR_7R_8$, —$NR_7R_8$, —$S(=O)R_9$, —$SO_2R_8$, —$SO_2NR_7R_8$, —$NR_7SO_2NR_8R_9$, —$NR_7SO_2R_9$, —$NR_7C(=O)R_8$, —$NR_7CO_2R_8$, —$NR_7C(=O)NR_8R_9$, halogen, cyano, aryl, substituted aryl, heterocyclo, or substituted heterocyclo;

$R_7$ is hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo;

$R_8$ is hydrogen, $C_1$-$C_8$ alkyl, substituted $C_1$-$C_8$ alkyl, cycloalkyl, or substituted cycloalkyl;

wherein when $R_7$ and $R_8$ are alkyl and/or substituted alkyl and are bonded to the same atom, $R_7$ and $R_8$ can be optionally linked together to form a four-, five-, or six-membered ring heterocyclo or substituted heterocyclo;

$R_9$ is $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo; and wherein when $R_8$ and $R_9$ are alkyl and are bonded to the same atom, $R_8$ and $R_9$ can be optionally linked together to form a four-, five-, or six-membered ring heterocyclo or substituted heterocyclo; with the provisos that:

(a) $R_2$ is not optionally substituted phenoxy attached to para-position of the phenyl ring;

(b) $R_7$ is not pyrazolyl, substituted pyrazolyl, alkyl substituted triazolyl, indazolyl, or substituted indazolyl when Z is —$NR_7R_8$; and (c) n is 1, 2, or 3 when Z is unsubstituted phenyl.

2. The compound according to claim 1 wherein $X_2$ and $X_3$ are N, and $X_1$ is —$CR_1$.

3. The compound according to claim 1 wherein Z is —$NR_7R_8$, —$NR_7SO_2NR_8R_9$, pyridyl, or substituted pyridyl.

4. The compound according to claim 1 or a pharmaceutically acceptable salt thereof, an enantiomer thereof or a diastereomer thereof, wherein:

Z is —$NR_7R_8$ or pyridyl, pyridazinyl, or pyrazinyl optionally substituted with one to three $R_{10}$;

$R_7$ is independently hydrogen, $C_1$-$C_8$ alkyl, substituted $C_1$-$C_8$ alkyl, cycloalkyl, substituted cycloalkyl, alkenyl, substituted alkenyl, alkynyl, substituted alkynyl, aryl, substituted aryl, heterocyclo, or substituted heterocyclo;

$R_8$ is independently hydrogen, $C_1$-$C_8$ alkyl, substituted $C_1$-$C_8$ alkyl, cycloalkyl, or substituted cycloalkyl;

wherein when $R_7$ and $R_8$ are alkyl and/or substituted alkyl and are bonded to the same atom, $R_7$ and $R_8$ can be optionally linked together to form a four-, five-, or six-membered ring heterocyclo or substituted heterocyclo; and each $R_{10}$ is independently halogen, cyano, $C_1$-$C_8$ alkyl, substituted $C_1$-$C_8$ alkyl, cycloalkyl, substituted cycloalkyl, alkenyl, substituted alkenyl, alkynyl, and/or substituted alkynyl;

with the proviso that: $R_7$ is not pyrazolyl, substituted pyrazolyl, indazolyl, substituted indazolyl, or alkyl substituted triazolyl when Z is —$NR_7R_8$.

5. The compound according to claim 4 wherein $X_2$ and $X_3$ are N, and $X_1$ is —$CR_1$.

6. The compound according to claim 4 wherein Z is —$NR_7R_8$, pyridyl, or substituted pyridyl.

7. A pharmaceutical composition comprising one or more compound(s) according to claim 1 and a pharmaceutically-acceptable carrier or diluent.

8. A pharmaceutical composition comprising one or more compound(s) according to claim 4 and a pharmaceutically-acceptable carrier or diluent.

9. A method of treating asthma, adult respiratory distress syndrome, chronic obstructive pulmonary disease, chronic pulmonary inflammatory disease, diabetes, inflammatory bowel disease, rheumatoid arthritis, psoriatic arthritis, traumatic arthritis, rubella arthritis, gouty arthritis or osteoarthritis comprising administering to a patient in need of such treatment a pharmaceutical composition according to claim 1.

10. A method of treating asthma, adult respiratory distress syndrome, chronic obstructive pulmonary disease, chronic pulmonary inflammatory disease, diabetes, inflammatory bowel disease, rheumatoid arthritis, psoriatic arthritis, traumatic arthritis, rubella arthritis, gouty arthritis or osteoarthritis in a mammal comprising administering to the mammal in need of such treatment at least one compound according to claim 4.

* * * * *

UNITED STATES PATENT AND TRADEMARK OFFICE
CERTIFICATE OF CORRECTION

PATENT NO. : 7,923,556 B2
APPLICATION NO. : 12/570010
DATED : April 12, 2011
INVENTOR(S) : Stephen Wrobleski et al.

It is certified that error appears in the above-identified patent and that said Letters Patent is hereby corrected as shown below:

Title Page, (Attorney, Agent, or Firm), delete "Lauralee L. Duncan" and insert -- Laurelee L. Duncan --, therefor.

In the Claims:

Claim 9, col. 322, line 42, delete "pharmaceutical composition" and insert -- therapeutically effective amount of a compound --; and Claim 10, col. 322, line 50, after "treatment" insert -- a therapeutically effective amount of --, therefor.

Signed and Sealed this
Twenty-fifth Day of September, 2012

David J. Kappos
*Director of the United States Patent and Trademark Office*